United States Patent
Borroni et al.

(10) Patent No.: US 11,541,132 B2
(45) Date of Patent: Jan. 3, 2023

(54) RADIOLABELED COMPOUNDS

(71) Applicant: Hoffmann-La Roche Inc., Little Falls, NJ (US)

(72) Inventors: Edilio Borroni, Basel (CH); Luca Gobbi, Basel (CH); Michael Honer, Basel (CH); Martin Edelmann, Basel (CH); Dale Mitchell, Margate (GB); David Hardick, Margate (GB); Wolfgang Schmidt, Margate (GB); Christopher Steele, Margate (GB); Mushtaq Mulla, Margate (GB)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/907,010

(22) Filed: Jun. 19, 2020

(65) Prior Publication Data

US 2020/0316232 A1 Oct. 8, 2020

Related U.S. Application Data

(63) Continuation of application No. PCT/EP2018/085464, filed on Dec. 18, 2018.

(30) Foreign Application Priority Data

Dec. 21, 2017 (EP) ..................................... 17209716

(51) Int. Cl.
- *A61K 51/00* (2006.01)
- *A61M 36/14* (2006.01)
- *A61K 51/04* (2006.01)

(52) U.S. Cl.
CPC ................................ *A61K 51/0459* (2013.01)

(58) Field of Classification Search
CPC .................................................. A61K 51/0459
USPC ........................................................ 424/1.89
See application file for complete search history.

(56) References Cited

U.S. PATENT DOCUMENTS

| 2011/0250135 A1* | 10/2011 | Schmitt-Willich | C07D 213/81 |
| | | | 424/1.89 |
| 2013/0164259 A1* | 6/2013 | Cheng | C07D 403/12 |
| | | | 544/364 |

FOREIGN PATENT DOCUMENTS

WO    WO-2014207508 A1 * 12/2014 ................ A61P 3/06

OTHER PUBLICATIONS

Frank et al. J. Label. Compd Radiopharm. 2007: 50: 746-769. (Year: 2007).*
Patani et al. Chem. Rev. 1996, 96, 3147-3176. (Year: 1996).*
Brockschnieder, D., et al., "Preclinical Characterization of a Novel Class of 18F-labeled PET Tracers for amyloid-β" J Nucl Med 53(11):1794-1801 (Nov. 1, 2012).
"International Preliminary Report on Patentability—PCT/EP2018/085464" (Report dated Jun. 23, 2020),:pp. 1-8 (Jul. 2, 2020).
"International Search Report—PCT/EP2018/085464":pp. 1-5 (dated Mar. 19, 2019).
Zollinger, M., et al., "Absorption, distribution, metabolism, and excretion (ADME) of 14C-sonidegib (LDE225) in healthy volunteers" Cancer Chemother Pharmacol 74(1):63-75 (Jul. 1, 2014).

* cited by examiner

*Primary Examiner* — Michael G. Hartley
*Assistant Examiner* — Sean R Donohue
(74) *Attorney, Agent, or Firm* — Bradley E. Davis

(57) ABSTRACT

The present invention relates to radiolabeled compounds of formula I

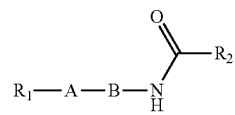

wherein either A, B, $R_1$, $R_2$, is labeled with a radionuclide selected from $^3H$, $^{11}C$ and $^{18}F$ and its use for imaging alpha synuclein and/or Abeta deposits in mammals.

4 Claims, 6 Drawing Sheets

RADIOLABELED COMPOUNDS

CROSS-REFERENCE TO RELATED APPLICATIONS

Figure 1:
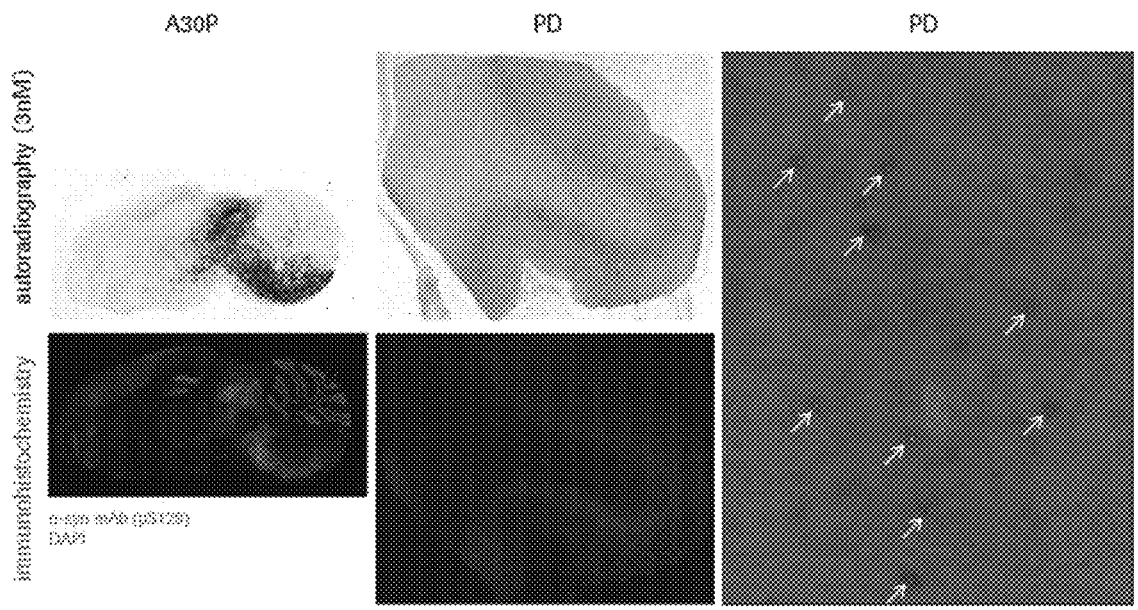

This application is a continuation of International Application No. PCT/EP2018/085464 having an international filing date of Dec. 18, 2018, and which claims benefit under 35 U.S.C. § 119 to European Patent Application No. 17209716.4, filed Dec. 21, 2017; all of which are incorporated by reference in their entirety.

The present invention relates to radiolabeled compounds of formula I

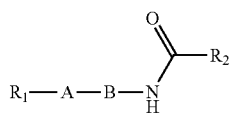

wherein

A is heterocycloalkyl,

B is aryl or heteroaryl both optionally substituted by $C_{1-7}$alkyl or halogen, $R_1$ is selected from aryl, heteroaryl optionally substituted by $C_{1-7}$alkyl, $C_{1-7}$alkoxy, cyano, halogen, —C(O)O—$C_{1-7}$alkyl, —N($C_{1-7}$alkyl)$_2$, halo-$C_{1-7}$alkoxy, —SO$_2$—$C_{1-7}$alkyl, $C_{2-7}$alkynyl, $R_2$ is selected from aryl, heteroaryl optionally substituted by halogen, $C_{1-7}$alkoxy, halo-$C_{1-7}$alkoxy, hydroxyl, —N($C_{1-7}$alkyl)$_2$, halo-$C_{1-7}$alkoxy-($C_{1-7}$-alkoxy)$_n$, hydroxyl-halo-$C_{1-7}$alkoxy, hydroxyl-($C_{1-7}$alkoxy)$_n$, cyano, $C_{1-7}$alkyl, $C_{2-7}$alkynoxy, $C_{2-7}$alkynoxy-($C_{1-7}$-alkoxy)$_n$, halo-$C_{1-7}$alkoxy substituted by —O—Si($C_{1-7}$alky)$_2$-$C_{1-7}$alkyl, heterocycloalkyl optionally substituted by $C_{1-7}$alkyl, n is 1, 2 wherein either A, B, $R_1$, $R_2$, is labeled with a radionuclide selected from $^3$H, $^{11}$C or $^{18}$F.

It has been found that the radiolabelled compounds of formula I may be used as PET (Positron Emission Tomography) and/or autoradiography radiotracers for the labelling and diagnostic molecular imaging of aggregates of α-synuclein (aSyn). Molecular imaging is based on the selective and specific interaction of a molecular probe (e.g. a radiotracer) with a biological target (for instance a receptor, an enzyme, an ion channel, a misfolded protein or any other cellular or extracellular component that is able to bind or retain the molecular probe) which is visualized through PET, nuclear magnetic resonance, near infrared or other methods. PET, a nuclear medical imaging modality, is ideally suited to produce three-dimensional images that provide important information on the distribution of a biological target in a given organ, or on the metabolic activity of such organ or cell or on the ability of a drug to enter such organ, bind to a biological target and/or modify biological processes. Since PET is a non-invasive imaging technique it can be used to investigate the pathophysiology of a disease and the action of a drug on a given molecular target or cellular processes in humans and in animals. The availability of a PET radiotracer specific for a given molecular target can facilitate diagnosis and monitoring of progression of a disease by demonstrating and quantifying pathophysiological changes taking place as a consequence of the disease. In addition, a PET radiotracer may facilitate drug development by supporting patient stratification and the understanding of the mechanism of action of a drug.

The human brain is a complex organ, consisting of millions of intercommunicating neurons. The understanding of abnormalities relating to diseases is the key to the future development of effective diagnosis and novel therapeutics. The study of biochemical abnormalities in human is rapidly becoming an essential and integral component of drug discovery and development process. Over recent years, there has been a growing use of human medical imaging to assess pathologies, disease processes and drug action. These imaging modalities include PET, MRI, CT, ultrasound, EEG, SPECT and others (*British Medical Bulletin*, 2003, 65, 169-177). Therefore, the use of non-invasive imaging modalities, e.g. PET, is an invaluable tool for the development of drugs in the future. Non-invasive nuclear imaging techniques can be used to obtain basic and diagnostic information about the physiology and biochemistry of a variety of living subjects. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. The use of radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject. Currently, radiotracers are available for obtaining useful information concerning cardiac function, myocardial blood flow, lung perfusion, liver function, brain blood flow, regional brain glucose and oxygen metabolism, function of several brain receptors and enzymes and visualization of amyloid beta plaques and tau deposits in Alzheimer's disease (*PET Molecular Imaging and Its Biological Applications*, Eds. Michael E. Phelps, Springer, New York, 2004. Ametamy S. et al., *Chem. Rev.*, 2008, 108, 1501-1516 Nordberg A. et al. *Nat. Rev. Neurol.*, 2010, 6, 78-87).

Furthermore,

PET imaging provides a non-invasive and quantitative assay of normal and abnormal neurochemistry in human at an early stage of the drug development to enhance the efficient and effective discovery of therapeutics.

Understanding disease mechanisms in human using non-invasive techniques is intimately connected with future developments in the diagnosis and management of diseases and of novel therapeutics.

The radionuclides commonly used in PET include $^{11}$C, $^{13}$N, $^{15}$O or $^{18}$F. In principle, it is possible to label all drugs by replacing one of the parent compound atoms with a PET nuclide, but only a few are found applicable as imaging agents in vivo in humans. The radioactive half-time of $^{11}$C, $^{13}$N, 150 and $^{18}$F are 20, 10, 2 and 110 min, respectively. These short half-lives endow a number of advantages to their use as tracers to probe biological processes in vivo using PET. Repeat studies in the same subject within the same day are made possible.

Tritium labeled compounds are particularly valuable and widely used for studies involving high resolution autoradiography. The physical (nuclear) properties of tritium, the low maximum beta energy (18 keV) of the radiation and the high maximum specific activity (29 Ci/mg atom of hydrogen), makes tritium the ideal isotope for determining the precise localization of compounds, drugs and hormones for example, in biological specimens.

Parkinson's disease (PD) is the most common neurodegenerative movement disorder and is typically associated with neuronal loss in the substantia nigra and inclusions containing the aggregates of the synaptic protein α-synuclein known as Lewy bodies (LBs) and Lewy neurites (LNs), respectively, in the cell bodies and processes of surviving neurons. Post mortem examination of PD brain sections also revealed abundant LBs and LNs in cortical regions.

Presently, detection of aSyn aggregates is only possible by histological analysis of autopsy material. In vivo imaging of aSyn pathology would provide novel insights into deposition of aSyn aggregates in the human brain and allow examining non-invasively the degree of aSyn pathology for the staging of PD and the differentiation of PD from other neurodegenerative disorders. In addition, such an imaging tool would permit quantifying changes in aSyn deposition over time, assessing its correlation with neurodegeneration and cognition and analyzing the efficacy of an anti-aSyn therapy in a proof-of-mechanism study.

Aggregates of aSyn share a common amyloid structure, based on 3-sheet units assembling into oligomers and larger fibrils. Compared to other amyloids involved in neurodegenerative processes such as Aβ or tau, both encountered in Alzheimer's disease (AD) as well as in PD and with PET tracers available, PET tracer development for aSyn aggregates is particularly challenging. In particular, a tracer for aSyn must have high affinity for aSyn (<20 nM or even higher), as LBs are present in lower density when compared to plaques and NFTs as found in AD. Furthermore, an aSyn PET tracer should ideally possess high selectivity over the structurally related Aβ and tau since PD can be a mixed pathology. In addition, a successful PET tracer should readily cross the blood-brain barrier, have appropriate lipophilicity (log D 1-3) and show rapid clearance from blood.

One object of the present invention is to find an imaging tool which will improve diagnosis by identifying potential patients with excess of aSyn aggregates in the brain, which may be likely to develop Parkinson's disease. It will also be useful to monitor the progression of the disease. When an anti-aSyn aggregate drug becomes available, imaging aSyn pathology in the brain may provide an essential tool for monitoring treatment.

SHORT DESCRIPTION OF THE FIGURES

FIG. 1: Binding of radioligand [$^3$H]Example-3 binding (3 nM) to A30P transgenic mouse brain sections (top left) and human PD cortical tissue sections (top middle) showing good co-localization with the anti-aSyn mAb pS129 (bottom). At higher magnification, hot spots of the autoradiograms show good co-localization with LBs stained by the aSyn mAb pS129 (right image, arrows).

Figure 2:
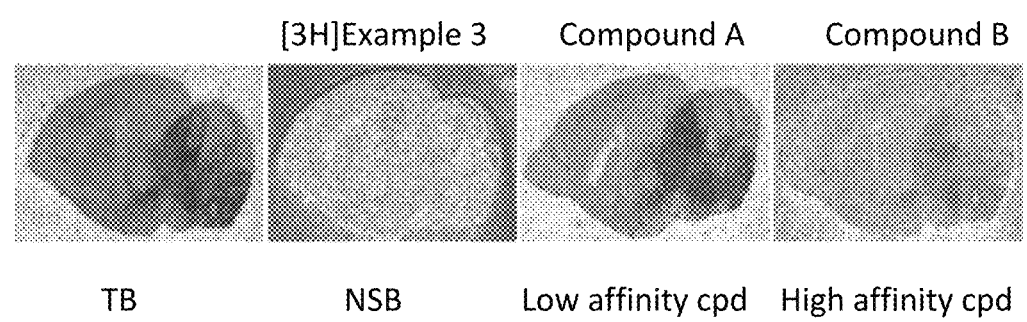

FIG. 2: Principle of the in vitro displacement screening assay using the specific binding of the screening radioligand [$^3$H]Example-3 to A30P transgenic mouse brain sections and assessing the displacement potency of novel compounds. Maximal displacement (100%) is defined by co-incubation with 3 μM cold compound Example 3.

Figure 3:
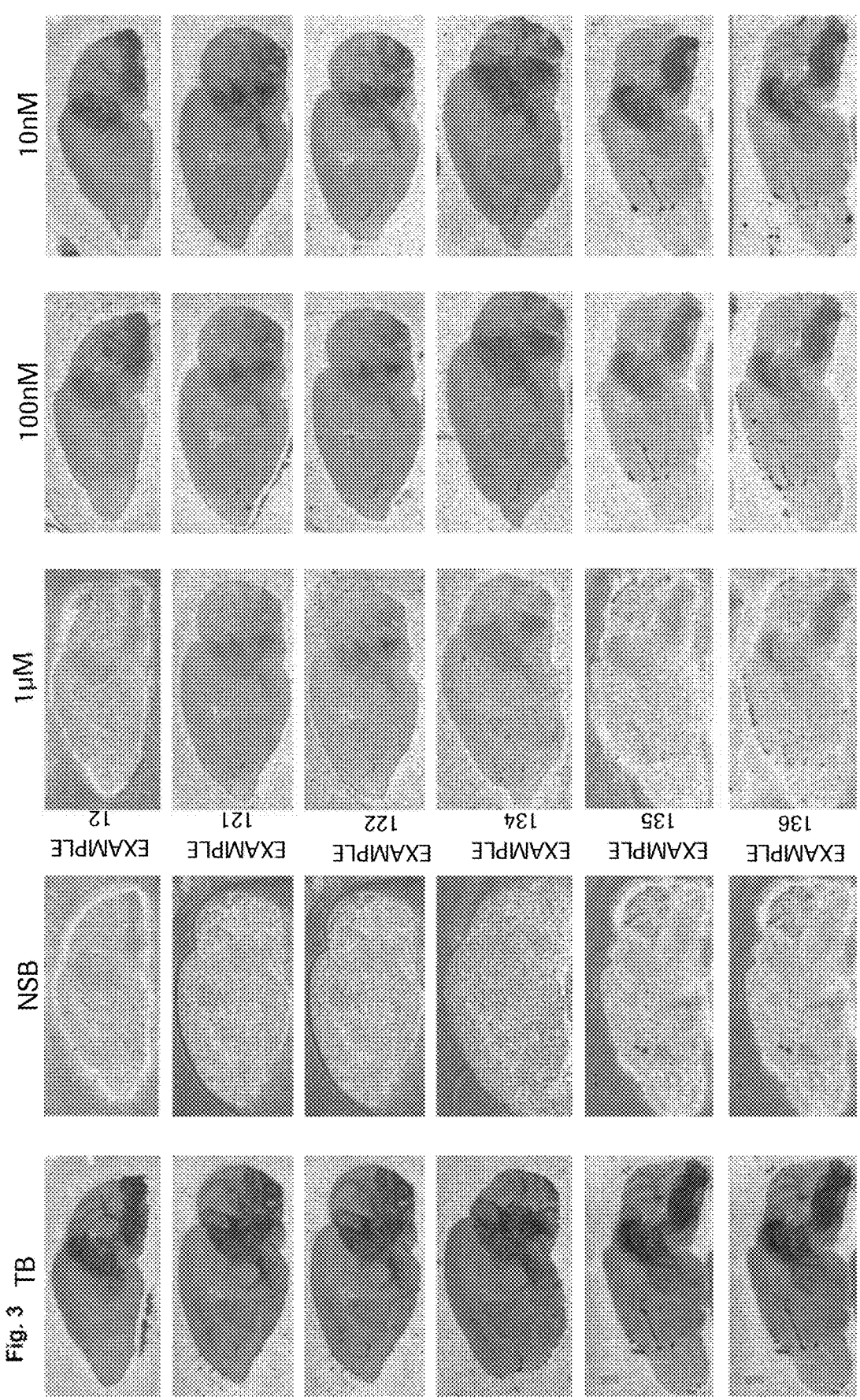

FIG. 3: In vitro displacement screening results of six novel compounds showing high affinity for aSyn aggregates in A30P transgenic mouse brain sections.

Figure 4:
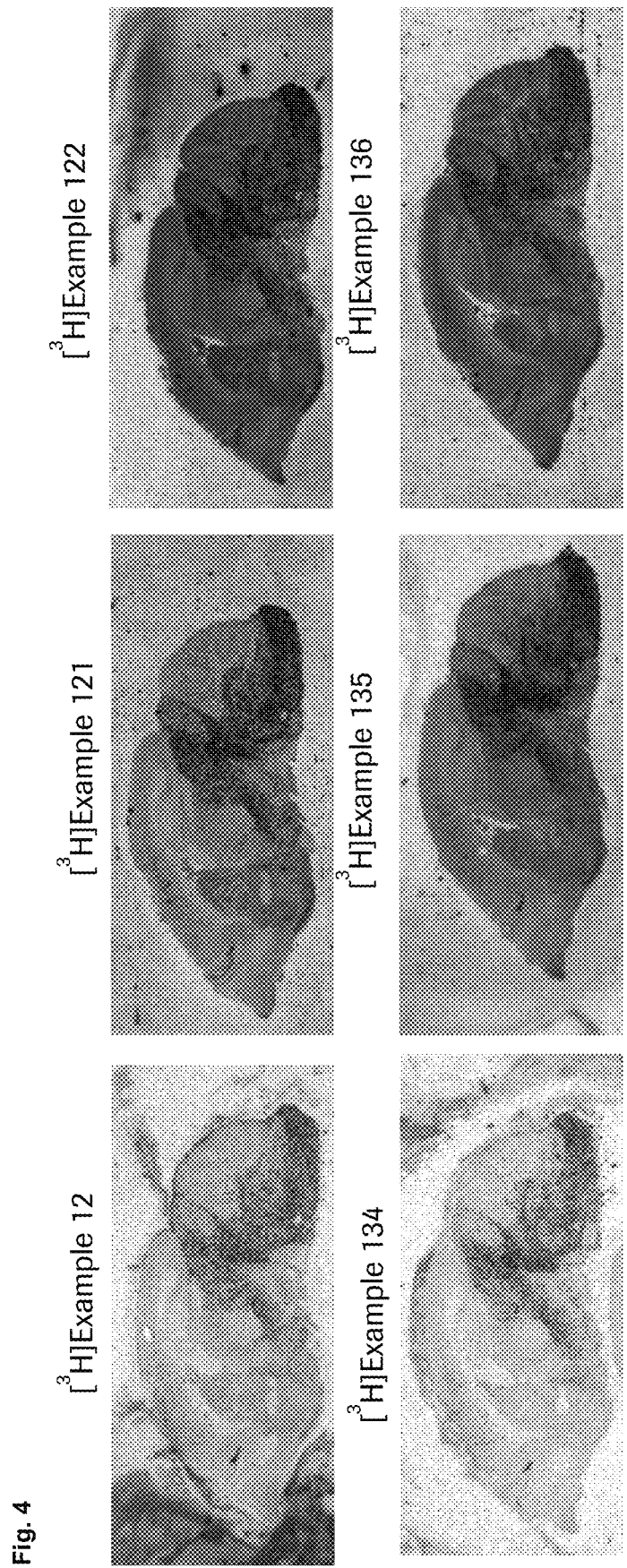

FIG. 4: In vitro autoradiography of tritiated compounds which have been identified as high affinity displacers in the screening assay. All ligands (at 10 nM) show strong binding to aSyn in A30P transgenic mouse brain sections.

Figure 5:
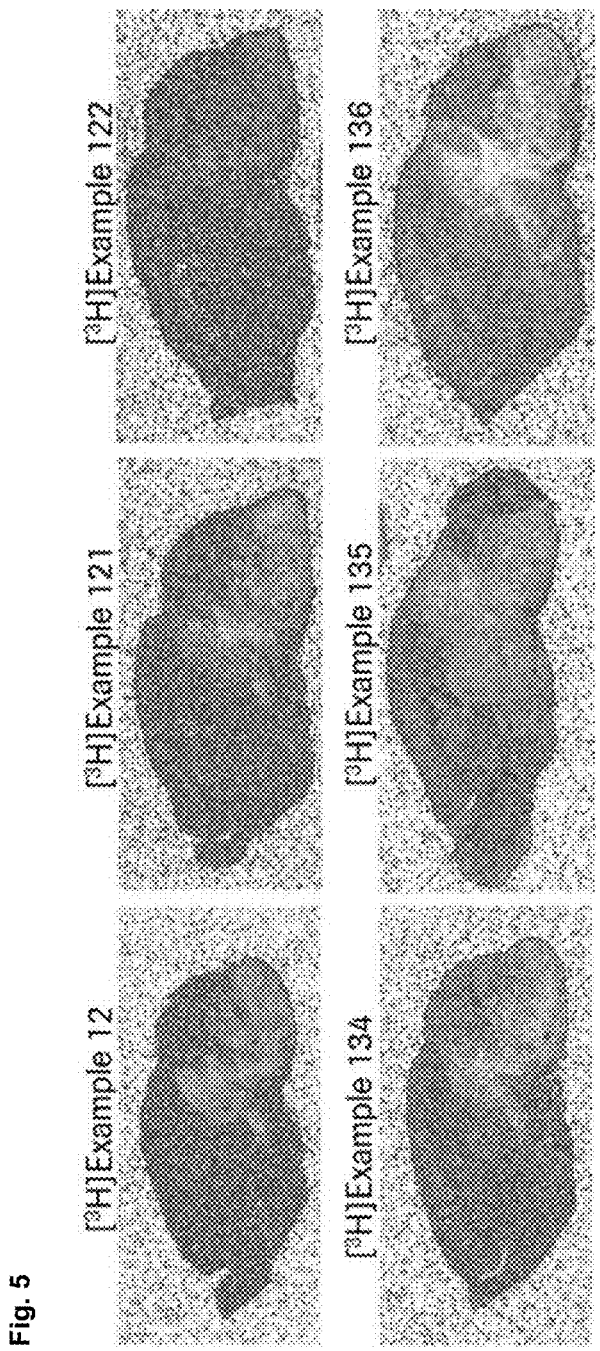

FIG. 5: Ex vivo autoradiography of tritiated compounds after i.v. injection in A30P mice and sacrificing the animal at 30 min p.i.

Figure 6:
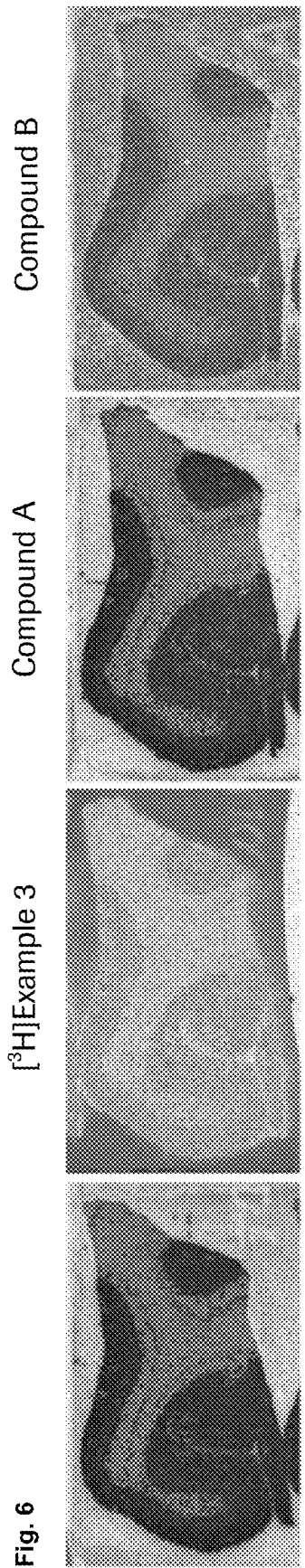

FIG. 6: Principle of the Aβ counterscreen based on an in vitro displacement assay using the specific binding of the screening radioligand [$^3$H]Example 3 to human AD brain sections and assessing the displacement potency of novel compounds. Maximal displacement (100%) is defined by co-incubation with 3 μM cold compound Example 3.

Figure 7:
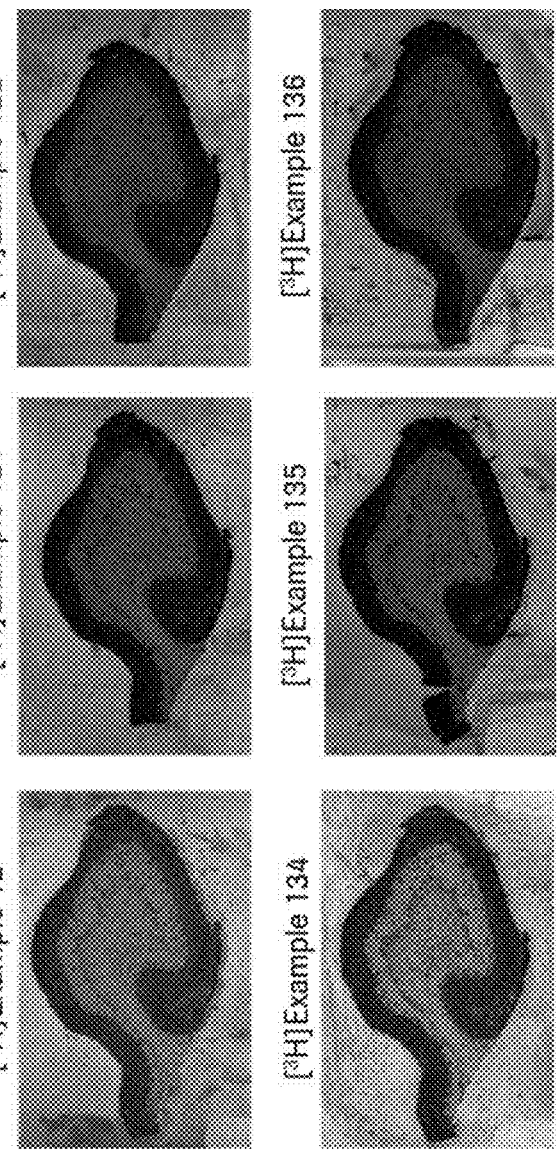

FIG. 7: In vitro autoradiography of AD tissue sections using tritiated compounds which have been identified as high affinity displacers in the A30P screening assay. All ligands (at 10 nM) show strong binding to Aβ in human AD brain sections.

Figure 8:
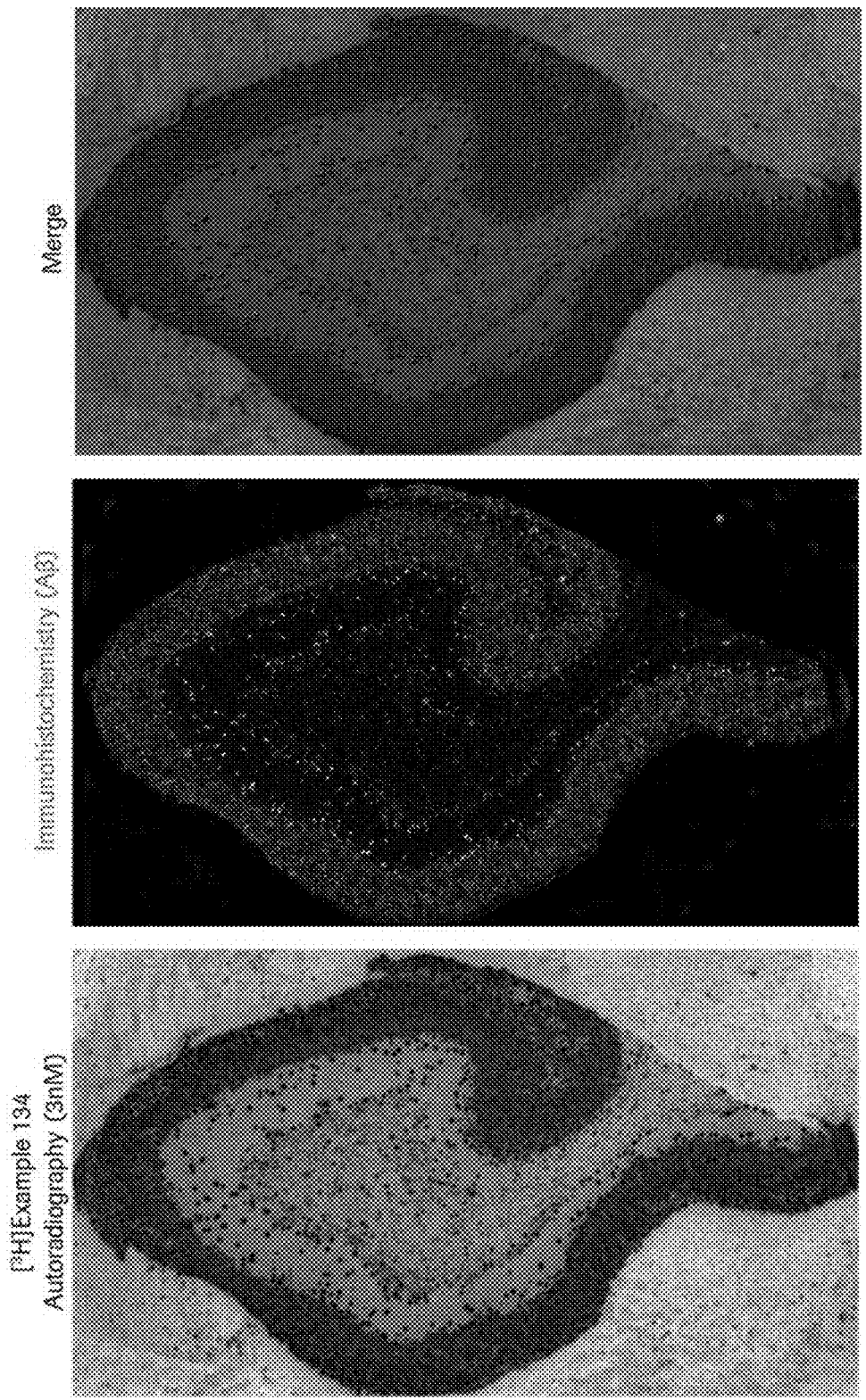

FIG. 8: Binding of radioligand [$^3$H]Example 134 (3 nM) to a human AD cortical tissue section showing an autoradiographical distribution pattern (left) which corresponds to the staining pattern of an anti-AD mAb (middle). Merged images of autoradiography and immunohistochemistry show co-localization of hot spots of the autoradiograms with Aβ plaques stained by an Aβ mAb (right).

DETAILED DESCRIPTION OF THE INVENTION

Definitions

Unless otherwise indicated, the following definitions are set forth to illustrate and define the meaning and scope of the various terms used to describe the invention herein.

The terms "compound(s) of the formula (I)", "compound(s) of formula (I)", "compound(s) of this invention" or "compound(s) of the present invention" refer to any compound selected from the genus of compounds as defined by the formula (I) including stereoisomers, tautomers, solvates, and salts (e.g. pharmaceutically acceptable salts) thereof.

It must be noted that, as used in the specification and the claims, the singular forms "a", "an" and "the" include plural referents unless the context clearly dictates otherwise.

The use of "or" or "and" means "and/or" unless stated otherwise.

When indicating the number of, the term "one or more" means from one substituent to the highest chemically? possible number of substitution, i.e. replacement of one hydrogen up to replacement of all hydrogens by substituents.

The term "optional" or "optionally" denotes that a subsequently described event or circumstance may but need not occur, and that the description includes instances where the event or circumstance occurs and instances in which it does not.

Any formula given herein is also intended to represent isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Substitution with heavier isotopes such as deuterium (i.e., $^2$H) may afford certain therapeutic advantages resulting from greater metabolic stability, for example increased in vivo half-life or reduced dosage requirements. Substitution with $^2$H may in particular be used to prevent the formation of undesired radiometabolites or to block radiodefluorination. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Furthermore, several methods exist for incorporating $^{11}$C (Peter J. H. Scott, *Angew. Chem. Int. Ed.* 2009, 48, 6001-6004) or $^{18}$F (Sean Preshlock et al., *Chem. Rev.* 2016, 116, 719-766. Frederic Dolle (2008) Fluorine-18 chemistry for molecular imaging with positron emission tomography. In *Fluorine and Health: Molecular Imaging, Biomedical Materials and Pharmaceuticals* (Tressaud, A. and Haufe, G., eds), pp. 3-66, Elsevier) into compounds.

The term "substituent" denotes an atom or a group of atoms replacing a hydrogen atom on the parent molecule.

The term "halogen" refers to fluorine, chlorine, bromine and iodine, and in some embodiments more specifically fluorine, chlorine and bromine.

The term "alkoxy" denotes a group of the formula —O—R', wherein R' is an alkyl group. Examples of alkoxy moieties include methoxy, ethoxy, isopropoxy, and tert-butoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "alkynyl" denotes a monovalent linear or branched hydrocarbon group of 2 to 12 carbon atoms with at least one triple bond. In particular embodiments, alkynyl has 2 to 7 carbon atoms, and in more particular embodiments 2 to 4 carbon atoms. Examples of alkynyl groups include ethynyl and propynyl.

The term "alkynoxy" denotes a group of the formula —O—R', wherein R' is an alkynyl group.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "hydroxyl-haloalkoxy" denotes an haloalkoxy group wherein at least one of the hydrogen atoms of the haloalkoxy group has been replaced by a hydroxyl group.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indo-lyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 12 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. In particular embodiments, heterocycloalkyl is a benzo-fused heterocyclic group of 9-12 ring atoms. Examples are benzo[d][1,3]dioxolyl, 2,3-dihydrobenzo[b][1,4]dioxinyl, 3,4-dihydro-2H-benzo[b][1,4]oxazinyl. Examples for monocyclic saturated heterocycloalkyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-azabicyclo[3.3.1]nonyl. Examples for partly unsaturated heterocycloalkyl are dihydrofuryl, imidazolinyl, dihydrooxazolyl, tetrahydro-pyridinyl, or dihydropyranyl.

The term "hydroxyalkyl" denotes an alkyl group wherein at least one of the hydrogen atoms of the alkyl group has been replaced by a hydroxy group. Examples of hydroxyalkyl include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "alkoxyalkyl" denotes an alkyl group wherein at least one of the hydrogen atoms of the alkyl group has been replaced by an alkoxy group. Exemplary alkoxyalkyl groups include 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

The term "half maximal inhibitory concentration" (IC50) denotes the concentration of a particular compound required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099).

The term "subject" denotes a vertebrate. In certain embodiments, the vertebrate is a mammal. Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

The term "pharmaceutically acceptable salts" denotes salts which are not biologically or otherwise undesirable. Pharmaceutically acceptable salts include both acid and base addition salts.

The terms "pharmaceutically acceptable excipient" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The present invention relates to radiolabeled compounds of formula I

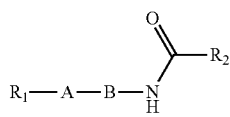

wherein

A is heterocycloalkyl,

B is aryl or heteroaryl both optionally substituted by $C_{1-7}$alkyl or halogen, $R_1$ is selected from aryl, heteroaryl optionally substituted by $C_{1-7}$alkyl, $C_{1-7}$alkoxy, cyano, halogen, —C(O)O—$C_{1-7}$alkyl, —N($C_{1-7}$alkyl)$_2$, halo-$C_{1-7}$alkoxy, —SO$_2$—$C_{1-7}$alkyl, $C_{2-7}$alkynyl, $R_2$ is selected from aryl, heteroaryl optionally substituted by halogen, $C_{1-7}$alkoxy, halo-$C_{1-7}$alkoxy, hydroxyl, —N($C_{1-7}$alkyl)$_2$, halo-$C_{1-7}$alkoxy-($C_{1-7}$-alkoxy)$_n$, hydroxyl-halo-$C_{1-7}$alkoxy, hydroxyl-($C_{1-7}$alkoxy), cyano, $C_{1-7}$alkyl, $C_{2-7}$alkynoxy, $C_{2-7}$alkynoxy-($C_{1-7}$-alkoxy)$_n$, halo-$C_{1-7}$ alkoxy substituted by —O—Si($C_{1-7}$alky)$_2$-$C_{1-7}$alkyl and heterocycloalkyl optionally substituted by $C_{1-7}$alkyl, n is 1, 2 wherein either A, B, $R_1$, $R_2$, is labeled with a radionuclide selected from $^3$H, $^{11}$C or $^{18}$F.

In a particular embodiment, the invention relates to compounds of formula I, wherein A is heterocycloalkyl, B is aryl or heteroaryl both optionally substituted by $C_{1-7}$alkyl or halogen, $R_1$ is selected from aryl, heteroaryl optionally substituted by $C_{1-7}$alkyl, $C_{1-7}$alkoxy, cyano, halogen, C(O)O—$C_{1-7}$alkyl, —N($C_{1-7}$alkyl)$_2$, halo-$C_{1-7}$alkoxy, —SO$_2$—$C_{1-7}$alkyl and $R_2$ is selected from aryl, heteroaryl optionally substituted by halogen, $C_{1-7}$alkoxy, halo-$C_{1-7}$alkoxy, hydroxyl, —N($C_{1-7}$alkyl)$_2$, halo-$C_{1-7}$alkoxy-($C_{1-7}$-alkoxy)$_n$, $C_{1-7}$alky-Si—O-halo-$C_{1-7}$ alkoxy, hydroxyl-halo-$C_{1-7}$alkoxy, hydroxyl-($C_{1-7}$alkoxy), cyano, $C_{1-7}$alkyl, heterocycloalkyl optionally substituted by $C_{1-7}$alkyl.

In a particular embodiment, the invention relates to radiolabeled compounds of formula I, wherein A is selected from piperazinyl and hexahydropyrrolo[3,4-c]pyrrol-2(1H)-yl.

In a particular embodiment, the invention relates to radiolabeled compounds of formula I, wherein B is selected from a 5- or 6-membered aryl or a 5- or 6-membered heteroaryl, preferably selected from phenyl, pyridinyl, piperazinyl, pyrimidinyl, pyrazinyl.

In a particular embodiment, the invention relates to radiolabeled compounds of formula I, wherein A is piperazinyl and B is phenyl.

In a particular embodiment, the invention relates to radiolabeled compounds of formula I, wherein A is piperazinyl and B is pyridinyl.

In a particular embodiment, the invention relates to radiolabeled compounds of formula I, wherein $R_2$ is selected from a 5- or 6-membered aryl or 5- or 6-membered heteroaryl group.

In a particular embodiment, the invention relates to radiolabeled compounds of formula I, wherein $R_2$ is selected from phenyl, pyridinyl.

In a particular embodiment, the invention relates to radiolabeled compounds of formula I, wherein $R_2$ is substituted by halogen, $C_{1-7}$alkoxy, hydroxyl, 6-membered heterocycloalkyl, $C_{1-7}$alkyl, halo-$C_{1-7}$alkoxy, halo-$C_{1-7}$alkoxy-($C_{1-7}$-alkoxy)$_n$ where n is 1, 2.

In a particular embodiment, the invention relates to radiolabeled compounds of formula I, wherein $R_2$ is labeled with a radionuclide selected from $^3$H, $^{18}$F and $^{11}$C.

In a particular embodiment, the invention relates to radiolabeled compounds of formula I selected from the group consisting of.

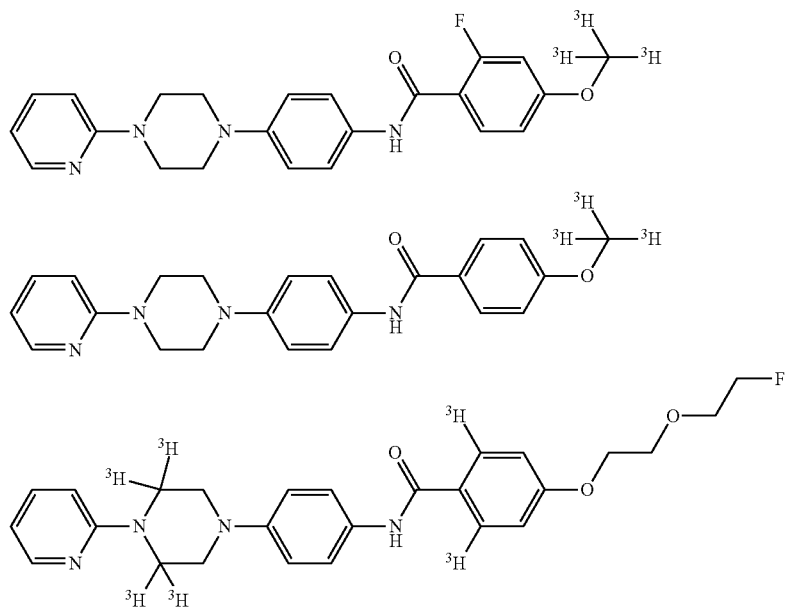

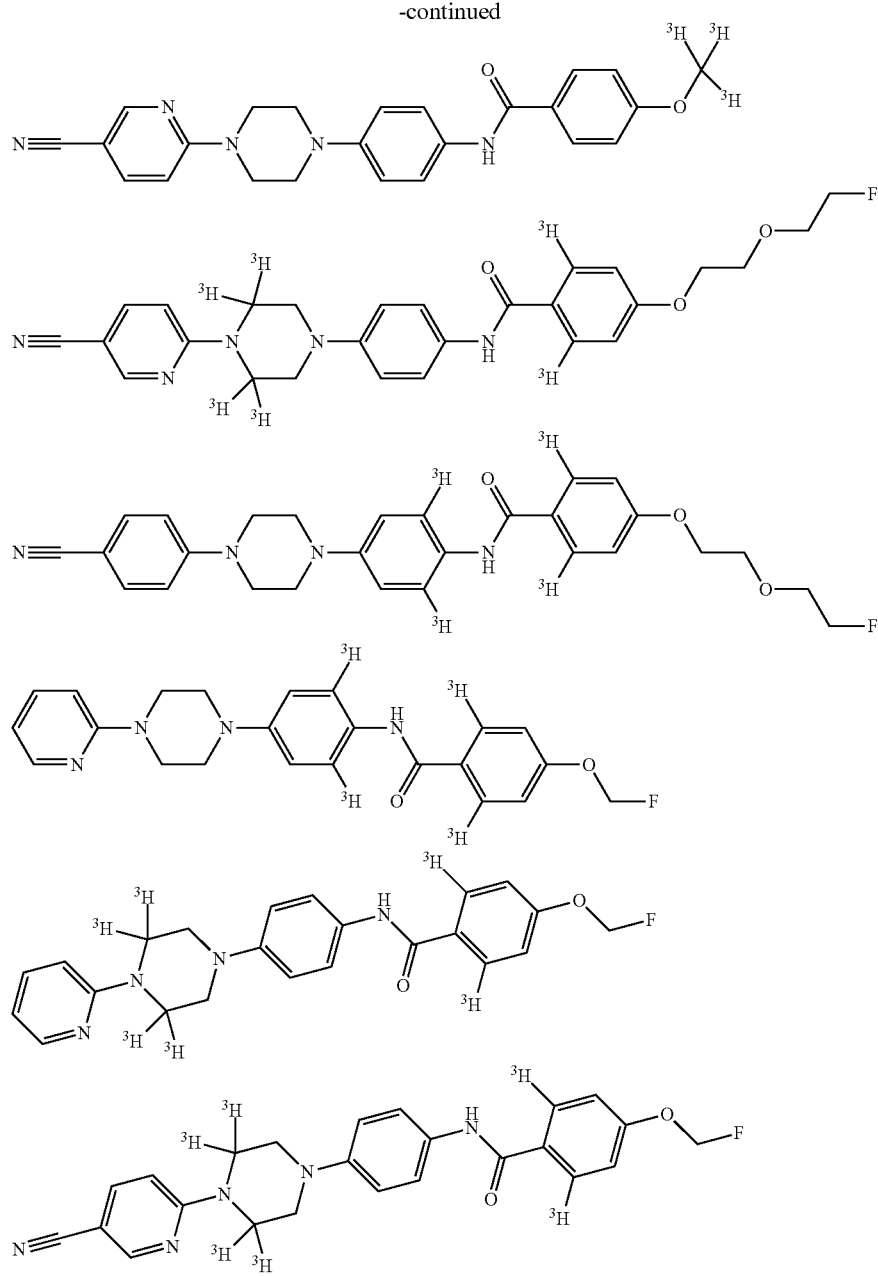

In another embodiment the present invention relates to the use of the radiolabeled compounds of the present invention in an alpha synuclein and/or Abeta binding study.

In another embodiment the present invention relates to the use of the radiolabeled compounds of the present invention in diagnostic imaging of alpha synuclein and/or Abeta aggregates in the brain of a mammal.

In another embodiment, the present invention relates to a pharmaceutical composition comprising a radiolabeled compound of the present invention and a pharmaceutical acceptable carrier.

In a further embodiment, the present invention relates to a method of imaging alpha synuclein and/or Abeta deposits in a mammal, comprising:

introducing into a mammal a detectable quantity of a pharmaceutical composition of the present invention; and detecting the compound associated with alpha synuclein and/or Abeta deposits.

In another embodiment, the present invention relates a use of a compound of the present invention for diagnostic imaging of alpha synuclein and/or Abeta deposits in the brain of a mammal.

The preparation of compounds of formula (I) of the present disclosure may be carried out in sequential or convergent synthetic routes. Syntheses of the disclosure are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral)

chromatography or crystallization. The substituents and indices used in the following description of the processes have the significance given herein.

Methods to Prepare Compounds of General Structure (A1) are Illustrated in Scheme 1.

Compounds of general structure (A1) can be prepared from intermediates of structure (B) by reacting the amino group of (B) with carboxylic acids of general structure $R_2COOH$ in the presence of amide coupling reagents such as HATU, EDC.HCl/HOBt or T3P. A base such as DIPEA or $Et_3N$ might be added and the reaction can be performed in solvents such as DMF or THF. Alternatively, compounds of structure (A1) can be prepared by reacting (B) with an acid chloride of general structure $R_2COCl$, in the presence of a base such as DIPEA or $Et_3N$ in a solvent such as DCM. Intermediates (B) can be prepared in two steps from piperazines of general structure (C) and nitro compounds (D). In a first step the piperazines (C) are reacted with nitro compounds (D) under nucleophilic aromatic substitution conditions to obtain intermediates (E). These for instance make use of a base such as $K_2CO_3$ or DIPEA in solvents such as DMSO, DMF or NMP. Reduction of nitro intermediates (E) to compounds (B) can be achieved by various reaction conditions, including but not limited to the use of $H_2$ in the presence of Pd/C in a solvent such as EtOH, or the use of hydrazine monohydrate with Raney Ni in a solvent such as EtOH or a solvent mixture consisting of EtOH/THF, or the use of $SnCl_2.2H_2O$ in EtOH or under Béchamp reduction conditions.

When intermediates of general structure (B) contain a pyridazine ring, the compounds can be prepared in one step starting from piperazines of structure (C) and 6-iodopyridazin-3-amine. This reaction can be catalyzed by using CuI in the presence of L-hydroxyproline and a base such as $K_3PO_4$ in a solvent such as DMSO.

When intermediates of general structure (B) contain a pyrazine ring, the compounds can be prepared in three steps from 2,5-dichloropyrazine. For instance, reaction of 2,5-dichloropyrazine with 1-(2-pyridyl)piperazine in the presence of a base such as $Cs_2CO_3$ in a solvent as for example DMF leads to 2-chloro-5-[4-(2-pyridyl)piperazin-1-yl]pyrazine. Reaction of this compound with $HNCPh_2$ in presence of a catalyst system such as $[Pd_2(dba)_3]$, BINAP, NaOtBu in Tol followed by deprotection of the amino group, for instance with $HONH_2 \cdot HCl$, $NaOAc \cdot 3H_2O$ in MeOH, leads to a pyrazine of general structure (B).

Scheme 1

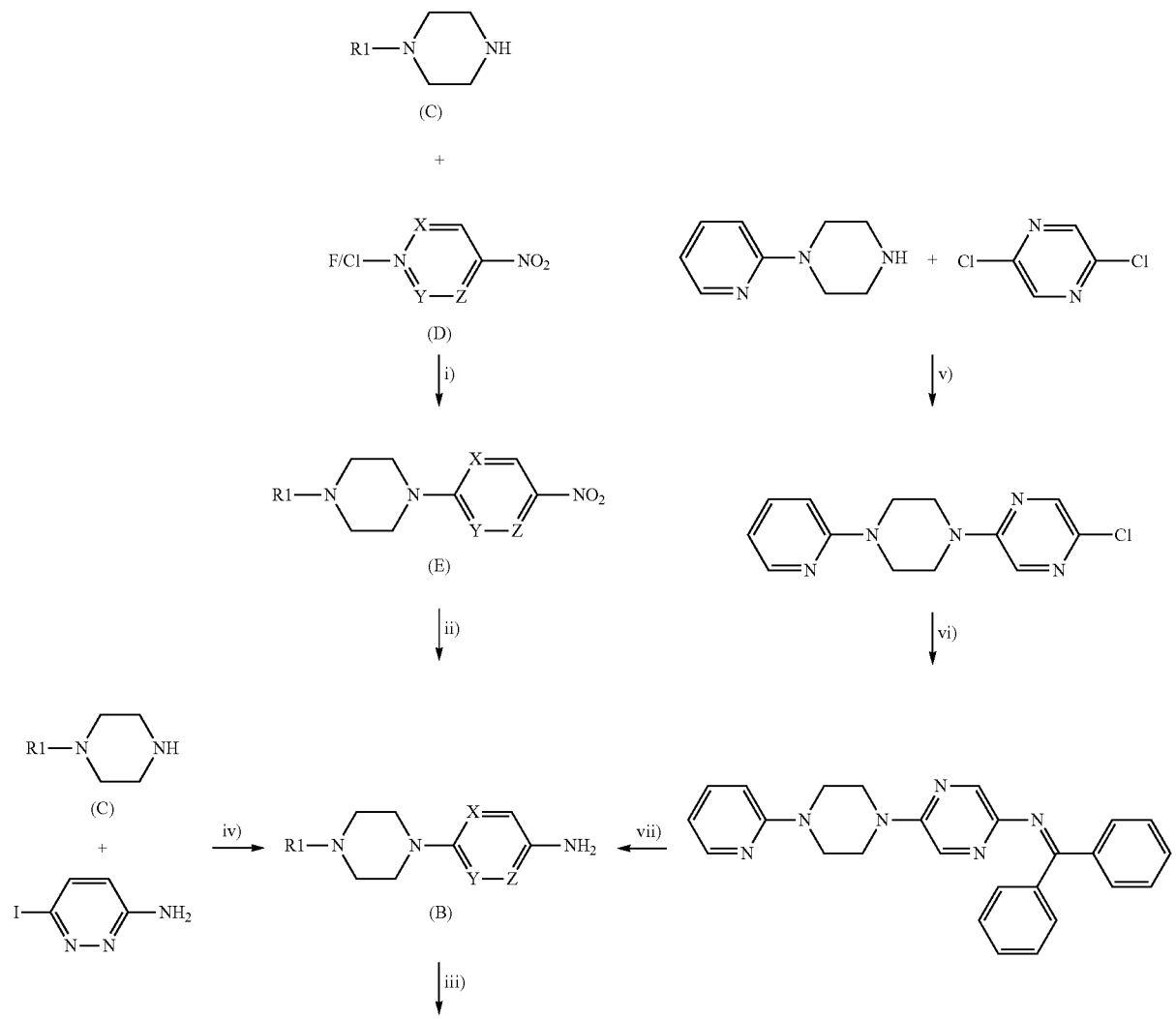

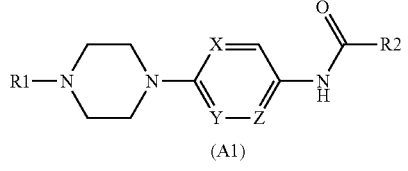

(A1)

X = CH, N or CMe
Y = CH or N
Z = CH or N

Conditions: i) (a) K₂CO₃, DMSO, 90° C.; or (b) K₂CO₃, DMF; or (c) DIPEA, NMP. ii) (a) H₂, Pd/C 10%, EtOH, rt; or (b) N₂H₄•H₂O, Raney-Ni, EtOH/THF or EtOH, rt; or (c) SnCl₂•2H₂O, EtOH, 70° C.; or (d) Fe, AcOH, H₂O. iii) (a) R₂COOH, HATU, DIPEA, or Et₃N, DMF, rt; or (b) R₂COCl, DIPEA, DCM, rt; or (c) R₂COOH, EDC•HCl, HOBt, DIPEA, DMF, rt; or (d) R₂COCl, Et₃N, THF or DCM, 0° C. to rt; or (e) R₂COOH, T3P, DIPEA, THF, rt. iv) CuI, L-hydroxyproline, K₃PO₄, DMSO, 100° C. v) Cs₂CO₃, DMF, 55° C. vi) HNCPh₂, [Pd₂(dba)₃], BINAP, NaOtBu, Tol, reflux. vii), HONH₂•HCl, NaOAc•3H₂O, MeOH, rt.

When compounds of general structure (A1) contain an $R_2$ consisting of a phenol substituent, as for example structure (A2) in Scheme 2, the compounds can be prepared in one step starting from an acetic acid ester of general structure (F) by saponification of the ester bond. A wide range of other ester groups might be used. Saponification of the ester can be achieved for example using aqueous NaOH in a solvent such as MeOH. Compounds of general structure (F) can be prepared according to the methods described in Scheme 1 above.

Phenols of structure (A2) can be further elaborated by alkylation to obtain for example compounds of general structure (A3). This can be for instance achieved by reaction with an alkylating reagent such as TsO(CH₂)₂O(CH₂)₂OH in presence of a base as $Cs_2CO_3$ in a solvent as DMF.

Scheme 2

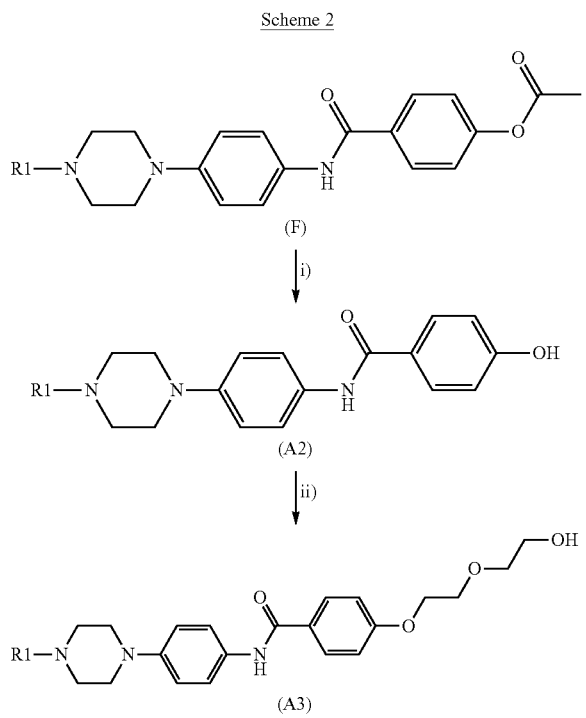

Conditions: i) NaOH$_{aq}$, MeOH, rt. ii) TsO(CH₂)₂O(CH₂)₂OH, Cs₂CO₃, DMF, rt.

In a certain embodiment of this invention the reagent R₂COOH used in Scheme 1 consists of 4-[2-(2-fluoroethoxy)ethoxy]benzoic acid (K) (Scheme 3). Compound (K) can be prepared in four steps by first introducing one tosyl group onto diethyleneglycol (G), for instance by reaction with TsCl, Ag₂O and KI in DCM at 0° C. Fluorination of (H) can be performed for example with DAST in DCM to obtain (I). Intermediate (I) is used to alkylate 4-hydroxybenzoic acid methyl esther in the presence of a base such as Cs₂CO₃ in a solvent as DMF. The resulting compound (J) is then transformed to (K) by saponification of the ester, for instance using aqueous NaOH in MeOH.

Scheme 3

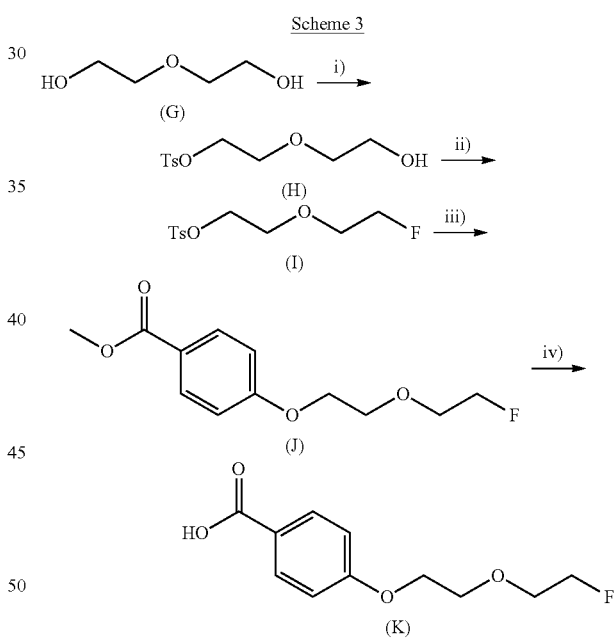

Conditions: i) TsCl, Ag₂O, KI, DCM, 0° C. to rt. ii) DAST, DCM, 0° C. to rt. iii) 4-OH—BzOMe, Cs₂CO₃, DMF, 50° C. iv) NaOH$_{aq}$, MeOH, rt.

In a further embodiment of this invention, the compounds possess the general structures (A4) or (A5) as depicted in Scheme 4. Compounds of general structure (A4) can be prepared for instance by reaction of an aniline of general structure (B2) (prepared as described in Scheme 1) with a reagent obtained by the reaction of an ester such as (N) with Me₃Al in a solvent such as dioxane. Compound (N) can be prepared starting from epoxide (L) by reaction with a fluoride source such as TBAF in a solvent such as Tol, leading to intermediate (M). Alcohol (M) can be transformed into silyl ether (N) for instance by the use of TBDM-SCl, imidazole and DMAP in DCM.

Further elaboration of general structures (A4) by removing the silicon protecting group with a reagent such as TBAF in a solvent as for example THF leads to compounds of general structure (A5).

Scheme 4

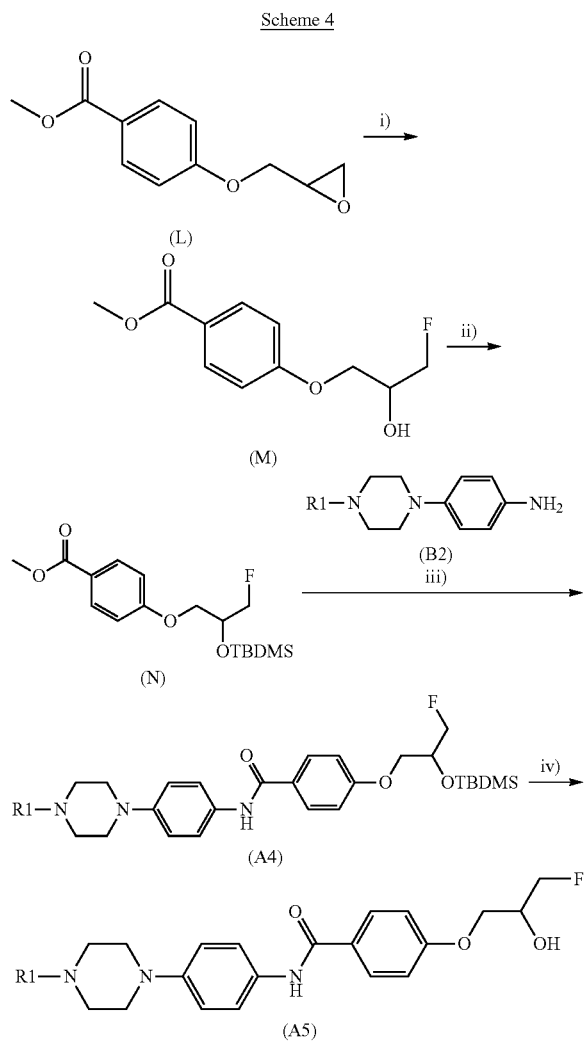

Conditions: i) TBAF, Tol, 80° C. ii) TBDMSCl, Imid, DMAP, DCM, rt.
iii) Me₃Al, dioxane, 90° C. iv) TBAF, THF, rt.

In a further embodiment of this invention the reagent R₂COCl used in Scheme 1 consists of 4-(fluoromethoxy) benzoyl chloride (Q) (Scheme 5). Compound (Q) can be prepared from ester (O) by saponicfication to (P) with, for instance, aqueous NaOH in a mixture of THF/EtOH followed by chlorination, for example using oxalyl chloride in the presence of DMF in a solvent as DCM.

Scheme 5

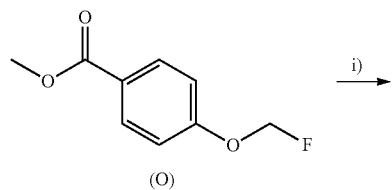

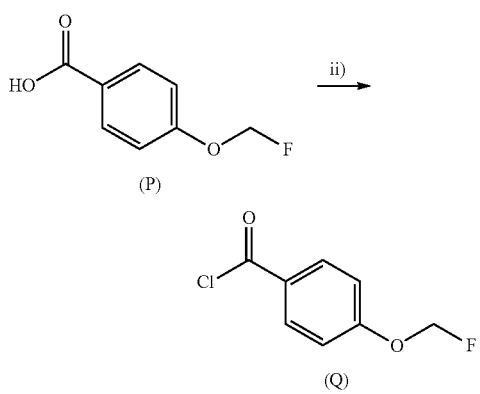

Conditions: i) NaOH$_{aq}$, THF/EtOH, rt. ii) (COCl)₂, DMF, DCM, rt.

In a certain embodiment of this invention, the compounds are 4-methoybenzamides of general structure (A6) (Scheme 6). Such compounds can be prepared according to the methods illustrated in Scheme 1 or alternatively starting from 4-methoxybenzoyl chloride. Reaction of 4-methoxy benzoyl chloride with 4-bromoaniline in the presence of a base as DIPEA in a solvent as DCM leads to intermediate (R). Reaction of (R) with 1-Cbz-piperazine under Buchwald cross coupling conditions, using for instance [Pd₂(dba)₃], XPhos and tBuONa in dioxane gives intermediate (S). Deprotection of the amine group can be achieved under reducing conditions, such as for example the use of 1-methyl-1,4-cyclohexadiene and Pd/C in EtOH. This yields intermediate (T) that can be derivatized into a range of final compounds of general structure (A6) by aromatic nucleophilic substitution of aryls of general structure R₁Br in the presence of a base such as DIPEA in a solvent as NMP.

Scheme 6

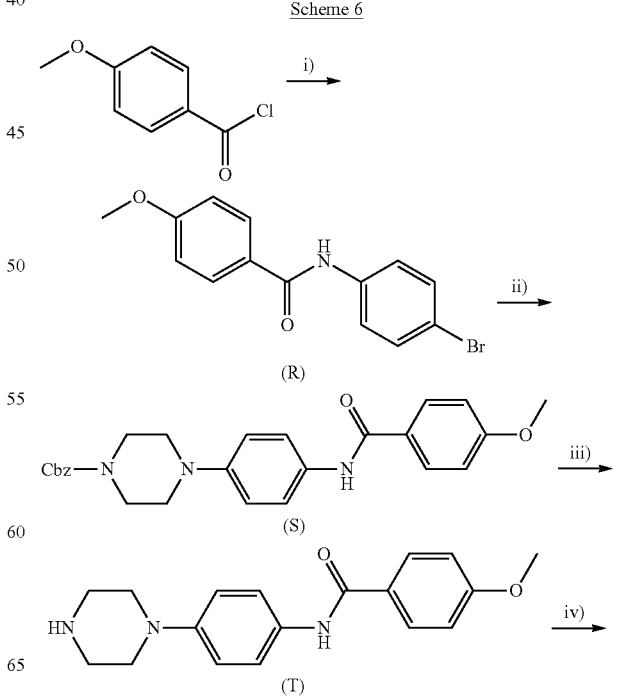

-continued

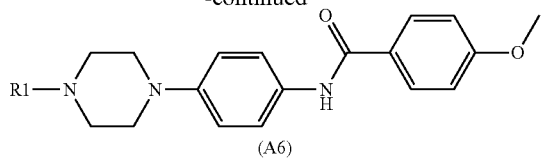

(A6)

Conditions: i) 4-Bromoaniline, DIPEA, DCM. ii) 1-Cbz-piperazine, [Pd₂(dba)₃], XPhos, tBuONa, dioxane. iii) 1-Methyl-1,4-cyclohexadiene, Pd/C, EtOH. iv) (a) R₁Br, [Pd(OAc)₂], RuPhos, Cs₂CO₃, dioxane; or (b) R₁Br, DIPEA, NMP, 120° C.

Scheme 7 illustrates a further method for preparing compounds of the type (A1) with the particular structure (A7). In this embodiment of the invention, the synthesis starts from 1-(4-nitrophenyl)piperazine (U) that is reacted with aryl bromides of structure R₁Br under Buchwald cross coupling conditions. This transformation can for instance be performed using [Pd(OAc)₂], RuPhos and Cs₂CO₃ in dioxane. The following reduction and amide bond formation steps can be performed using one of the several methods described above. For example, use of Fe and NH₄Cl in EtOH/H₂O reduces compounds of general structure (V) to anilines of the type (B2). Such anilines lead to the final products (A7) by reaction with R₂COOH, HATU and DIPEA in DMF.

Scheme 7

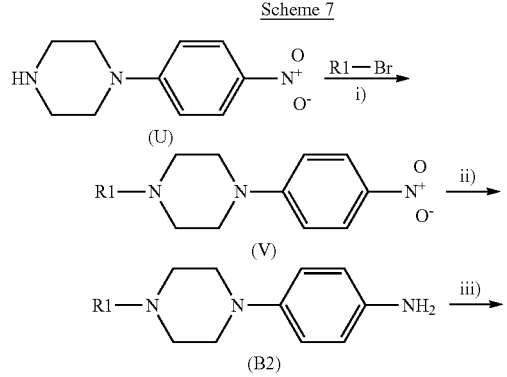

-continued

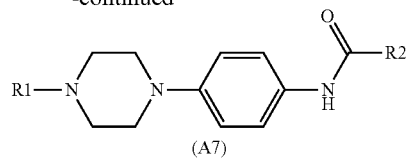

(A7)

Conditions: i) [Pd(OAc)₂], RuPhos, Cs₂CO₃, dioxane. ii) Fe, NH₄Cl, EtOH/H₂O. iii) R₂COOH, HATU, DIPEA, DMF.

In a certain embodiment of this invention, the compounds possess the structure (AC) or (AH) (Scheme 8). Such compounds can be prepared from a common intermediate (W) (WO2014/139978 A1, WO2015/144605 A1). Preparation of the (S,S)-enantiomer (AC) can be performed starting by reaction of (W) with 2-chloropyridine under nucleophilic aromatic substitution conditions, as for example heating in the presence of Et₃N in a solvent as DMA or NMP. The thus obtained intermediate (X) is then transformed in the corresponding amine (Y) by Boc deprotection. Several conditions can be used for this step, as for example reaction with TFA in DCM. Transformation of intermediate (Y) to the final compound (AC) can be achieved in analogy to the several methods described above. For instance reaction of (Y) with 4-fluoronitrobenzene and K₂CO₃ in DMSO at 90° C. yields (Z). Reduction of nitro compound (Z) to aniline (AB) can be performed for example with H₂, Pd/C and AcOH in EtOH. (AB) can then be subjected to amide coupling conditions to get to compound (AC), for example by reaction with Me₃Al and 4-methoxybenzoic acid methyl ester in dioxane. Preparation of the (R,R)-enantiomer (AH) can be achieved by reacting intermediate (W) with 4-fluoronitrobenzene and K₂CO₃ in DMSO to yield (AD). Removal of the Boc protecting group from (AD) can be achieved for example with TFA in DCM. The so obtained amine intermediate (AE) can further be elaborated into compound (AF) by reaction with 2-chloropyridine and Et₃N in DMA or NMP by heating. Nitro intermediate (AF) can be reduced to aniline (AG) using several of the conditions described above, as for example H₂, Pd/C and AcOH in EtOH. Aniline (AG) can finally be transformed in the desired product (AH) using amide coupling conditions, as for instance reaction with 4-methoxybenzoic acid, HATU and DIPEA in DMF.

Scheme 8

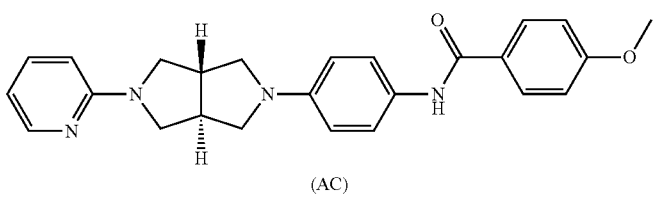

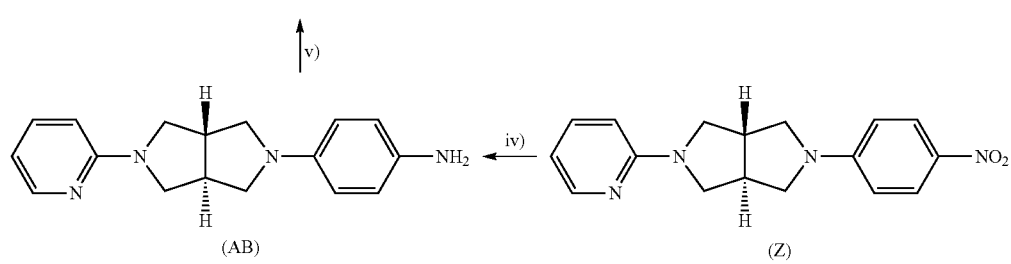

-continued

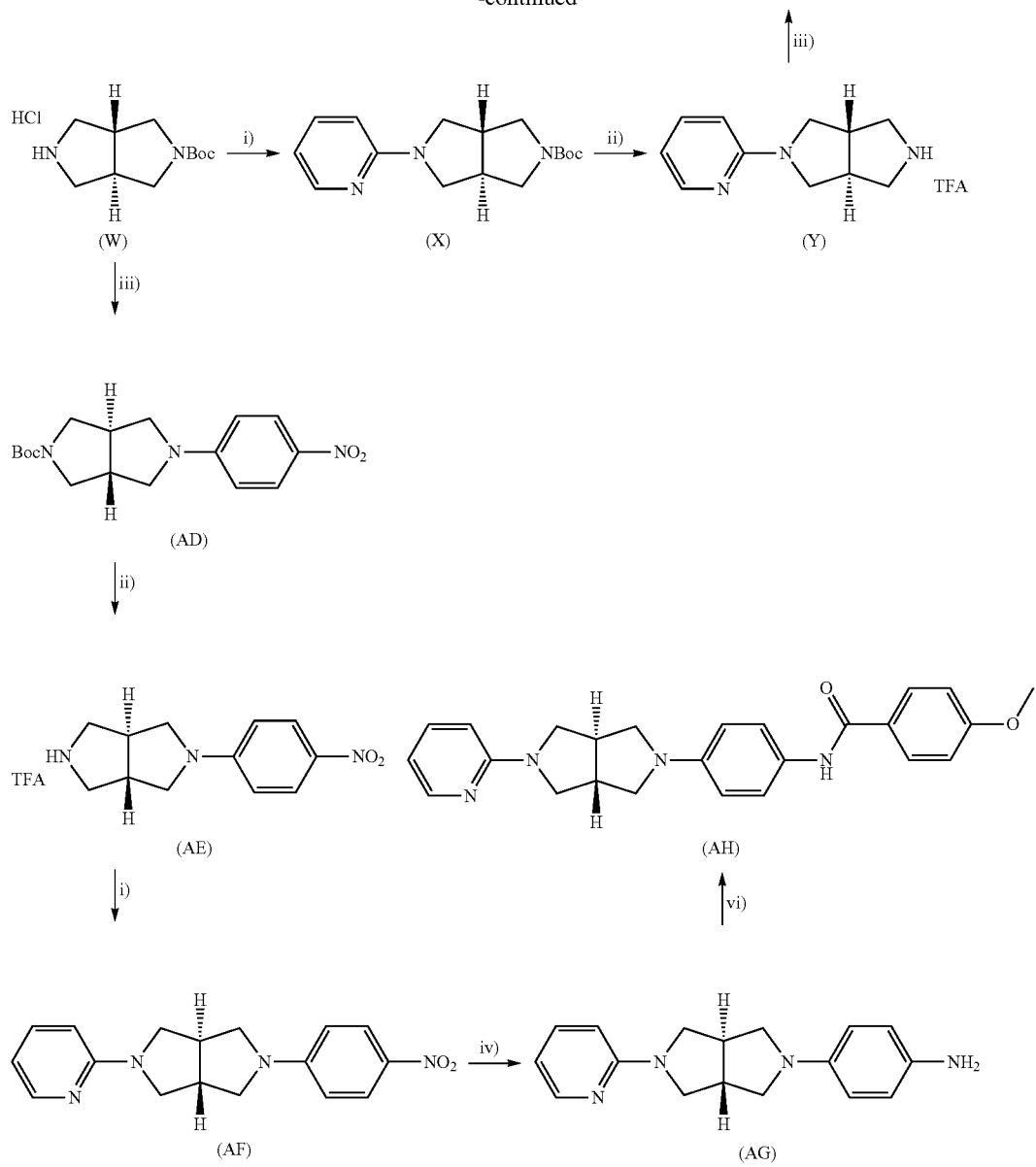

Conditions: i) 2-Cl-Pyridine, Et₃N, DMA or NMP, μw 160-170° C. ii) TFA, DCM, rt.
iii) 4-Fluoronitrobenzene, K₂CO₃, DMSO, 90° C. iv) H₂, Pd/C, AcOH, EtOH, rt. v) Me₃Al,
4-MeO—BzOMe, dioxane, 90° C. vi) 4-MeO—BzOH, HATU, DIPEA, DMF, rt.

Compounds of the present invention can be labeled with tritium using a range of different methods. Scheme 9 illustrates two approaches. In the first approach, a compound of general structure (AI) or (AJ) is tritiated by direct isotope exchange reaction catalyzed by Crabtree's or Kerr's catalyst under an atmosphere of [³H]H₂, in a solvent such as DMF, DCM or chlorobenzene. Compounds of general structure (AJ) possessing a 2-piridyl substituent in position R₁ typically lead to higher incorporation of tritium and thus higher specific activities.

Alternatively, when the compounds possess a methoxy group like in the general structure (AL), labelling can be achieved by alkylation of a phenolic precursor (AK) using a reagent such as [³H]methylnosylate in presence of a base as for example Cs₂CO₃ in solvents as THF or DMSO.

Scheme 9

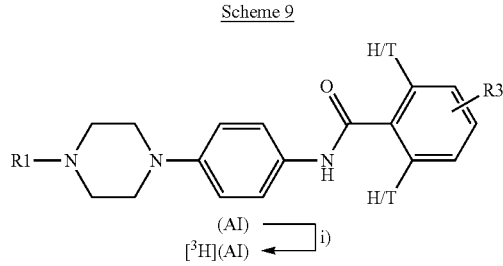

-continued

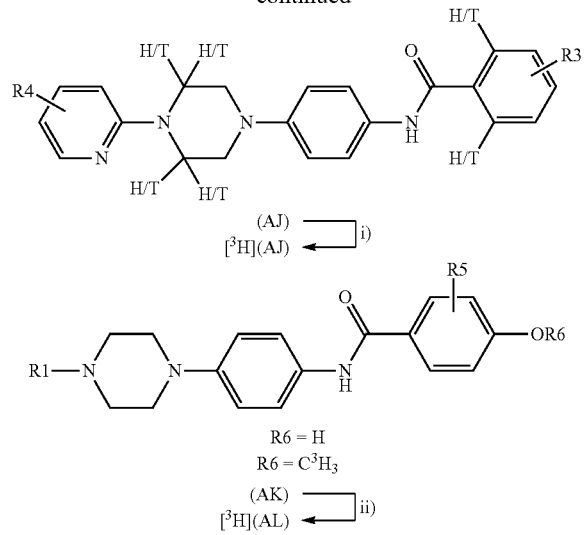

(AJ) ⇌ i)
[³H](AJ)

R6 = H
R6 = C³H₃

(AK) ⇌ ii)
[³H](AL)

Conditions: i) [Ir(COD)(PCy₃)(Py)]PF₆ or [Ir(ImMes)(PPhMe₂)(COD)]PF₆, DMF or DCM or PhCl, rt-90° C. ii) [³H]MeONs, Cs₂CO₃, THF or DMSO, 45-70° C.

Materials and Methods

Human Tissue Samples

Human PD brain tissue blocks were obtained from the Banner Sun Health Research Institute (Sun City, Ariz., USA). Pathological diagnosis of PD was made according to standard criteria based on neuropathological data.

Animals

The transgenic mouse strain A30P carries a mutant form of the human aSyn gene which is associated with the development of a familial form of PD. The mouse line B6.D2-Tg(Thy1-SNCA*30P)31Pjk was generated in-house and animals were used for this study at the onset of hind limb mobility problems and a resting tremor phenotype which typically occurred at an age of 12-16 months.

Radioligands

The screening radioligand [³H]Example-3, [³H]Example-12, [³H]Example-121, [³H]Example-122, [³H]Example-134, [³H]Example-135 and [³H]Example-136 were synthesized in-house (specific activity 77 Ci/mmol, radiochemical purity 99.5%). All other [³H]radioligands were also tritiated at Roche with a specific activity of >71 Ci/mmol. Radiochemical purity was >95% for all ligands.

Autoradiography

Ten µm thick A30P transgenic mouse brain sections and human PD brain sections are generated with a cryostat (Leica CM3050) at −17° C. chamber temperature and −15° C. object temperature. Sections are transferred to Histobond+ microscope slides (Marienfeld Laboratory Glassware). After drying for 3 hours at room temperature the sections are stored at −20° C. The sections are incubated with the radioligand (0.3-30 nM) and the respective cold compound (at various concentrations) in 50 mM Tris buffer, pH 7.4 at room temperature for 30 min. After washing 3×10 min at 4° C. in 50 mM Tris buffer, pH 7.4 and 3 quick dips in H₂O dist. at 4° C. the sections are dried at 4° C. for 3 h. The sections are placed in a FujiFilm Cassette, exposed to an Imaging Plate (BAS-IP TR 2025) for five days and afterwards scanned with a FujiFilm IP reader (BAS-5000) with a resolution of 25 µM per pixel.

Data Analysis

The signal intensity (Dens—PSL/mm2) in the region of interest (ROI) of the autoradiogram is quantified with the software MCID analysis (version 7.0, Imaging Research Inc.). The specific binding (SB) of radioligand [³H]Example-3 binding was calculated by subtracting non-specific binding (NSB) in midbrain and pons determined in presence of 3 µM cold EXAMPLE 3 from the total binding (TB) in midbrain and pons which was obtained with radioligand only. The % displacement by various compounds was calculated as following: % displacement=100−(SBcompound/SBEXAMPLE 3 only)*100.

Immunohistochemistry

Antibody staining of sections is performed after exposure and scanning of the tissue sections undergoing classical autoradiographical analysis. Brain sections were hydrated in PBS and blocked in 1% bovine serum albumin, 1% ovalbumin and 1% normal goat serum in PSB for 20 min. This is followed by overnight incubation at 4° C. with a mixture of anti-aSyn pS129 monoclonal antibody (generated in-house; 1 µg/mL) in blocking buffer. After washing with PBS+0.01% Tween20 and incubation with a fluorescent dye-labeled secondary antibody autofluorescence of lipofuscin is reduced by quenching through incubation in 0.3% Sudan Black in 70% EtOH for 3 min. After rinsing the slides in 70% EtOH and two times in H₂O dist., slides are embedded with Aquapolymount mounting medium, dried for at least 3 h at RT and scanned with the MetaSystem Metafer image analysis system (or Pannoramic p250).

Ex Vivo Autoradiography

Radiotracers are intravenously injected in A30P mice (1 mCi/kg) to analyze penetration through the blood-brain barrier and target-related retention in aSyn expressing brain regions. Animals are sacrificed at 15 or 30 min after tracer administration, brains are sampled and frozen. Brain sections are generated with a cryostat (Leica CM3050) at −17° C. chamber temperature and −15° C. object temperature and sections are exposed to an Imaging Plate (BAS-IP TR 2025) for five days and afterwards scanned with a FujiFilm IP reader (BAS-5000) with a resolution of 25 µM per pixel.

Results aSyn In Vitro Binding Assay

This in vitro binding assay assesses the affinity of compounds for native aSyn aggregates in tissue sections by autoradiography. The tritiated compounds are incubated in vitro with tissue sections from A30P transgenic mouse brains and human PD brain tissue. [³H]Example-3 shows strong binding to aSyn aggregates in A30P transgenic mouse brain tissue with histologically confirmed high aSyn load in midbrain and pons using the aSyn-specific antibody pS129 (FIG. 1, right image). Radioligand binding and antibody staining show excellent co-localization with strong signals in midbrain, pons and subthalamic regions and weaker signals in cortical areas. Human brain tissue samples from PD patients are characterized by a much lower density of aSyn aggregates compared to the overexpressing transgenic mouse model A30P. As a consequence, macroscopic co-localization of radioligand binding and aSyn mAb signals on human PD tissue sections is challenging (FIG. 1, middle image) but can be clearly demonstrated at higher magnification (FIG. 1, right image). The hot spots of the autoradiograms show good co-localization with LBs stained by the aSyn mAb pS129.

ASyn In Vitro Displacement Assay

This in vitro displacement binding assay assesses the affinity of novel compounds for native aSyn aggregates. The compounds are co-incubated with the screening radioligand [³H]Example-3 and the compound's displacement potency of [³H]Example-3 binding is determined by in vitro autoradiography using A30P transgenic mouse brain sections (FIG. 2). Total binding (TB) is determined at 3 nM [$^3$H] Example-3 while non-specific binding (NSB) is determined by co-incubation with 3 μM unlabeled Example-3. The NSB level is defined as 100% displacement. Several high-affinity displacers are identified (FIG. 3) and selected for tritiation and a direct binding test using autoradiography (FIG. 4).

In Vivo Binding/Ex Vivo Autoradiography

Upon intravenous administration in A30P mice, all radiotracers reveal good penetration through the blood-brain barrier and a clear target-related retention in midbrain, pons and subthalamic regions as visualized by ex vivo autoradiography (FIG. 5). No significant off-target binding is observed in brain regions devoid of aSyn pathology.

Aβ In Vitro Displacement Assay

This in vitro displacement binding assay assesses the affinity of novel compounds for native Aβ aggregates in human AD brain tissue samples. The compounds are co-incubated with the screening radioligand [$^3$H]Example 3 and the compound's displacement potency of [$^3$H]Example 3 binding is determined by in vitro autoradiography using AD brain tissue sections (FIG. 6). TB is determined at 3 nM [$^3$H]Example 3 while NSB is determined by co-incubation with 3 μM unlabeled Example 3. The NSB level is defined as 100% displacement.

Aβ In Vitro Binding Assay

This direct in vitro binding assay assesses the affinity of radiotracers for native Aβ aggregates in tissue sections by autoradiography. The tritiated compounds are incubated in vitro with sections from human AD brain samples and show strong binding to Aβ aggregates (FIG. 7). Radioligand binding and Aβ mAb staining show excellent co-localization as exemplified for [$^3$H]Example-134 (FIG. 8). The hot spots of the autoradiograms show good co-localization with Aβ plaques stained by the Aβ mAb MOAB-2.

EXAMPLES

Example 1

2-Fluoro-4-methoxy-N-(4-(4-(pyridin-2-yl)piperazin-1-yl)phenyl)benzamide

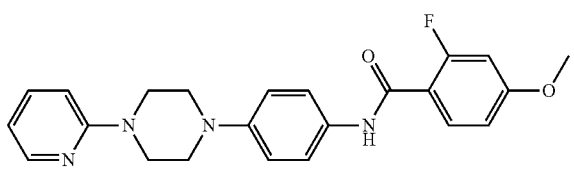 [SMILES: COc1ccc(C(=O)Nc2ccc(N3CCN(c4ccccn4)CC3)cc2)c(F)c1]

a) 1-(4-Nitrophenyl)-4-(pyridin-2-yl)piperazine

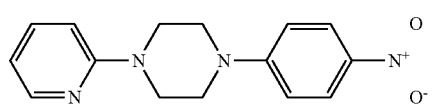

1-(Pyridin-2-yl)piperazine (4.90 g, 30 mmol) was dissolved at 22° C. in DMSO (10 ml) under an inert atmosphere. K$_2$CO$_3$ (6.22 g, 45 mmol) was added at 22° C. followed by 1-fluoro-4-nitrobenzene (4.66 g, 3.5 ml, 33 mmol). The reaction mixture was heated to 90° C. and stirred at this temperature for 90 min. The mixture was diluted with H$_2$O (150 ml) and extracted with DCM (3×150 ml). The organic layers were washed with sat. aq. NaCl (1×150 ml), dried over MgSO$_4$ (35 g), filtered over a glass-frit and washed with DCM (2×100 ml). The filtrate was evaporated at 40° C. and finally dried in HV to mainly remove DMSO. The residue (9.18 g) was partially dissolved in DCM/MeOH 1:1 (60 ml), adsorbed on 32 g Isolute HM-N 9800, evaporated and then purified by flash chromatography (silica gel, 330 g; MeOH in DCM 0% to 5%). Pure fractions corresponding to the product were collected to give after evaporation at 40° C. the title compound (6.89 g, 81%) as an orange solid. LC-MS: m/z=285.1 [M+H]$^+$.

b) 4-(4-(Pyridin-2-yl)piperazin-1-yl)aniline

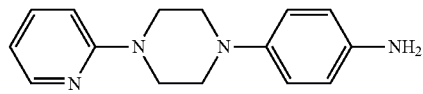

1-(4-Nitrophenyl)-4-(pyridin-2-yl)piperazine (6.77 g, 23.8 mmol) was suspended in EtOH (290 ml) and placed under inert atmosphere at 22° C. and a slurry of Pd/C 10% (2.53 g, 2.38 mmol) in EtOH (50 ml) was added. The reaction vessel was again inerted, then set under H$_2$ and reacted at 22° C. for 15 h. The catalyst was filtered over a membrane filter, washed with EtOH (2×50 ml) and the filtrate was evaporated. The residue was dissolved in DCM/MeOH 1:1 (20 ml), adsorbed on 12.5 g Isolute HM-N 9800, evaporated and then purified by flash chromatography (silica gel, 330 g, MeOH in DCM 1% to 5%). Fractions containing pure product were collected to give after evaporation at 40° C. the title compound (5.02 g, 83%) as a light yellow solid. LC-MS: m/z=255.2 [M+H]$^+$.

c) 2-Fluoro-4-methoxy-N-(4-(4-(pyridin-2-yl)piperazin-1-yl)phenyl)benzamide

2-Fluoro-4-methoxybenzoic acid (854 mg, 5.02 mmol) was dissolved in DMF (15 ml) to give a light yellow solution. DIPEA (1.18 g, 1.59 ml, 9.12 mmol) and HATU (2.08 g, 5.47 mmol) were added, and the reaction mixture was stirred at rt for 30 min. Then 4-(4-(pyridin-2-yl)piperazin-1-yl)aniline (1.16 g, 4.56 mmol) was added and the reaction mixture was stirred at rt for 1 h. H$_2$O was added and the product was extracted three times with DCM. The combined organic layers were dried over Na$_2$SO$_4$, filtered and evaporated. The crude material was suspended in DCM and filtered to provide 1.29 g (70%) of the title compound as a light grey solid. LC-MS m/z=407.2 [M+H]$^+$.

Example 2

4-Hydroxy-N-[4-[4-(2-pyridyl)piperazin-1-yl]phenyl]benzamide

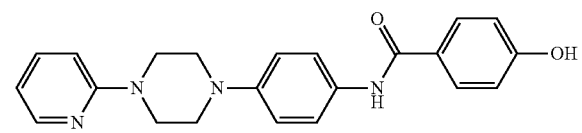

a) [4-[[4-[4-(2-Pyridyl)piperazin-1-yl]phenyl]carbamoyl]phenyl] acetate

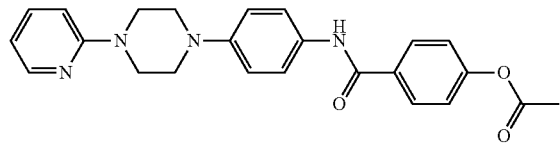 [SMILES: CC(=O)Oc1ccc(C(=O)Nc2ccc(N3CCN(c4ccccn4)CC3)cc2)cc1]

4-Acetoxybenzoic acid (1.59 g, 8.8 mmol) was dissolved at 22° C. in DCM (65 ml) under an inert atmosphere. Oxalyl chloride (1.68 g, 1.16 ml, 13.2 mmol) was added at 22° C. followed by DMF (32.2 mg, 34.1 µl, 440 µmol) and the reaction mixture was stirred at 22° C. for 2 h. The mixture was evaporated at 40° C. and the resulting acid chloride was dissolved in DCM (32.3 ml) and added dropwise (5 min) at 22° C. to a solution of 4-(4-(pyridin-2-yl)piperazin-1-yl) aniline (Intermediate 1.b) (2.24 g, 8.8 mmol) and DIPEA (4.55 g, 6.15 ml, 35.2 mmol) in DCM (80 ml) keeping the internal temperature below 20° C. (ice-bath). Stirring was continued at 22° C. for 30 min. The reaction was stopped by adding at 22° C. MeOH (5.64 g, 7.12 ml, 176 mmol). Stirring was continued for 1 h before filtering through a membrane-filter. Solids were washed with DCM (2×35 ml) and the cake was dried for 2 min (air dried by suction). Then the cake was washed with $H_2O$ (2×35 ml) and dried in HV to give the title compound (3.20 g, 87%) as white solid. LC-MS: m/z=417.3 $[M+H]^+$.

b) 4-Hydroxy-N-[4-[4-(2-pyridyl)piperazin-1-yl]phenyl]benzamide 4-((4-(4-(Pyridin-2-yl)piperazin-1-yl)phenyl)carbamoyl) phenyl acetate (3.06 g, 7.34 mmol) was suspended in MeOH (100 ml) under inert atmosphere at 22° C. NaOH (1 M aq., 29.4 ml, 29.4 mmol) was added. The mixture was stirred at 22° C. for 6 h to give a clear solution. The solution was treated with HCl (1 M aq., 29.4 ml, 29.4 mmol) leading to precipitation of the product. The mixture was stirred for an additional 60 min, filtered over a glass frit, washed with $H_2O$/MeOH 1:1 (1×60 ml), $H_2O$ (2×60 ml) and dried under HV to give the title compound (2.57 g, 94%) as white solid. LC-MS: m/z=375.3 $[M+H]^+$.

Example 3

4-Methoxy-N-[4-(4-pyridin-2-ylpiperazin-1-yl)phenyl]benzamide

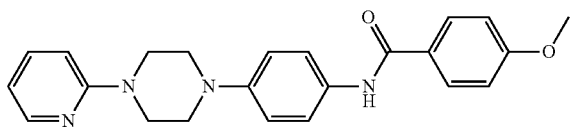 [SMILES: COc1ccc(C(=O)Nc2ccc(N3CCN(c4ccccn4)CC3)cc2)cc1]

The title compound was prepared in analogy to 2-fluoro-4-methoxy-N-(4-(4-(pyridin-2-yl)piperazin-1-yl)phenyl) benzamide (Example 1, step c) from 4-(4-(pyridin-2-yl) piperazin-1-yl)aniline (Intermediate 1.b) (500 mg, 1.97 mmol) and 4-methoxybenzoic acid (329 mg, 2.16 mmol). Yield 474 mg (61%). Off-white solid. LC-MS: m/z=389.2 $[M+H]^+$.

Example 4

6-Methoxy-N-[4-[4-(5-methyl-2-pyridyl)piperazin-1-yl]phenyl]pyridine-3-carboxamide

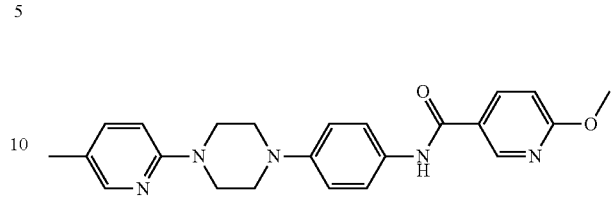

a) 1-(5-Methylpyridin-2-yl)-4-(4-nitrophenyl)piperazine

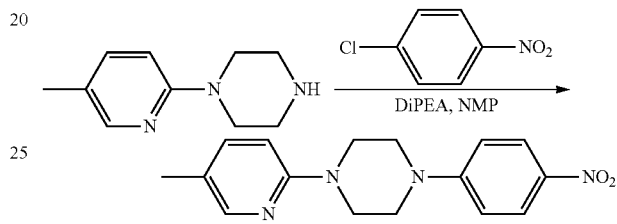

1-(5-Methylpyridin-2-yl)piperazine (3.1 g, 17.5 mmol), 1-chloro-4-nitrobenzene (3.84 g, 24 mmol) and DIPEA (4.6 ml, 3.38 g 26 mmol) were combined at room temperature in NMP (3 ml) then stirred and heated to 125° C. for 4.5 h. The cooled mixture was partitioned between $NaHCO_3$ and EtOAc and extracted with EtOAc (3×). The combined organic phases were then washed with $H_2O$ and concentrated onto silica. The crude solid was dry-loaded onto a silica column and purified by flash column chromatography eluting with DCM to DCM/EtOAc 1:1 to afford the title compound 2.7 g (52%). This material was used in the following step with no further characterization.

b) 4-(4-(5-Methylpyridin-2-yl)piperazin-1-yl)aniline

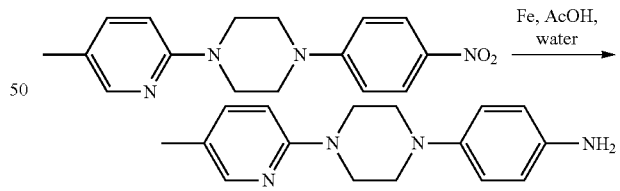

1-(5-Methylpyridin-2-yl)-4-(4-nitrophenyl)piperazine (2.7 g, 9.05 mmol), iron powder (2.3 g, 41 mmol), acetic acid (5 ml) and $H_2O$ (5 ml) were combined and refluxed for 2 h. Then another portion of iron powder (2.3 g, 41 mmol) and acetic acid (5 ml) were added and the mixture was stirred and heated for another 2 h. The mixture was cooled, filtered and concentrated and the residue partitioned between $NaHCO_3$ and DCM and extracted into DCM (3×). The combined organic phases were washed with $H_2O$ and dried and evaporated onto silica. The crude solid adsorbed onto silica was dry-loaded onto a silica column and purified by flash column chromatography eluting with isohexane 100% to EtOAc 100% to MeOH 50%. The product was obtained as a beige solid 1.89 g (78%).

¹H NMR (400 MHz, CDCl₃): δ 8.04 (d, J=2.0 Hz, 1H), 7.33 (dd, J=2.3, 8.4 Hz, 1H), 6.88-6.85 (m, 2H), 6.68-6.62 (m, 3H), 3.64-3.60 (m, 4H), 3.16-3.13 (m, 4H), 2.21 (s, 3H).

c) 6-Methoxy-N-(4-(4-(6-methylpyridin-3-yl)piperazin-1-yl)phenyl)nicotinamide

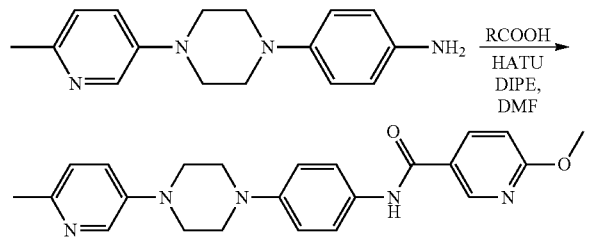

This compound was synthesized following the general procedure B.

Yield: 120 mg.

¹H NMR (400 MHz, CDCl₃) δ 8.68 (d, J=2.3 Hz, 1H), 8.10-8.05 (m, 2H), 7.58 (s, 1H), 7.52 (d, J=8.8 Hz, 2H), 7.35 (dd, J=2.3, 8.4 Hz, 1H), 7.01-6.97 (m, 2H), 6.83 (d, J=8.7 Hz, 1H), 6.66 (d, J=8.7 Hz, 1H), 4.00 (s, 3H), 3.67-3.63 (m, 4H), 3.31-3.27 (m, 4H), 2.22 (s, 3H). LC-MS: Rt=2.59 min, m/z=404, [M+H]⁺.

Example 5

4-Methyl-N-(4-(4-(pyridin-2-yl)piperazin-1-yl)phenyl)benzamide

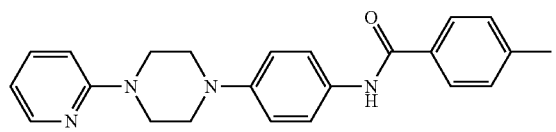

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (100 mg, 393 μmol) and 4-methylbenzoic acid (58.9 mg, 433 μmol). Yield 96 mg (66%). White solid. LC-MS: m/z=373.2 [M+H]⁺.

Example 6

4-(4-Methylpiperazin-1-yl)-N-(4-(4-(pyridin-2-yl)piperazin-1-yl)phenyl)benzamide

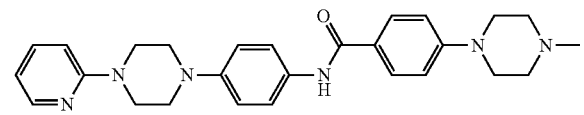

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (100 mg, 393 μmol) and 4-(4-methylpiperazin-1-yl)benzoic acid (95.3 mg, 433 μmol). Yield 38 mg (21%). Off-white solid. LC-MS: m/z=229.2 [M+2H]²⁺.

Example 7

4-(Dimethylamino)-N-(4-(4-(pyridin-2-yl)piperazin-1-yl)phenyl)benzamide

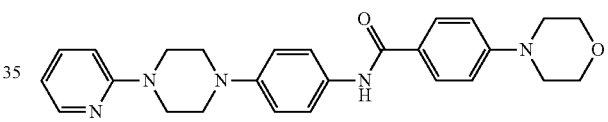

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (70 mg, 275 μmol) and 4-(dimethylamino)benzoic acid (50 mg, 303 μmol). Yield 27 mg (24%). Off-white solid. LC-MS: m/z=201.7 [M+2H]²⁺.

Example 8

4-Morpholino-N-(4-(4-(pyridin-2-yl)piperazin-1-yl)phenyl)benzamide

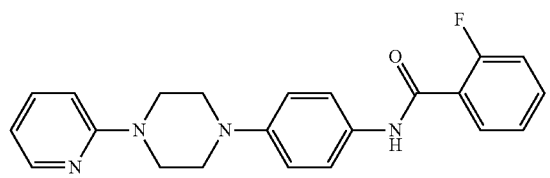 [SMILES: O=C(Nc1ccc(N2CCN(c3ccccn3)CC2)cc1)c1ccccc1F]

4-Morpholinobenzoic acid (122 mg, 590 μmol) was dissolved in DMF (5 ml). 4-(4-(Pyridin-2-yl)piperazin-1-yl)aniline (Intermediate 1.b) (100 mg, 393 μmol), HOBt (117 mg, 865 μmol), EDCl (188 mg, 983 μmol) and Et₃N (39.8 mg, 54.5 μl, 393 μmol) were added and the reaction mixture was stirred at rt for 7 h. Then additional 30 mg of 4-(4-(pyridin-2-yl)piperazin-1-yl)aniline (Intermediate 1.b) were added and the mixture was stirred for 16.5 h. H₂O was added and the product was extracted with DCM (3×). The combined organic layers were dried over Na₂SO₄ and evaporated. The crude material was suspended in DCM and filtered to provide 25 mg (14%) of the title compound as an off-white solid. LC-MS: m/z=222.7 [M+2H]²⁺.

Example 9

2-Fluoro-N-(4-(4-(pyridin-2-yl)piperazin-1-yl)phenyl)benzamide

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (100 mg, 393 μmol) and 2-fluorobenzoic acid (60.6 mg, 433 μmol). The product was purified with preparative HPLC to yield 78 mg (53%) of the title compound as a white solid. LC-MS: m/z=377.2 [M+H]$^+$.

Example 10

2-Fluoro-4-methyl-N-(4-(4-(pyridin-2-yl)piperazin-1-yl)phenyl)benzamide

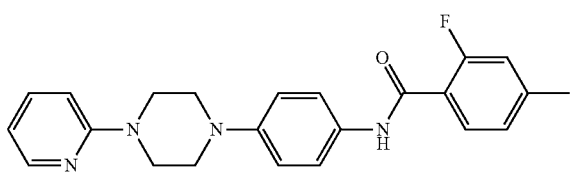 [SMILES: Cc1ccc(C(=O)Nc2ccc(N3CCN(c4ccccn4)CC3)cc2)c(F)c1]

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (100 mg, 393 μmol) and 2-fluoro-4-methylbenzoic acid (66.7 mg, 433 μmol). The product was purified with preparative HPLC to yield 27 mg (18%) of the title compound as a white solid. LC-MS: m/z=391.3 [M+H]$^+$.

Example 11

4-Methoxy-2-methyl-N-(4-(4-(pyridin-2-yl)piperazin-1-yl)phenyl)benzamide

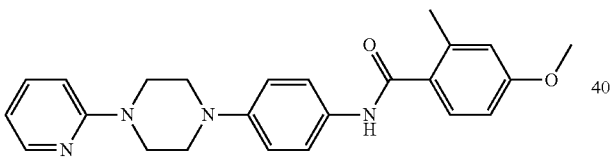

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (100 mg, 393 μmol) and 4-methoxy-2-methylbenzoic acid (71.9 mg, 433 μmol). The product was isolated as a white solid. Yield 78 mg (49%). LC-MS: m/z=202.2 [M+2H]$^{2+}$.

Example 12

4-(2-(2-Fluoroethoxy)ethoxy)-N-(4-(4-(pyridin-2-yl)piperazin-1-yl)phenyl)benzamide

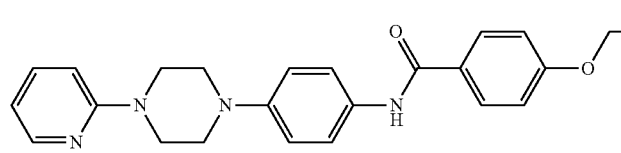

a) Methyl 4-[2-(2-fluoroethoxy)ethoxy]benzoate

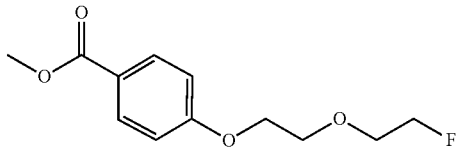 [SMILES: COC(=O)c1ccc(OCCOCCF)cc1]

2-(2-Fluoroethoxy)ethyl 4-methylbenzenesulfonate (CAS Nr. 1118567-11-5) (892 mg, 3.4 mmol) was dissolved under inert atmosphere at 22° C. in DMF (17 ml). Methyl 4-hydroxybenzoate (517 mg, 3.4 mmol) was added followed by Cs$_2$CO$_3$ (2.22 g, 6.8 mmol), then the mixture was warmed to 50° C. and stirred at 50° C. for 4 h. H$_2$O (50 ml) was added and the product was extracted with EtOAc (3×50 ml). The organic layers were combined and dried over MgSO$_4$ (5 g), filtered over a glass-frit (D3), washed with EtOAc (2×20 ml) and the filtrate was evaporated. The residue was purified by flash chromatography (silica gel, 40 g; EtOAc in heptane 0% to 50%). The corresponding pure fractions were collected to give after evaporation a colorless oil. LC-MS analysis of this material indicated the presence of 2% phenolic starting material. The solid was thus dissolved in DCM (20 ml) and washed with 10% Na$_2$CO$_3$ (2×20 ml) and H$_2$O (1×20 ml). The aqueous layers were back-extracted with DCM (1×20 ml). The organic layers were combined, dried over MgSO$_4$ (2 g), filtered over a glass-frit (D3) and washed with DCM (2×10 ml). The solvent was evaporated to give after drying in HV the title compound (715 mg, 87%) as colorless oil. LC-MS: m/z=243.1 [M+H]$^+$.

b) 4-[2-(2-Fluoroethoxy)ethoxy]benzoic acid

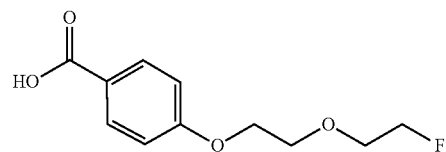 [SMILES: O=C(O)c1ccc(OCCOCCF)cc1]

Methyl 4-(2-(2-fluoroethoxy)ethoxy)benzoate (597.6 mg, 2.47 mmol) was dissolved under inert atmosphere at 22° C. in MeOH (12 ml) and NaOH (1 M aq. sol., 9.87 ml, 9.87 mmol,) was added. The reaction mixture was stirred at 22° C. for 4 h. MeOH was removed under reduced pressure and the remaining mixture was diluted with H$_2$O (10 ml), washed with DCM (2×10 ml) and treated with HCl (1 M aq., 9.87 ml, 9.87 mmol). The product was extracted with EtOAc (2×15 ml), the organic layers were combined and washed with H$_2$O (1×10 ml), then dried over MgSO$_4$ (2 g), filtered over a glass-frit (D3), washed with EtOAc (2×10 ml) and the filtrate was evaporated at 40° C. to give the title compound (540.4 mg, 96%) as white solid. LC-MS: m/z=229.1 [M+H]⁺.

c) 4-(2-(2-Fluoroethoxy)ethoxy)-N-(4-(4-(pyridin-2-yl)piperazin-1-yl)phenyl)benzamide The title compound was prepared in analogy to 2-fluoro-4-methoxy-N-(4-(4-(pyridin-2-yl)piperazin-1-yl)phenyl) benzamide (Example 1, step c) from 4-(4-(pyridin-2-yl) piperazin-1-yl)aniline (Intermediate 1.b) (100 mg, 393 μmol) and 4-(2-(2-fluoroethoxy)ethoxy)benzoic acid (98.7 mg, 433 μmol). The product was isolated as a white solid. 122 mg (67%). LC-MS: m/z=233.2 [M+2H]²⁺.

Example 13

4-Methoxy-N-[4-[4-(1,3-thiazol-2-yl)piperazin-1-yl] phenyl]benzamide

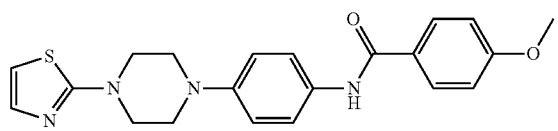

a) 2-[4-(4-Nitrophenyl)piperazin-1-yl]-1,3-thiazole

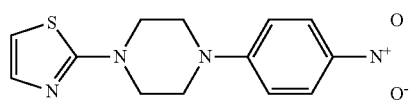

2-(Piperazin-1-yl)thiazole (596 mg, 3.52 mmol) was dissolved in DMSO (2.5 ml). K₂CO₃ (734 mg, 7.41 mmol) and 1-fluoro-4-nitrobenzene (500 mg, 3.54 mmol) were added and the solution was stirred at 90° C. for 20 min. The solution was diluted in H₂O and extracted with DCM. The combined organic layers were washed with brine, dried over MgSO₄, filtered and concentrated under vacuum. The crude product was purified by flash-column chromatography (0 to 5% MeOH in DCM) to yield 2-[4-(4-nitrophenyl)piperazin-1-yl]-1,3-thiazole (966 mg, 94%). LC-MS: m/z=291.1 [M+H]⁺.

b) 4-[4-(1,3-Thiazol-2-yl)piperazin-1-yl]aniline

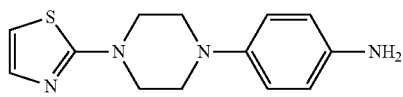

2-[4-(4-Nitrophenyl)piperazin-1-yl]-1,3-thiazole (965 mg, 3.32 mmol) was combined with EtOH (2.8 ml) and THF (5.6 ml) to give an orange suspension. Hydrazine mono hydrate (666 mg, 645 μl, 13.3 mmol) and a Raney Nickel (50% slurry in H₂O, 14.2 mg, 166 μmol) were added. The resulting mixture was stirred under N₂ at rt for 45 min. The reaction mixture was filtered under N2 through Celite. The filtrate was evaporated to dryness to afford the desired product 4-[4-(1,3-thiazol-2-yl)piperazin-1-yl]aniline (818.5 mg, 90%) as a brown solid. LC-MS: m/z=261.1 [M+H]⁺.

c) 4-Methoxy-N-[4-[4-(1,3-thiazol-2-yl)piperazin-1-yl]phenyl]benzamide

The title compound was prepared in analogy to 2-fluoro-4-methoxy-N-(4-(4-(pyridin-2-yl)piperazin-1-yl)phenyl) benzamide (Example 1, step c) from 4-[4-(1,3-thiazol-2-yl) piperazin-1-yl]aniline (53 mg, 204 μmol) and 4-methoxybenzoic acid (34.1 mg, 224 μmol). Yield 12.5 mg (15%). Off-white solid. LC-MS: m/z=395.2 [M+H]⁺.

Example 14

N-(4-(4-(Pyridin-2-yl)piperazin-1-yl)phenyl)-2,3-dihydrobenzo[b][1,4]dioxine-6-carboxamide

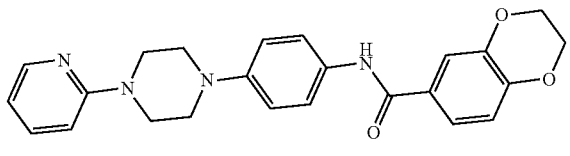 [SMILES: O=C(Nc1ccc(N2CCN(c3ccccn3)CC2)cc1)c1ccc2c(c1)OCCO2]

The title compound was prepared in analogy to 2-fluoro-4-methoxy-N-(4-(4-(pyridin-2-yl)piperazin-1-yl)phenyl) benzamide (Example 1, step c) from 4-(4-(pyridin-2-yl) piperazin-1-yl)aniline (Intermediate 1.b) (70 mg, 275 μmol) and 2,3-dihydrobenzo[b][1,4]dioxine-6-carboxylic acid (49.6 mg, 275 μmol). Yield 65 mg (57%). Off-white solid. LC-MS: m/z=417.2 [M+H]⁺.

Example 15

N-(4-(4-(Pyridin-2-yl)piperazin-1-yl)phenyl)benzo [d][1,3]dioxole-5-carboxamide

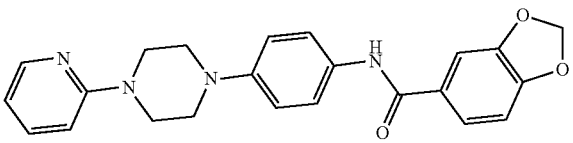 [SMILES: O=C(Nc1ccc(N2CCN(c3ccccn3)CC2)cc1)c1ccc2c(c1)OCO2]

The title compound was prepared in analogy to 2-fluoro-4-methoxy-N-(4-(4-(pyridin-2-yl)piperazin-1-yl)phenyl) benzamide (Example 1, step c) from 4-(4-(pyridin-2-yl) piperazin-1-yl)aniline (Intermediate 1.b) (70 mg, 275 μmol) and benzo[d][1,3]dioxole-5-carboxylic acid (45.7 mg, 275 μmol). Yield 71 mg (64%). Off-white solid. LC-MS: m/z=403.2 [M+H]⁺.

Example 16

N-(4-(4-(Pyridin-2-yl)piperazin-1-yl)phenyl)imidazo [1,2-a]pyridine-7-carboxamide

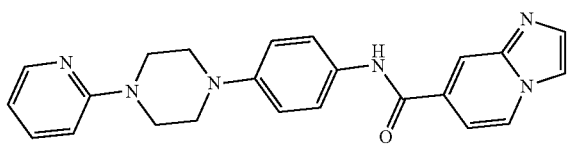 [SMILES: O=C(Nc1ccc(N2CCN(c3ccccn3)CC2)cc1)c1ccn2ccnc2c1]

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (70 mg, 275 µmol) and imidazo[1,2-a]pyridine-7-carboxylic acid (44.6 mg, 275 µmol). Yield 47 mg (43%). Yellow solid. LC-MS: m/z=397.3 [M–H]⁻.

Example 17

N-(4-(4-(Pyridin-2-yl)piperazin-1-yl)phenyl)imidazo[1,2-a]pyridine-6-carboxamide

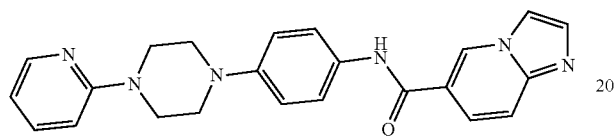

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (70 mg, 275 µmol) and imidazo[1,2-a]pyridine-6-carboxylic acid (44.6 mg, 275 µmol). The product was purified by preparative HPLC yielding 8.5 mg (7.7%) of the title compound as white solid. LC-MS: m/z=200.2 [M+2H]$^{2+}$.

Example 18

2-Fluoro-4-methoxy-N-[4-[4-(1,3-thiazol-2-yl)piperazin-1-yl]phenyl]benzamide

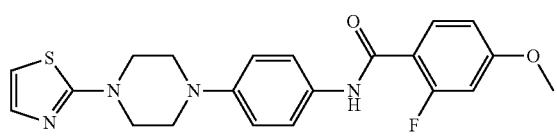 [SMILES: COc1ccc(C(=O)Nc2ccc(N3CCN(c4nccs4)CC3)cc2)c(F)c1]

2-Fluoro-4-methoxybenzoic acid (35.9 mg, 211 µmol) was combined with DMF (0.6 ml) to give a colorless solution. HATU (87.6 mg, 230 µmol) and DIPEA (49.6 mg, 67.1 µl, 384 µmol) were added and the reaction mixture was stirred at rt for 30 min. 4-[4-(1,3-Thiazol-2-yl)piperazin-1-yl]aniline (Intermediate 13.b, 50 mg, 192 µmol) dissolved in 0.1 ml DMF was added and the reaction mixture was stirred at rt for 1 h. H₂O was added (10 ml) and the brown solution was extracted with DCM (3×10 ml). The combined organic layers were washed with brine (1×10 ml), dried over MgSO₄, filtered and evaporated. The remaining brown oil was diluted with DCM (ca. 2 ml) and left over night at 4° C. Solids were collected by filtration, washed with DCM and dried under high vacuum to give 2-fluoro-4-methoxy-N-[4-[4-(1,3-thiazol-2-yl)piperazin-1-yl]phenyl]benzamide (12.4 mg, 15% yield) as white solid. The filtrate was evaporated and the residue was purified by preparative HPLC to yield a second portion of product (8.5 mg, 7.7%) as white solid. Combined yield 20.9 mg (23%). LCMS: m/z=413.2 [M+H]⁺.

Example 19

4-Methoxy-2-methyl-N-[6-[4-(2-pyridyl)piperazin-1-yl]-3-pyridyl]benzamide

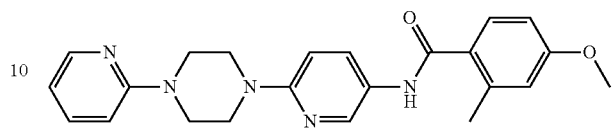

a) 1-(5-Nitropyridin-2-yl)-4-(pyridin-2-yl)piperazine

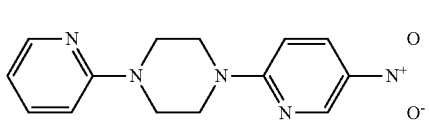

To a solution of 1-(pyridin-2-yl)piperazine (5.00 g, 30.6 mmol) in DMF (150 ml) under N₂ at 25° C. was added K₂CO₃ (8.46 g, 61.3 mmol) and the mixture was stirred at 25° C. for 30 min. 2-Chloro-5-nitropyridine (5.32 g, 33.7 mmol) was added at 25° C. and stirring was continued at 25° C. for 4 h. The reaction mixture was poured into H₂O (100 ml) and extracted with EtOAc (4×250 ml). The organic phase was washed with brine, dried over Na₂SO₄ and solvents were evaporated. The resulting crude was purified by flash chromatography (30-80% EtOAc in hexane) to get 1-(5-nitropyridin-2-yl)-4-(pyridin-2-yl)piperazine (8.0 g, 92%) as yellow solid. LC-MS: m/z=286.3 [M+H]⁺.

b) 6-[4-(Pyridin-2-yl)piperazin-1-yl]pyridin-3-amine

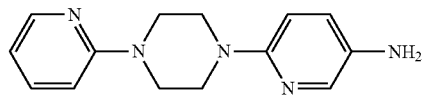

To a solution of 1-(5-nitropyridin-2-yl)-4-(pyridin-2-yl)piperazine (2.5 g, 8.76 mmol) in EtOH (150 ml) was added Raney-Ni (50% in H₂O) (6 ml) at 25° C. Hydrazine monohydrate (2.9 ml, 59.6 mmol) was added over a period of 15 min. The resulting reaction mixture was heated to 45° C. for 1 h. After total consumption of starting material (monitored by TLC) Raney-Ni was filtered off, washed with EtOH (2×100 ml) and the filtrate was concentrated under vacuum. The resulting crude product was purified by flash chromatography (amino modified silica gel; 60% EtOAc in hexane) to get 6-[4-(pyridin-2-yl)piperazin-1-yl]pyridin-3-amine (1.7 g, 76%) as grey solid. LC-MS: m/z=255.7 [M+H]⁺.

c) 4-Methoxy-2-methyl-N-[6-[4-(2-pyridyl)piperazin-1-yl]-3-pyridyl]benzamide

To a solution of 4-methoxy-2-methylbenzoic acid (100 mg, 0.65 mmol) in DMF (2.5 ml) were added DIPEA (0.3 ml, 1.95 mmol), HATU (370 mg, 0.97 mmol) and 6-[4-(pyridin-2-yl)piperazin-1-yl]pyridin-3-amine (166 mg, 0.65 mmol). The reaction mixture was stirred at 25° C. for 16 h. After total consumption of starting material (monitored by TLC) the reaction mixture was poured into H$_2$O (20 ml) and extracted with EtOAc (2×50 ml). The organic phase was dried over Na$_2$SO$_4$ and solvents were evaporated. The resulting crude material was purified by preparative HPLC to get the title compound (60 mg, 23%) as off-white solid. LC-MS: m/z=404.1 [M+H]$^+$.

Example 20

4-(Dimethylamino)-N-[4-[4-(1,3-thiazol-2-yl)piperazin-1-yl]phenyl]benzamide

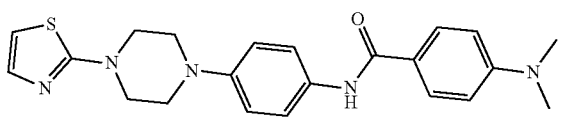 [SMILES: CN(C)c1ccc(C(=O)Nc2ccc(N3CCN(c4nccs4)CC3)cc2)cc1]

The title compound was prepared in analogy to 2-fluoro-4-methoxy-N-(4-(4-(pyridin-2-yl)piperazin-1-yl)phenyl)benzamide (Example 1, step c) from 4-[4-(1,3-thiazol-2-yl)piperazin-1-yl]aniline (Intermediate 13.b, 50 mg, 192 μmol) and 4-(dimethylamino)benzoic acid (34.9 mg, 211 μmol). The product was purified by preparative HPLC to yield 11.7 mg (14%) of the title compound as white solid. LC-MS: m/z=408.2 [M+H]$^+$; 204.7 [M+2H]$^{2+}$.

Example 21

2-Fluoro-4-methyl-N-[4-[4-(1,3-thiazol-2-yl)piperazin-1-yl]phenyl]benzamide

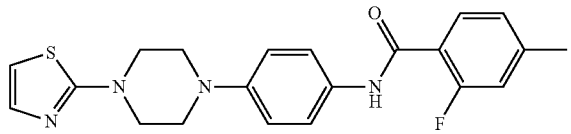 [SMILES: Cc1ccc(C(=O)Nc2ccc(N3CCN(c4nccs4)CC3)cc2)c(F)c1]

The title compound was prepared in analogy to 2-fluoro-4-methoxy-N-(4-(4-(pyridin-2-yl)piperazin-1-yl)phenyl)benzamide (Example 1, step c) from 4-[4-(1,3-thiazol-2-yl)piperazin-1-yl]aniline (Intermediate 13.b, 50 mg, 192 μmol) and 2-fluoro-4-methylbenzoic acid (32.6 mg, 211 μmol). The product was purified by preparative HPLC to yield 30.4 mg (38%) of the title compound off-white solid. LC-MS: m/z=397.2 [M+H]$^+$.

Example 22

4-(4-Methylpiperazin-1-yl)-N-[6-[4-(2-pyridyl)piperazin-1-yl]-3-pyridyl]benzamide

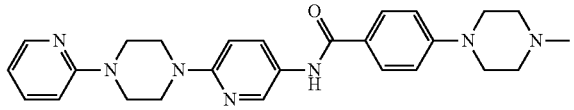

To a solution of 4-(4-methylpiperazin-1-yl)benzoic acid (100 mg, 0.45 mmol) in DMF (3 ml) were added DIPEA (0.23 ml, 1.36 mmol), HATU (259 mg, 0.68 mmol) and 6-[4-(pyridin-2-yl)piperazin-1-yl]pyridin-3-amine (Intermediate 19.b) (116 mg, 0.45 mmol). Then the reaction mixture was stirred at 25° C. for 16 h. After total consumption of the starting material (monitored by TLC) the reaction mixture was poured into H$_2$O (20 ml) and extracted with EtOAc (2×50 ml). The combined organic phases were dried over Na$_2$SO$_4$ and solvents were evaporated. The product was purified by preparative HPLC to get the title compound (24 mg, 12%) as yellow solid. LC-MS: m/z=458.2 [M+H]$^+$.

Example 23

2-Fluoro-4-methyl-N-[6-[4-(2-pyridyl)piperazin-1-yl]-3-pyridyl]benzamide

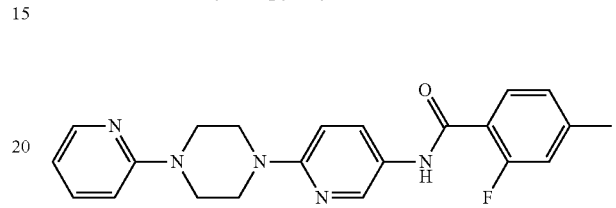

The title compound was prepared in analogy to 4-(4-methylpiperazin-1-yl)-N-[6-[4-(2-pyridyl)piperazin-1-yl]-3-pyridyl]benzamide (Example 22) from 6-[4-(pyridin-2-yl)piperazin-1-yl]pyridin-3-amine (Intermediate 19.b) (116 mg, 0.45 mmol) and 2-fluoro-4-methylbenzoic acid (100 mg, 0.65 mmol). Yield 77 mg (30%). White solid. LC-MS: m/z=392.4 [M+H]$^+$.

Example 24

4-Methoxy-N-[6-[4-(2-pyridyl)piperazin-1-yl]-3-pyridyl]benzamide

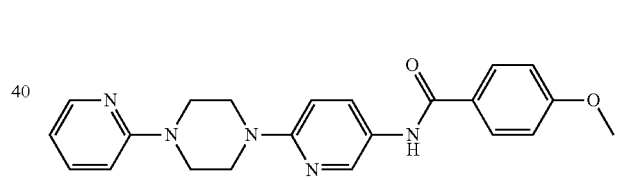

The title compound was prepared in analogy to 4-(4-methylpiperazin-1-yl)-N-[6-[4-(2-pyridyl)piperazin-1-yl]-3-pyridyl]benzamide (Example 22) from 6-[4-(pyridin-2-yl)piperazin-1-yl]pyridin-3-amine (Intermediate 19.b) (101 mg, 0.39 mmol) and 4-methoxybenzoic acid (50 mg, 0.33 mmol). Yield 17 mg (13%). Off-white solid. LC-MS: m/z=390.2 [M+H]$^+$.

Example 25

5-Methyl-N-[4-[4-(1,3-thiazol-2-yl)piperazin-1-yl]phenyl]pyridine-2-carboxamide

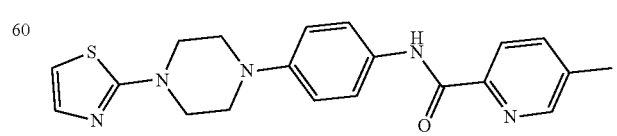

The title compound was prepared in analogy to 2-fluoro-4-methoxy-N-(4-(4-(pyridin-2-yl)piperazin-1-yl)phenyl)

benzamide (Example 1, step c) from 4-[4-(1,3-thiazol-2-yl)piperazin-1-yl]aniline (Intermediate 13.b) (100 mg, 384 µmol) and 5-methylpicolinic acid (57.9 mg, 422 µmol). The product was purified by preparative HPLC to yield 21.8 mg (14%) of the title compound as light green solid. LC-MS: m/z=380.2 [M+H]$^+$.

Example 26

4-Morpholin-4-yl-N-[4-[4-(1,3-thiazol-2-yl)piperazin-1-yl]phenyl]benzamide

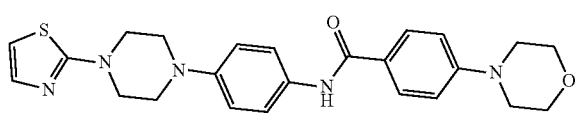 [SMILES: O=C(Nc1ccc(N2CCN(c3nccs3)CC2)cc1)c1ccc(N2CCOCC2)cc1]

The title compound was prepared in analogy to 2-fluoro-4-methoxy-N-(4-(4-(pyridin-2-yl)piperazin-1-yl)phenyl)benzamide (Example 1, step c) from 4-[4-(1,3-thiazol-2-yl)piperazin-1-yl]aniline (Intermediate 13.b) (100 mg, 384 µmol) and 4-morpholinobenzoic acid (87.6 mg, 422 µmol). Yield 78 mg (43%). Light yellow solid. LC-MS: m/z=448.3 [M–H]$^-$.

Example 27

4-Methyl-N-[4-[4-(1,3-thiazol-2-yl)piperazin-1-yl]phenyl]benzamide

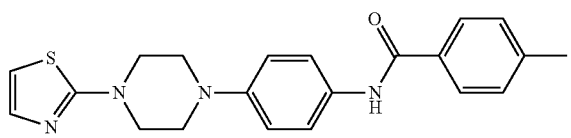 [SMILES: Cc1ccc(C(=O)Nc2ccc(N3CCN(c4nccs4)CC3)cc2)cc1]

The title compound was prepared in analogy to 2-fluoro-4-methoxy-N-(4-(4-(pyridin-2-yl)piperazin-1-yl)phenyl)benzamide (Example 1, step c) from 4-[4-(1,3-thiazol-2-yl)piperazin-1-yl]aniline (Intermediate 13.b) (55.8 mg, 214 µmol) and 4-methylbenzoic acid (32.1 mg, 236 µmol). The product was purified by preparative HPLC to yield 50.2 mg (59%) of the title compound as off-white solid. LC-MS: m/z=379.2 [M+H]$^+$.

Example 28

4-(4-Methylpiperazin-1-yl)-N-[4-[4-(1,3-thiazol-2-yl)piperazin-1-yl]phenyl]benzamide

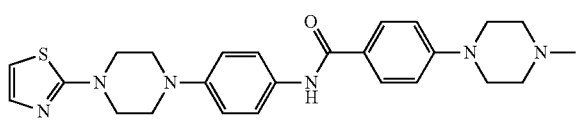

The title compound was prepared in analogy to 2-fluoro-4-methoxy-N-(4-(4-(pyridin-2-yl)piperazin-1-yl)phenyl)benzamide (Example 1, step c) from 4-[4-(1,3-thiazol-2-yl)piperazin-1-yl]aniline (Intermediate 13.b) (79 mg, 303 µmol) and 4-(4-methylpiperazin-1-yl)benzoic acid (73.5 mg, 334 µmol). Yield 24.9 mg (14%). Off-white solid. LC-MS: m/z=463.2 [M+H]$^+$.

Example 29

2-Fluoro-4-methoxy-N-(2-methyl-4-(4-(pyridin-2-yl)piperazin-1-yl)phenyl)benzamide

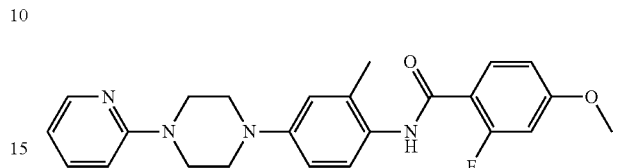

The title compound was prepared in analogy to N-(4-(4-(4-cyanophenyl)piperazin-1-yl)phenyl)-6-methoxynicotinamide (Example 157) and the general synthesis of sub-series 2. Final amide coupling step by procedure B. Yield: 4 mg.
$^1$H NMR (400 MHz, DMSO): δ 9.37 (d, J=3.0 Hz, 1H), 8.15 (dd, J=1.6, 4.9 Hz, 1H), 7.70 (dd, J=8.7, 8.7 Hz, 1H), 7.60-7.54 (m, 1H), 7.30 (J=8.7 Hz, 1H), 6.97 (d, J=2.3 Hz, 1H), 6.95-6.88 (m, 3H), 6.85 (dd, J=2.4, 8.7 Hz, 1H), 6.68 (dd, J=4.9, 6.8 Hz, 1H), 3.84 (s, 3H), 3.64 (dd, J=5.1, 5.1 Hz, 4H), 3.23 (dd, J=5.0, 5.0 Hz, 4H), 2.22 (s, 3H). LC-MS: Rt=2.76 min, m/z=421 [M+H]$^+$.

Example 30

4-(Dimethylamino)-N-(4-(4-(6-methylpyridin-2-yl)piperazin-1-yl)phenyl)benzamide

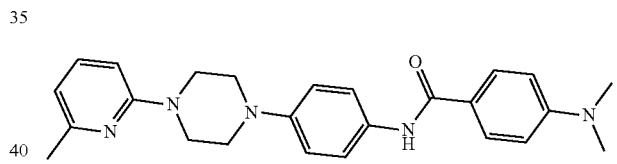

The title compound was prepared in analogy to N-(4-(4-(4-cyanophenyl)piperazin-1-yl)phenyl)-6-methoxynicotinamide (Example 157) and the general synthesis of sub-series 2. Final amide coupling step by procedure B. Yield: 70 mg.
$^1$H NMR (400 MHz, CDCl$_3$): δ 7.77 (d, J=8.9 Hz, 2H), 7.59 (s, 1H), 7.56-7.50 (m, 2H), 7.40 (dd, J=7.8, 7.8 Hz, 1H), 6.98 (d, J=8.9 Hz, 2H), 6.71 (d, J=8.9 Hz, 2H), 6.54-6.48 (m, 2H), 3.72-3.67 (m, 4H), 3.26 (dd, J=5.1, 5.1 Hz, 4H), 3.04 (s, 6H), 2.42 (s, 3H). LC-MS: Rt=2.72 min, m/z=416 [M+H]$^+$.

Example 31

4-(Dimethylamino)-N-[6-[4-(2-pyridyl)piperazin-1-yl]-3-pyridyl]benzamide

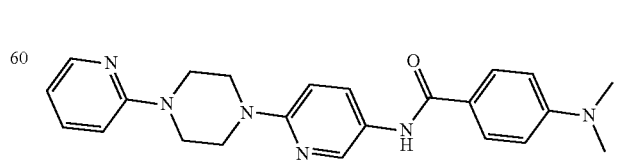

The title compound was prepared in analogy to 4-(4-methylpiperazin-1-yl)-N-[6-[4-(2-pyridyl)piperazin-1-yl]-

3-pyridyl]benzamide (Example 22) from 6-[4-(pyridin-2-yl)piperazin-1-yl]pyridin-3-amine (Intermediate 19.b) (155 mg, 0.61 mmol) and 4-(dimethylamino)benzoic acid (100 mg, 0.61 mmol). Yield 36 mg (15%). Off-white solid. LC-MS: m/z=403.1 [M+H]⁺.

Example 32

4-Morpholino-N-[6-[4-(2-pyridyl)piperazin-1-yl]-3-pyridyl]benzamide

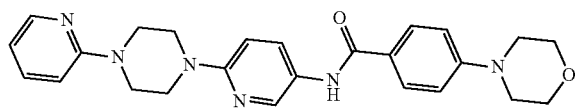 [SMILES: O=C(Nc1ccc(N2CCN(c3ccccn3)CC2)nc1)c1ccc(N2CCOCC2)cc1]

The title compound was prepared in analogy to 4-(4-methylpiperazin-1-yl)-N-[6-[4-(2-pyridyl)piperazin-1-yl]-3-pyridyl]benzamide (Example 22) from 6-[4-(pyridin-2-yl)piperazin-1-yl]pyridin-3-amine (Intermediate 19.b) (123 mg, 0.48 mmol) and 4-(morpholin-4-yl)benzoic acid (100 mg, 0.48 mmol). Yield 28 mg (13%). Off-white solid. LC-MS: m/z=445.1 [M+H]⁺.

Example 33

5-Methyl-N-[6-[4-(2-pyridyl)piperazin-1-yl]-3-pyridyl]pyridine-2-carboxamide

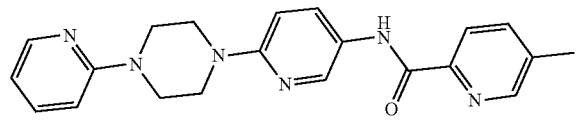 [SMILES: Cc1ccc(C(=O)Nc2ccc(N3CCN(c4ccccn4)CC3)nc2)nc1]

The title compound was prepared in analogy to 4-(4-methylpiperazin-1-yl)-N-[6-[4-(2-pyridyl)piperazin-1-yl]-3-pyridyl]benzamide (Example 22) from 6-[4-(pyridin-2-yl)piperazin-1-yl]pyridin-3-amine (Intermediate 19.b, 186 mg, 0.73 mmol) and 5-methylpyridine-2-carboxylic acid (100 mg, 0.73 mmol). Yield 28 mg (10%). Off-white solid. LC-MS: m/z=375.2 [M+H]⁺.

Example 34

2-Fluoro-4-methoxy-N-[6-[4-(2-pyridyl)piperazin-1-yl]-3-pyridyl]benzamide

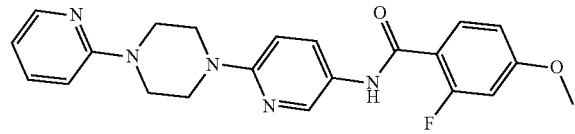 [SMILES: COc1ccc(C(=O)Nc2ccc(N3CCN(c4ccccn4)CC3)nc2)c(F)c1]

To a solution of 6-[4-(pyridin-2-yl)piperazin-1-yl]pyridin-3-amine (Intermediate 19.b) (100 mg, 0.39 mmol) in THF (2.5 ml) cooled with an ice/H₂O bath were added Et₃N (0.1 ml, 0.78 mmol) and 2-fluoro-4-methoxybenzoyl chloride (74 mg, 0.39 mmol). The mixture was stirred 1 h at 0° C. The reaction mixture was washed with H₂O (10 ml) and extracted with EtOAc (2×30 ml). The combined organic layers were dried over Na₂SO₄ and concentrated.

The resulting crude material was purified by preparative HPLC to get the title compound (56 mg, 35%) as off-white solid. LC-MS: m/z=408.2 [M+H]⁺.

Example 35

4-Methyl-N-[6-[4-(2-pyridyl)piperazin-1-yl]-3-pyridyl]benzamide

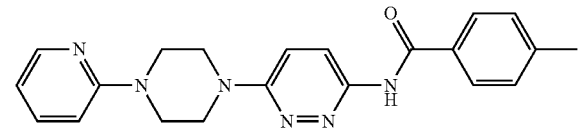

The title compound was prepared in analogy to 4-(4-methylpiperazin-1-yl)-N-[6-[4-(2-pyridyl)piperazin-1-yl]-3-pyridyl]benzamide (Example 22) from 6-[4-(pyridin-2-yl)piperazin-1-yl]pyridin-3-amine (Intermediate 19.b, 188 mg, 0.73 mmol) and 4-methylbenzoic acid (100 mg, 0.73 mmol). Yield 55 mg (20%). Off-white solid. LC-MS: m/z=371.1 [M+H]⁺.

Example 36

4-(Dimethylamino)-N-[6-[4-(2-pyridyl)piperazin-1-yl]pyridazin-3-yl]benzamide

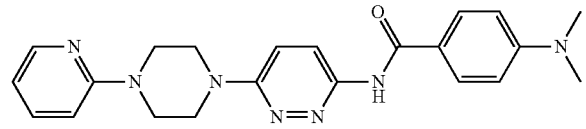

a) 6-[4-(Pyridin-2-yl)piperazin-1-yl]pyridazin-3-amine

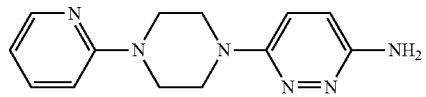

To a solution of 1-(pyridin-2-yl)piperazine (600 mg, 3.68 mmol) in DMSO (10 ml) was added 6-iodopyridazin-3-amine (813 mg, 3.68 mmol) and the reaction mixture was degassed by passing through it N₂ for 15 min. K₃PO₄ (1.17 g, 5.51 mmol), L-hydroxyproline (193 mg, 1.48 mmol) and CuI (140 mg, 0.74 mmol) were added to the reaction mixture. After degassing with a N₂ steam for 15 min, the reaction mixture was stirred at 100° C. for 16 h. The reaction mixture was poured into H₂O (50 ml) and extracted with a mixture of 15% IPA/CHCl₃ (3×100 ml). The combined organic layers were washed with brine, dried over Na₂SO₄ and solvents were evaporated. The resulting crude was purified by column chromatography (amine modified silica, 10% MeOH/DCM) to get 6-[4-(pyridin-2-yl)piperazin-1-yl]pyridazin-3-amine (160 mg, 26%) as grey solid. LC-MS: m/z=257.1 [M+H]⁺.

b) 4-(Dimethylamino)-N-[6-[4-(2-pyridyl)piperazin-1-yl]pyridazin-3-yl]benzamide

To a solution of 4-(dimethylamino)benzoic acid (75 mg, 0.46 mmol) in DMF (2.5 ml) were added DIPEA (0.23 ml, 1.36 mmol), EDC.HCl (130 mg, 0.68 mmol), HOBt (73 mg, 0.55 mmol) and 6-[4-(pyridin-2-yl)piperazin-1-yl]pyridazin-3-amine (117 mg, 0.46 mmol). The reaction mixture was stirred 16 h at 25° C. The mixture was poured into H$_2$O (20 ml) and extracted with EtOAc (2×50 ml). The combined organic layers were dried over Na$_2$SO$_4$ and solvents were evaporated. The resulting crude material was purified by preparative HPLC to get the title compound (36 mg, 20%) as off-white solid. LC-MS: m/z=404.2 [M+H]$^+$.

Example 37

4-Methyl-N-(4-(4-(pyridin-3-yl)piperazin-1-yl)phenyl)benzamide

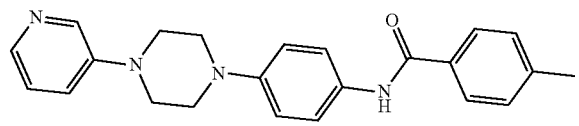 [SMILES: Cc1ccc(C(=O)Nc2ccc(N3CCN(c4cccnc4)CC3)cc2)cc1]

a) 1-(4-Nitrophenyl)-4-pyridin-3-ylpiperazine

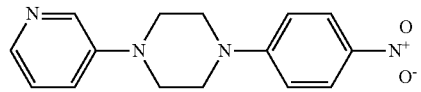

1-Fluoro-4-nitrobenzene (500 mg, 3.54 mmol) was combined with DMSO (3.5 ml) to give a yellow solution. K$_2$CO$_3$ (735 mg, 5.32 mmol) and 1-(pyridin-3-yl)piperazine (868 mg, 5.32 mmol) were added and the yellow reaction mixture was stirred at 90° C. for 3 h. The reaction mixture was diluted with H$_2$O (20 ml) and washed with DCM (3×20 ml). The combined organic layers were washed with brine (1×20 ml), dried over MgSO$_4$ and evaporated under reduced pressure to get the crude material as a yellow solid. The crude product was purified by chromatography (50 g silica gel cartridge, DCM to DCM/MeOH 95:5, 0-10% in 20 min) to afford 1-(4-nitrophenyl)-4-(pyridin-3-yl)piperazine (747 mg, 70%) as an orange solid. LC-MS: m/z=285.2 [M+H]$^+$.

b) 4-(4-Pyridin-3-ylpiperazin-1-yl)aniline

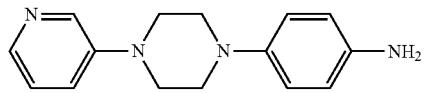 [SMILES: Nc1ccc(N2CCN(c3cccnc3)CC2)cc1]

1-(4-Nitrophenyl)-4-(pyridin-3-yl)piperazine (720 mg, 2.53 mmol) was combined with EtOH (100 ml) to give an orange slurry. Pd/C 10% (270 mg, 253 µmol) was added and the reaction mixture was stirred 80 min under H$_2$ at rt. The catalyst was filtered off over Dicalite, the volatiles were evaporated and the crude material was purified by flash chromatography (70 g silica gel cartridge, DCM to DCM/MeOH 95:5, 0-40% in 25 min). Yield 815 mg (100%). Light yellow solid. LC-MS: m/z=255.2 [M+H]$^+$.

c) 4-Methyl-N-(4-(4-(pyridin-3-yl)piperazin-1-yl)phenyl)benzamide

The title compound was prepared in analogy to 2-fluoro-4-methoxy-N-(4-(4-(pyridin-2-yl)piperazin-1-yl)phenyl)benzamide (Example 1, step c) from 4-(4-(pyridin-3-yl)piperazin-1-yl)aniline (70 mg, 275 µmol) and 4-methylbenzoic acid (41.2 mg, 303 µmol). The product was purified by flash chromatography (DCM to 90:2 DCM:MeOH). Residual DIPEA was removed by washing with 0.1 M citric acid and extraction with DCM. Yield 49 mg (46%). Off-white solid. LC-MS: m/z=187.1 [M+2H]$^{2+}$.

Example 38

4-Methoxy-N-(4-(4-(pyridin-3-yl)piperazin-1-yl)phenyl)benzamide

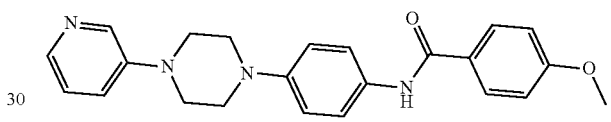

4-Methoxybenzoic acid (46.1 mg, 303 µmol) was combined with DMF (0.6 ml) to give a colorless solution. HATU (126 mg, 330 µmol) and DIPEA (71.1 mg, 96.1 µl, 550 µmol) were added and the reaction mixture was stirred 30 min at rt. 4-(4-(Pyridin-3-yl)piperazin-1-yl)aniline (Intermediate 37.b) (70 mg, 275 µmol) was added followed by more DMF (0.3 ml). The resulting slurry was stirred at rt for 4 h. H$_2$O was added (15 ml), then 0.1 M citric acid. After addition of DCM (5 ml) a solid formed, which was collected by filtration and washed with MeOH. The material was dried under vacuum to yield 4-methoxy-N-(4-(4-(pyridin-3-yl)piperazin-1-yl)phenyl)benzamide (35 mg, 31%). Off-white solid. LC-MS: m/z=195.1 [M+2H]$^{2+}$.

Example 39

4-Morpholino-N-(4-(4-(pyridin-3-yl)piperazin-1-yl)phenyl)benzamide

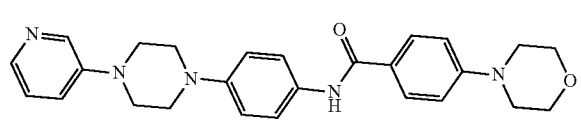 [SMILES: O=C(Nc1ccc(N2CCN(c3cccnc3)CC2)cc1)c1ccc(N2CCOCC2)cc1]

The title compound was prepared in analogy to 4-methoxy-N-(4-(4-(pyridin-3-yl)piperazin-1-yl)phenyl)benzamide (Example 38) from 4-(4-pyridin-3-ylpiperazin-1-yl)aniline (Intermediate 37.b) (70 mg, 275 µmol) and 4-morpholinobenzoic acid (62.7 mg, 303 µmol). 101 mg (79%). Off-white solid. LC-MS: m/z=222.7 [M+2H]$^{2+}$.

Example 40

2-Fluoro-4-methoxy-N-[6-[4-(2-pyridyl)piperazin-1-yl]pyridazin-3-yl]benzamide

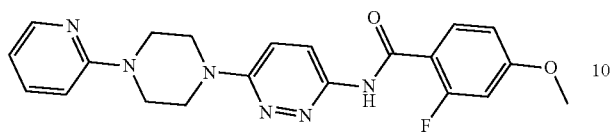

The title compound was prepared in analogy to 4-(dimethylamino)-N-[6-[4-(2-pyridyl)piperazin-1-yl]pyridazin-3-yl]benzamide (Example 36, step b) from 6-[4-(pyridin-2-yl)piperazin-1-yl]pyridazin-3-amine (Intermediate 36.a) (83 mg, 0.44 mmol) and 2-fluoro-4-methoxybenzoic acid (75 mg, 0.44 mmol). 18 mg (10%). Off-white solid. LC-MS: m/z=409.1 [M+H]$^+$.

Example 41

4-Methoxy-N-[4-[4-(4-pyridyl)piperazin-1-yl]phenyl]benzamide

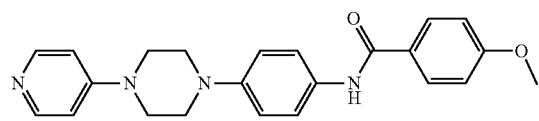

a) 4-[4-(4-Pyridyl)piperazin-1-yl]aniline

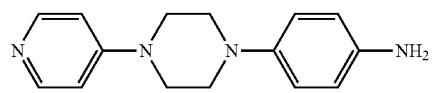 [SMILES: Nc1ccc(N2CCN(c3ccncc3)CC2)cc1]

To a solution of 1-(pyridin-4-yl)piperazine (300 mg, 1.81 mmol) in DMSO (5 ml) in a sealed tube at 25° C. were added 4-iodoaniline (477 mg, 2.18 mmol), K$_3$PO$_4$ (1.16 g, 5.45 mmol) and the reaction mixture was degassed with argon for 15 min. L-Hydroxyproline (95 mg, 0.73 mmol) and CuI (69 mg, 0.36 mmol) were added to the reaction mixture and it was again degassed for 15 min. Then the reaction mixture was stirred at 100° C. for 16 h. The reaction mixture was poured into H$_2$O (50 ml) and extracted with 15% IPA in CHCl$_3$ (3×100 ml). The combined organic layers were washed with brine, dried over Na$_2$SO$_4$ and solvents were evaporated. The resulting crude product was purified by column chromatography (amine-modified silica; 5% MeOH in DCM) to get 4-[4-(4-pyridyl)piperazin-1-yl]aniline (240 mg, 52%) as grey sticky solid. LC-MS: m/z=255.1 [M+H]$^+$.

b) 4-Methoxy-N-[4-[4-(4-pyridyl)piperazin-1-yl]phenyl]benzamide

To a solution of 4-methoxybenzoic acid (100 mg, 0.66 mmol) in DMF (3 ml) were added DIPEA (0.33 ml, 1.97 mmol), EDC.HCl (168 mg, 0.99 mmol), HOBt (107 mg, 0.79 mmol) and 4-[4-(4-pyridyl)piperazin-1-yl]aniline (167 mg, 0.66 mmol). Then the reaction mixture was stirred at 25° C. for 16 h. The reaction mixture was poured into H$_2$O (20 ml) and extracted with EtOAc (2×50 ml). The combined organic layers were dried (Na$_2$SO$_4$) and evaporated. The resulting material was purified by prep-HPLC to get 4-methoxy-N-[4-[4-(4-pyridyl)piperazin-1-yl]phenyl]benzamide (17 mg, 7%) as off-white solid. LC-MS: m/z=389.1 [M+H]$^+$.

Example 42

4-Methyl-N-(4-(4-(pyridin-2-yl)piperazin-1-yl)phenyl)-3,4-dihydro-2H-benzo[b][1,4]oxazine-7-carboxamide

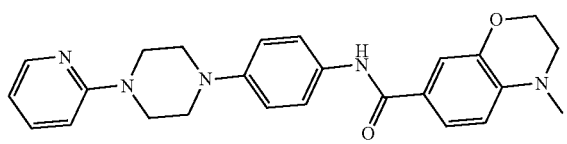 [SMILES: CN1CCOc2cc(C(=O)Nc3ccc(N4CCN(c5ccccn5)CC4)cc3)ccc21]

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (70 mg, 275 µmol) and 4-methyl-3,4-dihydro-2H-benzo[b][1,4]oxazine-7-carboxylic acid (58.5 mg, 303 µmol). Yield 55 mg (44%). White solid. LC-MS: m/z=430.1 [M+H]$^+$.

Example 43

4-Methoxy-N-(5-(4-(pyridin-2-yl)piperazin-1-yl)pyridin-2-yl)benzamide

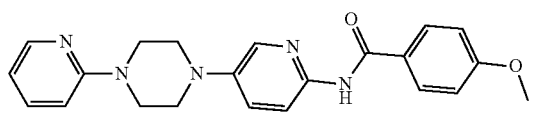

a) 1-(6-Nitropyridin-3-yl)-4-pyridin-2-ylpiperazine

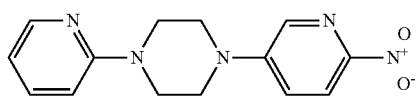

5-Fluoro-2-nitropyridine (500 mg, 3.52 mmol) was combined with DMSO (5 ml) to give a yellow solution. K$_2$CO$_3$ (730 mg, 5.28 mmol) and 1-(pyridin-2-yl)piperazine (862 mg, 804 µl) were added and the reaction mixture was stirred at 90° C. for 2 hours. The reaction mixture was diluted with H$_2$O (20 ml) and washed with DCM (3×20 ml). The combined organic layers were washed with brine (1×20 ml), dried over MgSO$_4$ and evaporated under reduced pressure to get the crude material as an orange solid. This crude product was used without further purification in the next step. LC-MS: m/z=286.2 [M+H]$^+$.

b) 5-(4-(Pyridin-2-yl)piperazin-1-yl)pyridin-2-amine

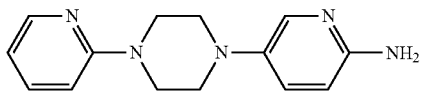

1-(6-Nitropyridin-3-yl)-4-pyridin-2-ylpiperazine (1.33 g, 4.67 mmol) was dissolved in EtOH (50 ml) and under an inert atmosphere Pd/C 10% (200 mg, 4.67 mmol) was added. The reaction mixture was stirred under $H_2$ at rt for 2 h, then solids were removed by filtration over Celite. The filtrate was concentrated under vacuum and the crude material was purified by flash chromatography (DCM to 20:1:0.1 DCM:MeOH:$NH_3$ aq.) to yield the title compound (878 mg, 70%) as a light brown solid. LC-MS: m/z=128.6 $[M+2H]^{2+}$.

c) 4-Methoxy-N-(5-(4-(pyridin-2-yl)piperazin-1-yl)pyridin-2-yl)benzamide

The title compound was prepared in analogy to 2-fluoro-4-methoxy-N-(4-(4-(pyridin-2-yl)piperazin-1-yl)phenyl)benzamide (Example 1, step c) from 5-(4-(pyridin-2-yl)piperazin-1-yl)pyridin-2-amine (70 mg, 274 µmol) and 4-methoxybenzoic acid (45.9 mg, 302 µmol).

Yield 107 mg (56%). White solid. LC-MS: m/z=195.7 $[M+2H]^{2+}$.

Example 44

2-Fluoro-4-methoxy-N-(5-(4-(pyridin-2-yl)piperazin-1-yl)pyridin-2-yl)benzamide

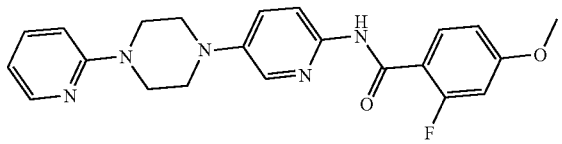 [SMILES: COc1ccc(C(=O)Nc2ccc(N3CCN(c4ccccn4)CC3)cn2)c(F)c1]

The title compound was prepared in analogy to 4-methoxy-N-(5-(4-(pyridin-2-yl)piperazin-1-yl)pyridin-2-yl)benzamide (Example 43, step c) from 5-(4-(pyridin-2-yl)piperazin-1-yl)pyridin-2-amine (Intermediate 43.b) (70 mg, 274 µmol) and 2-fluoro-4-methoxybenzoic acid (51.3 mg, 302 µmol). Yield 85 mg (75%). White solid. LC-MS: m/z=204.7 $[M+2H]^{2+}$.

Example 45

4-Methyl-N-(5-(4-(pyridin-2-yl)piperazin-1-yl)pyridin-2-yl)benzamide

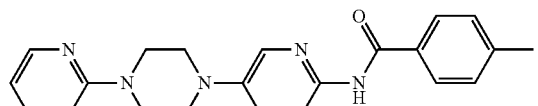

The title compound was prepared in analogy to 4-methoxy-N-(5-(4-(pyridin-2-yl)piperazin-1-yl)pyridin-2-yl)benzamide (Example 43.c) from 5-(4-(pyridin-2-yl)piperazin-1-yl)pyridin-2-amine (Intermediate 43.b (70 mg, 274 µmol) and 4-methylbenzoic acid (41.1 mg, 302 µmol). Yield 61 mg (59%). White solid. LC-MS: m/z=187.6 $[M+2H]^{2+}$.

Example 46

4-(Dimethylamino)-N-(5-(4-(pyridin-2-yl)piperazin-1-yl)pyridin-2-yl)benzamide

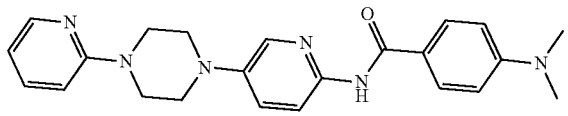

The title compound was prepared in analogy to 4-methoxy-N-(5-(4-(pyridin-2-yl)piperazin-1-yl)pyridin-2-yl)benzamide (Example 43.c) from 5-(4-(pyridin-2-yl)piperazin-1-yl)pyridin-2-amine (Intermediate 43.b) (70 mg, 274 µmol) and 4-(dimethylamino)benzoic acid (49.8 mg, 302 µmol). Yield 40 mg (35%). White solid. LC-MS: m/z=202.3 $[M+2H]^{2+}$.

Example 47

2-Fluoro-N-(5-(4-(pyridin-2-yl)piperazin-1-yl)pyridin-2-yl)benzamide

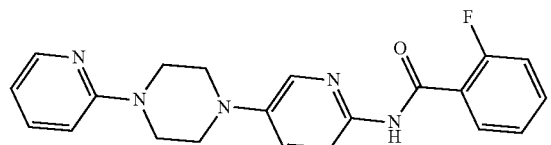

The title compound was prepared in analogy to 4-methoxy-N-(5-(4-(pyridin-2-yl)piperazin-1-yl)pyridin-2-yl)benzamide (Example 43.c) from 5-(4-(pyridin-2-yl)piperazin-1-yl)pyridin-2-amine (Intermediate 43.b) (70 mg, 274 µmol) and 2-fluorobenzoic acid (42.3 mg, 302 µmol). Yield 71 mg (67%). White solid. LC-MS: m/z=189.6 $[M+2H]^{2+}$.

Example 48

4-Morpholino-N-[6-[4-(2-pyridyl)piperazin-1-yl]pyridazin-3-yl]benzamide

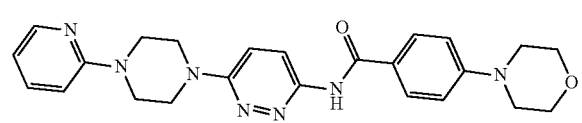

The title compound was prepared in analogy to 4-(dimethylamino)-N-[6-[4-(2-pyridyl)piperazin-1-yl]pyridazin-3-yl]benzamide (Example 36, step b) from 6-[4-(pyridin-2-yl)piperazin-1-yl]pyridazin-3-amine (Intermediate 36.a) (93 mg, 0.36 mmol) and 4-morpholinobenzoic acid (75 mg, 0.36 mmol). Yield 16 mg (10%). Off-white solid. LC-MS: m/z=446.0 $[M+H]^+$.

Example 49

4-Methoxy-N-{4-[4-(pyrimidin-2-yl)piperazin-1-yl]phenyl}benzamide

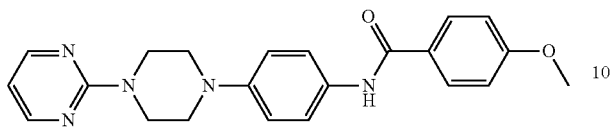

a) 4-[4-(Pyrimidin-2-yl)piperazin-1-yl]aniline

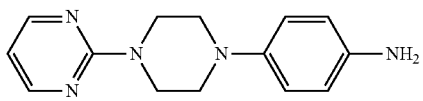 [SMILES: Nc1ccc(N2CCN(c3ncccn3)CC2)cc1]

The title compound was prepared in analogy to 4-[4-(4-pyridyl)piperazin-1-yl]aniline (Intermediate 41.a) from 2-(piperazin-1-yl)pyrimidine (300 mg, 1.83 mmol). Yield 255 mg (55%). Black sticky solid. LC-MS: m/z=256.1 [M+H]⁺.

b) 4-Methoxy-N-{4-[4-(pyrimidin-2-yl)piperazin-1-yl]phenyl}benzamide

The title compound was prepared in analogy to 4-methoxy-N-[4-[4-(4-pyridyl)piperazin-1-yl]phenyl]benzamide (Example 41, step b) from 4-[4-(pyrimidin-2-yl)piperazin-1-yl]aniline (168 mg, 0.66 mmol) and 4-methoxybenzoic acid (100 mg, 0.66 mmol). Yield 45 mg (18%). Off-white solid. LC-MS: m/z=390.2 [M+H]⁺.

Example 50

N-(4-(4-(5-Cyanopyridin-2-yl)piperazin-1-yl)phenyl)-4-methoxybenzamide

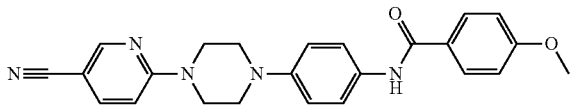

a) 6-[4-(4-Aminophenyl)piperazin-1-yl]pyridine-3-carbonitrile

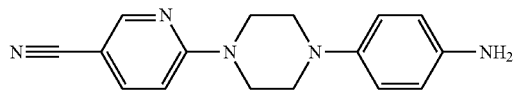

Method A

The title compound was prepared in analogy to 4-[4-(4-pyridyl)piperazin-1-yl]aniline (Intermediate 41.a) from 2-(piperazin-1-yl)pyridine-4-carbonitrile (300 mg, 1.59 mmol). Yield 180 mg (40%). Black sticky solid. LC-MS: m/z=280.2 [M+H]⁺.

Method B i) 6-[4-(4-nitrophenyl)piperazin-1-yl]pyridine-3-carbonitrile

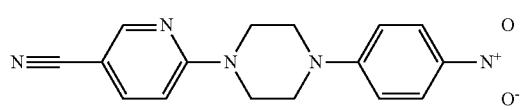

6-(Piperazin-1-yl)nicotinonitrile (3.76 g, 20 mmol) was dissolved at 20-25° C. in DMSO (15 ml) under inert atmosphere. K₂CO₃ (4.15 g, 30 mmol) was added at 20-25° C. followed by 1-fluoro-4-nitrobenzene (3.1 g, 2.33 ml, 22 mmol). The reaction mixture was heated to 90° C. and stirred at this temperature for 90 min. The mixture was allowed to cool to 20-25° C., leading to precipitation of the product and an instirrable solid that was left standing at 22° C. over night. The mixture was mainly dissolved in H₂O and DCM and the aqueous layer (containing some solid product) was extracted with DCM. The organic layers were dried over MgSO₄, filtered over a glass-frit (D3), washed with DCM, and the filtrate was evaporated under reduced pressure at 40° C. The residue was partially dissolved in DCM/MeOH 10:1 (40 ml), adsorbed on Isolute HM-N 9800, evaporated and then purified by flash chromatography (silica gel, MeOH in DCM 1% to 5%). Pure product-fractions were combined and evaporated at 40° C. to give after drying in HV the title compound (5.59 g, 90%) as an orange solid. LCMS m/z=310.2 [M+H]⁺.

ii) 6-[4-(4-Aminophenyl)piperazin-1-yl]pyridine-3-carbonitrile

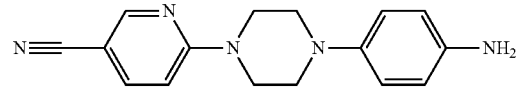

6-(4-(4-Nitrophenyl)piperazin-1-yl)nicotinonitrile (10.2 g, 33 mmol) was suspended at 20-25° C. in EtOH (470 ml), and under inert atmosphere at 20-25° C. was added a slurry of Pd/C, 10% (3.51 g, 3.3 mmol) in EtOH (50 ml). The reaction mixture was set under H₂ and reacted at 20-25° C. for 20 h. The catalyst was filtered off over a membrane-filter, washed with EtOH and DCM/MeOH 4:1, and the filtrate was evaporated at 40° C. to give the crude product as light yellow solid. This material was suspended in DCM/MeOH 2:1, adsorbed on Isolute HM-N 9800, evaporated and then purified by flash chromatography (silica gel, MeOH in DCM 1% to 5%). The corresponding pure fractions were collected to give after evaporation at 40° C. the title compound (5.92 g, 64%) as an off-white solid. LC-MS m/z=280.1 [M+H]⁺.

b) N-(4-(4-(5-Cyanopyridin-2-yl)piperazin-1-yl)phenyl)-4-methoxybenzamide

The title compound was prepared in analogy to 4-methoxy-N-[4-[4-(4-pyridyl)piperazin-1-yl]phenyl]benzamide (Example 41, step b) from 6-[4-(4-aminophenyl) piperazin-1-yl]pyridine-3-carbonitrile (184 mg, 0.66 mmol) and 4-methoxybenzoic acid (100 mg, 0.66 mmol). Yield 26 mg (10%). Off-white solid. LC-MS: m/z=414.4 [M+H]⁺.

Example 51

4-Morpholino-N-(5-(4-(pyridin-2-yl)piperazin-1-yl)pyridin-2-yl)benzamide

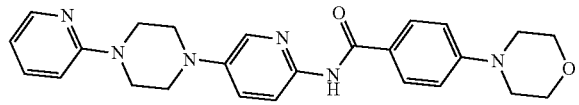 [SMILES: O=C(Nc1ccc(N2CCN(c3ccccn3)CC2)cn1)c1ccc(N2CCOCC2)cc1]

The title compound was prepared in analogy to 4-methoxy-N-(5-(4-(pyridin-2-yl)piperazin-1-yl)pyridin-2-yl)benzamide (Example 43, step c) from 5-[4-(2-pyridyl)piperazin-1-yl]pyridin-2-amine (Intermediate 43.b) (70 mg, 274 µmol) and 4-morpholinobenzoic acid (62.5 mg, 302 µmol). Yield 53 mg (43%). White solid. LC-MS: m/z=223.2 [M+2H]²⁺.

Example 52

2-Fluoro-4-methyl-N-(5-(4-(pyridin-2-yl)piperazin-1-yl)pyridin-2-yl)benzamide

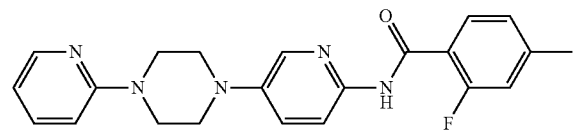 [SMILES: Cc1ccc(C(=O)Nc2ccc(N3CCN(c4ccccn4)CC3)cn2)c(F)c1]

The title compound was prepared in analogy to 4-methoxy-N-(5-(4-(pyridin-2-yl)piperazin-1-yl)pyridin-2-yl)benzamide (Example 43, step c) from 5-(4-(pyridin-2-yl)piperazin-1-yl)pyridin-2-amine (Intermediate 43.b) (55 mg, 215 µmol) and 2-fluoro-4-methylbenzoic acid (36 mg, 237 µmol). Yield 62 mg (73%). Off-white solid. LC-MS: m/z=196.7 [M+2H]²⁺.

Example 53

5-Methyl-N-(5-(4-(pyridin-2-yl)piperazin-1-yl)pyridin-2-yl)picolinamide

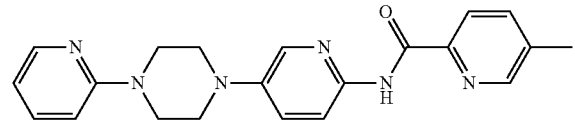 [SMILES: Cc1ccc(C(=O)Nc2ccc(N3CCN(c4ccccn4)CC3)cn2)nc1]

The title compound was prepared in analogy to 4-methoxy-N-(5-(4-(pyridin-2-yl)piperazin-1-yl)pyridin-2-yl)benzamide (Example 43, step c) from 5-(4-(pyridin-2-yl)piperazin-1-yl)pyridin-2-amine (Intermediate 43.b) (55 mg, 215 µmol) and 5-methylpicolinic acid (32 mg, 237 µmol). Yield 12 mg (14%). Off-white solid. LC-MS: m/z=188.2 [M+2H]²⁺.

Example 54

3-Methyl-N-(5-(4-(pyridin-2-yl)piperazin-1-yl)pyridin-2-yl)benzamide

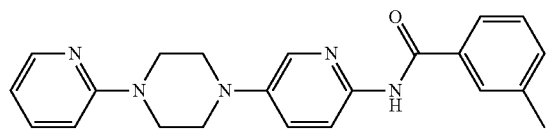 [SMILES: Cc1cccc(C(=O)Nc2ccc(N3CCN(c4ccccn4)CC3)cn2)c1]

The title compound was prepared in analogy to 4-methoxy-N-(5-(4-(pyridin-2-yl)piperazin-1-yl)pyridin-2-yl)benzamide (Example 43, step c) from 5-(4-(pyridin-2-yl)piperazin-1-yl)pyridin-2-amine (Intermediate 43.b) (40 mg, 157 µmol) and 3-methylbenzoic acid (33 mg, 242 µmol). Yield 40 mg (67%). Grey solid. LC-MS: m/z=187.7 [M+2H]²⁺.

Example 55

4-Methoxy-N-{4-[4-(1,3,5-triazin-2-yl)piperazin-1-yl]phenyl}benzamide

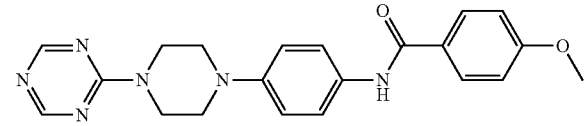

a) 4-[4-(1,3,5-Triazin-2-yl)piperazin-1-yl]aniline

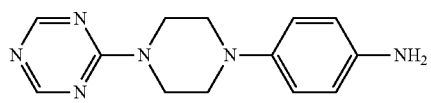 [SMILES: Nc1ccc(N2CCN(c3ncncn3)CC2)cc1]

The title compound was prepared in analogy to 4-[4-(4-pyridyl)piperazin-1-yl]aniline (Intermediate 41.a) from 2-piperazin-1-yl-1,3,5-triazine (300 mg, 1.84 mmol). Yield 175 mg (37%). Grey sticky solid. LC-MS: m/z=257.1 [M+H]⁺.

b) 4-Methoxy-N-{4-[4-(1,3,5-triazin-2-yl)piperazin-1-yl]phenyl}benzamide

The title compound was prepared in analogy to 4-methoxy-N-[4-[4-(4-pyridyl)piperazin-1-yl]phenyl]benzamide (Example 41, step b) from 4-[4-(1,3,5-triazin-2-yl)piperazin-1-yl]aniline (168 mg, 0.66 mmol) and 4-methoxybenzoic acid (100 mg, 0.66 mmol). Yield 22 mg (9%). Off-white solid. LC-MS: m/z=391.2 [M+H]⁺.

Example 56

4-Methoxy-N-{4-[4-(pyrimidin-4-yl)piperazin-1-yl]phenyl}benzamide

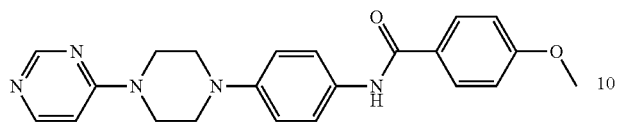

a) 4-[4-(Pyrimidin-4-yl)piperazin-1-yl]aniline

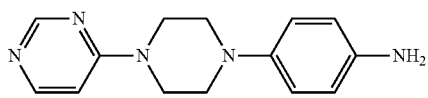

The title compound was prepared in analogy to 4-[4-(4-pyridyl)piperazin-1-yl]aniline (Intermediate 41.a) from 4-(piperazin-1-yl)pyrimidine (300 mg, 1.83 mmol). Yield 188 mg (40%). Black solid. LC-MS: m/z=256.0 [M+H]$^+$.

b) 4-Methoxy-N-{4-[4-(pyrimidin-4-yl)piperazin-1-yl]phenyl}benzamide

The title compound was prepared in analogy to 4-methoxy-N-[4-[4-(4-pyridyl)piperazin-1-yl]phenyl]benzamide (Example 41, step b) from 4-[4-(pyrimidin-4-yl)piperazin-1-yl]aniline (168 mg, 0.66 mmol) and 4-methoxybenzoic acid (100 mg, 0.66 mmol). Yield 42 mg (16%). Off-white solid. LC-MS: m/z=390.2 [M+H]$^+$.

Example 57

N-[4-[4-(4-Cyanophenyl)piperazin-1-yl]phenyl]-4-methoxy-benzamide

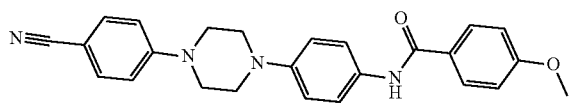 [SMILES: COc1ccc(C(=O)Nc2ccc(N3CCN(c4ccc(C#N)cc4)CC3)cc2)cc1]

a) 4-[4-(4-Aminophenyl)piperazin-1-yl]benzonitrile

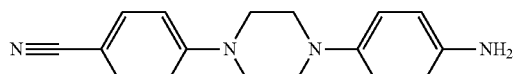

The title compound was prepared in analogy to 4-[4-(4-pyridyl)piperazin-1-yl]aniline (Intermediate 41.a) from 4-(piperazin-1-yl)benzonitrile (300 mg, 1.60 mmol). Yield 210 mg (47%). Black solid. LC-MS: m/z=279.2 [M+H]$^+$.

b) N-[4-[4-(4-Cyanophenyl)piperazin-1-yl]phenyl]-4-methoxy-benzamide

The title compound was prepared in analogy to 4-methoxy-N-[4-[4-(4-pyridyl)piperazin-1-yl]phenyl]benzamide (Example 41, step b) from 4-[4-(4-aminophenyl)piperazin-1-yl]benzonitrile (183 mg, 0.66 mmol) and 4-methoxybenzoic acid (100 mg, 0.66 mmol). Yield 26 mg (10%). Off-white solid. LC-MS: m/z=413.2 [M+H]$^+$.

Example 58

4-Methoxy-N-[4-[4-(6-methoxypyridin-3-yl)piperazin-1-yl]phenyl]benzamide

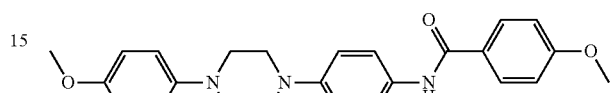

a) 4-(4-(6-Methoxypyridin-3-yl)piperazin-1-yl)aniline

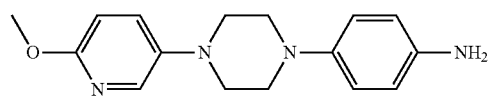

1-(6-Methoxypyridin-3-yl)-4-(4-nitrophenyl)piperazine (80 mg, 255 μmol) (CAS Nr. 158399-77-0) was combined with EtOH (5.0 ml) to give a yellow slurry. Pd/C 10% (27.1 mg, 25.5 μmol) was added and the reaction mixture was stirred under H$_2$ at rt for 80 min. The catalyst was filtered off over Dicalite, volatiles were evaporated and the crude material was purified by preparative TLC (silica gel, 2 mm, 9:1 DCM/MeOH) to obtain 4-(4-(6-methoxypyridin-3-yl)piperazin-1-yl)aniline (44 mg, 59%) as an off-white solid. LC-MS: m/z=285.2 [M+H]$^+$.

b) 4-Methoxy-N-[4-[4-(6-methoxypyridin-3-yl)piperazin-1-yl]phenyl]benzamide The title compound was prepared in analogy to 2-fluoro-4-methoxy-N-(4-(4-(pyridin-2-yl)piperazin-1-yl)phenyl)benzamide (Example 1, step c) from 4-(4-(6-methoxypyridin-3-yl)piperazin-1-yl)aniline (43.7 mg, 154 μmol) and 4-methoxybenzoic acid (25.7 mg, 169 μmol). Yield 4.5 mg (6.6%). White solid. LC-MS: m/z=419.2 [M+H]$^+$.

Example 59

4-Methoxy-N-(2-(4-(pyridin-2-yl)piperazin-1-yl)pyrimidin-5-yl)benzamide

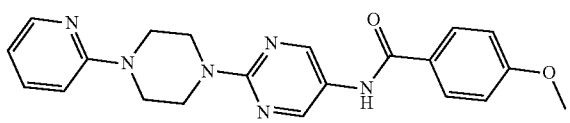

a) 5-Nitro-2-(4-(pyridin-2-yl)piperazin-1-yl)pyrimidine

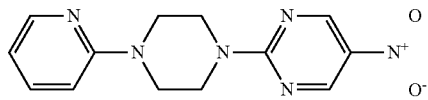

2-Chloro-5-nitropyrimidine (2.0 g, 12 mmol) was dissolved in THF (60 ml). 1-(Pyridin-2-yl)piperazine (2.2 g, 2.1 ml, 14 mmol) was added. After completion of the reaction as monitored by TLC, the mixture was concentrated under vacuum. The crude was diluted with H$_2$O and extracted with EtOAc and additional portions of DCM. The combined organic layers were dried with MgSO$_4$ and concentrated under vacuum. The product was purified by flash chromatography (silica gel, 120 g, 0% to 5% MeOH in DCM) to yield 5-nitro-2-(4-(pyridin-2-yl)piperazin-1-yl)pyrimidine (1.07 g, 30%) as an orange solid. LC-MS: m/z=287.2 [M+H]$^+$.

b) 2-(4-(Pyridin-2-yl)piperazin-1-yl)pyrimidin-5-amine

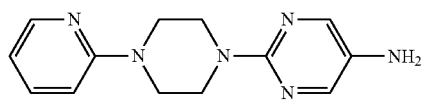

5-Nitro-2-(4-(pyridin-2-yl)piperazin-1-yl)pyrimidine (1.07 g, 3.74 mmol) was dissolved in EtOH (50 ml). The solution was purged with Ar and Pd/C 10% (350 mg, 3.74 mmol) was added. The reaction mixture was stirred under H$_2$ at rt for 2.5 h. The solution was filtered over Celite, washed with EtOH and concentrated under vacuum to yield 2-(4-(pyridin-2-yl)piperazin-1-yl)pyrimidin-5-amine (870 mg 89% yield) as light green solid. LC-MS: m/z=129.1 [M+2H]2+.

c) 4-Methoxy-N-(2-(4-(pyridin-2-yl)piperazin-1-yl)pyrimidin-5-yl)benzamide

The title compound was prepared in analogy to 2-fluoro-4-methoxy-N-(4-(4-(pyridin-2-yl)piperazin-1-yl)phenyl)benzamide (Example 1, step c) from 2-(4-(pyridin-2-yl)piperazin-1-yl)pyrimidin-5-amine (60 mg, 234 µmol) and 4-methoxybenzoic acid (39.2 mg, 258 µmol). Yield 58 mg (60%). White solid. LC-MS: m/z=391.2 [M+H]$^+$.

Example 60

2-Fluoro-4-methoxy-N-(2-(4-(pyridin-2-yl)piperazin-1-yl)pyrimidin-5-yl)benzamide

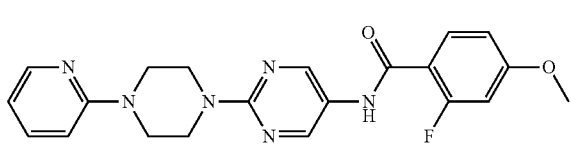 [SMILES: COc1ccc(C(=O)Nc2cnc(N3CCN(c4ccccn4)CC3)nc2)c(F)c1]

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b) (60 mg, 234 µmol) and 2-fluoro-4-methoxybenzoic acid (43.8 mg, 258 µmol). Yield 82 mg (82%). White solid. LC-MS: m/z=409.2 [M+H]$^+$.

Example 61

2-Fluoro-N-(2-(4-(pyridin-2-yl)piperazin-1-yl)pyrimidin-5-yl)benzamide

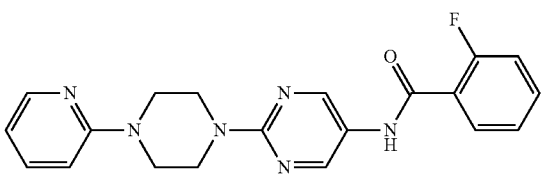 [SMILES: O=C(Nc1cnc(N2CCN(c3ccccn3)CC2)nc1)c1ccccc1F]

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b) (60 mg, 234 µmol) and 2-fluorobenzoic acid (36.1 mg, 258 µmol). Yield 51 mg (56%). White solid. LC-MS: m/z=379.2 [M+H]$^+$.

Example 62

4-(Dimethylamino)-N-(2-(4-(pyridin-2-yl)piperazin-1-yl)pyrimidin-5-yl)benzamide

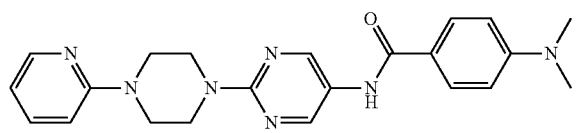

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b) (60 mg, 234 µmol) and 4-(dimethylamino)benzoic acid (42.5 mg, 258 µmol). Yield 75 mg (76%). Off-white solid. LC-MS: m/z=202.7 [M+2H]2+.

Example 63

4-Morpholino-N-(2-(4-(pyridin-2-yl)piperazin-1-yl)pyrimidin-5-yl)benzamide

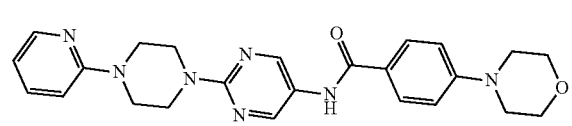 [SMILES: O=C(Nc1cnc(N2CCN(c3ccccn3)CC2)nc1)c1ccc(N2CCOCC2)cc1]

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2- yl)piperazin-1-yl)pyrimidin-5-amine (Intermediate 59.b) (60 mg, 234 µmol) and 4-morpholinobenzoic acid (53.4 mg, 258 µmol). Yield 74 mg (68%). Off-white solid. LC-MS: m/z=446.3 [M+H]⁺.

Example 64

3-Methyl-N-(2-(4-(pyridin-2-yl)piperazin-1-yl)pyrimidin-5-yl)benzamide

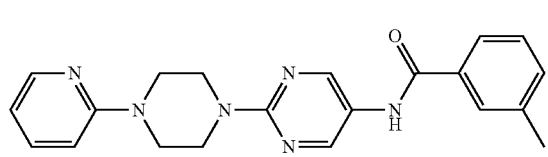 [SMILES: Cc1cccc(C(=O)Nc2cnc(N3CCN(c4ccccn4)CC3)nc2)c1]

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b) (60 mg, 234 µmol) and 3-methylbenzoic acid (35.1 mg, 258 µmol). Yield 71 mg (77%). Light brown solid. LC-MS: m/z=375.2 [M+H]⁺.

Example 65

N-[4-[4-(4-Cyano-2-pyridyl)piperazin-1-yl]phenyl]-4-methoxy-benzamide

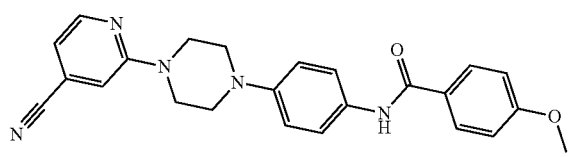 [SMILES: COc1ccc(C(=O)Nc2ccc(N3CCN(c4cc(C#N)ccn4)CC3)cc2)cc1]

a) 2-[4-(4-Aminophenyl)piperazin-1-yl]pyridine-4-carbonitrile

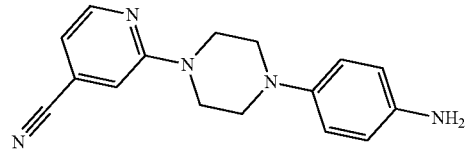 [SMILES: N#Cc1ccnc(N2CCN(c3ccc(N)cc3)CC2)c1]

The title compound was prepared in analogy to 4-[4-(4-pyridyl)piperazin-1-yl]aniline (Intermediate 41.a) from 2-(piperazin-1-yl)pyridine-4-carbonitrile (300 mg, 1.59 mmol). Yield 150 mg (34%). Off-white solid. LC-MS: m/z=279.2 [M+H]⁺.

b) N-[4-[4-(4-Cyano-2-pyridyl)piperazin-1-yl]phenyl]-4-methoxy-benzamide

The title compound was prepared in analogy to 4-methoxy-N-[4-[4-(4-pyridyl)piperazin-1-yl]phenyl]benzamide (Example 41, step b) from 2-[4-(4-aminophenyl)piperazin-1-yl]pyridine-4-carbonitrile (184 mg, 0.66 mmol) and 4-methoxybenzoic acid (100 mg, 0.66 mmol). Yield 32 mg (12%). Off-white solid. LC-MS: m/z=414.2 [M+H]⁺.

Example 66

4-Methoxy-N-{4-[4-(thiophen-2-yl)piperazin-1-yl]phenyl}benzamide

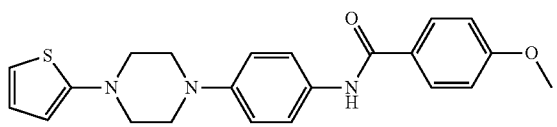 [SMILES: COc1ccc(C(=O)Nc2ccc(N3CCN(c4cccs4)CC3)cc2)cc1]

a) 4-[4-(Thiophen-2-yl)piperazin-1-yl]aniline

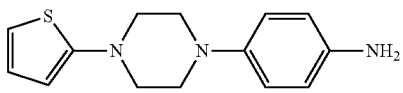

The title compound was prepared in analogy to 4-[4-(4-pyridyl)piperazin-1-yl]aniline (Intermediate 41.a) from 1-(thiophen-2-yl)piperazine (300 mg, 1.78 mmol). Yield 220 mg (48%). Off-white solid. LC-MS: m/z=260.0 [M+H]⁺.

b) 4-Methoxy-N-{4-[4-(thiophen-2-yl)piperazin-1-yl]phenyl}benzamide

The title compound was prepared in analogy to 4-methoxy-N-[4-[4-(4-pyridyl)piperazin-1-yl]phenyl]benzamide (Example 41, step b) from 4-[4-(thiophen-2-yl)piperazin-1-yl]aniline (171 mg, 0.66 mmol) and 4-methoxybenzoic acid (100 mg, 0.66 mmol). Yield 10 mg (4%). Grey solid. LC-MS: m/z=394.1 [M+H]⁺.

Example 67

4-Methoxy-N-{4-[4-(2-methoxypyridin-3-yl)piperazin-1-yl]phenyl}benzamide

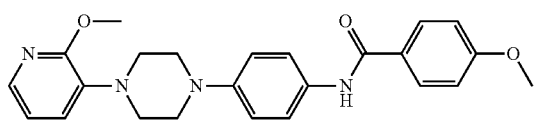 [SMILES: COc1ccc(C(=O)Nc2ccc(N3CCN(c4cccnc4OC)CC3)cc2)cc1]

a) 4-[4-(2-Methoxypyridin-3-yl)piperazin-1-yl]aniline

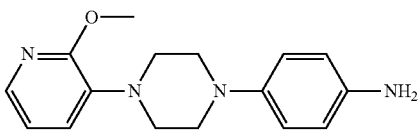 [SMILES: COc1ncccc1N1CCN(c2ccc(N)cc2)CC1]

The title compound was prepared in analogy to 4-[4-(4-pyridyl)piperazin-1-yl]aniline (Intermediate 41.a) from 1-(2-methoxypyridin-3-yl)piperazine (250 mg, 1.09 mmol). Yield 130 mg (42%). Black sticky solid. LC-MS: m/z=285.4 [M+H]$^+$.

b) 4-Methoxy-N-{4-[4-(2-methoxypyridin-3-yl)piperazin-1-yl]phenyl}benzamide

The title compound was prepared in analogy to 4-methoxy-N-[4-[4-(4-pyridyl)piperazin-1-yl]phenyl]benzamide (Example 41, step b) from 4-[4-(2-methoxypyridin-3-yl)piperazin-1-yl]aniline (187 mg, 0.66 mmol) and 4-methoxybenzoic acid (100 mg, 0.66 mmol). Yield 14 mg (5%). Off-white solid. LC-MS: m/z=419.1 [M+H]$^+$.

Example 68

4-Methoxy-N-{4-[4-(6-methoxypyridin-2-yl)piperazin-1-yl]phenyl}benzamide

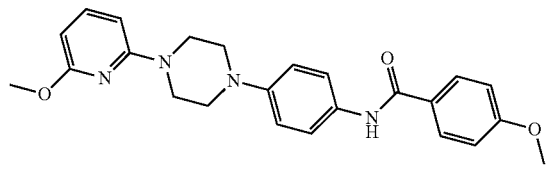

a) 4-[4-(6-Methoxypyridin-2-yl)piperazin-1-yl]aniline

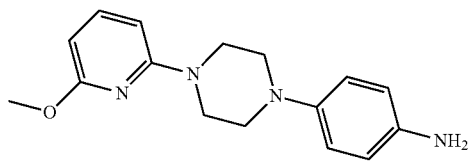 [SMILES: COc1cccc(N2CCN(c3ccc(N)cc3)CC2)n1]

The title compound was prepared in analogy to 4-[4-(4-pyridyl)piperazin-1-yl]aniline (Intermediate 41.a) from 1-(6-methoxypyridin-2-yl)piperazine (300 mg, 1.55 mmol). Yield 172 mg (39%). Off-white solid. LC-MS: m/z=285.1 [M+H]$^+$.

b) 4-Methoxy-N-{4-[4-(6-methoxypyridin-2-yl)piperazin-1-yl]phenyl}benzamide

The title compound was prepared in analogy to 4-methoxy-N-[4-[4-(4-pyridyl)piperazin-1-yl]phenyl]benzamide (Example 41, step b) from 4-[4-(6-methoxypyridin-2-yl)piperazin-1-yl]aniline (183 mg, 0.66 mmol) and 4-methoxybenzoic acid (100 mg, 0.66 mmol). Yield 62 mg (23%). Off-white solid. LC-MS: m/z=419.1 [M+H]$^+$.

Example 69

4-Methoxy-N-{4-[4-(2-methoxyphenyl)piperazin-1-yl]phenyl}benzamide

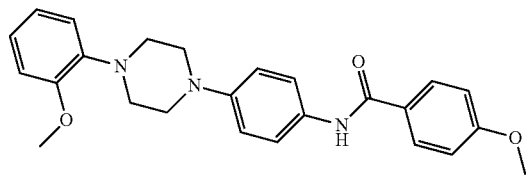 [SMILES: COc1ccc(C(=O)Nc2ccc(N3CCN(c4ccccc4OC)CC3)cc2)cc1]

a) 4-[4-(2-Methoxyphenyl)piperazin-1-yl]aniline

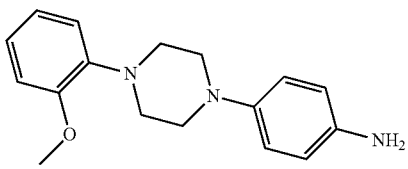 [SMILES: COc1ccccc1N1CCN(c2ccc(N)cc2)CC1]

The title compound was prepared in analogy to 4-[4-(4-pyridyl)piperazin-1-yl]aniline (Intermediate 41.a) from 1-(2-methoxyphenyl)piperazine (300 mg, 1.56 mmol). Yield 190 mg (43%). Black sticky solid. LC-MS: m/z=284.2 [M+H]$^+$.

b) 4-Methoxy-N-{4-[4-(2-methoxyphenyl)piperazin-1-yl]phenyl}benzamide

The title compound was prepared in analogy to 4-methoxy-N-[4-[4-(4-pyridyl)piperazin-1-yl]phenyl]benzamide (Example 41, step b) from 4-[4-(2-methoxyphenyl)piperazin-1-yl]aniline (186 mg, 0.66 mmol) and 4-methoxybenzoic acid (100 mg, 0.66 mmol). Yield 30 mg (11%). Off-white solid. LC-MS: m/z=418.2 [M+H]$^+$.

Example 70

N-{4-[4-(2-Cyanophenyl)piperazin-1-yl]phenyl}-4-methoxybenzamide

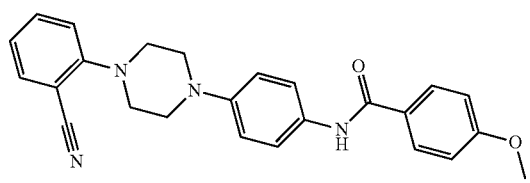 [SMILES: COc1ccc(C(=O)Nc2ccc(N3CCN(c4ccccc4C#N)CC3)cc2)cc1]

a) 2-[4-(4-Aminophenyl)piperazin-1-yl]benzonitrile

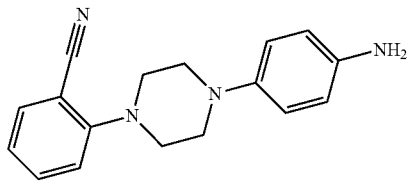 [SMILES: N#Cc1ccccc1N1CCN(c2ccc(N)cc2)CC1]

The title compound was prepared in analogy to 4-[4-(4-pyridyl)piperazin-1-yl]aniline (Intermediate 41.a) from 2-(piperazin-1-yl)benzonitrile (400 mg, 2.13 mmol). Yield 160 mg (27%). Black sticky solid. LC-MS: m/z=279.3[M+H]$^+$.

b) N-{4-[4-(2-Cyanophenyl)piperazin-1-yl]phenyl}-4-methoxybenzamide

The title compound was prepared in analogy to 4-methoxy-N-[4-[4-(4-pyridyl)piperazin-1-yl]phenyl]benzamide (Example 41, step b) from 2-[4-(4-aminophenyl)piperazin-1-yl]benzonitrile (184 mg, 0.66 mmol) and 4-methoxybenzoic acid (100 mg, 0.66 mmol). Yield 40 mg (15%). Off-white solid. LC-MS: m/z=413.1 [M+H]$^+$.

Example 71

N-{4-[4-(2-Fluorophenyl)piperazin-1-yl]phenyl}-4-methoxybenzamide

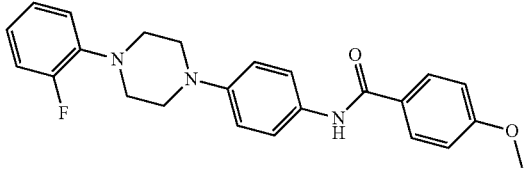 [SMILES: COc1ccc(C(=O)Nc2ccc(N3CCN(c4ccccc4F)CC3)cc2)cc1]

a) 4-[4-(2-Fluorophenyl)piperazin-1-yl]aniline

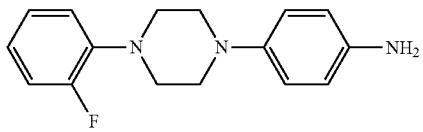

The title compound was prepared in analogy to 4-[4-(4-pyridyl)piperazin-1-yl]aniline (Intermediate 41.a) from 1-(2-fluorophenyl)piperazine (500 mg, 2.77 mmol). Yield 250 mg (33%). Brown sticky solid. LC-MS: m/z=272.0 [M+H]$^+$.

b) N-{4-[4-(2-Fluorophenyl)piperazin-1-yl]phenyl}-4-methoxybenzamide

The title compound was prepared in analogy to 4-methoxy-N-[4-[4-(4-pyridyl)piperazin-1-yl]phenyl]benzamide (Example 41, step b) from 4-[4-(2-fluorophenyl)piperazin-1-yl]aniline (179 mg, 0.66 mmol) and 4-methoxy- benzoic acid (100 mg, 0.66 mmol). Yield 26 mg (10%). Grey solid. LC-MS: m/z=406.1 [M+H]$^+$.

Example 72

4-Methoxy-2-methyl-N-(2-(4-(pyridin-2-yl)piperazin-1-yl)pyrimidin-5-yl)benzamide

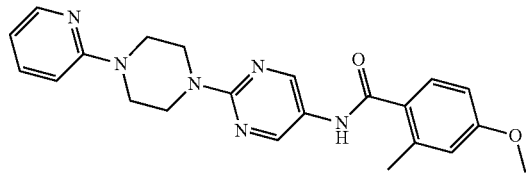 [SMILES: COc1ccc(C(=O)Nc2cnc(N3CCN(c4ccccn4)CC3)nc2)c(C)c1]

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b) (60 mg, 234 µmol) and 4-methoxy-2-methylbenzoic acid (42.8 mg, 258 µmol). Yield 77 mg (78%). Off-white solid. LC-MS: m/z=405.2 [M+H]$^+$.

Example 73

4-(4-Methylpiperazin-1-yl)-N-(2-(4-(pyridin-2-yl)piperazin-1-yl)pyrimidin-5-yl)benzamide

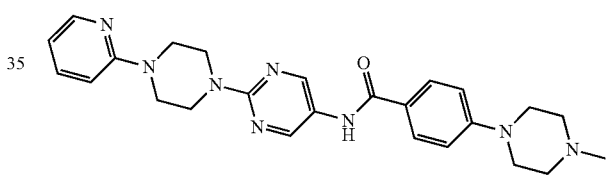

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b) (60 mg, 234 µmol) and 4-(4-methylpiperazin-1-yl)benzoic acid (56.7 mg, 258 µmol). Yield 79 mg (70%). Light red solid. LC-MS: m/z=230.3 [M+2H]$^2$.

Example 74

4-Methyl-N-(2-(4-(pyridin-2-yl)piperazin-1-yl)pyrimidin-5-yl)benzamide

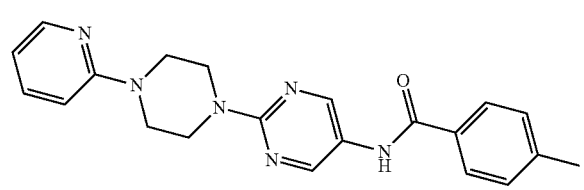 [SMILES: Cc1ccc(C(=O)Nc2cnc(N3CCN(c4ccccn4)CC3)nc2)cc1]

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b)

(60 mg, 234 μmol) and 4-methylbenzoic acid (35.1 mg, 258 μmol). Yield 63 mg (69%). Off-white solid. LC-MS: m/z=375.2 [M+H]⁺.

Example 75

5-Methyl-N-(2-(4-(pyridin-2-yl)piperazin-1-yl)pyrimidin-5-yl)picolinamide

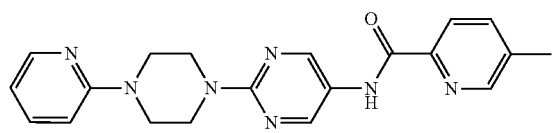 [SMILES: Cc1ccc(C(=O)Nc2cnc(N3CCN(c4ccccn4)CC3)nc2)nc1]

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b) (60 mg, 234 μmol) and 5-methylpicolinic acid (35.3 mg, 258 μmol). Yield 6 mg (6%). Off-white solid. LC-MS: m/z=376.2 [M+H]⁺.

Example 76

5-Methoxy-N-(5-(4-(pyridin-2-yl)piperazin-1-yl)pyridin-2-yl)picolinamide

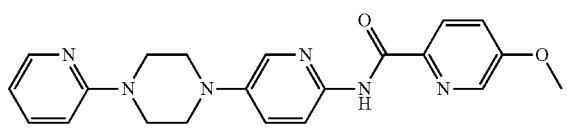 [SMILES: COc1ccc(C(=O)Nc2ccc(N3CCN(c4ccccn4)CC3)cn2)nc1]

The title compound was prepared in analogy to 4-methoxy-N-(5-(4-(pyridin-2-yl)piperazin-1-yl)pyridin-2-yl)benzamide (Example 43, step c) from 5-(4-(pyridin-2-yl)piperazin-1-yl)pyridin-2-amine (Intermediate 43.b) (40 mg, 157 μmol) and 5-methoxypicolinic acid (39.6 mg, 259 μmol). Yield 45 mg (47%). Off-white solid. LC-MS: m/z=391.2 [M+H]⁺.

Example 77

5-Methoxy-N-(4-(4-(pyridin-3-yl)piperazin-1-yl)phenyl)picolinamide

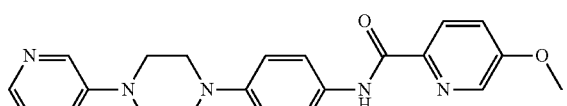

The title compound was prepared in analogy to 4-methyl-N-(4-(4-(pyridin-3-yl)piperazin-1-yl)phenyl)benzamide (Example 37, step c) from 4-(4-(pyridin-3-yl)piperazin-1-yl)aniline (Intermediate 37.b) (60 mg, 236 μmol) and 5-methoxypicolinic acid (39.7 mg, 260 μmol). Off white solid. LC-MS: m/z=390.2 [M+H]⁺.

Example 78

5-Methoxy-N-(4-(4-(pyridin-2-yl)piperazin-1-yl)phenyl)picolinamide

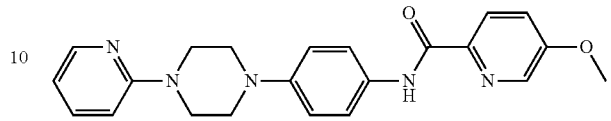

The title compound was prepared in analogy to 2-fluoro-4-methoxy-N-(4-(4-(pyridin-2-yl)piperazin-1-yl)phenyl)benzamide (Example 1, step c) from 4-(4-(pyridin-2-yl)piperazin-1-yl)aniline (Intermediate 1.b) (60 mg, 236 μmol) and 5-methoxypicolinic acid (39.7 mg, 260 μmol). Yield 51 mg (53%). Light brown solid. LC-MS: m/z=390.2 [M+H]⁺.

Example 79

5-Methoxy-N-(2-(4-(pyridin-2-yl)piperazin-1-yl)pyrimidin-5-yl)picolinamide

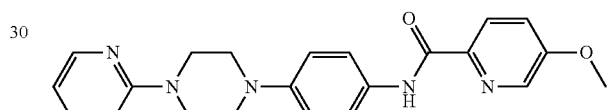

The title compound was prepared in analogy to 4-methoxy-N-(2-(4-(pyridin-2-yl)piperazin-1-yl)pyrimidin-5-yl)benzamide (Example 59, step c) from 2-(4-(pyridin-2-yl)piperazin-1-yl)pyrimidin-5-amine (Intermediate 59.b) (60 mg, 234 μmol) and 5-methoxypicolinic acid (39.4 mg, 258 μmol). Yield 45 mg (47%). White solid. LC-MS: m/z=392.2 [M+H]⁺.

Example 80

4-Methoxy-2-methyl-N-[5-(4-pyridin-2-ylpiperazin-1-yl)pyridin-2-yl]benzamide

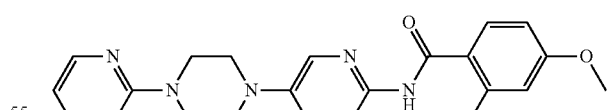

The title compound was prepared in analogy to 4-methoxy-N-(5-(4-(pyridin-2-yl)piperazin-1-yl)pyridin-2-yl)benzamide (Example 43, step c) from 5-(4-(pyridin-2-yl)piperazin-1-yl)pyridin-2-amine (Intermediate 43.b) (70 mg, 274 μmol) and 4-methoxy-2-methylbenzoic acid (50.1 mg, 302 μmol). Yield 21 mg (18%). White solid. 1H NMR (300 MHz, CHLOROFORM-d) δ ppm 2.54 (s, 3H) 3.22-3.28 (m, 4H) 3.69-3.75 (m, 4H) 3.83 (s, 3H) 6.65-6.80 (m, 4H) 7.28-7.41 (m, 1H) 7.49-7.56 (m, 2H) 7.85 (br s, 1H) 8.23 (d, J=4.84 Hz, 1H) 8.27 (d, J=8.98 Hz, 1H) 8.44 (br s, 1H).

Example 81

4-(4-Methylpiperazin-1-yl)-N-[5-(4-pyridin-2-ylpip-erazin-1-yl)pyridin-2-yl]benzamide

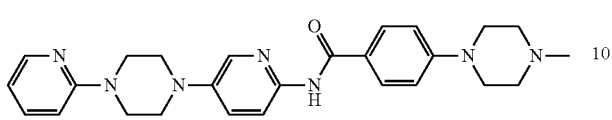

The title compound was prepared in analogy to 4-methoxy-N-(5-(4-(pyridin-2-yl)piperazin-1-yl)pyridin-2-yl)benzamide (Example 43, step c) from 5-(4-(pyridin-2-yl)piperazin-1-yl)pyridin-2-amine (Intermediate 43.b) (70 mg, 274 μmol) and 4-(4-methylpiperazin-1-yl)benzoic acid (66.4 mg, 302 μmol). Yield 55 mg (42%). White solid. LC-MS: m/z=458.3 [M+H]$^+$.

Example 82

4-Methoxy-N-[4-[4-(4-methoxy-2-pyridyl)piperazin-1-yl]phenyl]benzamide

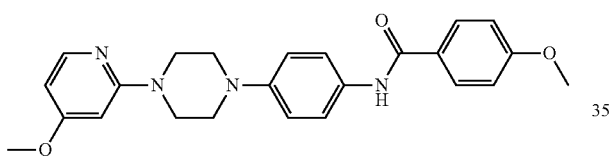

a) 4-[4-(4-Methoxy-2-pyridyl)piperazin-1-yl]aniline

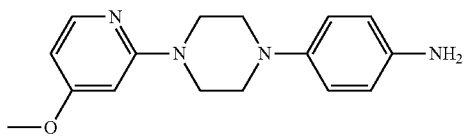 [SMILES: COc1ccnc(N2CCN(c3ccc(N)cc3)CC2)c1]

The title compound was prepared in analogy to 4-[4-(4-pyridyl)piperazin-1-yl]aniline (Intermediate 41.a) from 1-(4-methoxypyridin-2-yl)piperazine (300 mg, 1.55 mmol). Yield 208 mg (47%). Black sticky solid. LC-MS: m/z=285.3 [M+H]$^+$.

b) 4-Methoxy-N-[4-[4-(4-methoxy-2-pyridyl)piper-azin-1-yl]phenyl]benzamide

The title compound was prepared in analogy to 4-methoxy-N-[4-[4-(4-pyridyl)piperazin-1-yl]phenyl]benz-amide (Example 41, step b) from 4-[4-(4-methoxy-2-pyridyl)piperazin-1-yl]aniline (187 mg, 0.66 mmol) and 4-methoxybenzoic acid (100 mg, 0.66 mmol). 152 mg (55%). Grey solid. LC-MS: m/z=419.0 [M+H]$^+$.

Example 83

Acetic acid; 4-Methoxy-N-[4-[4-(3-methyl-4-pyridyl)piperazin-1-yl]phenyl]benzamide

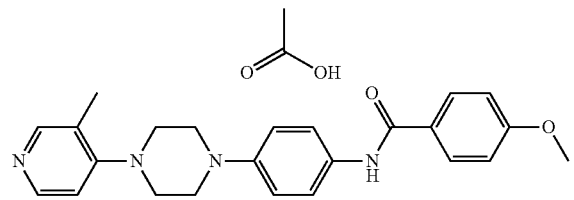

a) 4-[4-(3-Methylpyridin-4-yl)piperazin-1-yl]aniline

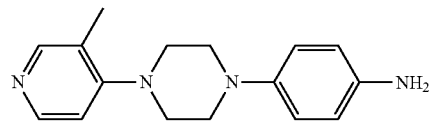 [SMILES: Cc1cnccc1N1CCN(c2ccc(N)cc2)CC1]

The title compound was prepared in analogy to 4-[4-(4-pyridyl)piperazin-1-yl]aniline (Intermediate 41.a) from 1-(3-methylpyridin-4-yl)piperazine (300 mg, 1.69 mmol). Yield 220 mg (48%). Brown sticky solid. LC-MS: m/z=269.2[M+H]$^+$.

b) Acetic acid; 4-methoxy-N-[4-[4-(3-methyl-4-pyridyl)piperazin-1-yl]phenyl]benzamide The title compound was prepared in analogy to 4-methoxy-N-[4-[4-(4-pyridyl)piperazin-1-yl]phenyl]benz-amide (Example 41, step b) from 4-[4-(3-methylpyridin-4-yl)piperazin-1-yl]aniline (176 mg, 0.66 mmol) and 4-methoxybenzoic acid (100 mg, 0.66 mmol). Yield 64 mg (24%). Brown solid. LC-MS: m/z=403.1 [M+H]$^+$.

Example 84

2-Fluoro-4-methoxy-N-(5-(4-(pyridin-2-yl)piper-azin-1-yl)pyrazin-2-yl)benzamide

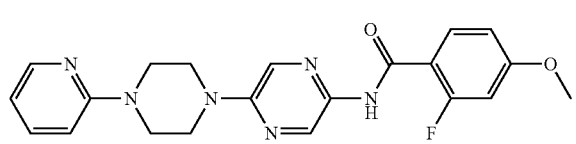

a) 2-Chloro-5-(4-(pyridin-2-yl)piperazin-1-yl)pyra-zine

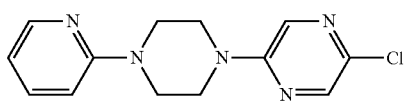 [SMILES: Clc1cnc(N2CCN(c3ccccn3)CC2)cn1]

1-(Pyridin-2-yl)piperazine (1.64 g, 1.53 ml, 10.1 mmol), 2,5-dichloropyrazine (1.5 g, 10.1 mmol) and Cs₂CO₃ (5.25 g, 16.1 mmol) were dissolved in DMF (40 ml). The solution was stirred 17 h at 55° C. The solution was diluted with H₂O, then extracted with DCM (4×). The combined organic layers were washed with brine, dried over MgSO₄, filtered and concentrated under vacuum. The crude material was purified by flash chromatography (DCM to DCM/0.6% MeOH) to yield 2-chloro-5-(4-(pyridin-2-yl)piperazin-1-yl)pyrazine (1.57 g, 55%). Light yellow solid. LC-MS: m/z=276.1. [M+H]⁺.

b) N-(Diphenylmethylene)-5-(4-(pyridin-2-yl)piperazin-1-yl)pyrazin-2-amine

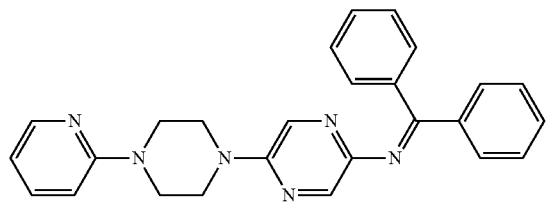 [SMILES: c1ccc(C(=Nc2cnc(N3CCN(c4ccccn4)CC3)cn2)c2ccccc2)cc1]

2-Chloro-5-(4-(pyridin-2-yl)piperazin-1-yl)pyrazine (1.56 g, 5.66 mmol) was dissolved in Tol (31 ml) under Ar. Diphenylmethaneimine (1.13 g, 1.04 ml, 6.22 mmol), BINAP (352 mg, 566 µmol) and NaOtBu (761 mg, 7.92 mmol) were added. The flask was purged with Ar for 5 min, then [Pd₂(dba)₃] (155 mg, 170 µmol) was added. The reaction was stirred 24 h under Ar at 115° C. The reaction mixture was diluted in H₂O, extracted with DCM (3×). The combined organic layers were dried with MgSO₄, filtered and concentrated under vacuum.

The crude material was purified by flash chromatography (DCM to DCM/0.4% MeOH) to yield N-(diphenylmethylene)-5-(4-(pyridin-2-yl)piperazin-1-yl)pyrazin-2-amine (1.87 g, 75% yield). Yellow solid. LC-MS: m/z=421.3[M+H]⁺.

c) 5-(4-(Pyridin-2-yl)piperazin-1-yl)pyrazin-2-amine

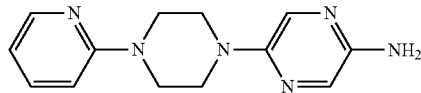

N-(Diphenylmethylene)-5-(4-(pyridin-2-yl)piperazin-1-yl)pyrazin-2-amine (1.87 g, 4.44 mmol) was dissolved in MeOH (85 ml). Hydroxylammonium chloride (617 mg, 8.87 mmol) and NaOAc trihydrate (1.21 g, 8.87 mmol) were added. The reaction was stirred for 30 min at rt. The reaction mixture was concentrated under vacuum. The crude material was purified by flash chromatography (DCM to 98:2 DCM:MeOH to remove benzophenone oxime, then to 15% MeOH in DCM). 5-(Pyridin-2-yl)piperazin-1-yl)pyrazin-2-amine (1.08 g, 95%) was isolated as light brown solid. LC-MS: m/z=257.2 [M+H]⁺.

d) 2-Fluoro-4-methoxy-N-(5-(4-(pyridin-2-yl)piperazin-1-yl)pyrazin-2-yl)benzamide 2-Fluoro-4-methoxybenzoic acid (39.8 mg, 234 µmol) was dissolved in DMF (707 µl). HATU (107 mg, 281 µmol) and DIPEA (60.5 mg, 81.8 µl, 468 µmol) were added and the reaction mixture was stirred at rt for 30 min. 5-(4-(Pyridin-2-yl)piperazin-1-yl)pyrazin-2-amine (60 mg, 234 µmol) was added. The solution was stirred 2 h at rt. The solution was diluted in 0.1 M citric acid, then extracted with two portions DCM. The combined organic layers were washed with brine, dried with MgSO₄, filtered and concentrated under vacuum. The crude material was purified by flash chromatography (0% to 20% 98:2 DCM:MeOH in DCM) to yield 2-fluoro-4-methoxy-N-(5-(4-(pyridin-2-yl)piperazin-1-yl)pyrazin-2-yl)benzamide (12 mg, 12%) as off-white solid. LC-MS: m/z=409.2 [M+H]⁺.

Example 85

4-Methoxy-N-(5-(4-(pyridin-2-yl)piperazin-1-yl)pyrazin-2-yl)benzamide

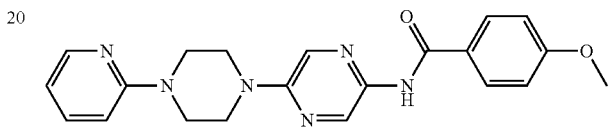

The title compound was prepared in analogy to 2-fluoro-4-methoxy-N-(5-(4-(pyridin-2-yl)piperazin-1-yl)pyrazin-2-yl)benzamide (Example 84, step d) from 4-methoxybenzoic acid (35.6 mg, 234 µmol) and 5-(4-(pyridin-2-yl)piperazin-1-yl)pyrazin-2-amine (Intermediate 84.c) (60 mg, 234 µmol). Yield 67 mg (70%). White solid. LC-MS: m/z=391.2 [M+H]⁺.

Example 86

4-(Dimethylamino)-N-(5-(4-(pyridin-2-yl)piperazin-1-yl)pyrazin-2-yl)benzamide

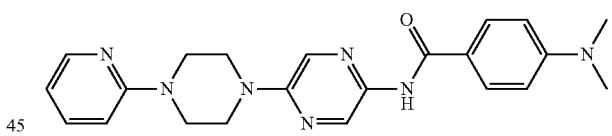

The title compound was prepared in analogy to 2-fluoro-4-methoxy-N-(5-(4-(pyridin-2-yl)piperazin-1-yl)pyrazin-2-yl)benzamide (Example 84, step d) from 4-(dimethylamino) benzoic acid (38.4 mg, 234 µmol) and 5-(4-(pyridin-2-yl) piperazin-1-yl)pyrazin-2-amine (Intermediate 84 c) (60 mg, 234 µmol). Yield 15 mg (15%). Light brown solid. LC-MS: m/z=404.2 [M+H]⁺.

Example 87

4-(4-Methylpiperazin-1-yl)-N-(5-(4-(pyridin-2-yl)piperazin-1-yl)pyrazin-2-yl)benzamide

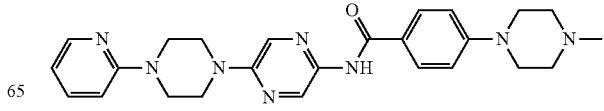

The title compound was prepared in analogy to 2-fluoro-4-methoxy-N-(5-(4-(pyridin-2-yl)piperazin-1-yl)pyrazin-2-yl)benzamide (Example 84, step d) from 4-(4-methylpiperazin-1-yl)benzoic acid (51.6 mg, 234 μmol) and 5-(4-(pyridin-2-yl)piperazin-1-yl)pyrazin-2-amine (Intermediate 84.c) (60 mg, 234 μmol). Yield 43 mg (38%). Brown solid. LC-MS: m/z=459.2 [M+H]⁺.

Example 88

4-Morpholino-N-(5-(4-(pyridin-2-yl)piperazin-1-yl)pyrazin-2-yl)benzamide

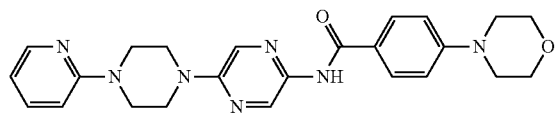

The title compound was prepared in analogy to 2-fluoro-4-methoxy-N-(5-(4-(pyridin-2-yl)piperazin-1-yl)pyrazin-2-yl)benzamide (Example 84, step d) from 4-morpholinobenzoic acid (48.5 mg, 234 μmol) and 5-(4-(pyridin-2-yl)piperazin-1-yl)pyrazin-2-amine (Intermediate 84.c) (60 mg, 234 μmol). Yield 55 mg (50%). Off-white solid. LC-MS: m/z=446.2 [M+H]⁺.

Example 89

4-Methyl-N-(5-(4-(pyridin-2-yl)piperazin-1-yl)pyrazin-2-yl)benzamide

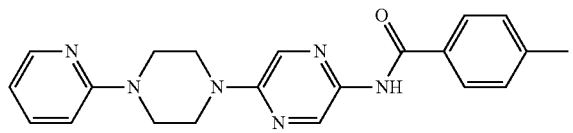 [SMILES: Cc1ccc(C(=O)Nc2cnc(N3CCN(c4ccccn4)CC3)cn2)cc1]

The title compound was prepared in analogy to 2-fluoro-4-methoxy-N-(5-(4-(pyridin-2-yl)piperazin-1-yl)pyrazin-2-yl)benzamide (Example 84, step d) from 4-methylbenzoic acid (31.9 mg, 234 μmol) and 5-(4-(pyridin-2-yl)piperazin-1-yl)pyrazin-2-amine (Intermediate 84.c) (60 mg, 234 μmol). Yield 73 mg (79%). Off-white solid. LC-MS: m/z=375.2 [M+H]⁺.

Example 90

5-Methyl-N-(5-(4-(pyridin-2-yl)piperazin-1-yl)pyrazin-2-yl)picolinamide

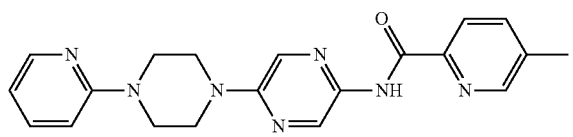 [SMILES: Cc1ccc(C(=O)Nc2cnc(N3CCN(c4ccccn4)CC3)cn2)nc1]

The title compound was prepared in analogy to 2-fluoro-4-methoxy-N-(5-(4-(pyridin-2-yl)piperazin-1-yl)pyrazin-2-yl)benzamide (Example 84, step d) from 5-methylpicolinic acid (32.1 mg, 234 μmol) and 5-(4-(pyridin-2-yl)piperazin-1-yl)pyrazin-2-amine (Intermediate 84.c) (60 mg, 234 μmol). Yield 20 mg (22%). Off-white solid. LC-MS: m/z=376.2 [M+H]⁺.

Example 91

N-(4-(4-(5-Cyanopyridin-2-yl)piperazin-1-yl)phenyl)-6-methoxypicolinamide

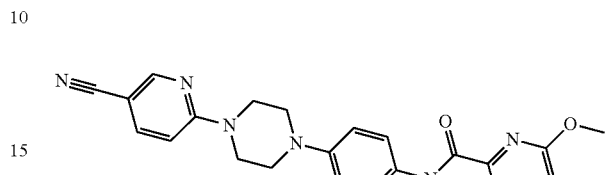

The title compound was prepared in analogy to 2-fluoro-4-methoxy-N-(4-(4-(pyridin-2-yl)piperazin-1-yl)phenyl)benzamide (Example 1, step c) from 6-[4-(4-aminophenyl)piperazin-1-yl]pyridine-3-carbonitrile (Intermediate 50.a) (60 mg, 215 μmol) and 6-methoxypicolinic acid (32.9 mg, 215 μmol). Yield 38 mg (41%). Light brown solid. LC-MS: m/z=415.0 [M+H]⁺.

Example 92

N-(4-(4-(4-Cyanophenyl)piperazin-1-yl)phenyl)-4-morpholinobenzamide

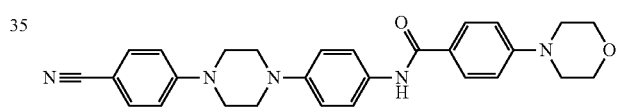

The title compound was prepared in analogy to 2-fluoro-4-methoxy-N-(4-(4-(pyridin-2-yl)piperazin-1-yl)phenyl)benzamide (Example 1, step c) from 4-(4-(4-aminophenyl)piperazin-1-yl)benzonitrile (Intermediate 57.a) (60 mg, 216 μmol) and 4-morpholinobenzoic acid (44.7 mg, 216 μmol). 19 mg (18%). White solid. LC-MS: m/z=468.2 [M+H]⁺.

Example 93

N-(4-(4-(4-Cyanophenyl)piperazin-1-yl)phenyl)-6-methoxypicolinamide

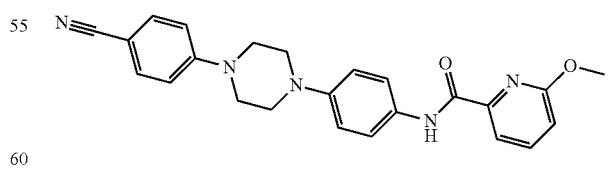

The title compound was prepared in analogy to 2-fluoro-4-methoxy-N-(4-(4-(pyridin-2-yl)piperazin-1-yl)phenyl)benzamide (Example 1, step c) from 4-(4-(4-aminophenyl)piperazin-1-yl)benzonitrile (Intermediate 57.a) (60 mg, 216 μmol) and 6-methoxypicolinic acid (33 mg, 216 μmol). 61 mg (65%). Off-white solid. LC-MS: m/z=414.2 [M+H]⁺.

Example 94

4-Morpholino-N-(4-(4-(thiophen-2-yl)piperazin-1-yl)phenyl)benzamide

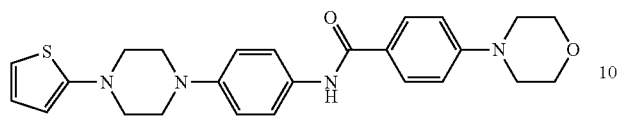

The title compound was prepared in analogy to 2-fluoro-4-methoxy-N-(4-(4-(pyridin-2-yl)piperazin-1-yl)phenyl)benzamide (Example 1, step c) from 4-(4-(thiophen-2-yl)piperazin-1-yl)aniline (Intermediate 66.a) (60 mg, 231 µmol) and 4-morpholinobenzoic acid (47.9 mg, 231 µmol). 67 mg (61%). Light brown solid. LC-MS: m/z=449.2 [M+H]$^+$.

Example 95

N-(5-(4-(5-Cyanopyridin-2-yl)piperazin-1-yl)pyridin-2-yl)-4-methoxybenzamide

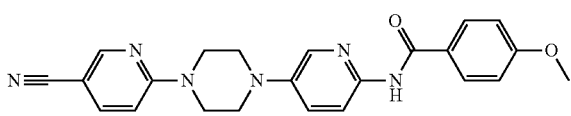

a) 6-(4-(6-Nitropyridin-3-yl)piperazin-1-yl)nicotinonitrile

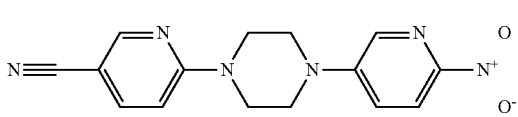

6-(Piperazin-1-yl)nicotinonitrile (331 mg, 1.76 mmol) was dissolved in DMSO (1.25 ml). K$_2$CO$_3$ (365 mg, 2.64 mmol) and 5-fluoro-2-nitropyridine (250 mg, 1.76 mmol) were added and the solution was stirred 25 min at 90° C. The solution was diluted in H$_2$O and extracted with DCM. The combined organic layers were washed with brine, dried over MgSO$_4$, filtered and concentrated under vacuum. The crude product was purified by flash-column chromatography (DCM to 5% MeOH in DCM) to yield 6-(4-(6-nitropyridin-3-yl)piperazin-1-yl)nicotinonitrile (358 mg, 62%). LC-MS: m/z=311.1 [M+H]$^+$.

b) 6-(4-(6-Aminopyridin-3-yl)piperazin-1-yl)nicotinonitrile

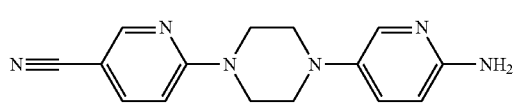 [SMILES: N#Cc1ccc(N2CCN(c3ccc(N)nc3)CC2)nc1]

6-(4-(6-Nitropyridin-3-yl)piperazin-1-yl)nicotinonitrile (356 mg, 1.09 mmol) was dissolved in EtOH (15 ml) and the solution was placed under Ar. Pd/C 10% (127 mg, 1.09 mmol) was added, and the reaction was stirred at rt under H$_2$ for 80 min. The reaction mixture was filtered over Celite and washed with EtOH and 9:1 DCM:MeOH, then concentrated under vacuum to yield 6-(4-(6-aminopyridin-3-yl)piperazin-1-yl)nicotinonitrile (319 mg, 99%) as yellow solid. LC-MS: m/z=281.2 [M+H]$^+$.

c) N-(5-(4-(5-Cyanopyridin-2-yl)piperazin-1-yl)pyridin-2-yl)-4-methoxybenzamide The title compound was prepared in analogy to 2-fluoro-4-methoxy-N-(4-(4-(pyridin-2-yl)piperazin-1-yl)phenyl)benzamide (Example 1, step c) from 6-(4-(6-aminopyridin-3-yl)piperazin-1-yl)nicotinonitrile (60 mg, 214 µmol) and 4-methoxybenzoic acid (32.6 mg, 214 µmol). 56 mg (60%). Off-white solid. LC-MS: m/z=415.2 [M+H]$^+$.

Example 96

N-(5-(4-(4-Cyanophenyl)piperazin-1-yl)pyridin-2-yl)-4-methoxybenzamide

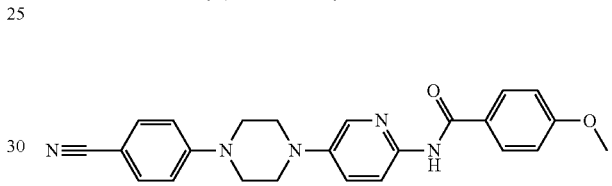

a) 4-(4-(6-Nitropyridin-3-yl)piperazin-1-yl)benzonitrile

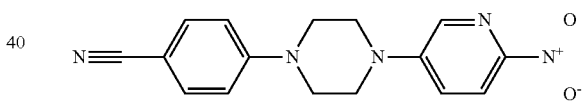

4-(Piperazin-1-yl)benzonitrile (329 mg, 1.76 mmol) was dissolved in DMSO (1.25 ml).
K$_2$CO$_3$ (365 mg, 2.64 mmol) and 5-fluoro-2-nitropyridine (250 mg, 1.76 mmol) were added and the solution was stirred 15 min at 90° C. The solution was diluted in H$_2$O and extracted with DCM. The combined organic layers were washed with brine, dried over MgSO$_4$, filtered and concentrated under vacuum. The crude product was purified by flash chromatography (DCM to 5% MeOH in DCM) to yield 4-(4-(6-nitropyridin-3-yl)piperazin-1-yl)benzonitrile (448 mg, 78.2%) as yellow solid. LC-MS: m/z=310.2 [M+H]$^+$.

b) 4-(4-(6-Aminopyridin-3-yl)piperazin-1-yl)benzonitrile

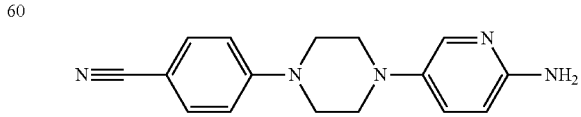

4-(4-(6-Nitropyridin-3-yl)piperazin-1-yl)benzonitrile (445 mg, 1.44 mmol) was dissolved in EtOH (20 ml) and the solution was placed under Ar. Pd/C 10% (159 mg, 1.44 mmol) was added, and the reaction was stirred at rt under H₂ for 2 h. The reaction mixture was filtered over Celite and washed with EtOH and 4:1 DCM:MeOH, then concentrated under vacuum to yield 4-(4-(6-aminopyridin-3-yl)piperazin-1-yl)benzonitrile (414 mg, 62%; 60% purity) still containing starting material. This material was used as such in the following step. LC-MS: m/z=280.2 [M+H]⁺.

c) N-(5-(4-(4-Cyanophenyl)piperazin-1-yl)pyridin-2-yl)-4-methoxybenzamide

The title compound was prepared in analogy to 2-fluoro-4-methoxy-N-(4-(4-(pyridin-2-yl)piperazin-1-yl)phenyl)benzamide (Example 1, step c) from 4-(4-(6-aminopyridin-3-yl)piperazin-1-yl)benzonitrile (60 mg, 215 μmol) and 4-methoxybenzoic acid (32.7 mg, 215 μmol). Yield 25 mg (27%). White solid. LC-MS: m/z=414.2 [M+H]⁺.

Example 97

N-(2-(4-(4-Cyanophenyl)piperazin-1-yl)pyrimidin-5-yl)-4-methoxybenzamide

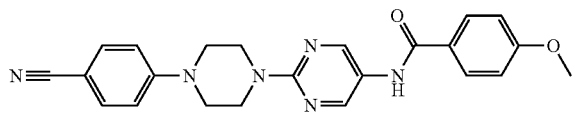 [SMILES: COc1ccc(C(=O)Nc2cnc(N3CCN(c4ccc(C#N)cc4)CC3)nc2)cc1]

a) 4-(4-(5-Nitropyrimidin-2-yl)piperazin-1-yl)benzonitrile

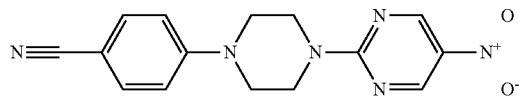

2-Chloro-5-nitropyrimidine (270 mg, 1.69 mmol) was dissolved in THF (60 ml) and 4-(piperazin-1-yl)benzonitrile (317 mg, 1.69 mmol) was added. The reaction mixture turned immediately yellow. The reaction mixture was concentrated under vacuum. The crude was diluted in H₂O and extracted with EtOAc and DCM. The combined organic layers were dried with MgSO₄ and concentrated under vacuum. The crude product was purified with flash chromatography (silica gel, 120 g, 0% to 5% MeOH in DCM) to yield 4-(4-(5-nitropyrimidin-2-yl)piperazin-1-yl)benzonitrile (150 mg, 27% yield) as an orange solid. LC-MS: m/z=311.1 [M+H]⁺.

b) 4-(4-(5-Aminopyrimidin-2-yl)piperazin-1-yl)benzonitrile

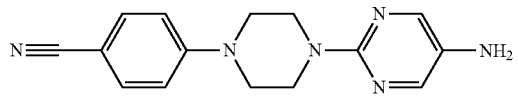

4-(4-(5-Nitropyrimidin-2-yl)piperazin-1-yl)benzonitrile (150 mg, 483 μmol) was dissolved in EtOH (6 ml) and the solution was placed under Ar. Pd/C 10% (53.5 mg, 483 μmol) was added and the reaction was stirred 80 min under H₂ at rt. The reaction mixture was filtered over Celite and washed with EtOH and 9:1 DCM:MeOH, then concentrated under vacuum to yield 4-(4-(5-aminopyrimidin-2-yl)piperazin-1-yl)benzonitrile (110 mg, 69%). LCMS: m/z=281.1 [M+H]⁺.

c) N-(2-(4-(4-Cyanophenyl)piperazin-1-yl)pyrimidin-5-yl)-4-methoxybenzamide

The title compound was prepared in analogy to 2-fluoro-4-methoxy-N-(4-(4-(pyridin-2-yl)piperazin-1-yl)phenyl)benzamide (Example 1, step c) from 4-(4-(5-aminopyrimidin-2-yl)piperazin-1-yl)benzonitrile (35 mg, 125 μmol) and 4-methoxybenzoic acid (19 mg, 125 μmol). Yield 20 mg (37%). Off-white solid. LC-MS: m/z=415.2 [M+H]⁺.

Example 98

N-(2-(4-(5-Cyanopyridin-2-yl)piperazin-1-yl)pyrimidin-5-yl)-4-methoxybenzamide

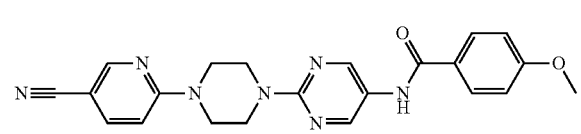 [SMILES: COc1ccc(C(=O)Nc2cnc(N3CCN(c4ccc(C#N)cn4)CC3)nc2)cc1]

a) 6-(4-(5-Nitropyrimidin-2-yl)piperazin-1-yl)nicotinonitrile

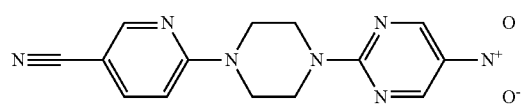

2-Chloro-5-nitropyrimidine (270 mg, 1.69 mmol) was dissolved in THF (60 ml) and 6-(piperazin-1-yl)nicotinonitrile (319 mg, 1.69 mmol) was added. The reaction mixture turned immediately yellow. The reaction mixture was concentrated under vacuum. The crude was diluted in H₂O and extracted with EtOAc and DCM. The combined organic layers were dried with MgSO₄ and concentrated under vacuum. The crude product was purified with flash chromatography (silica gel, 120 g, 0% to 5% MeOH in DCM) to yield 6-(4-(5-nitropyrimidin-2-yl)piperazin-1-yl)nicotinonitrile (246 mg, 44% yield) as an orange solid. LC-MS: m/z=312.1 [M+H]⁺.

b) 6-(4-(5-Aminopyrimidin-2-yl)piperazin-1-yl)nicotinonitrile

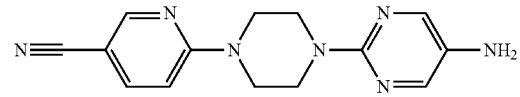

6-(4-(5-Nitropyrimidin-2-yl)piperazin-1-yl)nicotinonitrile (270 mg, 867 µmol) was dissolved in EtOH (11 ml) and the solution was placed under Ar. Pd/C 10% (96.3 mg, 867 µmol) was added and the reaction was stirred overnight under H₂ at rt. The reaction mixture was filtered over Celite and washed with EtOH and 9:1 DCM:MeOH, then concentrated under vacuum to yield 6-(4-(5-aminopyrimidin-2-yl)piperazin-1-yl)nicotinonitrile (157 mg, 58%) as an off-white solid. LC-MS: m/z=282.2 [M+H]⁺.

c) N-(2-(4-(5-Cyanopyridin-2-yl)piperazin-1-yl)pyrimidin-5-yl)-4-methoxybenzamide The title compound was prepared in analogy to 2-fluoro-4-methoxy-N-(4-(4-(pyridin-2-yl)piperazin-1-yl)phenyl)benzamide (Example 1, step c) from 6-(4-(5-aminopyrimidin-2-yl)piperazin-1-yl)nicotinonitrile (50 mg, 178 µmol) and 4-methoxybenzoic acid (27 mg, 178 µmol). Yield 45 mg (58%). White solid. LC-MS: m/z=416.2 [M+H]⁺.

Example 99

N-(2-(4-(5-Cyanopyridin-2-yl)piperazin-1-yl)pyrimidin-5-yl)-4-morpholinobenzamide

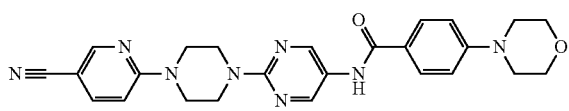 [SMILES: N#Cc1ccc(N2CCN(c3ncc(NC(=O)c4ccc(N5CCOCC5)cc4)cn3)CC2)nc1]

The title compound was prepared in analogy to N-(2-(4-(5-cyanopyridin-2-yl)piperazin-1-yl)pyrimidin-5-yl)-4-methoxybenzamide (Example 98, step c) from 6-(4-(5-aminopyrimidin-2-yl)piperazin-1-yl)nicotinonitrile (Intermediate 98.b) (50 mg, 178 µmol) and 4-morpholinobenzoic acid (36.8 mg, 178 µmol). 15 mg (17%). Off-white solid. LC-MS: m/z=471.2 [M+H]⁺.

Example 100

N-[4-[4-(6-Cyano-2-pyridyl)piperazin-1-yl]phenyl]-4-methoxy-benzamide

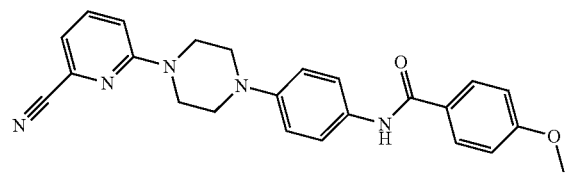 [SMILES: COc1ccc(C(=O)Nc2ccc(N3CCN(c4cccc(C#N)n4)CC3)cc2)cc1]

a) 6-[4-(4-Nitrophenyl)piperazin-1-yl]pyridine-2-carbonitrile

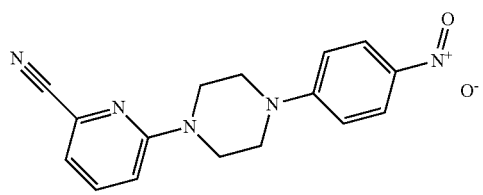

To a solution under N₂ of 6-(piperazin-1-yl)pyridine-2-carbonitrile (750 mg, 3.98 mmol) in DMF (5 ml) was added K₂CO₃ (1.38 mg, 4.38 mmol) and the mixture was stirred at 25° C. for 30 min. After that 4-fluoronitrobenzene (618 mg, 4.38 mmol) was added and the reaction mixture was stirred for 16 h at 25° C. After total consumption of starting materials (monitored by TLC) the reaction mixture was poured into H₂O (50 ml) and extracted with EtOAc (3×100 ml). The combined organic phases were dried over Na₂SO₄ and concentrated under vacuum. The resulting crude was purified by flash chromatography (40% EtOAc/Hexane) to get 6-[4-(4-nitrophenyl)piperazin-1-yl]pyridine-2-carbonitrile (760 mg, 62%) as yellow solid.

b) 6-[4-(4-Aminophenyl)piperazin-1-yl]pyridine-2-carbonitrile

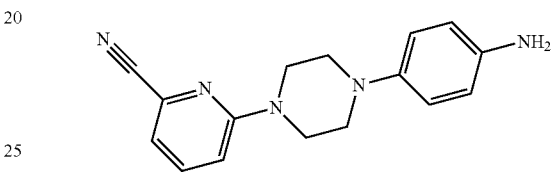

To a solution of 6-[4-(4-nitrophenyl)piperazin-1-yl]pyridine-2-carbonitrile (750 mg, 2.43 mmol) in EtOH (10 ml) was added Raney-Ni (50% in H₂O) (2.5 ml). N₂H₄.H₂O (1.1 ml, 24.2 mmol) was added over a 15 min period. The reaction mixture was then heated to 45° C. for 1 h. Raney-Ni was filtered off, washed with EtOH and the filtrate concentrated under vacuum. The resulting crude product was purified by flash chromatography (amine modified silica gel, 60-80% EtOAc/Hexane) to get 6-[4-(4-aminophenyl)piperazin-1-yl]pyridine-2-carbonitrile (580 mg, 86%) as grey solid. LC-MS: m/z=280.2 [M+H]⁺.

c) N-[4-[4-(6-Cyano-2-pyridyl)piperazin-1-yl]phenyl]-4-methoxy-benzamide

To a solution of 6-[4-(4-aminophenyl)piperazin-1-yl]pyridine-2-carbonitrile (250 mg, 0.75 mmol) in THF (2.5 ml) cooled with an ice/H₂O bath were added Et₃N (0.2 ml, 1.5 mmol) and 4-methoxybenzoyl chloride (0.1 ml, 0.75 mmol). The reaction mixture was stirred 1 h at 0° C. The reaction mixture was diluted with H₂O (20 ml) and extracted with EtOAc (2×50 ml). The combined organic layers were dried over Na₂SO₄ and concentrated. The resulting crude product was purified by flash chromatography to get the title compound (135 mg, 43%) as off-white solid. LC-MS: m/z=414.1 [M+H]⁺.

Example 101

4-Methoxy-N-[4-(4-phenylpiperazin-1-yl)phenyl]benzamide

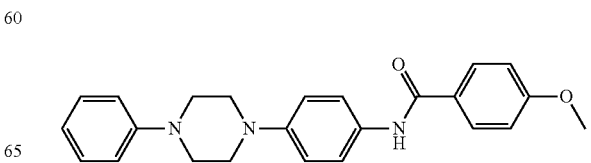

a) 1-(4-Nitrophenyl)-4-phenylpiperazine

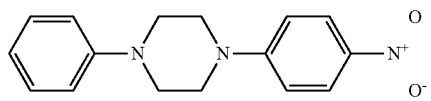

The title compound was prepared in analogy to 6-[4-(4-nitrophenyl)piperazin-1-yl]pyridine-2-carbonitrile (Intermediate 100.a) from 1-phenylpiperazine (500 mg, 3.08 mmol) and 1-fluoro-4-nitrobenzene (478 mg, 3.39 mmol). Crude yield 500 mg. Yellow solid. This material was used without any further purification in the next step.

b) 4-(4-Phenylpiperazin-1-yl)aniline

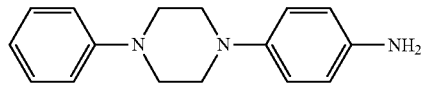 [SMILES: Nc1ccc(N2CCN(c3ccccc3)CC2)cc1]

The title compound was prepared in analogy to 6-[4-(4-aminophenyl)piperazin-1-yl]pyridine-2-carbonitrile (Intermediate 100.b) from 1-(4-nitrophenyl)-4-phenylpiperazine (500 mg, 1.77 mmol). Yield 405 mg (90%). Grey solid. LC-MS: m/z=253.9 [M+H]$^+$.

c) 4-Methoxy-N-[4-(4-phenylpiperazin-1-yl)phenyl]benzamide

The title compound was prepared in analogy to N-[4-[4-(6-cyano-2-pyridyl)piperazin-1-yl]phenyl]-4-methoxy-benzamide (Example 100, step c) from 4-(4-phenylpiperazin-1-yl)aniline (100 mg, 0.39 mmol) and 4-methoxybenzoyl chloride (0.05 ml, 0.39 mmol). Yield 55 mg (36%). Off-white solid. LC-MS: m/z=388.3 [M+H]$^+$.

Example 102

4-Methoxy-N-[4-[4-(4-methyl-2-pyridyl)piperazin-1-yl]phenyl]benzamide

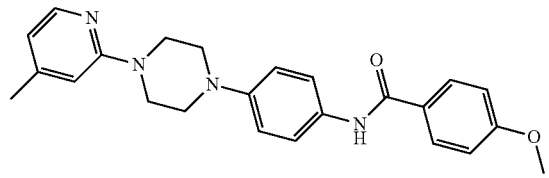

a) 1-(4-Methylpyridin-2-yl)-4-(4-nitrophenyl)piperazine

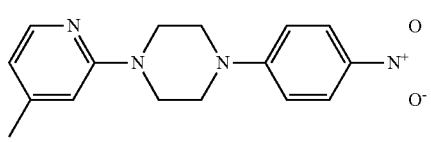

The title compound was prepared in analogy to 6-[4-(4-nitrophenyl)piperazin-1-yl]pyridine-2-carbonitrile (Intermediate 100.a) from 1-(4-methylpyridin-2-yl)piperazine (500 mg, 2.82 mmol) and 1-fluoro-4-nitrobenzene (438 mg, 3.10 mmol). Yield 330 mg (39%). Yellow solid. LC-MS: m/z=299.1 [M+H]$^+$.

b) 4-[4-(4-Methylpyridin-2-yl)piperazin-1-yl]aniline

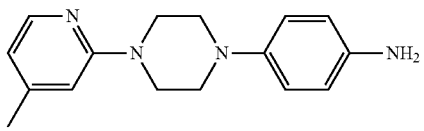

The title compound was prepared in analogy to 6-[4-(4-aminophenyl)piperazin-1-yl]pyridine-2-carbonitrile (Intermediate 100.b) from 1-(4-methylpyridin-2-yl)-4-(4-nitrophenyl)piperazine (500 mg, 1.68 mmol). Yield 360 mg (80%). Brown sticky solid. LC-MS: m/z=268.9 [M+H]$^+$.

c) 4-Methoxy-N-[4-[4-(4-methyl-2-pyridyl)piperazin-1-yl]phenyl]benzamide

To a solution of 4-methoxybenzoic acid (100 mg, 0.66 mmol) in THF (5 ml) were added DIPEA (0.43 ml, 2.63 mmol), T3P (50% sol in EA) (1 ml, 1.64 mmol) and 4-[4-(4-methylpyridin-2-yl)piperazin-1-yl]aniline (176 mg, 0.66 mmol). Then the reaction mixture was stirred at 25° C. for 16 h. The reaction mixture was poured into H$_2$O (20 ml) and extracted with EtOAc (2×50 ml). The combined organic phases were dried over Na$_2$SO$_4$ and solvents were evaporated. The resulting crude material was purified by flash chromatography (5% MeOH/DCM) to get the product (26 mg, 10%) as off-white solid. LC-MS: m/z=403.3 [M+H]$^+$.

Example 103

N-[4-[4-(3-Cyanophenyl)piperazin-1-yl]phenyl]-4-methoxy-benzamide

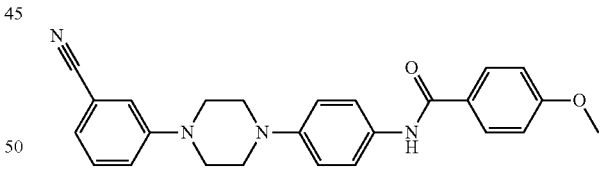

a) 3-[4-(4-Nitrophenyl)piperazin-1-yl]benzonitrile

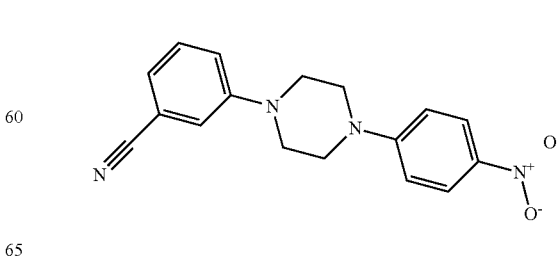

The title compound was prepared in analogy to 6-[4-(4-nitrophenyl)piperazin-1-yl]pyridine-2-carbonitrile (Intermediate 100.a) from 3-(piperazin-1-yl)benzonitrile (400 mg, 1.66 mmol) and 1-fluoro-4-nitrobenzene (258 mg, 1.83 mmol). Yield 410 mg (80%). Yellow solid.

b) 3-[4-(4-Aminophenyl)piperazin-1-yl]benzonitrile

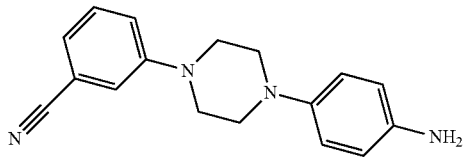 [SMILES: N#Cc1cccc(N2CCN(c3ccc(N)cc3)CC2)c1]

3-[4-(4-Nitrophenyl)piperazin-1-yl]benzonitrile (50 mg, 0.16 mmol) and SnCl$_2$.2H$_2$O (366 mg, 1.62 mmol) were suspended in EtOH (2.5 ml) and heated to 70° C. for 20 h. EtOH was evaporated and the remaining mixture was diluted with H$_2$O (10 ml), neutralized with aq. NaHCO$_3$ solution and extracted with EtOAc (2×30 ml). The combined organic layers were dried over Na$_2$SO$_4$ and concentrated to give 3-[4-(4-aminophenyl)piperazin-1-yl]benzonitrile (40 mg, 89%) as brown solid. This material was used with no further purification in the following. LC-MS: m/z=278.9 [M+H]$^+$.

c) N-[4-[4-(3-Cyanophenyl)piperazin-1-yl]phenyl]-4-methoxy-benzamide

The title compound was prepared in analogy to N-[4-[4-(6-cyano-2-pyridyl)piperazin-1-yl]phenyl]-4-methoxy-benzamide (Example 100.c) from 3-[4-(4-aminophenyl)piperazin-1-yl]benzonitrile (40 mg, 0.14 mmol) and 4-methoxybenzoyl chloride (0.02 ml, 0.14 mmol). Yield 45 mg (76%). Off-white solid. LC-MS: m/z=413.3 [M+H]$^+$.

Example 104

N-[4-[4-(3-Fluorophenyl)piperazin-1-yl]phenyl]-4-methoxy-benzamide

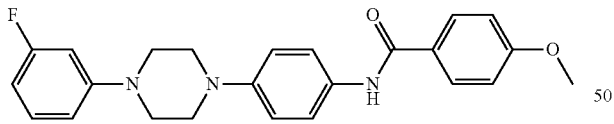

a) 1-(3-Fluorophenyl)-4-(4-nitrophenyl)piperazine

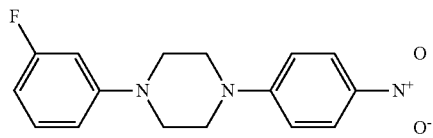

The title compound was prepared in analogy to 6-[4-(4-nitrophenyl)piperazin-1-yl]pyridine-2-carbonitrile (Intermediate 100.a) from 1-(3-fluorophenyl)piperazine (500 mg, 2.77 mmol) and 1-fluoro-4-nitrobenzene (430 mg, 3.05 mmol). Yield 410 mg (80%). Yellow solid. LC-MS: m/z=302.0 [M+H]$^+$.

b) 4-[4-(3-Fluorophenyl)piperazin-1-yl]aniline

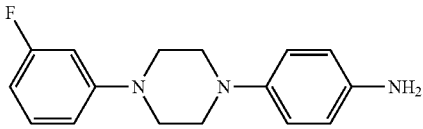 [SMILES: Nc1ccc(N2CCN(c3cccc(F)c3)CC2)cc1]

The title compound was prepared in analogy to 6-[4-(4-aminophenyl)piperazin-1-yl]pyridine-2-carbonitrile (Intermediate 100.b) from 1-(3-fluorophenyl)-4-(4-nitrophenyl)piperazine (500 mg, 1.68 mmol). Yield 360 mg (80%). Off-white solid. LC-MS: m/z=272.0 [M+H]$^+$.

c) N-[4-[4-(3-Fluorophenyl)piperazin-1-yl]phenyl]-4-methoxy-benzamide

The title compound was prepared in analogy to 4-methoxy-N-[4-[4-(4-methyl-2-pyridyl)piperazin-1-yl]phenyl]benzamide (Example 102, step c) from 4-[4-(3-fluoro-phenyl)piperazin-1-yl]aniline (178 mg, 0.66 mmol) and 4-methoxybenzoic acid (100 mg, 0.66 mmol). Yield 55 mg (21%). White solid. LC-MS: m/z=406.3 [M+H]$^+$.

Example 105

N-[4-[4-(4-Fluorophenyl)piperazin-1-yl]phenyl]-4-methoxy-benzamide

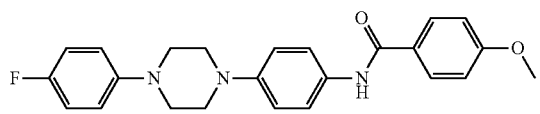 [SMILES: COc1ccc(C(=O)Nc2ccc(N3CCN(c4ccc(F)cc4)CC3)cc2)cc1]

a) 1-(4-Fluorophenyl)-4-(4-nitrophenyl)piperazine

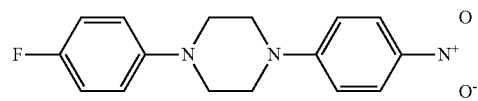

The title compound was prepared in analogy to 6-[4-(4-nitrophenyl)piperazin-1-yl]pyridine-2-carbonitrile (Intermediate 100.a) from 1-(4-fluorophenyl)piperazine (500 mg, 2.77 mmol) and 1-fluoro-4-nitrobenzene (430 mg, 3.05 mmol). Yield 540 mg (65%). Yellow solid. LC-MS: m/z=302.2 [M+H]$^+$.

b) 4-[4-(4-Fluorophenyl)piperazin-1-yl]aniline

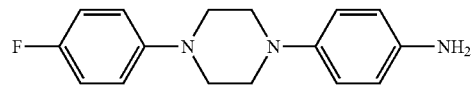 [SMILES: Nc1ccc(N2CCN(c3ccc(F)cc3)CC2)cc1]

The title compound was prepared in analogy to 6-[4-(4-aminophenyl)piperazin-1-yl]pyridine-2-carbonitrile (Intermediate 100.b) from 1-(4-fluorophenyl)-4-(4-nitrophenyl)piperazine (500 mg, 1.68 mmol). Yield 380 mg (84%). Off-white solid. LC-MS: m/z=217.9 [M+H]+.

c) N-[4-[4-(4-Fluorophenyl)piperazin-1-yl]phenyl]-4-methoxy-benzamide

The title compound was prepared in analogy to 4-methoxy-N-[4-[4-(4-methyl-2-pyridyl)piperazin-1-yl]phenyl]benzamide (Example 102.c) from 4-[4-(4-fluorophenyl)piperazin-1-yl]aniline (178 mg, 0.66 mmol) and 4-methoxybenzoic acid (100 mg, 0.66 mmol). Yield 27 mg (10%). Off-white solid. LC-MS: m/z=406.2 [M+H]+.

Example 106

N-[3-Fluoro-4-[4-(2-pyridyl)piperazin-1-yl]phenyl]-4-methoxy-benzamide

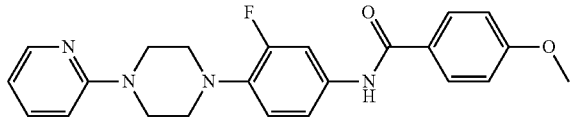 [SMILES: COc1ccc(C(=O)Nc2ccc(N3CCN(c4ccccn4)CC3)c(F)c2)cc1]

To a solution of 3-fluoro-4-[4-(2-pyridyl)piperazin-1-yl]aniline (CAS Nr. 202133-31-1) (200 mg, 0.730 mmol) in THF (10 ml) at 0° C. under N₂ was added Et₃N (0.2 ml, 1.51 mmol) and 4-methoxybenzoyl chloride (0.1 ml, 0.73 mmol). The mixture was stirred 1 h at 0° C. The reaction mixture was diluted with H₂O and extracted with EtOAc (2×50 ml) and the organic layers were washed with brine, dried over Na₂SO₄ and concentrated under reduced pressure. The resulting crude product was purified by flash chromatography to get N-[3-fluoro-4-[4-(2-pyridyl)piperazin-1-yl]phenyl]-4-methoxy-benzamide (270 mg, 89%) as off-white solid. LC-MS: m/z=407.3 [M+H]+.

Example 107

N-[4-[4-(5-Cyano-2-pyridyl)piperazin-1-yl]-3-fluoro-phenyl]-4-methoxy-benzamide

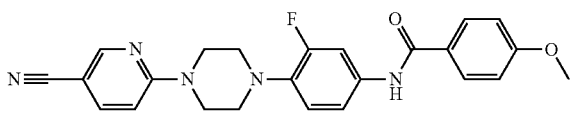 [SMILES: COc1ccc(C(=O)Nc2ccc(N3CCN(c4ccc(C#N)cn4)CC3)c(F)c2)cc1]

a) 6-[4-(4-Amino-2-fluoro-phenyl)piperazin-1-yl]pyridine-3-carbonitrile

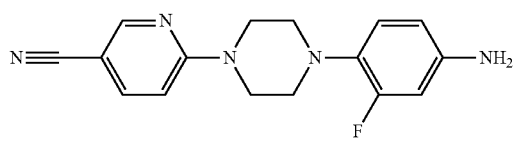 [SMILES: N#Cc1ccc(N2CCN(c3ccc(N)cc3F)CC2)nc1]

6-[4-(2-Fluoro-4-nitro-phenyl)piperazin-1-yl]pyridine-3-carbonitrile (400 mg, 1.22 mmol) and SnCl₂.2H₂O (2.76 g, 12.2 mmol) were suspended in EtOH (10 ml) and heated to 70° C. for 16 h. EtOH was evaporated and the residue was diluted with H₂O, neutralized with aq. NaHCO₃ solution and extracted with DCM (2×100 ml). The combined organic layers were dried over Na₂SO₄ and concentrated to give 6-[4-(4-amino-2-fluoro-phenyl)piperazin-1-yl]pyridine-3-carbonitrile (270 mg, 74%) as off-white solid. This material was used in the following step without further purification. LC-MS: m/z=298.3 [M+H]+.

b) N-[4-[4-(5-Cyano-2-pyridyl)piperazin-1-yl]-3-fluoro-phenyl]-4-methoxy-benzamide The title compound was prepared in analogy to N-[3-fluoro-4-[4-(2-pyridyl)piperazin-1-yl]phenyl]-4-methoxy-benzamide (Example 106) from 6-[4-(4-amino-2-fluoro-phenyl)piperazin-1-yl]pyridine-3-carbonitrile (200 mg, 0.67 mmol) and 4-methoxybenzoyl chloride (0.09 ml, 0.67 mmol). Yield 18 mg (6%). White solid. LC-MS: m/z=432.2 [M+H]+.

Example 108

N-(4-(4-(5-Cyanopyridin-2-yl)piperazin-1-yl)phenyl)-4-hydroxybenzamide

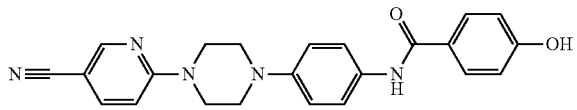 [SMILES: N#Cc1ccc(N2CCN(c3ccc(NC(=O)c4ccc(O)cc4)cc3)CC2)nc1]

a) [4-[[4-[4-(5-Cyano-2-pyridyl)piperazin-1-yl]phenyl]carbamoyl]phenyl] acetate

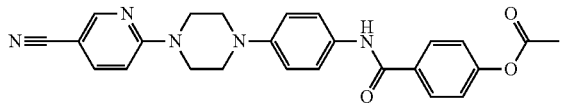 [SMILES: CC(=O)Oc1ccc(C(=O)Nc2ccc(N3CCN(c4ccc(C#N)cn4)CC3)cc2)cc1]

To a solution of 4-acetoxybenzoic acid (1.29 g, 7.16 mmol) in DCM (60 ml) were added oxalyl chloride (1.36 g, 940 µl, 10.7 mmol) and DMF (26.2 mg, 27.7 µl, 358 µmol) and the mixture stirred at 20-25° C. for 1.5 h. The reaction mixture was concentrated under vacuum. The crude product was dissolved in DCM (30 ml) and added to a solution of 6-[4-(4-aminophenyl)piperazin-1-yl]pyridine-3-carbonitrile (Intermediate 50.a) (2.0 g, 7.16 mmol) and DIPEA (3.7 g, 5.0 ml, 28.6 mmol) in DCM (60 ml). The light brown suspension was stirred at 20-25° C. for 30 min. Then MeOH (6 ml) was added to quench the reaction. The suspension was stirred for 1 h and filtered. The cake was washed with DCM (10 ml) and dried on the filter for 2 min. Then the cake was washed with H₂O (25 ml) and finally dried under vacuum at 40° C. to obtain the desired product (2.91 g, 92%) as colorless crystals. LC MS m/z=442.3 [M+H]+.

b) N-[4-[4-(5-Cyano-2-pyridyl)piperazin-1-yl]phenyl]-4-hydroxy-benzamide

To a suspension of 4-((4-(4-(5-cyanopyridin-2-yl)piperazin-1-yl)phenyl)carbamoyl)phenyl acetate (2.8 g, 6.34 mmol) in MeOH (84 ml) was added NaOH 1M in H₂O (25.4 ml, 25.4 mmol), and the suspension was stirred for 1 h. Most of MeOH was removed under vacuum. Then HCl 1M in H₂O (25.4 ml, 25.4 mmol) was added to reach pH 4-5. The resulting suspension was filtered, the cake washed with H₂O (25 ml) and then dried under vacuum at 40° C. to obtain the desired product (2.48 g, 98%) as white crystals. LC-MS: m/z=400.3 [M+H]⁺.

Example 109

4-Methoxy-N-[4-[4-(p-tolyl)piperazin-1-yl]phenyl]benzamide

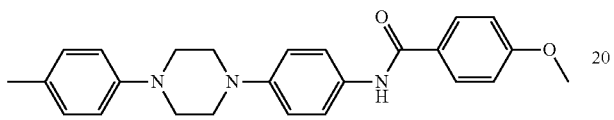

The title compound was prepared in analogy to N-[4-[4-(6-cyano-2-pyridyl)piperazin-1-yl]phenyl]-4-methoxy-benzamide (Example 100, step c) from 4-[4-(p-tolyl)piperazin-1-yl]aniline (CAS Nr. 68944-99-0) (100 mg, 0.370 mmol) and 4-methoxybenzoyl chloride (0.06 ml, 0.41 mmol). Yield 46 mg (29%). Off-white solid. LC-MS: m/z=402.3 [M+H]⁺.

Example 110

4-Methoxy-N-[4-[4-(4-methoxyphenyl)piperazin-1-yl]phenyl]benzamide

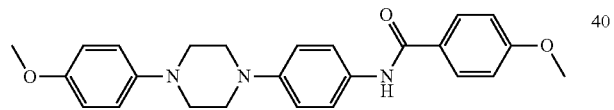

The title compound was prepared in analogy to N-[4-[4-(6-cyano-2-pyridyl)piperazin-1-yl]phenyl]-4-methoxy-benzamide (Example 100, step c) from 4-[4-(4-methoxyphenyl)piperazin-1-yl]aniline (CAS Nr. 74852-62-3) (75.0 mg, 0.260 mmol) and 4-methoxybenzoyl chloride (0.04 ml, 0.290 mmol). Yield 80 mg (69%). White solid. LC-MS: m/z=418.2 [M+H]⁺.

Example 111

4-Methoxy-N-[4-[4-(4-methylsulfonylphenyl)piperazin-1-yl]phenyl]benzamide

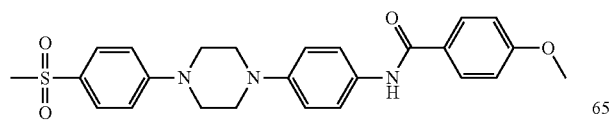

a) 1-(4-Methylsulfonylphenyl)-4-(4-nitrophenyl)piperazine

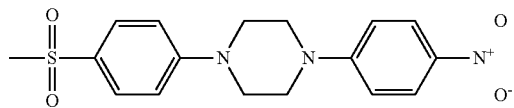

The title compound was prepared in analogy to 6-[4-(4-nitrophenyl)piperazin-1-yl]pyridine-2-carbonitrile (Intermediate 100.a) from 1-(4-methylsulfonylphenyl)piperazine (730.0 mg, 3.04 mmol) and 1-fluoro-4-nitrobenzene (471 mg, 3.34 mmol). Yield 520 mg (43%). Yellow solid.

b) 4-[4-(4-Methylsulfonylphenyl)piperazin-1-yl]aniline

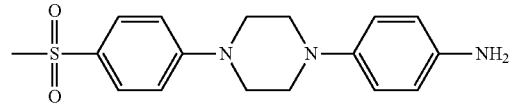

1-(4-Methylsulfonylphenyl)-4-(4-nitrophenyl)piperazine (500 mg, 1.38 mmol) and SnCl₂.2H₂O (3.12 g, 13.8 mmol) were suspended in EtOH (10 ml) and heated to 70° C. for 16 h. EtOH was evaporated under reduced pressure and the residue was diluted with H₂O, neutralised with aq. NaHCO₃ solution and extracted with DCM (2×100 ml). The combined organic layers were dried over Na₂SO₄ and concentrated to give 4-[4-(4-methylsulfonylphenyl)piperazin-1-yl]aniline (220 mg 46%) as off-white solid. This material was used without further purification in the next step. LC-MS: m/z=232.2 [M+H]⁺.

c) 4-Methoxy-N-[4-[4-(4-methylsulfonylphenyl)piperazin-1-yl]phenyl]benzamide

The title compound was prepared in analogy to N-[4-[4-(6-cyano-2-pyridyl)piperazin-1-yl]phenyl]-4-methoxy-benzamide (Example 100.c) from 4-[4-(4-methylsulfonylphenyl)piperazin-1-yl]aniline (100 mg, 0.300 mmol) and 4-methoxybenzoyl chloride (0.04 ml, 0.330 mmol). Yield 57 mg (39%). White solid. LC-MS: m/z=466.3 [M+H]⁺.

Example 112

N-[4-[4-(4-Cyanophenyl)piperazin-1-yl]-3-methylphenyl]-4-methoxy-benzamide

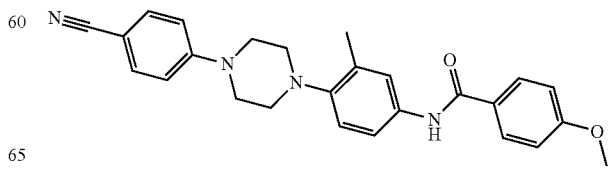

a) 4-[4-(2-Methyl-4-nitro-phenyl)piperazin-1-yl]benzonitrile

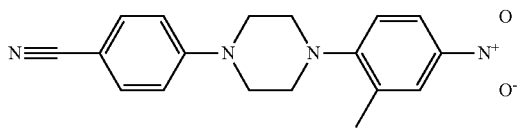

To a solution under N₂ of 1-(4-cyanophenyl)piperazine (543 mg, 2.9 mmol) in DMF (10 ml) was added K₂CO₃ (672 mg, 4.83 mmol) and the mixture was stirred at 25° C. for 5 min. After that 2-fluoro-5-nitrotoluene (300 mg, 1.93 mmol) was added. The reaction vessel was sealed and the mixture was stirred 16 h at 100° C. After cooling to 25° C., the reaction mixture was diluted with H₂O (30 ml) and extracted with EtOAc (2×100 ml). The organic phases were washed with brine, dried over Na₂SO₄ and concentrated under reduced pressure. The crude product was purified by flash chromatography (20% EtOAc/hexane) to get 4-[4-(2-methyl-4-nitro-phenyl)piperazin-1-yl]benzonitrile (440 mg, 63%) as orange solid.

b) 4-[4-(4-Amino-2-methyl-phenyl)piperazin-1-yl]benzonitrile

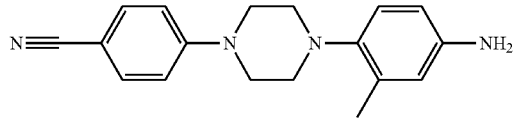 [SMILES: Cc1cc(N)ccc1N1CCN(c2ccc(C#N)cc2)CC1]

4-[4-(2-Methyl-4-nitro-phenyl)piperazin-1-yl]benzonitrile (400 mg, 1.24 mmol) and SnCl₂.2H₂O (2.80 g, 12.4 mmol) were suspended in EtOH (10 ml) and heated to 70° C. for 20 h. EtOH was evaporated under reduced pressure and the residue was diluted with H₂O (20 ml), neutralised with aq. NaHCO₃ solution and extracted with DCM (2×100 ml). The combined organic layers were dried over Na₂SO₄ and concentrated to give the title compound (200 mg, 51%) as off-white solid. This material was used without further purification in the next step.

c) N-[4-[4-(4-Cyanophenyl)piperazin-1-yl]-3-methyl-phenyl]-4-methoxy-benzamide The title compound was prepared in analogy to N-[4-[4-(6-cyano-2-pyridyl)piperazin-1-yl]phenyl]-4-methoxy-benzamide (Example 100, step c) from 4-[4-(4-amino-2-methyl-phenyl)piperazin-1-yl]benzonitrile (200 mg, 0.680 mmol) and 4-methoxybenzoyl chloride (0.1 ml, 0.750 mmol). Yield 75 mg (23%). Off-white solid. LC-MS: m/z=427.3 [M+H]⁺.

Example 113

N-[4-[4-(5-Cyano-2-pyridyl)piperazin-1-yl]-3-methyl-phenyl]-4-methoxy-benzamide

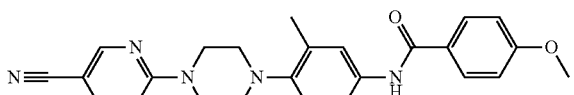

a) 6-[4-(2-Methyl-4-nitro-phenyl)piperazin-1-yl]pyridine-3-carbonitrile

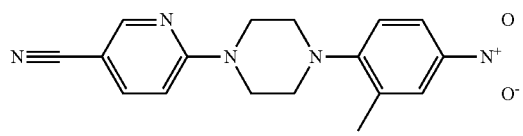

The title compound was prepared in analogy to 4-[4-(2-methyl-4-nitro-phenyl)piperazin-1-yl]benzonitrile (Intermediate 112.a) from 6-piperazinonicotinonitrile (546 mg, 2.9 mmol) and 2-fluoro-5-nitrotoluene (300 mg, 1.93 mmol). Yield 229 mg (32%). Yellow solid.

b) 6-[4-(4-Amino-2-methyl-phenyl)piperazin-1-yl]pyridine-3-carbonitrile

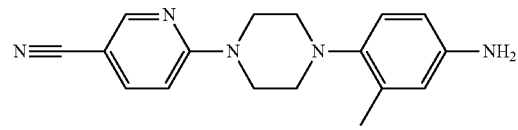 [SMILES: Cc1cc(N)ccc1N1CCN(c2ccc(C#N)cn2)CC1]

The title compound was prepared in analogy to 4-[4-(4-amino-2-methyl-phenyl)piperazin-1-yl]benzonitrile (Intermediate 112.b) from 6-[4-(2-methyl-4-nitro-phenyl)piperazin-1-yl]pyridine-3-carbonitrile (200 mg, 0.620 mmol). Yield 160 mg (84%). Off-white solid. LCMS: m/z=311.4 [M+NH4]⁺.

c) N-[4-[4-(5-Cyano-2-pyridyl)piperazin-1-yl]-3-methyl-phenyl]-4-methoxy-benzamide The title compound was prepared in analogy to N-[4-[4-(6-cyano-2-pyridyl)piperazin-1-yl]phenyl]-4-methoxy-benzamide (Example 100, step c) from 6-[4-(4-amino-2-methyl-phenyl)piperazin-1-yl]pyridine-3-carbonitrile (160 mg, 0.550 mmol) and 4-methoxybenzoyl chloride (0.08 ml, 0.60 mmol). Yield 120 mg (48%). Off-white solid. LC-MS: m/z=428.3 [M+H]⁺.

Example 114

N-[4-[4-(4-Cyanophenyl)piperazin-1-yl]phenyl]-2-fluoro-4-methoxy-benzamide

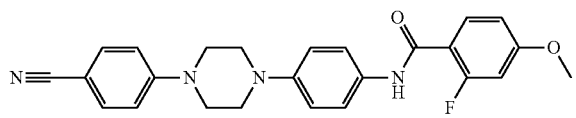

To a solution of 4-[4-(4-aminophenyl)piperazin-1-yl]benzonitrile (Intermediate 57.a) (250 mg, 0.900 mmol) in dry THF (10 ml) cooled with an ice/H₂O bath, were added Et₃N (0.29 ml, 2.25 mmol) and 2-fluoro-4-methoxybenzoyl chloride (186 mg, 0.990 mmol). The reaction mixture was stirred 1 h at 0° C. Then the reaction mixture was poured into H₂O (10 ml) and extracted with EtOAc (2×50 ml). The combined organic layers were dried over Na₂SO₄, and concentrated.

The resulting crude product was purified by flash chromatography (50% EtOAc/hexane) to get N-[4-[4-(4-cyanophenyl)piperazin-1-yl]phenyl]-2-fluoro-4-methoxy-benzamide (216 mg, 52%) as off-white solid. LC-MS: m/z=431.2 [M+H]⁺.

Example 115

N-[4-[4-(5-Cyano-2-pyridyl)piperazin-1-yl]phenyl]-2-fluoro-4-methoxy-benzamide

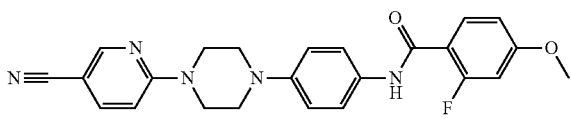

The title compound was prepared in analogy to N-[4-[4-(4-cyanophenyl)piperazin-1-yl]phenyl]-2-fluoro-4-methoxy-benzamide (Example 114) from 6-[4-(4-aminophenyl)piperazin-1-yl]pyridine-3-carbonitrile (Intermediate 50.a) (200 mg, 0.670 mmol) and 2-fluoro-4-methoxybenzoyl chloride (186 mg, 0.980 mmol). Yield 77 mg (19%). Off-white solid. LCMS: m/z=432.2 [M+H]⁺.

Example 116

N-[4-[4-(5-Cyano-2-pyridyl)piperazin-1-yl]phenyl]-4-(2-fluoroethoxy)benzamide

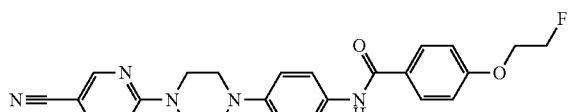

To a solution of 4-(2-fluoroethoxy)benzoic acid [CAS Nr. 145304-35-4] (150 mg, 0.810 mmol) in DMF (5 ml) were added DIPEA (0.42 ml, 2.44 mmol), EDC HCl (234 mg, 1.22 mmol), HOBt (165 mg, 1.22 mmol) and 6-[4-(4-aminophenyl)piperazin-1-yl]pyridine-3-carbonitrile (Intermediate 50.a) (227 mg, 0.810 mmol). The reaction mixture was stirred at 25° C. for 16 h. The reaction mixture was poured into H₂O (20 ml) and extracted with EtOAc (2×50 ml). The combined organic layers were dried over Na₂SO₄ and solvents were evaporated. The resulting crude product was purified by flash chromatography (amine silica gel, 50% EtOAc/Hexane) to get N-[4-[4-(5-cyano-2-pyridyl)piperazin-1-yl]phenyl]-4-(2-fluoroethoxy)benzamide (170 mg, 47%) as off-white solid. LC-MS: m/z=446.3 [M+H]⁺.

Example 117

N-[4-[4-(4-Cyanophenyl)piperazin-1-yl]phenyl]-4-(2-fluoroethoxy)benzamide

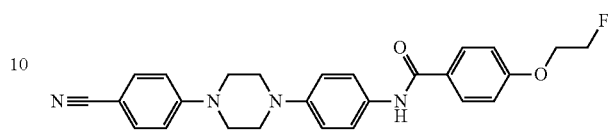

The title compound was prepared in analogy to N-[4-[4-(5-cyano-2-pyridyl)piperazin-1-yl]phenyl]-4-(2-fluoroethoxy)benzamide (Example 116) from 4-[4-(4-aminophenyl)piperazin-1-yl]benzonitrile (Intermediate 57.a) (227 mg, 0.810 mmol) and 4-(2-fluoroethoxy)benzoic acid (CAS Nr. 145304-35-4) (150 mg, 0.810 mmol). Yield 70 mg (19%). Light yellow solid. LC-MS: m/z=445.1 [M+H]⁺.

Example 118

4-(2-Fluoroethoxy)-N-[4-[4-(2-pyridyl)piperazin-1-yl]phenyl]benzamide

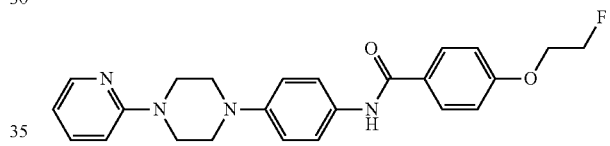

The title compound was prepared in analogy to N-[4-[4-(5-cyano-2-pyridyl)piperazin-1-yl]phenyl]-4-(2-fluoroethoxy)benzamide (Example 116) from 4-[4-(2-pyridyl)piperazin-1-yl]aniline (Intermediate 1.b) (249 mg, 0.980 mmol) and 4-(2-fluoroethoxy)benzoic acid (CAS Nr. 145304-35-4) (150 mg, 0.810 mmol). Yield 10 mg (3%). Off-white solid. LC-MS: m/z=421.0 [M+H]⁺.

Example 119

4-(2-Fluoroethoxy)-N-[4-[4-(4-thiazol-2-ylpiperazin-1-yl)phenyl]benzamide

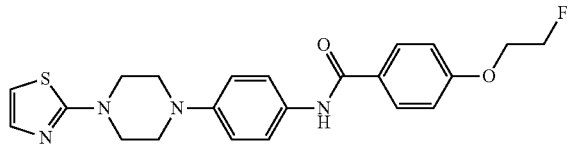 [SMILES: O=C(Nc1ccc(N2CCN(c3nccs3)CC2)cc1)c1ccc(OCCF)cc1]

The title compound was prepared in analogy to N-[4-[4-(5-cyano-2-pyridyl)piperazin-1-yl]phenyl]-4-(2-fluoroethoxy)benzamide (Example 116) from 4-(4-thiazol-2-ylpiperazin-1-yl)aniline (Intermediate 13.b) (254 mg, 0.980 mmol) and 4-(2-fluoroethoxy)benzoic acid (CAS Nr. 145304-35-4) (150 mg, 0.810 mmol). Yield 76 mg (20%). Light yellow solid. LCMS: m/z=427.2 [M+H]⁺.

Example 120

4-[2-[2-(2-Fluoroethoxy)ethoxy]ethoxy]-N-[4-(4-thiazol-2-ylpiperazin-1-yl)phenyl]benzamide

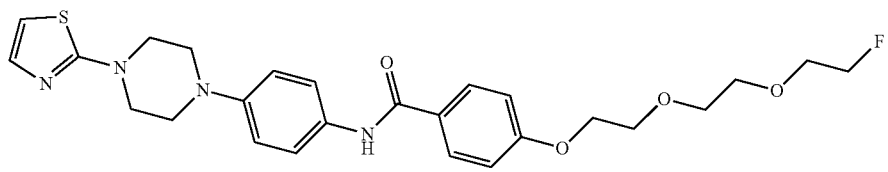 [SMILES: O=C(Nc1ccc(N2CCN(c3nccs3)CC2)cc1)c1ccc(OCCOCCOCCF)cc1]

The title compound was prepared in analogy to N-[4-[4-(5-cyano-2-pyridyl)piperazin-1-yl]phenyl]-4-(2-fluoroethoxy)benzamide (Example 116) from 4-(4-thiazol-2-ylpiperazin-1-yl)aniline (Intermediate 13.b) (115 mg, 0.440 mmol) and 4-[2-[2-(2-fluoroethoxy)ethoxy]ethoxy]benzoic acid (CAS Nr. 1269797-18-3) (100 mg, 0.370 mmol). Yield 105 mg (55%). Off-white solid. LC-MS: m/z=515.2 [M+H]+.

Example 121

N-(4-(4-(5-Cyanopyridin-2-yl)piperazin-1-yl)phenyl)-4-(2-(2-fluoroethoxy)ethoxy)benzamide

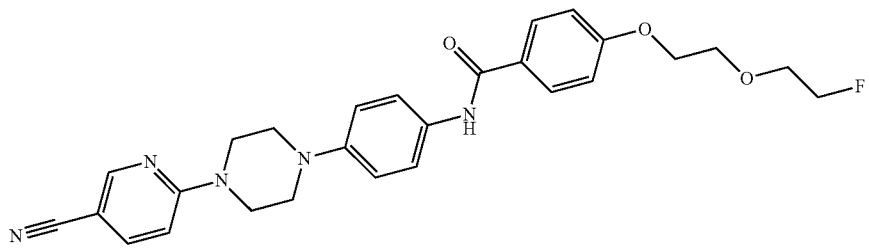 [SMILES: N#Cc1ccc(N2CCN(c3ccc(NC(=O)c4ccc(OCCOCCF)cc4)cc3)CC2)nc1]

a) 2-(2-Hydroxyethoxy)ethyl 4-methylbenzenesulfonate

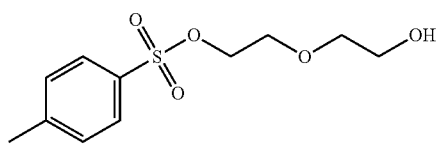 [SMILES: Cc1ccc(S(=O)(=O)OCCOCCO)cc1]

To a solution of diethyleneglycol (20.0 g, 17.9 ml, 188 mmol) in DCM (200 ml) under argon were added tosyl chloride (53.9 g, 283 mmol) and silver oxide (65.5 g, 283 mmol) and the suspension was cooled to 0-5° C. Then potassium iodide (6.26 g, 37.7 mmol) was added over 10 min in 5 portions. After the addition was completed, the reaction was warmed to 20-25° C. and stirred for 1.5 h. The dark grey suspension was filtered, the cake washed with DCM (100 ml), and the filtrate concentrated under vacuum at 40° C. A yellowish non-transparent emulsion was obtained which was purified by flash chromatography (SiO$_2$, Hept/EtOAc 5% to 90%) to obtain the desired product (11.6 g, 24%) as a colorless oil. LC-MS: m/z=415.2 [M+H]+.

b) 2-(2-Fluoroethoxy)ethyl 4-methylbenzenesulfonate

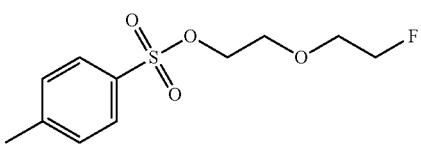 [SMILES: Cc1ccc(S(=O)(=O)OCCOCCF)cc1]

To a solution of 2-(2-hydroxyethoxy)ethyl 4-methylbenzenesulfonate (7.64 g, 29.3 mmol) in DCM (115 ml) under Ar was added at 0-5° C. diethylaminosulfur trifluoride (14.2 g, 11.6 ml, 88 mmol). The light yellow solution was warmed to 20-25° C. and was stirred for 1 h. The reaction mixture was cooled again to 5-10° C. and quenched with 1M NaHCO$_3$ (200 ml) and solid NaHCO$_3$ (11 g) was added to reach pH 7-8. The organic layer was concentrated under vacuum. Due to bad conversion, the crude was dissolved again in DCM (115 ml) under Ar and diethylaminosulfur trifluoride (7.1 g, 5.82 ml, 44 mmol) was added at 0-5° C. The light yellow solution was warmed to 20-25° C. and stirred for 1 h. The reaction mix was cooled again to 5-10° C. and quenched with 1M NaHCO$_3$ (200 ml), and solid NaHCO$_3$ (3 g) was added to reach pH 7-8. The organic layer was concentrated under vacuum to obtain the crude product as a yellow oil which was purified by MPLC over silica (eluent: heptane/ethyl acetate) to obtain the desired product (3.4 g, 44%) as a light yellow oil. $^1$H NMR (400 MHz, CHLOROFORM-d) δ ppm 1.56 (s, 1H) 1.90 (t, J=6.18 Hz, 1H) 2.45 (s, 3H) 3.50-3.57 (m, 2H) 3.63-3.74 (m, 4H) 4.16-4.25 (m, 2H) 7.31-7.41 (m, 2H) 7.76-7.85 (m, 2H). LCMS: m/z=261.2 [M−H]−.

c) Methyl 4-[2-(2-fluoroethoxy)ethoxy]benzoate

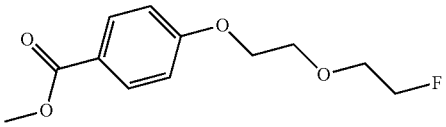 [SMILES: COC(=O)c1ccc(OCCOCCF)cc1]

To a solution of 2-(2-fluoroethoxy)ethyl 4-methylbenzenesulfonate (3.4 g, 13 mmol) in DMF (34 ml) were added methyl 4-hydroxybenzoate (1.97 g, 13 mmol,) and $Cs_2CO_3$ (8.45 g, 25.9 mmol). The yellow suspension was heated to 50° C. for 2 h. The reaction was quenched with $H_2O$ (200 ml) and extracted with EtOAc (3×200 ml). The combined organic layers were dried over $Na_2SO_4$ and concentrated under vacuum to obtain the crude product as yellow oil. Purification by MPLC over silica (eluent: heptane/ethyl acetate) provided the desired product (2.86, 91%) as colorless oil. LC MS: m/z=243.2 [M+H]$^+$.

d) 4-[2-(2-Fluoroethoxy)ethoxy]benzoic acid

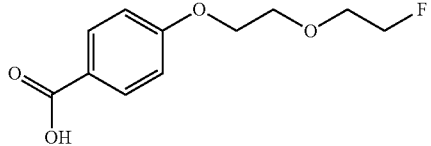 [SMILES: O=C(O)c1ccc(OCCOCCF)cc1]

To a solution of methyl 4-(2-(2-fluoroethoxy)ethoxy) benzoate (2.86 g, 11.8 mmol) in MeOH (29 ml) was added 2M aq.NaOH (23.6 ml, 47.2 mmol), and the colorless solution was stirred at 20-25° C. for 2 h. Most of MeOH was removed under vacuum. Then 2 M aq. HCl (23.6 ml, 47.2 mmol) was added over 1 min to reach pH 1-2 and an homogenous suspension was formed. The suspension was stirred for 1 h at 20-25° C., filtered, and the cake was washed with $H_2O$ (2×10 ml) and dried under vacuum to obtain the desired product (2.64 g, 98%) as colorless crystals. LC MS: m/z=229.2 [M+H]$^+$.

e) N-(4-(4-(5-Cyanopyridin-2-yl)piperazin-1-yl)phenyl)-4-(2-(2-fluoroethoxy)ethoxy)benzamide To a solution of 4-(2-(2-fluoroethoxy)ethoxy)benzoic acid (833 mg, 3.65 mmol) in DCM (30 ml) were added oxalyl chloride (695 mg, 479 µl, 5.48 mmol) and DMF (13.3 mg, 14.1 µl, 183 µmol) and the mixture was stirred at 20-25° C. for 1.5 h. The reaction mixture was concentrated under vacuum at 40° C. The crude acid chloride was dissolved in DCM (15 ml) and added to a solution of 6-[4-(4-aminophenyl)piperazin-1-yl]pyridine-3-carbonitrile (Intermediate 50.a) (1.02 g, 3.65 mmol) and DIPEA (1.89 g, 2.55 ml) in DCM (30 ml). The light yellow, thick suspension was stirred at 20-25° C. for 30 min. Then MeOH (3 ml) was added to quench the reaction. The resulting suspension was stirred for 1 h, filtered, and the cake was washed with DCM (10 ml) and dried on the filter for 2 min. Then the cake was washed with $H_2O$ (25 ml) and finally dried under vacuum at 40° C. to obtain the desired product (1.34 g, 75%) as colorless crystals. LC MS: m/z=490.2 [M+H]$^+$.

Example 122

N-(4-(4-(4-Cyanophenyl)piperazin-1-yl)phenyl)-4-(2-(2-fluoroethoxy)ethoxy)benzamide

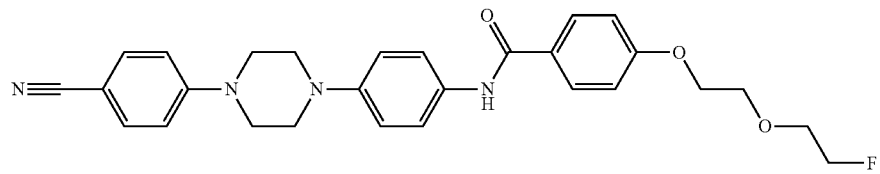 [SMILES: N#Cc1ccc(N2CCN(c3ccc(NC(=O)c4ccc(OCCOCCF)cc4)cc3)CC2)cc1]

To a solution of 4-(2-(2-fluoroethoxy)ethoxy)benzoic acid (Intermediate 121.d) (74.3 mg, 326 µmol) in DMF (2 ml) was added at 22° C. HATU (124 mg, 326 µmol) followed by N,N-diisopropylethylamine (80.1 mg, 108 µl, 620 µmol) and the mixture was stirred at 22° C. for 30 min. Then was added 4-(4-(4-aminophenyl)piperazin-1-yl)benzonitrile (Intermediate 57.a) (86.3 mg, 310 µmol) to give after 30 min a brown suspension. After stirring at 22° C. for a total 2 h the mixture was quenched with half-sat. $NaHCO_3$ (20 ml) and extracted with DCM (4×20 ml). The organic layers were dried and evaporated, and further dried in the HV at 50° C. The crude product was suspended in 6 ml DCM for 3 h. The solid was filtered off, washed with DCM (2×1 ml) and dried in HV to give a first portion of not yet clean product. The filtrate was treated with DCM/MeOH resulting after filtration in a second portion of product. The combined solids and the clear filtrate were purified separately by flash chromatography (silica gel; MeOH in DCM 0% to 4%) to give pure product. Combined yield 91 mg (60%). Off-white solid. LC-MS: m/z=489.5 [M+H]$^+$.

Example 123

N-[4-[4-(4-Cyanophenyl)piperazin-1-yl]phenyl]-4-[2-[2-(2-fluoroethoxy)ethoxy]ethoxy]benzamide

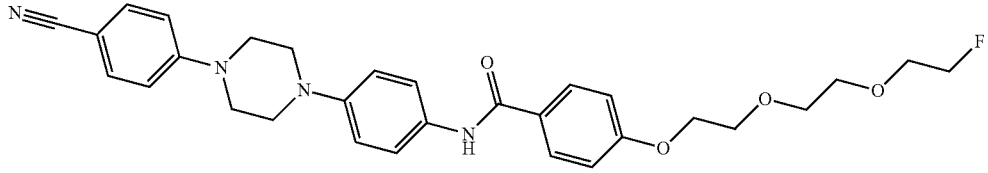 [SMILES: N#Cc1ccc(N2CCN(c3ccc(NC(=O)c4ccc(OCCOCCOCCF)cc4)cc3)CC2)cc1]

The title compound was prepared in analogy to N-[4-[4-(5-cyano-2-pyridyl)piperazin-1-yl]phenyl]-4-(2-fluoroethoxy)benzamide (Example 116) from 4-[4-(4-aminophenyl)

piperazin-1-yl]benzonitrile (Intermediate 57.a) (123 mg, 0.440 mmol) and 4-[2-[2-(2-fluoroethoxy)ethoxy]ethoxy]benzoic acid (CAS Nr. 1269797-18-3) (100 mg, 0.370 mmol). Yield 42 mg (21%). Off-white solid. LC-MS: m/z=533.3 [M+H]$^+$.

Example 124 rac-4-(2-((tert-Butyldimethylsilyl)oxy)-3-fluoropropoxy)-N-(4-(4-(pyridin-2-yl)piperazin-1-yl)phenyl)benzamide

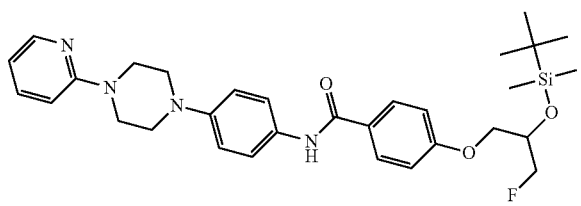 [SMILES: CC(C)(C)[Si](C)(C)OC(CF)COc1ccc(C(=O)Nc2ccc(N3CCN(c4ccccn4)CC3)cc2)cc1]

a) rac-Methyl 4-(3-fluoro-2-hydroxypropoxy)benzoate

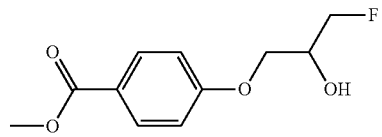 [SMILES: COC(=O)c1ccc(OCC(O)CF)cc1]

To a solution of methyl rac-4-(oxiran-2-ylmethoxy)benzoate (CAS Nr. 5535-03-5) (312 mg, 1.5 mmol) in Tol (3 ml) was added at 22° C. tetra-n-butylammonium fluoride, 1 M in THF (3.3 ml, 3.3 mmol). The mixture was warmed to 80° C. and stirred for 1 h. The mixture was evaporated, quenched with H$_2$O (6 ml) and set acidic (pH=1-2) by addition of 1 N aq. HCl (3.3 ml). The aqueous mixture was extracted with ethyl acetate (3×10 ml). The organic layers were washed with sat NaCl (2×10 ml), dried and evaporated. The residue was purified by flash chromatography (silica gel, 12 g, EtOAc in heptane 5% to 40% to 100%) to give the title compound (120 mg, 35%) as colorless oil. LC-MS: m/z=229.2 [M+H)]$^+$.

b) rac-Methyl 4-(2-((tert-butyldimethylsilyl)oxy)-3-fluoropropoxy)benzoate

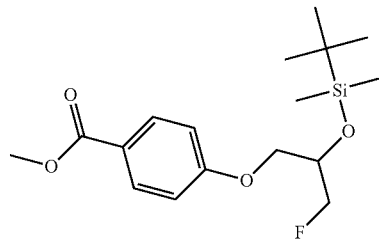

To a solution of methyl 4-(3-fluoro-2-hydroxypropoxy)benzoate (100 mg, 438 µmol) in DCM (1.5 ml) was added at 22° C. imidazole (59.7 mg, 876 µmol) followed by DMAP (5.35 mg, 43.8 µmol). Then was added dropwise a solution of TBDMS-Cl (79.3 mg, 526 µmol) in DCM (0.5 ml) and the mixture was stirred at 22° C. for 90 min to give ca. 60% conversion. After 3.5 h further imidazole (89.5 mg, 1.31 mmol) was added followed by a solution of TBDMS-Cl (119 mg, 789 µmol) in DCM (1 ml). The reaction mixture was stirred for 15 min at 22° C. to give complete conversion. The solid was filtered off and washed with DCM (2×2 ml). The filtrate was evaporated, adsorbed on Isolute HM-N and directly purified by flash chromatography (silica gel, 12 g, EtOAc in heptane 5% to 20% to 50%) to give the title compound (113 mg, 75%) as colorless oil. LC-MS: m/z=343.3 [M+H]$^+$.

c) rac-4-(2-((tert-Butyldimethylsilyl)oxy)-3-fluoropropoxy)-N-(4-(4-(pyridin-2-yl)piperazin-1-yl)phenyl)benzamide To a solution of 4-(4-(pyridin-2-yl)piperazin-1-yl)aniline (Intermediate 1.b) (58 mg, 228 µmol) in dioxane (2.3 ml) was added at 22° C. trimethylaluminum, 2 M in heptane (114 µl, 228 µmol). The resulting mixture was stirred at 22° C. for 1 h. Then was added a solution of methyl 4-(2-((tert-butyldimethylsilyl)oxy)-3-fluoropropoxy)benzoate (78.1 mg, 228 µmol) in dioxane (0.6 ml) and the reaction was heated to 90° C. and stirred at 90° C. for 1 h to give complete conversion. The mixture was cooled to 22° C., quenched with H$_2$O (1 ml), diluted with ethyl acetate (3 ml) and evaporated. The residue was treated with H$_2$O and extracted with EtOAc (3×10 ml). The organic layer was dried and evaporated. The residue (120 mg, 93%) was combined with crude product from a preliminary experiment (14 mg) and purified by flash chromatography (silica gel, 4 g, dissolved in DCM, MeOH in DCM 1% to 2% to 5%) to give the title compound (88 mg, 68%; corrected yield=61%) as a light yellow solid. LC-MS: m/z=565.4 [M+H]$^+$.

Example 125 rac-4-(3-Fluoro-2-hydroxypropoxy)-N-(4-(4-(pyridin-2-yl)piperazin-1-yl)phenyl)benzamide

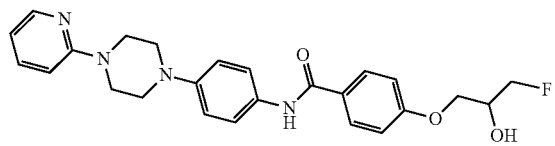 [SMILES: O=C(Nc1ccc(N2CCN(c3ccccn3)CC2)cc1)c1ccc(OCC(O)CF)cc1]

To a solution of 4-(2-((tert-butyldimethylsilyl)oxy)-3-fluoropropoxy)-N-(4-(4-(pyridin-2-yl)piperazin-1-yl)phenyl)benzamide (Example 124) (67 mg, 119 µmol) in THF (1.3 ml) was added at 22° C. tetra-n-butylammonium fluoride, 1 M in THF (130 µl, 130 µmol) and the mixture was stirred at 22° C. for 30 min to give complete conversion. The clear light yellow solution was treated dropwise with H$_2$O (3 ml) to precipitate the product. After stirring for 30 min the solid product was filtered off. The solid was washed with H$_2$O (2×2 ml) and H$_2$O/ACN 1:1 (2×1 ml). The solid was dried under high vacuum to give the title compound (40 mg, 75%) as off-white solid. LC-MS: m/z=451.4 [M+H]$^+$.

Example 126 rac-4-(2-((tert-Butyldimethylsilyl)oxy)-3-fluoropropoxy)-N-(4-(4-(thiazol-2-yl)piperazin-1-yl)phenyl)benzamide

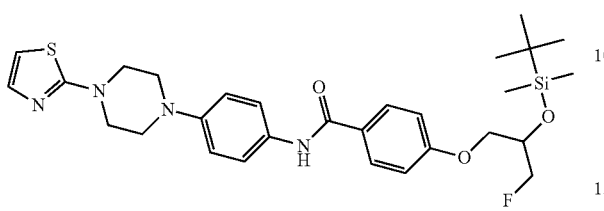

The title compound was prepared in analogy to rac-4-(2-((tert-butyldimethylsilyl)oxy)-3-fluoropropoxy)-N-(4-(4-(pyridin-2-yl)piperazin-1-yl)phenyl)benzamide (Example 124, step c) from 4-[4-(1,3-thiazol-2-yl)piperazin-1-yl]aniline (Intermediate 13.b) (78.1 mg, 300 μmol) and rac-methyl 4-(2-((tert-butyldimethylsilyl)oxy)-3-fluoropropoxy)benzoate (Intermediate 124.b) (103 mg, 300 μmol). Yield 81 mg (47%) as a light yellow solid. LC-MS: m/z=571.4 [M+H]⁺.

Example 127 rac-4-(2-((tert-Butyldimethylsilyl)oxy)-3-fluoropropoxy)-N-(4-(4-(4-cyanophenyl)piperazin-1-yl)phenyl)benzamide

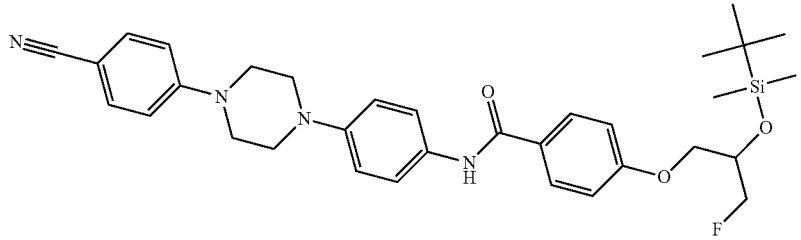 [SMILES: CC(C)(C)[Si](C)(C)OC(CF)COc1ccc(C(=O)Nc2ccc(N3CCN(c4ccc(C#N)cc4)CC3)cc2)cc1]

The title compound was prepared in analogy to rac-4-(2-((tert-butyldimethylsilyl)oxy)-3-fluoropropoxy)-N-(4-(4-(pyridin-2-yl)piperazin-1-yl)phenyl)benzamide (Example 124, step c) from 4-(4-(4-aminophenyl)piperazin-1-yl)benzonitrile (Intermediate 57.a) (83.5 mg, 300 μmol) and rac-methyl 4-(2-((tert-butyldimethylsilyl)oxy)-3-fluoropropoxy)benzoate (Intermediate 124.b) (103 mg, 300 μmol). Yield 120 mg (68%). Yellow solid. LC-MS: m/z=589.4 [M+H]⁺.

Example 128 rac-4-(2-((tert-Butyldimethylsilyl)oxy)-3-fluoropropoxy)-N-(4-(4-(4-cyanopyridin-2-yl)piperazin-1-yl)phenyl)benzamide

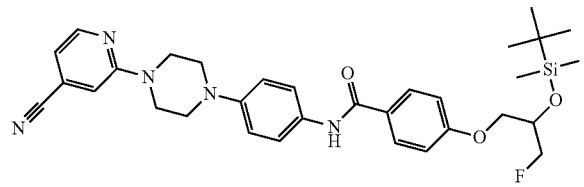 [SMILES: CC(C)(C)[Si](C)(C)OC(CF)COc1ccc(C(=O)Nc2ccc(N3CCN(c4cc(C#N)ccn4)CC3)cc2)cc1]

a) 2-[4-(4-Nitrophenyl)piperazin-1-yl]pyridine-4-carbonitrile

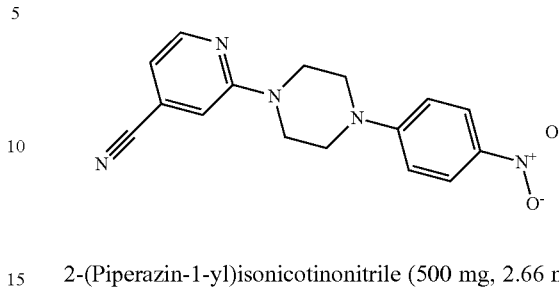

2-(Piperazin-1-yl)isonicotinonitrile (500 mg, 2.66 mmol) was combined with DMSO (1.90 ml) to give a light yellow solution. K₂CO₃ (551 mg, 3.98 mmol) and 1-fluoro-4-nitrobenzene (375 mg, 2.66 mmol) were added and the solution was stirred at 90° C. for 1 h. The reaction mixture was diluted with H₂O (50 ml) and extracted with DCM (3×50 ml). The combined organic layers were washed with brine (1×50 ml), dried over MgSO₄ and concentrated under vacuum. The crude product was purified by flash chromatography. (50 g SiO2 cartridge, DCM to DCM/MeOH 98:0.2) to yield the title compound (751 mg, 91%) as yellow solid. LC-MS: m/z=310.1 [M+H]⁺.

b) 2-[4-(4-Aminophenyl)piperazin-1-yl]pyridine-4-carbonitrile

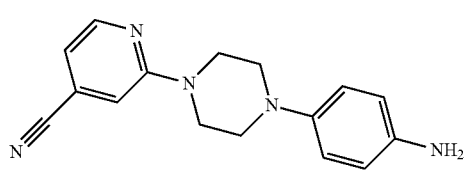 [SMILES: N#Cc1ccnc(N2CCN(c3ccc(N)cc3)CC2)c1]

2-[4-(4-Nitrophenyl)piperazin-1-yl]pyridine-4-carbonitrile (750 mg, 2.42 mmol) was dissolved in EtOH (30 ml) and placed under argon. Pd/C 10% (258 mg, 242 μmol) was added, and the reaction was stirred 4 h under H₂ at rt. The reaction mixture was filtered over Celite. The solids were washed with EtOH and 4:1 DCM:MeOH. The filtrate was concentrated under vacuum and the so obtained crude material was purified by flash chromatography. (70 g SiO2 cartridge, DCM to DCM/MeOH 98:2) to yield the title compound (413 mg, 58%) as an off-white solid. LC-MS: m/z=280.2 [M+H]⁺.

c) rac-4-(2-((tert-Butyldimethylsilyl)oxy)-3-fluoro-propoxy)-N-(4-(4-(4-cyanopyridin-2-yl)piperazin-1-yl)phenyl)benzamide The title compound was prepared in analogy to rac-4-(2-((tert-butyldimethylsilyl)oxy)-3-fluoropropoxy)-N-(4-(4-(pyridin-2-yl)piperazin-1-yl)phenyl)benzamide (Example 124, step c) from 2-[4-(4-aminophenyl)piperazin-1-yl]pyridine-4-carbonitrile (83.8 mg, 300 µmol) and rac-methyl 4-(2-((tert-butyldimethylsilyl)oxy)-3-fluoropropoxy)benzoate (Intermediate 124.b) (103 mg, 300 µmol). Yield 149 mg (84%). Light yellow solid. LC-MS: m/z=590.5 [M+H]$^+$.

Example 129 rac-N-(4-(4-(5-Cyanopyridin-2-yl)piperazin-1-yl)phenyl)-4-(3-fluoro-2-hydroxypropoxy)benzamide

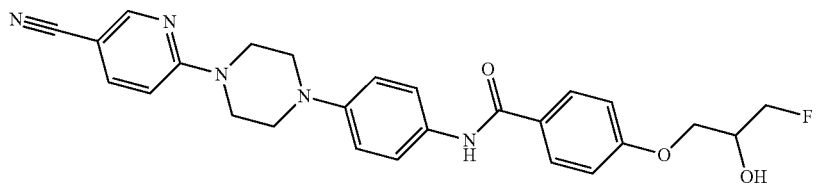 [SMILES: N#Cc1ccc(N2CCN(c3ccc(NC(=O)c4ccc(OCC(O)CF)cc4)cc3)CC2)nc1]

a) 4-(2-((tert-Butyldimethylsilyl)oxy)-3-fluoro-propoxy)-N-(4-(4-(5-cyanopyridin-2-yl)piperazin-1-yl)phenyl)benzamide

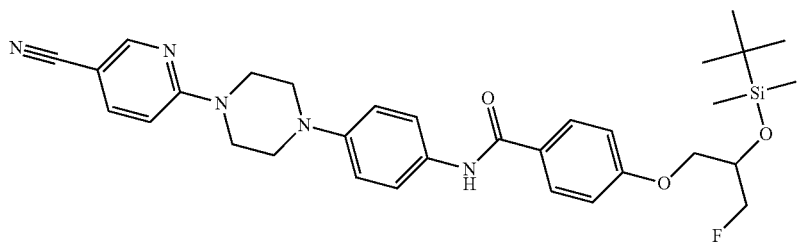 [SMILES: CC(C)(C)[Si](C)(C)OC(CF)COc1ccc(C(=O)Nc2ccc(N3CCN(c4ccc(C#N)cn4)CC3)cc2)cc1]

The title compound was prepared in analogy to rac-4-(2-((tert-butyldimethylsilyl)oxy)-3-fluoropropoxy)-N-(4-(4-(pyridin-2-yl)piperazin-1-yl)phenyl)benzamide (Example 124, step c) from 6-[4-(4-aminophenyl)piperazin-1-yl]pyridine-3-carbonitrile (Intermediate 50.a) (83.8 mg, 300 µmol) and rac-methyl 4-(2-((tert-butyldimethylsilyl)oxy)-3-fluoropropoxy)benzoate (Intermediate 124.b) (103 mg, 300 µmol). Yield 109 mg (62%). Yellow solid. LC-MS: m/z=590.4 [M+H]$^+$.

b) rac-N-(4-(4-(5-Cyanopyridin-2-yl)piperazin-1-yl)phenyl)-4-(3-fluoro-2-hydroxypropoxy)benzamide The title compound was prepared in analogy to rac-4-(3-fluoro-2-hydroxypropoxy)-N-(4-(4-(pyridin-2-yl)piperazin-1-yl)phenyl)benzamide (Example 125) from 4-(2-((tert-butyldimethylsilyl)oxy)-3-fluoropropoxy)-N-(4-(4-(5-cyanopyridin-2-yl)piperazin-1-yl)phenyl)benzamide (93 mg, 157 µmol). Yield 67 mg (90%). Light yellow solid. LC-MS: m/z=476.4 [M+H]$^+$.

Example 130 rac-4-(3-Fluoro-2-hydroxypropoxy)-N-(4-(4-(thiazol-2-yl)piperazin-1-yl)phenyl)benzamide

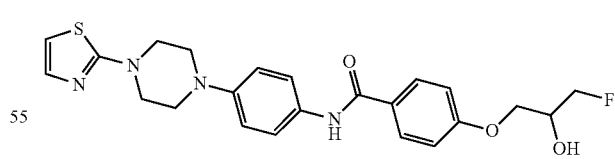

The title compound was prepared in analogy to rac-4-(3-fluoro-2-hydroxypropoxy)-N-(4-(4-(pyridin-2-yl)piperazin-1-yl)phenyl)benzamide (Example 125) from rac-4-(2-((tert-butyldimethylsilyl)oxy)-3-fluoropropoxy)-N-(4-(4-(thiazol-2-yl)piperazin-1-yl)phenyl)benzamide (Example 126) (70.4 mg, 123 µmol). Yield 46 mg (82%). Light yellow solid. LC-MS: m/z=457.3 [M+H]$^+$.

Example 131 rac-N-(4-(4-(4-Cyanophenyl)piperazin-1-yl)phenyl)-4-(3-fluoro-2-hydroxypropoxy)benzamide

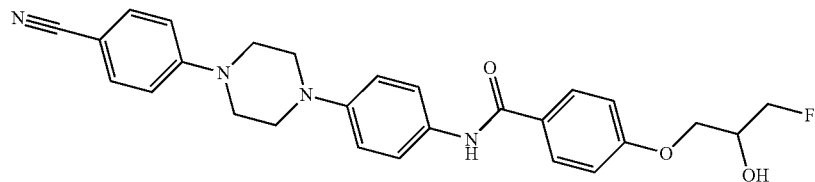 [SMILES: N#Cc1ccc(N2CCN(c3ccc(NC(=O)c4ccc(OCC(O)CF)cc4)cc3)CC2)cc1]

The title compound was prepared in analogy to rac-4-(3-fluoro-2-hydroxypropoxy)-N-(4-(4-(pyridin-2-yl)piperazin-1-yl)phenyl)benzamide (Example 125) from rac-4-(2-((tert-butyldimethylsilyl)oxy)-3-fluoropropoxy)-N-(4-(4-(4-cyanophenyl)piperazin-1-yl)phenyl)benzamide (Example 127) (101 mg, 172 μmol). Yield 73 mg (90%). Light yellow solid. LC-MS: m/z=475.3 [M+H]⁺.

Example 132

4-Methoxy-N-(4-((3aS,6aS)-5-(pyridin-2-yl)hexahydropyrrolo[3,4-c]pyrrol-2(1H)-yl)phenyl)benzamide

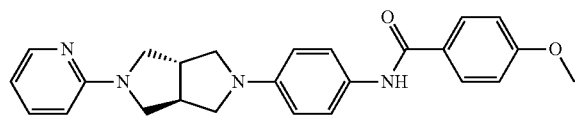

a) (3aR,6aR)-tert-Butyl 5-(pyridin-2-yl)hexahydropyrrolo[3,4-c]pyrrole-2(1H)-carboxylate

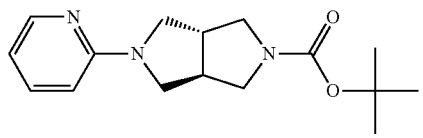 [SMILES: CC(C)(C)OC(=O)N1C[C@H]2CN(c3ccccn3)C[C@@H]2C1]

To a solution of (3aR,6aR)-tert-butyl hexahydropyrrolo[3,4-c]pyrrole-2(1H)-carboxylate hydrochloride (free base preparation: WO2014/139978 A1, WO2015/144605 A1) (995 mg, 4 mmol) in DMA (10 ml) was added at 22° C. 2-chloropyridine (1.36 g, 1.14 ml, 12 mmol) followed by Et₃N (1.62 g, 2.23 ml, 16 mmol) and the mixture was set under Ar and reacted in a microwave apparatus at 160° C. for 30 min. The precipitated TEA.HCl was filtered off, washed with DMA (1×5 ml) and the filtrate was evaporated under high vacuum at 70° C. (Kugelrohr oven—0.8 mbar). The red oil was dissolved in DCM and directly purified by flash chromatography (silica gel, 40 g, EtOAc in heptane 20% to 40%) to give the title compound (261 mg, 23%) as an off-white solid. LC-MS: m/z=290.3 [M+H]⁺.

b) (3aS,6aS)-2-(Pyridin-2-yl)octahydropyrrolo[3,4-c]pyrrole bis(2,2,2-trifluoroacetate)

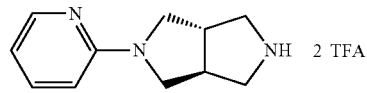

To a solution of (3aR,6aR)-tert-butyl 5-(pyridin-2-yl)hexahydropyrrolo[3,4-c]pyrrole-2(1H)-carboxylate (738 mg, 2.55 mmol) in DCM (7.2 ml) was added at 22° C. trifluoroacetic acid (5.82 g, 3.93 ml, 51 mmol). The reaction mixture was stirred at 22° C. for 30 min. The clear yellow solution was evaporated and the light brown oil was co-distilled with toluene (2 20×4 ml) to be solidified and dried under high vacuum at 55° C. to give the title compound (1.56 g, quant., ca. 68% purity) as off-white solid. LC-MS: m/z=190.2 [M+H]⁺. This material was used in the next step with no further purification.

c) (3aS,6aS)-2-(4-Nitrophenyl)-5-(pyridin-2-yl)octahydropyrrolo[3,4-c]pyrrole

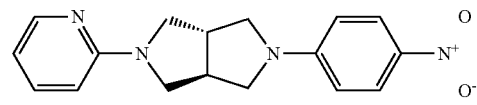

To a solution of (3aS,6aS)-2-(pyridin-2-yl)octahydropyrrolo[3,4-c]pyrrole bis (2,2,2-trifluoroacetate) (1.4 g, 2.28 mmol) in DMSO (5.6 ml) was added at 22° C. 1-fluoro-4-nitrobenzene (386 mg, 2.74 mmol) followed by K₂CO₃ (1.58 g, 11.4 mmol). The reaction mixture was heated to 90° C. and stirred at 90° C. for 30 min. The mixture was partitioned between H₂O (100 ml) and DCM (100 ml) and the aqueous layer was extracted with DCM (3×100 ml). The combined organic layers were dried and evaporated. The crude product was suspended in DCM (10 ml), the solid filtered off, washed with DCM (2×5 ml) and dried to give the title compound (584 mg, 82%) as yellow solid. LC-MS: m/z=311.3 [M+H]⁺.

d) 4-((3aS,6aS)-5-(Pyridin-2-yl)hexahydropyrrolo[3,4-c]pyrrol-2(1H)-yl)aniline

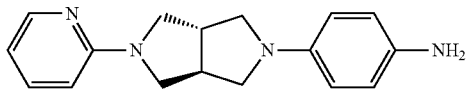

To a suspension of (3aS,6aS)-2-(4-nitrophenyl)-5-(pyridin-2-yl)octahydropyrrolo[3,4-c]pyrrole (530 mg, 1.71 mmol) in EtOH (21 ml) was added at 22° C. after inertisation Pd/C 10% (90.9 mg, 85.4 µmol). The reaction mixture was set under H₂ and stirred at 22° C. for 15 h. Acetic acid (21 ml) was added followed by new catalyst (90 mg). The mixture was stirred under H₂ for 2 h. The catalyst was filtered off, washed with EtOH (2×20 ml), the filtrate was evaporated and co-distilled with EtOH (1×20 ml). The residue was treated with sat. aq. NaHCO₃ (100 ml) and extracted with DCM (3×100 ml). The organic layers were dried and evaporated to give the title compound (405 mg, 85%) as light grey solid. MS: m/z=281.3 [M+H]⁺.

e) 4-Methoxy-N-(4-((3aS,6aS)-5-(pyridin-2-yl)hexahydropyrrolo[3,4-c]pyrrol-2(1H)-yl)phenyl)benzamide To a suspension of 4-((3aS,6aS)-5-(pyridin-2-yl)hexahydropyrrolo[3,4-c]pyrrol-2(1H)-yl)aniline (56.1 mg, 200 µmol) in dioxane (2 ml) was added at 22° C. trimethylaluminum, 2 M in heptane (100 µl, 200 µmol) and the reaction mixture was stirred at 22° C. for 1 h. Then was added a solution of methyl 4-methoxybenzoate (33.2 mg, 200 µmol) in dioxane (0.4 ml), heated to 90° C. and stirred at 90° C. for 60 min. After a total 2 h at 90° C. the mixture was cooled to 22° C., quenched with H₂O (1 ml), diluted with EtOAc (3 ml) and evaporated. The residue was treated with H₂O (10 ml) and extracted with DCM (4×10 ml). The organic layer was dried (Na₂SO₄) and evaporated. The residue was purified by trituration in DCM (1 ml), the solid was filtered off, washed with DCM (2×2 ml) and dried in HV to give the title compound (7.8 mg, 9%) as a light yellow solid. The drying agent after extraction (Na₂SO₄) was suspended with 50 ml DCM/MeOH 19:1 containing 2% triethylamine, filtered and washed with DCM/MeOH 19:1. The filtrate was evaporated and dried in HV to give a second portion of the title compound (16.8 mg, 20%) as light yellow solid. Combined yield 25 mg (29%). LC-MS: m/z=415.4 [M+H]⁺.

Example 133

4-Methoxy-N-(4-((3aR,6aR)-5-(pyridin-2-yl)hexahydropyrrolo[3,4-c]pyrrol-2(1H)-yl)phenyl)benzamide

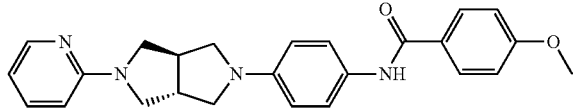 [SMILES: COc1ccc(C(=O)Nc2ccc(N3C[C@@H]4CN(c5ccccn5)C[C@H]4C3)cc2)cc1]

a) (3aR,6aR)-tert-Butyl 5-(4-nitrophenyl)hexahydropyrrolo[3,4-c]pyrrole-2(1H)-carboxylate

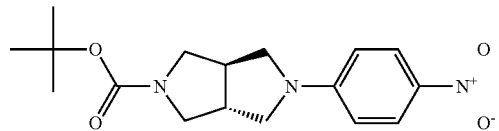

To a solution of (3aR,6aR)-tert-butyl hexahydropyrrolo[3,4-c]pyrrole-2(1H)-carboxylate hydrochloride (free base preparation: WO2014/139978 A1, WO2015/144605 A1) (1.99 g, 8 mmol) in DMSO (8 ml) was added at 22° C. 1-fluoro-4-nitrobenzene (1.24 g, 8.8 mmol) followed by K₂CO₃ (2.76 g, 20 mmol). The reaction mixture was warmed to 90° C. and stirred at 90° C. for 90 min. The mixture was partitioned between H₂O (100 ml) and DCM (100 ml) and the aqueous layer was extracted with DCM (3×100 ml). The organic layers were dried and evaporated. The residue was purified by flash chromatography (80 g silica gel, MeOH in DCM 0% to 2%) to give the title compound (1.9 g, 71%) as a yellow solid. LC-MS: m/z=334.2 [M+H]⁺.

b) (3aS,6aS)-2-(4-Nitrophenyl)octahydropyrrolo[3,4-c]pyrrole 2,2,2-trifluoroacetate

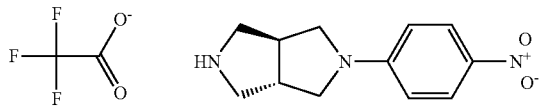

To a solution of (3aR,6aR)-tert-butyl 5-(4-nitrophenyl)hexahydropyrrolo[3,4-c]pyrrole-2(1H)-carboxylate (900 mg, 2.7 mmol) in DCM (9 ml) was added at 22° C. trifluoroacetic acid (6.16 g, 4.16 ml, 54 mmol) and the mixture was stirred at 22° C. for 60 min. The solvent was removed under reduced pressure to give the title compound (1.14 g, quant., ca. 82% purity) as yellow solid. LC-MS: m/z=234.2 [M+H]⁺. This material was used in the next step with no further purification.

c) (3aR,6aR)-2-(4-Nitrophenyl)-5-(pyridin-2-yl)octahydropyrrolo[3,4-c]pyrrole

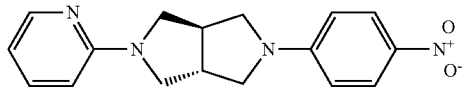

To a solution of (3aS,6aS)-2-(4-nitrophenyl)octahydropyrrolo[3,4-c]pyrrole 2,2,2-trifluoroacetate (550 mg, 1.58 mmol) in NMP (5.5 ml) was added at 22° C. 2-chloropyridine (899 mg, 749 µl, 7.92 mmol) followed by triethylamine (1.12 g, 1.55 ml, 11.1 mmol). The tube was inerted, sealed and reacted in microwave apparatus at 170° C. for 1.5 h. The mixture was quenched with sat aq. NaHCO₃ (50 ml) and extracted DCM (4×50 ml). The organic layers were dried and evaporated (at the end HV at 100° C. to remove NMP). The crude product was suspended in DCM, the solid filtered off, washed with DCM and dried to give the title compound (265 mg, 54%) as brown solid. LC-MS: m/z=311.2 [M+H]+.

d) 4-((3aR,6aR)-5-(Pyridin-2-yl)hexahydropyrrolo[3,4-c]pyrrol-2(1H)-yl)aniline

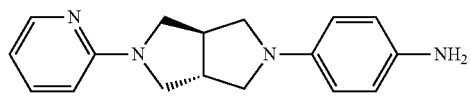

The title compound was prepared in analogy to 4-((3aS,6aS)-5-(pyridin-2-yl)hexahydropyrrolo[3,4-c]pyrrol-2(1H)-yl)aniline (Intermediate 132.d) from (3aR,6aR)-2-(4-nitrophenyl)-5-(pyridin-2-yl)octahydropyrrolo[3,4-c]pyrrole (468 mg, 1.51 mmol). 356 mg (84%). Light brown solid. MS: m/z=281.2 [M+H]+.

e) 4-Methoxy-N-(4-((3aR,6aR)-5-(pyridin-2-yl)hexahydropyrrolo[3,4-c]pyrrol-2(1H)-yl)phenyl)benzamide To a solution of 4-methoxybenzoic acid (29.2 mg, 192 μmol) in DMF (0.9 ml) was added at 22° C. HATU (73 mg, 192 μmol) followed by DIPEA (41.4 mg, 55.9 μl, 320 μmol) and the mixture was stirred at 22° C. for 30 min. Then was added 4-((3aR,6aR)-5-(pyridin-2-yl)hexahydropyrrolo[3,4-c]pyrrol-2(1H)-yl)aniline (44.9 mg, 160 μmol) to give after 5 minutes a thick suspension that was diluted by addition of DMF (0.45 ml). After stirring at 22° C. for further 3 h the mixture was quenched with H2O (10 ml) and extracted with DCM (5×10 ml). The organic layers were dried and evaporated and the crude product was suspended in 5 ml DCM for 1 h. The solid was filtered off, washed with DCM (2×1 ml) and dried under high vacuum to give the title compound (58 mg, 88%) as light grey solid. LC-MS: m/z=415.3 [M+H]+.

Example 134

4-(Fluoromethoxy)-N-(4-(4-(pyridin-3-yl)piperazin-1-yl)phenyl)benzamide

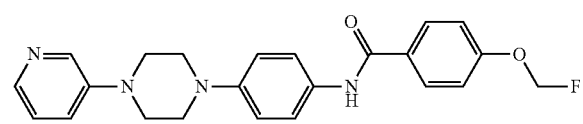 [SMILES: O=C(Nc1ccc(N2CCN(c3cccnc3)CC2)cc1)c1ccc(OCF)cc1]

a) 4-(Fluoromethoxy)benzoic acid

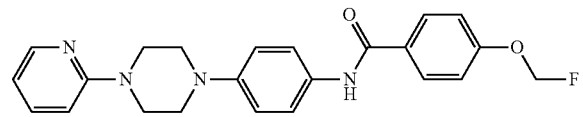

To a solution of methyl 4-(fluoromethoxy)benzoate (360 mg, 1.95 mmol) in THF (5 ml) and EtOH (5 ml) was added NaOH 1 M in H2O (3.91 ml, 3.91 mmol) and the clear and colorless solution was stirred at rt for 5 h. The organic solvents were removed by evaporation and the aqueous residue was treated dropwise with HCl 1 M in H2O (3.91 ml, 3.91 mmol). The resulting white suspension was filtered, washed with H2O and dried. Colorless solid (280 mg, 84%). LC-MS: m/z=169.1 [M−H]−.

b) 4-(Fluoromethoxy)-N-(4-(4-(pyridin-3-yl)piperazin-1-yl)phenyl)benzamide

To a solution of 4-(fluoromethoxy)benzoic acid (93.6 mg, 0.55 mmol) in DCM (8 ml) was added at 22° C. oxalyl chloride (105 mg, 72.2 μl, 825 μmol) followed by DMF (8.04 mg, 8.52 μl, 110 μmol) and the mixture was stirred at 22° C. for 90 min. The solvent and excess of oxalyl chloride were removed under reduced pressure to give the crude acid chloride that was used without further purification. To a solution of 4-(4-(pyridin-3-yl)piperazin-1-yl)aniline (Intermediate 37.b) (140 mg, 0.55 mmol) in DCM (6 ml) was added at 22° C. DIPEA (284 mg, 384 μl, 2.2 mmol) followed by a solution of the acid chloride in DCM (2 ml) and the mixture was stirred at 22° C. for 15 h. The thick suspension was evaporated, suspended in DCM/MeOH 3:1 (4 ml) and the solid was filtered off, washed with DCM/MeOH 3:1 (1×3 ml) and dried under high vacuum to give the title compound (150 mg, 67%) as off-white solid. LC-MS: m/z=407.3 [M+H)]+.

Example 135

4-(Fluoromethoxy)-N-[4-(4-pyridin-2-ylpiperazin-1-yl)phenyl]benzamide

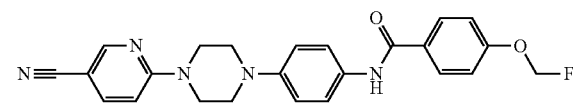

The title compound was prepared in analogy to 4-(fluoromethoxy)-N-(4-(4-(pyridin-3-yl)piperazin-1-yl)phenyl)benzamide (Example 134, step b) from 4-(fluoromethoxy)benzoic acid (Intermediate 134 a) (55 mg, 323 μmol) and 4-(4-(pyridin-2-yl)piperazin-1-yl)aniline (Intermediate 1.b) (82.2 mg, 323 μmol). Yield 91 mg (69%). Off-white solid. LC-MS: m/z=407.3 [M+H)]+.

Example 136

N-[4-[4-(5-Cyanopyridin-2-yl)piperazin-1-yl]phenyl]-4-(fluoromethoxy)benzamide

The title compound was prepared in analogy to 4-(fluoromethoxy)-N-(4-(4-(pyridin-3-yl)piperazin-1-yl)phenyl)benzamide (Example 134, step b) from 4-(fluoromethoxy)benzoic acid (Intermediate 134 a) (55 mg, 323 μmol) and 6-[4-(4-aminophenyl)piperazin-1-yl]pyridine-3-carbonitrile (Intermediate 50.a) (90.3 mg, 323 μmol). Yield 69 mg (49%). Off-white solid. LC-MS: m/z=430.4 [M−H]−.

Example 137

4-(2-(2-Hydroxyethoxy)ethoxy)-N-(4-(4-(pyridin-2-yl)piperazin-1-yl)phenyl)benzamide

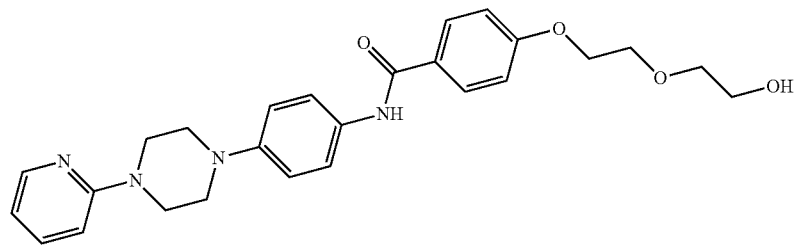 [SMILES: O=C(Nc1ccc(N2CCN(c3ccccn3)CC2)cc1)c1ccc(OCCOCCO)cc1]

a) 4-((4-(4-(Pyridin-2-yl)piperazin-1-yl)phenyl)carbamoyl)phenyl acetate

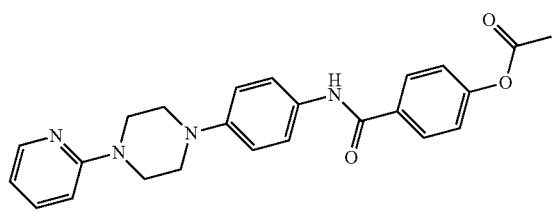 [SMILES: CC(=O)Oc1ccc(C(=O)Nc2ccc(N3CCN(c4ccccn4)CC3)cc2)cc1]

4-Acetoxybenzoic acid (1.5 g, 8.33 mmol) was dissolved in DCM (60 ml). Oxalyl chloride (1.58 g, 1.09 ml, 12.5 mmol) was added followed by DMF (30.4 mg, 32.2 µl, 416 µmol). The reaction mixture was stirred for 1.5 h at rt, then concentrated under vacuum. The crude product was dissolved in DCM (35 ml) and added dropwise to a stirred solution of 4-(4-(pyridin-2-yl)piperazin-1-yl)aniline (Intermediate 1.b) (2.12 g, 8.33 mmol) and DIPEA (4.31 g, 5.82 ml, 33.3 mmol) in DCM (70 ml) at RT. The reaction mixture was stirred at rt for 1.25 h. To the light brown suspension was added a mixture of MeOH (6 ml) and $H_2O$ (30 ml) and the reaction mixture was allowed to stir for 15 minutes before filtering off the product. The filter cake was washed with DCM (20 ml) and $H_2O$ (2×30 ml). Colorless solid (2.89 g, 83%), LCMS: m/z=417.3 [M+H]$^+$.

b) 4-Hydroxy-N-[4-(4-(pyridin-2-ylpiperazin-1-yl)phenyl]benzamide

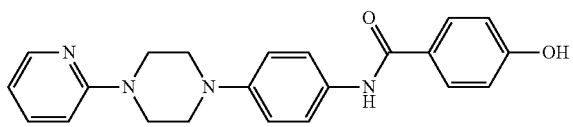 [SMILES: O=C(Nc1ccc(N2CCN(c3ccccn3)CC2)cc1)c1ccc(O)cc1]

To a suspension of 4-((4-(4-(pyridin-2-yl)piperazin-1-yl)phenyl)carbamoyl)phenyl acetate (1.68 g, 4.03 mmol) in dioxane (34 ml) and $H_2O$ (16.8 ml) was added NaOH 1M in $H_2O$ (16.1 ml, 16.1 mmol) and the rapidly formed solution was stirred at 60° C. for 1.3 h. Dioxane was evaporated and to the residue was added dropwise HCl 1 M in $H_2O$ (14.5 ml, 14.5 mmol). The mixture was filtered. The filter cake was washed with plenty of $H_2O$ and dried. Light grey solid (1.49 g; 99%). LC-MS: m/z=373.3 [M−H]$^-$.

c) 4-(2-(2-Hydroxyethoxy)ethoxy)-N-(4-(4-(pyridin-2-yl)piperazin-1-yl)phenyl)benzamide To a suspension of 4-hydroxy-N-(4-(4-(pyridin-2-yl)piperazin-1-yl)phenyl)benzamide (112 mg, 0.3 mmol) in DMF (2.2 ml) was added at 22° C. 2-(2-hydroxyethoxy)ethyl 4-methylbenzenesulfonate (CAS Nr. 118591-58-5) (85.9 mg, 330 µmol) followed by $Cs_2CO_3$ (108 mg, 330 µmol) and the mixture was stirred at 22° C. for 1 h. Then the mixture was warmed to 70° C. and stirred for 2 h. The mixture was cooled to 22° C. and treated dropwise with $H_2O$ (2.2 ml) to give precipitation of a solid. The suspension was stirred for 10 minutes, the solid was filtered off, washed with MeOH/$H_2O$ 1:1 (2×6 ml) and $H_2O$ (2×6 ml) and dried. The resulting solid was dissolved in DCM/MeOH 1:1 (10 ml), filtered and the filter washed with DCM/MeOH 1:1 (1×2 ml). The filtrate was evaporated and dried under high vacuum to give the title compound (60 mg, 43%) as white solid. LC-MS: m/z=463.3 [M+H]$^+$.

Example 138

4-Hydroxy-N-[4-(4-pyridin-3-ylpiperazin-1-yl)phenyl]benzamide

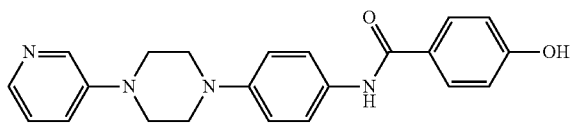 [SMILES: O=C(Nc1ccc(N2CCN(c3cccnc3)CC2)cc1)c1ccc(O)cc1]

a) [4-[[4-(4-Pyridin-3-ylpiperazin-1-yl)phenyl]carbamoyl]phenyl] acetate

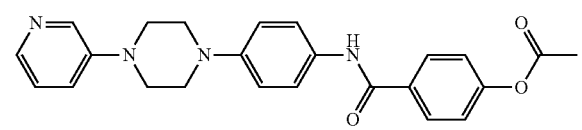 [SMILES: CC(=O)Oc1ccc(C(=O)Nc2ccc(N3CCN(c4cccnc4)CC3)cc2)cc1]

The title compound was prepared in analogy to 4-((4-(4-(pyridin-2-yl)piperazin-1-yl)phenyl)carbamoyl)phenyl acetate (Intermediate 137.a) from 4-acetoxybenzoic acid (819 mg, 4.55 mmol) and 4-(4-(pyridin-3-yl)piperazin-1-yl)

aniline (Intermediate 37.b) (1.10 g, 4.33 mmol). Yield 1.39 g (77%). LC-MS: m/z=417.2[M+H]⁺.

b) 4-Hydroxy-N-[4-(4-pyridin-3-ylpiperazin-1-yl)phenyl]benzamide

To a suspension of [4-[[4-(4-pyridin-3-ylpiperazin-1-yl)phenyl]carbamoyl]phenyl] acetate (1.39 g, 3.33 mmol) in MeOH (41.5 ml) was added 1 M aq. NaOH (13.3 ml, 13.3 mmol) and the resulting mixture was stirred for 20 min at rt. The reaction mixture was treated with 1 M HCl aq. (13.3 ml, 13.3 mmol) to give precipitation of the product. After stirring for 1 h at rt the solids were collected by filtration and washed with H₂O/MeOH 1:1 (30 ml) and H₂O (2×30 ml) and dried under high vacuum over night to obtain the product (1.01 g, 81%) as off-white solid. LC-MS: m/z=373.1 [M–H]⁻.

General Synthesis Sub-Series

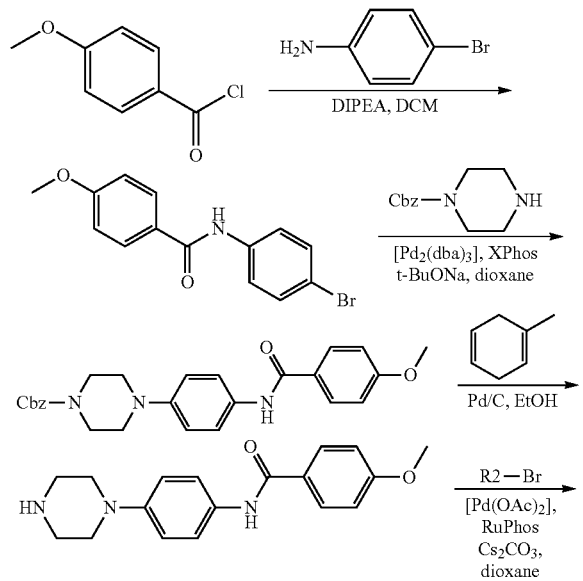

N-(4-Bromophenyl)-4-methoxybenzamide

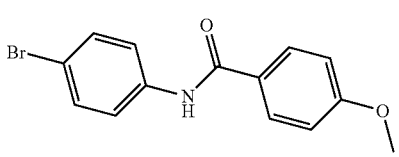 [SMILES: COc1ccc(C(=O)Nc2ccc(Br)cc2)cc1]

To a solution of 4-bromoaniline (5 g, 29.1 mmol) and DIPEA (14.2 ml, 81.4 mmol) in DCM (50 ml) at 0° C. was added dropwise a solution of 4-methoxybenzoyl chloride (5 g, 29.3 mmol) in DCM (50 ml). The reaction mixture was stirred at 0° C. for 30 minutes and then at rt for 1 h. The precipitate formed was collected by filtration, washed with DCM and dried to give the title compound (7.56 g, 85%) as a white solid.

¹H NMR (400 MHz, DMSO): δ 10.21 (s, 1H), 7.98-7.95 (m, 2H), 7.78-7.75 (m, 2H), 7.55-7.52 (m, 2H), 7.08 (d, J=8.9 Hz, 2H), 3.85 (s, 3H). LC-MS: Rt=1.64 min m/z=306, [M+H]⁺.

Benzyl 4-(4-(4-methoxybenzamido)phenyl)piperazine-1-carboxylate

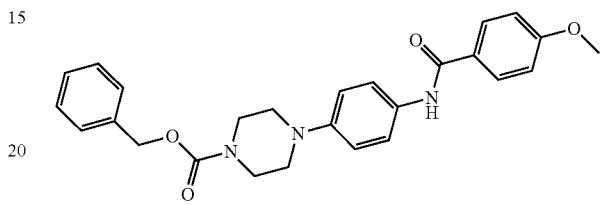

N-(4-Bromophenyl)-4-methoxybenzamide (2 g, 6.53 mmol), Cbz-piperazine (1.38 g, 7.18 mmol), XPhos (623 mg, 1.31 mmol) and NaOtBu (1.38 g, 14.4 mmol) were suspended in dioxane (20 ml) and degassed with nitrogen for 30 minutes. [Pd₂(dba)₃] (598 mg, 0.65 mmol) was then added and the reaction mixture was heated to 90° C. for 2 h under N₂. The reaction was allowed to cool to rt and diluted with H₂O. The precipitate formed was collected by filtration and washed with H₂O. The dry residue (3.7 g) was triturated with diethyl ether to afford the title compound (2.85 g, 98%) as a brown solid.

¹H NMR (400 MHz, DMSO): δ 9.92 (s, 1H), 7.94 (d, J=8.9 Hz, 2H), 7.62 (d, J=9.2 Hz, 2H), 7.40 (d, J=4.5 Hz, 4H), 7.38-7.31 (m, 1H), 7.05 (d, J=8.9 Hz, 2H), 6.95 (d, J=9.2 Hz, 2H), 5.12 (s, 2H), 3.84 (s, 3H), 3.59-3.56 (m, 4H), 3.09 (dd, J=5.0, 5.0 Hz, 4H). LC-MS: Rt=1.69 min, m/z=446, [M+H]⁺.

4-Methoxy-N-(4-(piperazin-1-yl)phenyl)benzamide

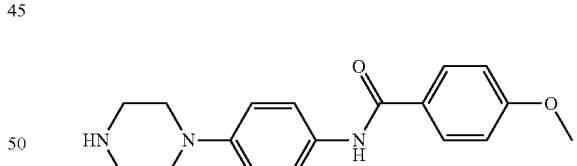

To a solution of benzyl 4-(4-(4-methoxybenzamido)phenyl)piperazine-1-carboxylate (2 g, 4.49 mmol) in EtOH (36 ml) was added Pd/C 10% (2 g), followed by 1-methyl-1,4-cyclohexadiene (5 ml, 44.9 mmol). The reaction mixture was heated to 85° C. and stirred at this temperature for 1 hour. After cooling to rt, the reaction mixture was filtered through a pad of Celite and washed with EtOH and MeOH. The filtrate was concentrated to furnish the title compound (1.33 g, 95%) as a brown solid.

¹H NMR (400 MHz, DMSO): δ d 9.88 (s, 1H), 7.94 (d, J=8.9 Hz, 2H), 7.59 (d, J=9.0 Hz, 2H), 7.05 (d, J=8.9 Hz, 2H), 6.90 (d, J=9.2 Hz, 2H), 3.84 (s, 3H), 3.02-2.98 (m, 4H), 2.83 (dd, J=4.9, 4.9 Hz, 4H). LC-MS: Rt=1.17 min, m/z=312, [M+H]⁺.

General Procedure A

Synthesis of 4-methoxy-N-(4-(4-(R₂-yl)piperazin-1-yl)phenyl)benzamides

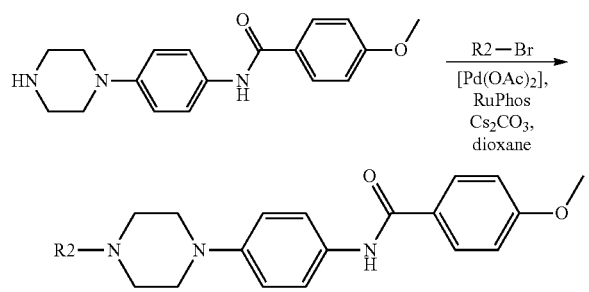

4-Methoxy-N-(4-(piperazin-1-yl)phenyl)benzamide (120 mg, 0.39 mmol), the R₂-(Het)aryl halide (1.1 eq.), Cs₂CO₃ (2.2 eq., 276 mg, 0.85 mmol), [Pd(OAc)₂] (0.1 eq., 9 mg, 0.04 mmol) and RuPhos (0.2 eq., 36 mg, 0.08 mmol) were combined in a reaction tube. Degassed dioxane (3 ml) was then added, the reaction tube flushed with nitrogen, sealed and the reaction mixture was stirred at 80° C. overnight. In case of incomplete conversions more reagents were added accordingly. After completion the reaction mixture was cooled to rt and H₂O added. The precipitate formed was collected by filtration, washed with H₂O and dried. The residue was dissolved in DCM/MeOH (2:1), adsorbed onto HM-N beads (Biotage) and evaporated. The resulting material was dry-loaded onto a silica column and purified by flash column chromatography eluting with 0.5 to 3% methanol/dichloromethane to afford the title compounds as yellow solids.

Examples Prepared Using General Procedure A

Example 139

N-(4-(4-(4-Cyano-2-methoxyphenyl)piperazin-1-yl)phenyl)-4-methoxybenzamide

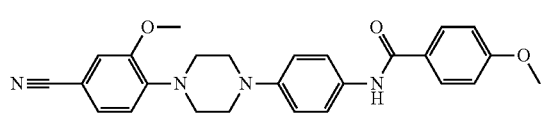 [SMILES: COc1ccc(C(=O)Nc2ccc(N3CCN(c4ccc(C#N)cc4OC)CC3)cc2)cc1]

Yield: 47 mg.

¹H NMR (400 MHz, DMSO): δ 9.92 (s, 1H), 7.95 (d, J=8.8 Hz, 2H), 7.63 (d, J=9.2 Hz, 2H), 7.38 (s, 2H), 7.07-7.03 (m, 3H), 6.99 (d, J=9.2 Hz, 2H), 3.88 (s, 3H), 3.85 (s, 3H), 3.25 (s, 4H) 4H-piperazine hidden under DMSO peak.

LC-MS: Rt=3.36 min, m/z=443 [M+H]⁺.

Example 140

N-(4-(4-(4-Cyano-3-methoxyphenyl)piperazin-1-yl)phenyl)-4-methoxybenzamide

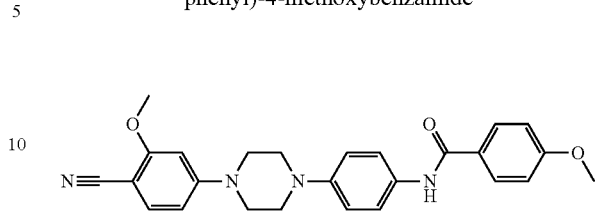

Yield: 33 mg.

¹H NMR (400 MHz, DMSO): δ 9.92 (s, 1H), 7.95 (d, J=8.9 Hz, 2H), 7.64 (d, J=9.2 Hz, 2H), 7.47 (d, J=8.5 Hz, 1H), 7.06 (d, J=9.0 Hz, 2H), 7.00 (d, J=9.2 Hz, 2H), 6.68-6.64 (m, 2H), 3.91 (s, 3H), 3.84 (s, 3H), 3.54 (dd, J=5.1, 5.1 Hz, 4H), 3.25 (dd, J=5.1, 5.1 Hz, 4H).

LC-MS: Rt=3.33 min, m/z=443 [M+H]⁺.

Example 141

N-(4-(4-(5-Fluoropyridin-2-yl)piperazin-1-yl)phenyl)-4-methoxybenzamide

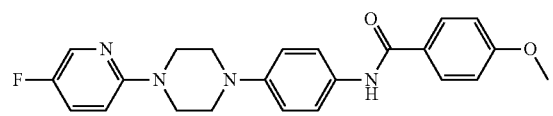

Yield: 5 mg.

¹H NMR (400 MHz, DMSO): δ 9.95 (s, 1H), 8.17 (d, J=3.3 Hz, 1H), 8.00-7.97 (m, 2H), 7.67 (d, J=9.1 Hz, 2H), 7.62-7.55 (m, 1H), 7.09 (d, J=8.8 Hz, 2H), 7.05-6.98 (m, 3H), 3.88 (s, 3H), 3.63 (dd, J=5.1, 5.1 Hz, 4H), 3.25 (dd, J=5.2, 5.2 Hz, 4H).

LC-MS: Rt=3.33 min, m/z=407 [M+H]⁺.

Example 142

N-(4-(4-(5-(Dimethylamino)pyridin-2-yl)piperazin-1-yl)phenyl)-4-methoxybenzamide

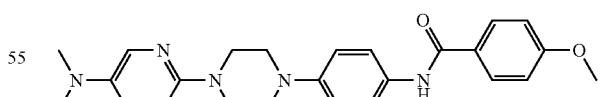

Yield: 28 mg.

¹H NMR (400 MHz, DMSO): δ 9.91 (s, 1H), 7.95 (d, J=8.9 Hz, 2H), 7.78 (d, J=3.0 Hz, 1H), 7.63 (d, J=9.2 Hz, 2H), 7.20 (dd, J=3.1, 9.2 Hz, 1H), 7.05 (d, J=8.9 Hz, 2H), 6.99 (d, J=9.2 Hz, 2H), 6.85 (d, J=9.0 Hz, 1H), 3.84 (s, 3H), 3.46 (dd, J=5.0, 5.0 Hz, 4H), 3.21 (dd, J=5.1, 5.1 Hz, 4H), 2.80 (s, 6H).

LC-MS: Rt=2.87 min, m/z=432 [M+H]⁺.

Example 143

N-(4-(4-(5-Cyanopyrimidin-2-yl)piperazin-1-yl)phenyl)-4-methoxybenzamide

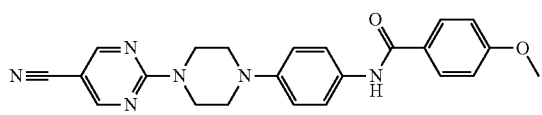 [SMILES: COc1ccc(C(=O)Nc2ccc(N3CCN(c4ncc(C#N)cn4)CC3)cc2)cc1]

Yield: 76 mg.

¹H NMR (400 MHz, DMSO): δ 9.92 (s, 1H), 8.80 (s, 2H), 7.95 (d, J=9.0 Hz, 2H), 7.64 (d, J=9.2 Hz, 2H), 7.05 (d, J=9.0 Hz, 2H), 6.99 (d, J=9.2 Hz, 2H), 4.01 (dd, J=5.2, 5.2 Hz, 4H), 3.84 (s, 3H), 3.21 (dd, J=5.1, 5.1 Hz, 4H).

LC-MS: Rt=3.41 min, m/z=415, [M+H]⁺.

Example 144

N-(4-(4-(4-Cyano-2-methylphenyl)piperazin-1-yl)phenyl)-4-methoxybenzamide

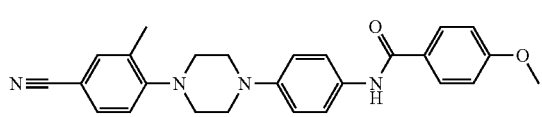 [SMILES: COc1ccc(C(=O)Nc2ccc(N3CCN(c4ccc(C#N)cc4C)CC3)cc2)cc1]

Yield: 32 mg.

¹H NMR (400 MHz, DMSO): δ 9.92 (s, 1H), 7.95 (d, J=8.9 Hz, 2H), 7.66-7.62 (m, 4H), 7.20-7.16 (m, 1H), 7.06 (d, J=9.0 Hz, 2H), 7.00 (d, J=9.2 Hz, 2H), 3.84 (s, 3H), 3.31-3.25 (m, 4H), 3.11 (dd, J=4.8, 4.8 Hz, 4H), 2.33 (s, 3H).

LC-MS: Rt=3.49 min, m/z=427 [M+H]⁺.

Example 145

N-(4-(4-(4-Cyano-2-fluorophenyl)piperazin-1-yl)phenyl)-4-methoxybenzamide

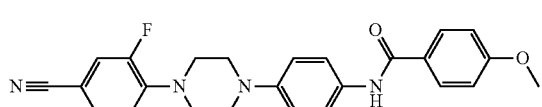

Yield: 39 mg.

¹H NMR (400 MHz, DMSO): δ 9.92 (s, 1H), 7.95 (d, J=8.9 Hz, 2H), 7.74 (dd, J=2.0, 13.3 Hz, 1H), 7.66-7.59 (m, 3H), 7.21 (dd, J=8.8, 8.8 Hz, 1H), 7.06 (d, J=8.9 Hz, 2H), 7.00 (d, J=9.2 Hz, 2H), 3.84 (s, 3H), 3.39-3.34 (m, 4H), 3.31-3.24 (m, 4H).

LC-MS: Rt=3.41 min, m/z=431 [M+H]⁺.

Example 146

N-(4-(4-(6-Fluoropyridin-2-yl)piperazin-1-yl)phenyl)-4-methoxybenzamide

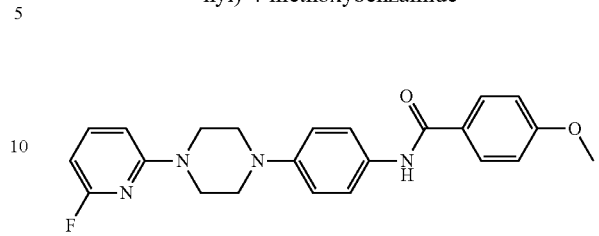

Yield: 10 mg.

¹H NMR (400 MHz, DMSO): δ 9.96 (s, 1H), 7.99 (d, J=8.8 Hz, 2H), 7.76 (q, J=8.3 Hz, 1H), 7.68 (d, J=8.8 Hz, 2H), 7.10 (d, J=8.6 Hz, 2H), 7.04 (d, J=8.8 Hz, 2H), 6.80 (d, J=8.1 Hz, 1H), 6.38-6.34 (m, 1H), 3.89 (s, 3H), 3.68 (s, 4H), 3.25 (d, J=4.3 Hz, 4H).

LC-MS: Rt=3.48 min, m/z=407 [M+H]⁺.

Example 147

N-(4-(4-(5-Cyanopyrazin-2-yl)piperazin-1-yl)phenyl)-4-methoxybenzamide

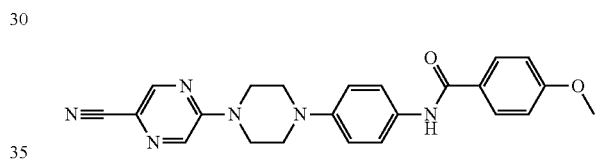

Yield: 39 mg.

¹H NMR (400 MHz, DMSO): δ 9.96 (s, 1H), 8.64 (d, J=1.3 Hz, 1H), 8.55 (d, J=1.3 Hz, 1H), 7.99 (d, J=8.8 Hz, 2H), 7.68 (d, J=9.1 Hz, 2H), 7.09 (d, J=8.8 Hz, 2H), 7.04 (d, J=9.1 Hz, 2H), 3.95 (dd, J=5.2, 5.2 Hz, 4H), 3.89 (s, 3H), 3.35-3.25 (m, 4H).

LC-MS: Rt=3.21 min, m/z=415 [M+H]⁺.

Example 148

N-(4-(4-(3-Fluoropyridin-2-yl)piperazin-1-yl)phenyl)-4-methoxybenzamide

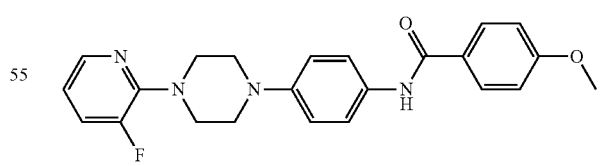

Yield: 41 mg.

¹H NMR (400 MHz, DMSO): δ 9.83 (s, 1H), 7.99-7.95 (m, 1H), 7.87 (d, J=8.8 Hz, 2H), 7.56 (d, J=9.1 Hz, 2H), 7.51-7.44 (m, 1H), 6.97 (d, J=8.8 Hz, 2H), 6.91 (d, J=9.1 Hz, 2H), 6.88-6.82 (m, 1H), 3.77 (s, 3H), 3.51-3.44 (m, 4H), 3.17 (dd, J=5.1, 5.1 Hz, 4H).

LC-MS: Rt=3.37 min, m/z=407 [M+H]⁺.

Example 149

N-(4-(4-(4-Chloropyridin-2-yl)piperazin-1-yl)phenyl)-4-methoxybenzamide

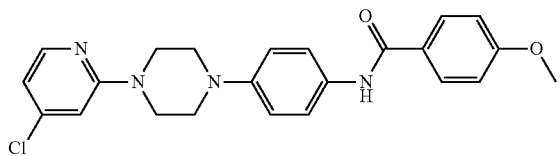

Yield: 6 mg.

$^1$H NMR (400 MHz, DMSO): δ 9.96 (s, 1H), 8.15 (d, J=5.6 Hz, 1H), 7.99 (d, J=8.8 Hz, 2H), 7.68 (d, J=8.8 Hz, 2H), 7.10 (d, J=8.8 Hz, 2H), 7.04 (d, J=9.3 Hz, 3H), 6.79 (dd, J=1.5, 5.3 Hz, 1H), 3.89 (s, 3H), 3.73 (dd, J=4.9, 4.9 Hz, 4H), 3.24 (dd, J=4.9, 4.9 Hz, 4H).

LC-MS: Rt=3.39 min, m/z=423 [M+H]$^+$.

Example 150

N-(4-(4-(4-Cyano-3-fluorophenyl)piperazin-1-yl)phenyl)-4-methoxybenzamide

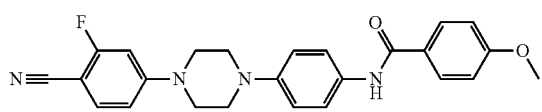 [SMILES: COc1ccc(C(=O)Nc2ccc(N3CCN(c4ccc(C#N)cc4F)CC3)cc2)cc1]

Yield: 35 mg.

$^1$H NMR (400 MHz, DMSO): δ 9.96 (s, 1H), 7.99 (d, J=8.8 Hz, 2H), 7.70-7.64 (m, 3H), 7.12-6.95 (m, 6H), 3.89 (s, 3H), 3.61 (dd, J=5.1, 5.1 Hz, 4H), 3.27 (dd, J=4.9, 4.9 Hz, 4H).

LC-MS: Rt=3.39 min, m/z=431 [M+H]$^+$.

Example 151

N-(4-(4-(5-Cyano-4-methylpyridin-2-yl)piperazin-1-yl)phenyl)-4-methoxybenzamide

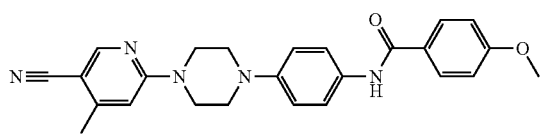 [SMILES: COc1ccc(C(=O)Nc2ccc(N3CCN(c4cc(C)c(C#N)cn4)CC3)cc2)cc1]

Yield: 38 mg.

$^1$H NMR (400 MHz, DMSO): δ 9.96 (s, 1H), 8.48 (s, 1H), 8.00 (d, J=8.8 Hz, 2H), 7.68 (d, J=9.1 Hz, 2H), 7.10 (d, J=8.8 Hz, 2H), 7.06-6.99 (m, 3H), 3.89 (s, 3H), 3.86 (dd, J=5.2, 5.2 Hz, 4H), 3.25 (dd, J=5.2, 5.2 Hz, 4H), 2.41 (s, 3H).

LC-MS: Rt=3.38 min, m/z=428 [M+H]$^+$.

Example 152

N-(4-(4-(4-Chloro-5-cyanopyridin-2-yl)piperazin-1-yl)phenyl)-4-methoxybenzamide

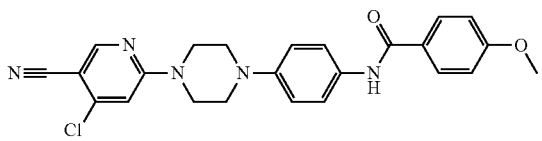 [SMILES: COc1ccc(C(=O)Nc2ccc(N3CCN(c4cc(Cl)c(C#N)cn4)CC3)cc2)cc1]

Yield: 7 mg.

$^1$H NMR (400 MHz, DMSO): δ 9.84 (s, 1H), 8.50 (s, 1H), 7.87 (d, J=8.8 Hz, 2H), 7.56 (d, J=9.1 Hz, 2H), 7.20 (s, 1H), 6.98 (d, J=8.8 Hz, 2H), 6.92 (d, J=9.1 Hz, 2H), 3.81 (dd, J=4.9, 4.9 Hz, 4H), 3.14 (dd, J=5.1, 5.1 Hz, 4H).

LC-MS: Rt=3.48 min, m/z=448 [M+H]$^+$.

Example 153

N-(4-(4-(4-Cyano-3-methylphenyl)piperazin-1-yl)phenyl)-4-methoxybenzamide

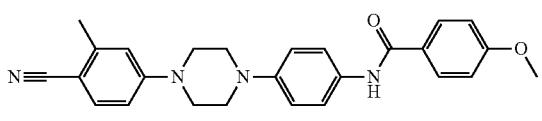

Yield: 51 mg.

$^1$H NMR (400 MHz, DMSO): δ 9.92 (s, 1H), 7.95 (d, J=8.9 Hz, 2H), 7.64 (d, J=9.0 Hz, 2H), 7.54 (d, J=8.8 Hz, 1H), 7.07-6.98 (m, 5H), 6.93 (dd, J=2.5, 8.8 Hz, 1H), 3.84 (s, 3H), 3.50 (dd, J=5.1, 5.1 Hz, 4H), 3.24 (dd, J=5.1, 5.1 Hz, 4H), 2.41 (s, 3H).

LC-MS: Rt=3.41 min, m/z=427 [M+H]$^+$.

Example 154

N-(4-(4-(6-Cyanopyridin-3-yl)piperazin-1-yl)phenyl)-4-methoxybenzamide

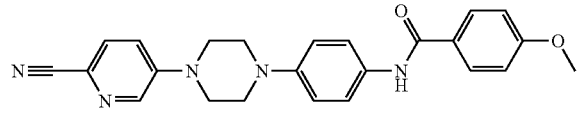

Yield: 15 mg.

$^1$H NMR (400 MHz, DMSO): δ 9.99 (s, 1H), 8.57 (d, J=2.5 Hz, 1H), 8.01 (d, J=8.6 Hz, 2H), 7.85 (d, J=8.8 Hz, 1H), 7.71 (d, J=9.1 Hz, 2H), 7.52 (dd, J=2.8, 8.8 Hz, 1H), 7.12 (d, J=8.6 Hz, 2H), 7.07 (d, J=8.8 Hz, 2H), 3.91 (s, 3H), 3.65 (dd, J=5.1, 5.1 Hz, 4H), 3.34-3.32 (m, 4H).

LC-MS: Rt=3.64 min, m/z=414 [M+H]$^+$.

Example 155

4-Methoxy-N-(4-(4-(2-methoxypyridin-4-yl)piperazin-1-yl)phenyl)benzamide

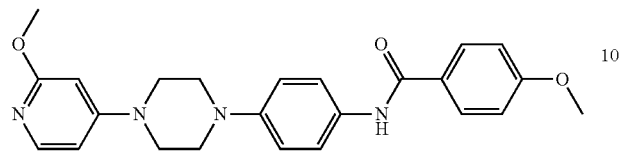

Yield: 44 mg.

$^1$H NMR (400 MHz, DMSO): δ 9.93 (s, 1H), 7.95 (d, J=8.9 Hz, 2H), 7.83 (d, J=6.0 Hz, 1H), 7.64 (d, J=9.0 Hz, 2H), 7.05 (d, J=8.9 Hz, 2H), 6.98 (d, J=9.2 Hz, 2H), 6.64 (dd, J=2.3, 6.1 Hz, 1H), 6.19 (d, J=2.1 Hz, 1H), 3.81 (d, J=21.0 Hz, 6H), 3.44 (dd, J=5.1, 5.1 Hz, 4H), 3.23-3.17 (m, 4H).

LC-MS: Rt=3.15 min, m/z=419 [M+H]$^+$.

Example 156

4-Methoxy-N-(4-(4-(6-methylpyridin-3-yl)piperazin-1-yl)phenyl)benzamide

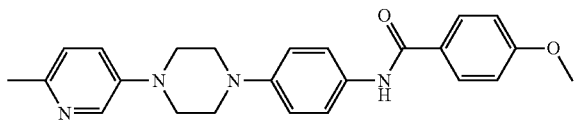

Yield: 43 mg.

$^1$H NMR (400 MHz, DMSO): δ 9.93 (s, 1H), 8.22 (d, J=2.8 Hz, 1H), 7.95 (d, J=8.9 Hz, 2H), 7.64 (d, J=8.9 Hz, 2H), 7.33 (dd, J=2.9, 8.5 Hz, 1H), 7.11 (d, J=8.5 Hz, 1H), 7.05 (d, J=8.8 Hz, 2H), 7.00 (d, J=9.0 Hz, 2H), 3.84 (s, 3H), 3.27 (d, J=4.5 Hz, 8H), 2.37 (s, 3H).

LC-MS: Rt=2.50 min, m/z=403 [M+H]$^+$.

General Synthesis Sub-Series 2

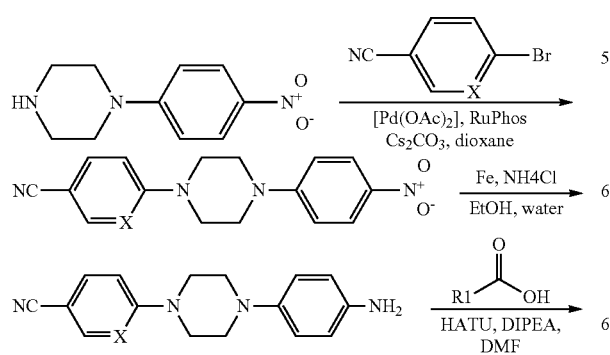

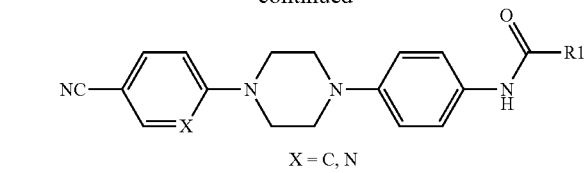

X = C, N 6-(4-(4-Nitrophenyl)piperazin-1-yl)nicotinonitrile

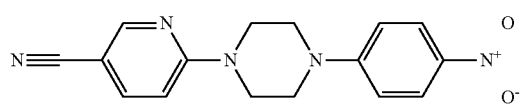

1-(4-Nitrophenyl)piperazine (1.5 g, 7.24 mmol), 6-bromopyridine-3-carbonitrile (1.46 g, 7.96 mmol), Cs$_2$CO$_3$ (5.19 g, 15.9 mmol) and RuPhos (675 mg, 1.45 mmol) were suspended in anhydrous dioxane (50 ml) and degassed for 5 minutes with nitrogen. [Pd(OAc)$_2$](162 mg, 0.72 mmol) was then added, the mixture further degassed (3 min) and the reaction vessel was sealed and heated at 90° C. overnight. After cooling to rt H$_2$O was added and the resulting precipitate collected by filtration. The precipitate was washed with H$_2$O (3×) and diethyl ether (3×) and dried to give the title compound (1.75 g, 80%) as a dark yellow solid.

$^1$H NMR (400 MHz, DMSO): δ 8.58 (d, J=1.5 Hz, 1H), 8.14 (d, J=9.3 Hz, 2H), 7.95 (dd, J=2.3, 9.1 Hz, 1H), 7.08 (d, J=9.6 Hz, 2H), 7.00 (d, J=9.3 Hz, 1H), 3.94-3.87 (m, 4H), 3.71 (dd, J=5.1, 5.1 Hz, 4H). LC-MS: Rt=1.60 min, m/z=310 [M+H]$^+$.

4-(4-(4-Nitrophenyl)piperazin-1-yl)benzonitrile

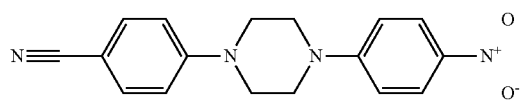

1-(4-Nitrophenyl)piperazine (1.5 g, 7.24 mmol), 4-bromobenzonitrile (1.45 g, 7.96 mmol), Cs$_2$CO$_3$ (5.19 g, 15.9 mmol) and RuPhos (675 mg, 1.45 mmol) were suspended in anhydrous dioxane (50 ml) and degassed for 5 min with nitrogen. [Pd(OAc)$_2$] (162 mg, 0.72 mmol) was then added, the mixture further degassed (3 min) and the reaction vessel was sealed and heated at 90° C. overnight. After cooling to rt H$_2$O was added and the resulting precipitate collected by filtration. The precipitate was washed with H$_2$O (3×) and diethyl ether (3×) and dried to give the title compound (1.70 g, 77%) as a dark yellow solid.

$^1$H NMR (400 MHz, DMSO): δ 8.14 (d, J=9.1 Hz, 2H), 7.67 (d, J=8.6 Hz, 2H), 7.12-7.05 (m, 4H), 3.72 (m, 4H), 3.62 (m, 4H). LC-MS: Rt=1.65 min, m/z=307 [M−H]$^−$.

6-[4-(4-Aminophenyl)piperazin-1-yl]pyridine-3-carbonitrile (corresponds to Intermediate 50.a)

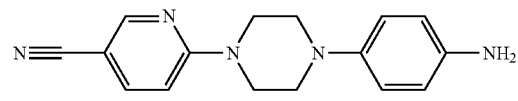

6-(4-(4-Nitrophenyl)piperazin-1-yl)nicotinonitrile (2.2 g, 7.11 mmol) was suspended in EtOH (71 ml) and H₂O (18 ml), NH₄Cl (228 mg, 4.27 mmol) was added and the mixture heated at 40° C. Iron powder (2.39 g, 42.7 mmol) was then added and the mixture was stirred at 90° C. for 2 h. After cooling to rt the reaction mixture was filtered and partitioned between DCM and saturated NaHCO₃. The aqueous phase was extracted with DCM (3×) and the combined organic phases dried (Na₂SO₄), filtered and evaporated. The residue was re-dissolved in chloroform and evaporated (3×) to provide the title compound (2.2 g, quant.) as a dark solid.

¹H NMR (400 MHz, DMSO): δ 8.55 (d, J=2.0 Hz, 1H), 7.91 (dd, J=2.4, 9.0 Hz, 1H), 7.03 (d, J=9.3 Hz, 1H), 6.80 (d, J=8.8 Hz, 2H), 6.56 (d, J=8.6 Hz, 2H), 4.70-4.64 (m, 2H), 3.82 (dd, J=4.9, 4.9 Hz, 4H), 3.03 (dd, J=4.9, 4.9 Hz, 4H). LC-MS: Rt=1.24 min, m/z=280 [M+H]⁺.

4-(4-(4-Aminophenyl)piperazin-1-yl)benzonitrile (corresponds to Intermediate 57.a)

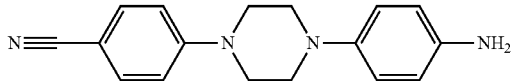

4-(4-(4-Nitrophenyl)piperazin-1-yl)benzonitrile (2.2 g, 7.14 mmol) was suspended in EtOH (71 ml) and H₂O (18 ml), NH₄Cl (228 mg, 4.27 mmol) was added and the mixture heated at 40° C. Iron powder (2.39 g, 42.7 mmol) was then added and the mixture was stirred at 90° C. for 2 h. After cooling to rt the reaction mixture was filtered and partitioned between DCM and saturated NaHCO₃. The aqueous phase was extracted with DCM (3×) and the combined organic phases dried (Na₂SO₄), filtered and evaporated. The residue was re-dissolved in chloroform and evaporated (3×) to provide the title compound (1.98 g, 99%) as a dark solid.

¹H NMR (400 MHz, DMSO): δ 7.62 (d, J=8.8 Hz, 2H), 7.09 (d, J=9.1 Hz, 2H), 6.76 (d, J=8.6 Hz, 2H), 6.54 (d, J=8.6 Hz, 2H), 4.63 (s, 2H), 3.47 (dd, J=4.7, 4.7 Hz, 4H), 3.04 (dd, J=4.7, 4.7 Hz, 4H). LC-MS: Rt=1.34 min, m/z=279 [M+H]⁺.

General Procedure B

Synthesis of N-(4-(4-(5-cyanopyridin-2-yl)piperazin-1-yl)phenyl)-R₁-amides and N-(4-(4-(4-cyanophenyl)piperazin-1-yl)phenyl)-R₁-amides

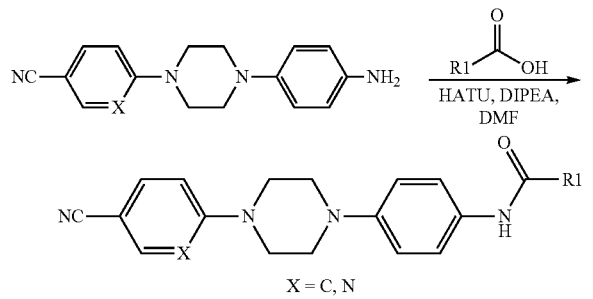

To a solution of the R₁-carboxylic acids (1.1 eq.) in anhydrous DMF (2 ml) and DIPEA (1.5 eq., 103 μL, 0.59 mmol) was added HATU (1.2 eq., 180 mg, 0.47 mmol) and the reaction mixture stirred for 30 minutes at rt. The amines 6-[4-(4-aminophenyl)piperazin-1-yl]pyridine-3-carbonitrile (110 mg, 0.39 mmol) or 4-(4-(4-aminophenyl)piperazin-1-yl)benzonitrile (110 mg, 0.4 mmol) were then added in DMF (2 ml) and the reaction was stirred at rt overnight. H₂O was then added and the resulting precipitate collected by filtration. The precipitate was washed with H₂O and dried. The crude solid was dissolved in DCM/MeOH (2:1), adsorbed onto HM-N beads (Biotage) and evaporated. The resulting material was dry-loaded onto a silica column and purified by flash column chromatography eluting with 0.5 to 3% MeOH/DCM to afford the title compounds as yellow solids.

Examples Prepared Using General Procedure B

Example 157

N-(4-(4-(4-Cyanophenyl)piperazin-1-yl)phenyl)-6-methoxynicotinamide

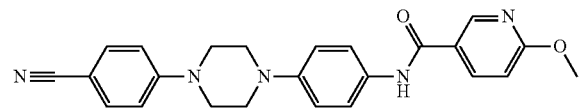

Yield: 19 mg.
¹H NMR (400 MHz, DMSO): δ 10.08 (s, 1H), 8.78 (d, J=2.1 Hz, 1H), 8.23 (dd, J=2.5, 8.7 Hz, 1H), 7.63 (dd, J=2.4, 9.1 Hz, 4H), 7.11 (d, J=9.2 Hz, 2H), 7.02 (d, J=9.2 Hz, 2H), 6.96 (d, J=8.7 Hz, 1H), 3.95 (s, 3H), 3.52 (dd, J=5.1, 5.1 Hz, 4H), 3.26 (dd, J=5.1, 5.1 Hz, 4H). LC-MS: Rt=3.33 min, m/z=414 [M+H]⁺.

Example 158

N-(4-(4-(4-Cyanophenyl)piperazin-1-yl)phenyl)-1-methyl-1H-pyrazole-4-carboxamide

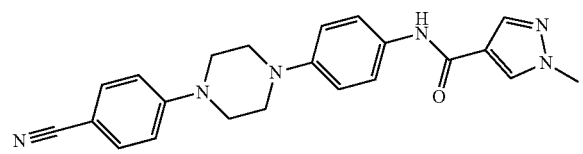 [SMILES: Cn1cc(C(=O)Nc2ccc(N3CCN(c4ccc(C#N)cc4)CC3)cc2)cn1]

Yield: 24 mg.
¹H NMR (400 MHz, DMSO): δ 9.65 (s, 1H), 8.27 (s, 1H), 7.99 (s, 1H), 7.60 (dd, J=9.0, 17.9 Hz, 4H), 7.11 (d, J=9.0 Hz, 2H), 6.99 (d, J=9.0 Hz, 2H), 3.90 (s, 3H), 3.51 (dd, J=5.1, 5.1 Hz, 4H), 3.24 (dd, J=5.1, 5.1 Hz, 4H). LC-MS: Rt=3.16 min, m/z=387 [M+H]⁺.

Example 159

N-(4-(4-(5-Cyanopyridin-2-yl)piperazin-1-yl)phenyl)-3,4-dimethoxybenzamide

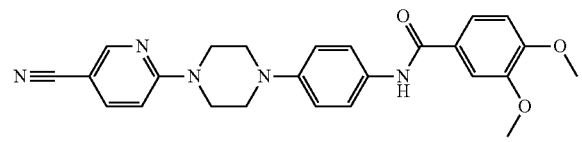 [SMILES: COc1ccc(C(=O)Nc2ccc(N3CCN(c4ccc(C#N)cn4)CC3)cc2)cc1OC]

Yield: 62 mg.
¹H NMR (400 MHz, DMSO): δ 9.94 (s, 1H), 8.57 (d, J=2.3 Hz, 1H), 7.93 (dd, J=2.3, 9.1 Hz, 1H), 7.69-7.62 (m, 3H), 7.58 (d, J=1.8 Hz, 1H), 7.12 (d, J=8.3 Hz, 1H), 7.05 (dd, J=8.7, 8.7 Hz, 3H), 3.90-3.83 (m, 10H), 3.30-3.22 (m, 4H). LC-MS: Rt=3.23 min, m/z=444 [M+H]⁺.

Example 160

N-(4-(4-(5-Cyanopyridin-2-yl)piperazin-1-yl)phenyl)-3-fluoro-4-methoxybenzamide

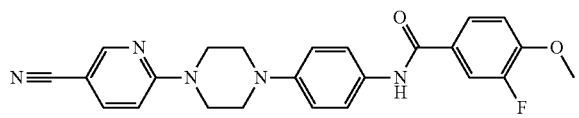 [SMILES: COc1ccc(C(=O)Nc2ccc(N3CCN(c4ccc(C#N)cn4)CC3)cc2)cc1F]

Yield: 66 mg.

¹H NMR (400 MHz, DMSO): δ 10.02 (s, 1H), 8.57 (d, J=2.3 Hz, 1H), 7.94 (dd, J=2.3, 9.1 Hz, 1H), 7.89 (s, 1H), 7.87 (s, 1H), 7.67 (d, J=8.8 Hz, 2H), 7.35 (dd, J=8.6, 8.6 Hz, 1H), 7.06 (dd, J=8.7, 8.7 Hz, 3H), 3.98 (s, 3H), 3.88 (dd, J=5.1, 5.1 Hz, 4H), 3.27 (dd, J=5.3, 5.3 Hz, 4H). LC-MS: Rt=3.29 min, m/z=432 [M+H]⁺.

Example 161

N-(4-(4-(5-Cyanopyridin-2-yl)piperazin-1-yl)phenyl)isonicotinamide

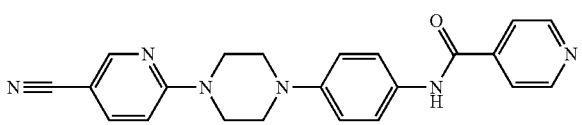

Yield: 32 mg.

¹H NMR (400 MHz, DMSO): δ 10.34 (s, 1H), 8.80-8.77 (m, 2H), 8.53 (d, J=2.1 Hz, 1H), 7.92-7.85 (m, 3H), 7.66 (d, J=9.2 Hz, 2H), 7.03 (d, J=9.2 Hz, 3H), 3.84 (dd, J=5.1, 5.1 Hz, 4H), 3.24 (dd, J=5.1, 5.1 Hz, 4H). LC-MS: Rt=2.89 min, m/z=385 [M+H]⁺.

Example 162

N-(4-(4-(5-Cyanopyridin-2-yl)piperazin-1-yl)phenyl)-5-methoxypicolinamide

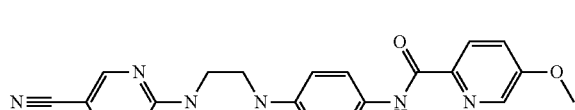

Yield: 36 mg.

¹H NMR (400 MHz, DMSO): δ 10.29 (s, 1H), 8.53 (d, J=2.0 Hz, 1H), 8.38 (d, J=2.6 Hz, 1H), 8.12 (d, J=9.0 Hz, 1H), 7.89 (dd, J=2.4, 9.0 Hz, 1H), 7.77 (d, J=9.2 Hz, 2H), 7.62 (dd, J=2.9, 8.8 Hz, 1H), 7.01 (dd, J=8.7, 8.7 Hz, 3H), 3.94 (s, 3H), 3.84 (dd, J=5.1, 5.1 Hz, 4H), 3.25-3.18 (m, 4H). LC-MS: Rt=3.43 min, m/z=415 [M+H]⁺.

Example 163

N-(4-(4-(4-Cyanophenyl)piperazin-1-yl)phenyl)-3-fluoro-4-methoxybenzamide

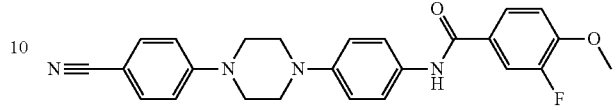

Yield: 33 mg.

¹H NMR (400 MHz, DMSO): δ 9.99 (s, 1H), 7.86 (s, 1H), 7.83 (s, 1H), 7.63 (dd, J=3.8, 9.0 Hz, 4H), 7.31 (dd, J=8.6, 8.6 Hz, 1H), 7.11 (d, J=9.2 Hz, 2H), 7.01 (d, J=9.2 Hz, 2H), 3.94 (s, 3H), 3.52 (dd, J=5.1, 5.1 Hz, 4H), 3.26 (dd, J=5.1, 5.1 Hz, 4H). LC-MS: Rt=3.42 min, m/z=431 [M+H]⁺.

Example 164

4-Cyano-N-(4-(4-(5-cyanopyridin-2-yl)piperazin-1-yl)phenyl)benzamide

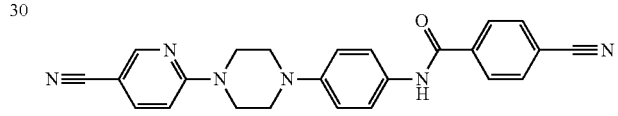

Yield: 27 mg.

¹H NMR (400 MHz, DMSO): δ 10.32 (s, 1H), 8.53 (d, J=2.0 Hz, 1H), 8.11 (d, J=8.5 Hz, 2H), 8.03 (d, J=8.5 Hz, 2H), 7.90 (dd, J=2.4, 9.0 Hz, 1H), 7.66 (d, J=9.0 Hz, 2H), 7.02 (d, J=9.0 Hz, 3H), 3.84 (dd, J=5.1, 5.1 Hz, 4H), 3.24 (dd, J=5.2, 5.2 Hz, 4H). LC-MS: Rt=3.29 min, m/z=409 [M+H]⁺.

Example 165

N-(4-(4-(4-Cyanophenyl)piperazin-1-yl)phenyl)pyrimidine-4-carboxamide

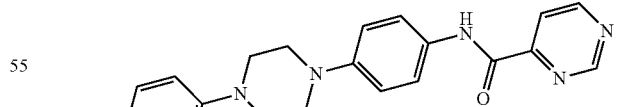

Yield: 34 mg.

¹H NMR (400 MHz, DMSO): δ 10.69 (s, 1H), 9.42 (d, J=1.4 Hz, 1H), 9.13 (d, J=5.1 Hz, 1H), 8.13 (dd, J=1.4, 5.1 Hz, 1H), 7.81 (d, J=9.2 Hz, 2H), 7.63 (d, J=9.0 Hz, 2H), 7.11 (d, J=9.0 Hz, 2H), 7.03 (d, J=9.2 Hz, 2H), 3.52 (dd, J=5.1, 5.1 Hz, 4H), 3.29 (dd, J=5.1, 5.1 Hz, 4H). LC-MS: Rt=3.34 min, m/z=385 [M+H]⁺.

Example 166

N-(4-(4-(4-Cyanophenyl)piperazin-1-yl)phenyl)-5-methoxypicolinamide

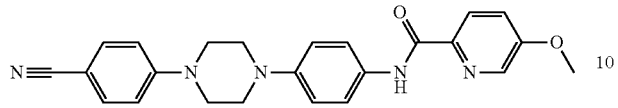

Yield: 22 mg.
$^1$H NMR (400 MHz, DMSO): δ 10.30 (s, 1H), 8.39 (d, J=2.6 Hz, 1H), 8.12 (d, J=8.7 Hz, 1H), 7.77 (d, J=9.0 Hz, 2H), 7.64-7.60 (m, 3H), 7.11 (d, J=9.2 Hz, 2H), 7.01 (d, J=9.2 Hz, 2H), 3.94 (s, 3H), 3.51 (dd, J=5.1, 5.1 Hz, 4H), 3.26 (dd, J=5.1, 5.1 Hz, 4H). LC-MS: Rt=3.52 min, m/z=414 [M+H]$^+$.

Example 167

N-(4-(4-(4-Cyanophenyl)piperazin-1-yl)phenyl)-4-methoxy-3-methylbenzamide

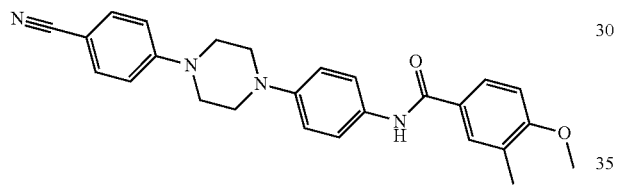

Yield: 45 mg.
$^1$H NMR (400 MHz, DMSO): δ 9.88 (s, 1H), 7.84 (dd, J=2.2, 8.5 Hz, 1H), 7.80 (d, J=1.8 Hz, 1H), 7.67-7.61 (m, 4H), 7.11 (d, J=9.2 Hz, 2H), 7.06 (d, J=8.7 Hz, 1H), 7.00 (d, J=9.2 Hz, 2H), 3.88 (s, 3H), 3.51 (dd, J=5.1, 5.1 Hz, 4H), 3.25 (dd, J=5.1, 5.1 Hz, 4H), 2.23 (s, 3H). LC-MS: Rt=3.52 min, m/z=427 [M+H]$^+$.

Example 168

N-(4-(4-(4-Cyanophenyl)piperazin-1-yl)phenyl)-4-methoxy-2-methylbenzamide

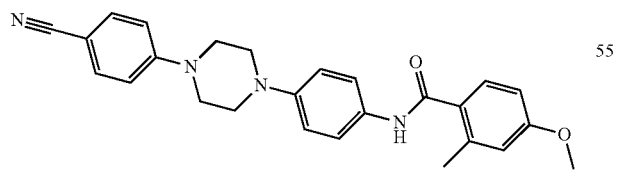

Yield: 39 mg.
$^1$H NMR (400 MHz, DMSO): δ 9.95 (s, 1H), 7.65-7.60 (m, 4H), 7.43 (d, J=8.3 Hz, 1H), 7.11 (d, J=9.2 Hz, 2H), 6.99 (d, J=9.2 Hz, 2H), 6.87-6.83 (m, 2H), 3.80 (s, 3H), 3.51 (dd, J=5.1, 5.1 Hz, 4H), 3.23 (dd, J=5.1, 5.1 Hz, 4H), 2.40 (s, 3H). LC-MS: Rt=3.39 min, m/z=427 [M+H]$^+$.

Example 169

N-(4-(4-(4-Cyanophenyl)piperazin-1-yl)phenyl)-3,4-dimethoxybenzamide

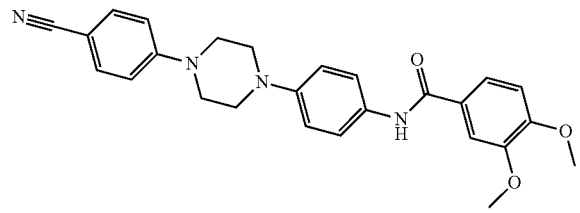 [SMILES: COc1ccc(C(=O)Nc2ccc(N3CCN(c4ccc(C#N)cc4)CC3)cc2)cc1OC]

Yield: 52 mg.
$^1$H NMR (400 MHz, DMSO): δ 9.91 (s, 1H), 7.66-7.60 (m, 5H), 7.54 (d, J=2.0 Hz, 1H), 7.10 (dd, J=8.9, 11.9 Hz, 3H), 7.01 (d, J=9.2 Hz, 2H), 3.85 (d, J=3.1 Hz, 6H), 3.52 (dd, J=5.1, 5.1 Hz, 4H), 3.26 (dd, J=5.1, 5.1 Hz, 4H). LC-MS: Rt=3.30 min, m/z=443 [M+H]$^+$.

Example 170

N-(4-(4-(5-Cyanopyridin-2-yl)piperazin-1-yl)phenyl)-4-methoxy-3-methylbenzamide

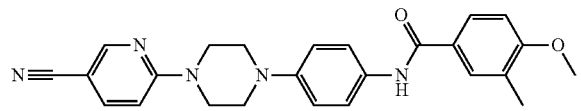 [SMILES: COc1ccc(C(=O)Nc2ccc(N3CCN(c4ccc(C#N)cn4)CC3)cc2)cc1C]

Yield: 37 mg.
$^1$H NMR (400 MHz, DMSO): δ 9.88 (s, 1H), 8.53 (d, J=2.4 Hz, 1H), 7.90 (dd, J=2.4, 9.0 Hz, 1H), 7.84 (dd, J=2.1, 8.5 Hz, 1H), 7.79 (d, J=1.8 Hz, 1H), 7.64 (d, J=9.0 Hz, 2H), 7.07-6.98 (m, 4H), 3.88 (s, 3H), 3.84 (dd, J=5.1, 5.1 Hz, 4H), 3.24-3.17 (m, 4H), 2.23 (s, 3H). LC-MS: Rt=3.45 min, m/z=428 [M+H]$^+$.

Example 171

N-(4-(4-(5-Cyanopyridin-2-yl)piperazin-1-yl)phenyl)-6-methoxynicotinamide

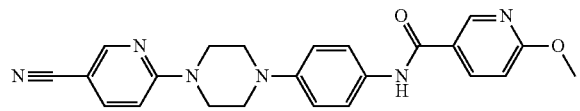 [SMILES: COc1ccc(C(=O)Nc2ccc(N3CCN(c4ccc(C#N)cn4)CC3)cc2)cn1]

Yield: 34 mg.
$^1$H NMR (400 MHz, DMSO): δ 10.08 (s, 1H), 8.78 (d, J=2.4 Hz, 1H), 8.53 (d, J=2.4 Hz, 1H), 8.23 (dd, J=2.5, 8.7 Hz, 1H), 7.90 (dd, J=2.3, 9.1 Hz, 1H), 7.63 (d, J=9.0 Hz, 2H), 7.02 (dd, J=6.5, 9.0 Hz, 3H), 6.95 (d, J=8.7 Hz, 1H), 3.95 (s, 3H), 3.84 (dd, J=5.1, 5.1 Hz, 4H), 3.23 (dd, J=5.1, 5.1 Hz, 4H). LC-MS: Rt=3.24 min, m/z=415 [M+H]$^+$.

Example 172

Methyl 6-(4-(4-(4-methoxybenzamido)phenyl)piperazin-1-yl)nicotinate

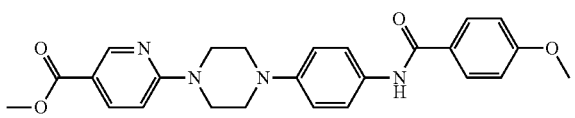

4-Methoxy-N-(4-(piperazin-1-yl)phenyl)benzamide (96 mg, 0.25 mmol), methyl 6-bromopyridine-3-carboxylate (1.1 eq.) and DIPEA (5 eq., 161.3 mg, 1.25 mmol) were combined in a reaction tube. NMP (1 ml) was then added, the reaction tube flushed with nitrogen, sealed and the reaction mixture was stirred at 120° C. for 2.5 h. After completion the reaction mixture was cooled to rt and H$_2$O added. The precipitate formed was collected by filtration, washed with H$_2$O and dried. The product was triturated with Et2O/MeOH (95:5). The resulting material was dried in vacuo to afford the title compound. Yield 81 mg.

$^1$H NMR (400 MHz, DMSO): δ 9.46 (s, 1H), 8.70 (d, J=2.0 Hz, 1H), 8.02-7.92 (m, 3H), 7.61 (d, J=8.9 Hz, 2H), 7.03 (d, J=8.8 Hz, 2H), 6.96 (d, J=8.9 Hz, 2H), 6.87 (d, J=9.0 Hz, 1H), 3.88-3.83 (m, 9H), 3.29 (dd, J=5.2, 5.2 Hz, 4H), 2.81 (bs, 4H). LC-MS: Rt=3.70 min, m/z=447 [M+H]$^+$.

General Synthesis Sub-Series 3

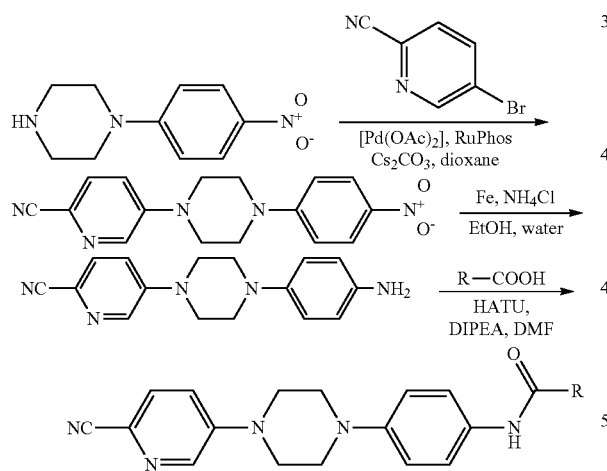

5-(4-(4-Nitrophenyl)piperazin-1-yl)picolinonitrile

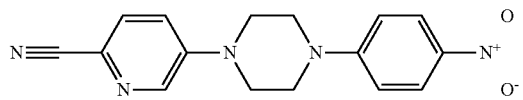

1-(4-Nitrophenyl)piperazine (622 mg, 3.0 mmol), 5-bromopicolinonitrile (500 mg, 2.73 mmol), Cs$_2$CO$_3$ (1.78 g, 5.46 mmol) and RuPhos (255 mg, 0.55 mmol) were suspended in anhydrous dioxane (15 ml) and degassed for 5 min with nitrogen. [Pd(OAc)$_2$] (61 mg, 0.27 mmol) was then added, the mixture further degassed (3 min) and the reaction vessel was sealed and heated at 90° C. for 4 h. After cooling to rt H$_2$O was added and the resulting precipitate collected by filtration. The precipitate was washed with H$_2$O (3×) and diethyl ether (3×) and dried to give the title compound (800 mg, 94%) as a yellow solid.

$^1$H NMR (400 MHz, DMSO): δ 8.49 (d, J=3.0 Hz, 1H), 8.15 (d, J=9.3 Hz, 2H), 7.84 (d, J=8.8 Hz, 1H), 7.43 (dd, J=3.0, 9.1 Hz, 1H), 7.10 (d, J=9.3 Hz, 2H), 3.73 (dd, J=5.8, 13.4 Hz, 8H). LC-MS: Rt=1.52 min, m/z=310 [M+H]$^+$.

5-(4-(4-Aminophenyl)piperazin-1-yl)picolinonitrile

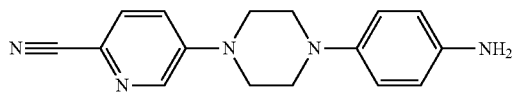

5-(4-(4-Nitrophenyl)piperazin-1-yl)picolinonitrile (830 mg, 2.68 mmol) was suspended in EtOH (32 ml) and H$_2$O (8 ml), NH$_4$Cl (86 mg, 1.61 mmol) was added and the mixture heated at 40° C. Iron powder (0.9 g, 16.1 mmol) was then added and the mixture was stirred at 90° C. for 2 h. Additional iron powder (450 mg, 8.0 mmol) was added and stirring continued at 95° C. for 5 h. After cooling to rt the reaction mixture was filtered and partitioned between DCM and saturated NaHCO$_3$. The aqueous phase was extracted with DCM (3×) and the combined organic phases dried (Na$_2$SO$_4$), filtered and evaporated. The residue was re-dissolved in chloroform and evaporated (3×) to provide the title compound (705 mg, 94%) as a dark solid.

$^1$H NMR (400 MHz, DMSO): δ 8.52 (d, J=2.8 Hz, 1H), 7.82 (d, J=8.6 Hz, 1H), 7.47 (dd, J=3.0, 9.1 Hz, 1H), 6.81 (d, J=8.8 Hz, 2H), 6.59-6.55 (m, 2H), 4.67 (s, 2H), 3.58 (dd, J=5.1, 5.1 Hz, 4H), 3.09 (dd, J=5.1, 5.1 Hz, 4H). LC-MS: Rt=1.27 min, m/z=280 [M+H]$^+$.

Example 173

N-(4-(4-(6-Cyanopyridin-3-yl)piperazin-1-yl)phenyl)-5-methoxypicolinamide

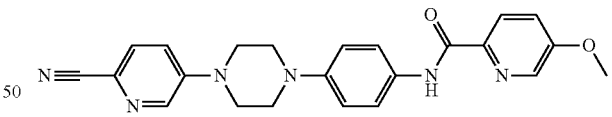

To a solution of 5-methoxypicolinic acid (1.1 eq., 36 mg, 236 μmol) in anhydrous DMF (2.5 ml) and DIPEA (1.5 eq., 56 μL, 322 μmol) was added HATU (1.2 eq., 98 mg, 258 μmol) and the reaction mixture was stirred for 20 min at rt. 5-(4-(4-Aminophenyl)piperazin-1-yl)picolinonitrile (60 mg, 215 μmol) was then added and the reaction was stirred at rt overnight. H$_2$O was then added and the resulting precipitate collected by filtration. The precipitate was washed with H$_2$O (3×) and diethyl ether (3×) and dried. The crude solid was dissolved in DCM/MeOH (2:1), adsorbed onto HM-N beads (Biotage) and evaporated. The resulting material was dry-loaded onto a silica column and purified by flash column chromatography eluting with 0.5 to 3% methanol/dichloromethane to afford the title compound (31 mg, 35%) as a yellow solid.

¹H NMR (400 MHz, DMSO): δ 10.34 (s, 1H), 8.55 (d, J=2.8 Hz, 1H), 8.43 (d, J=2.8 Hz, 1H), 8.16 (d, J=8.6 Hz, 1H), 7.82 (dd, J=7.5, 8.7 Hz, 3H), 7.66 (dd, J=2.9, 8.7 Hz, 1H), 7.50 (dd, J=3.0, 9.1 Hz, 1H), 7.06 (d, J=9.1 Hz, 2H), 3.99 (s, 3H), 3.63 (dd, J=5.2, 5.2 Hz, 4H), 3.32 (dd, J=5.1, 5.1 Hz, 4H). LC-MS: Rt=3.80 min, m/z=415 [M+H]⁺.

Example 174

N-[4-[4-(5-Cyano-2-pyridyl)piperazin-1-yl]phenyl]-4-prop-2-ynoxy-benzamide

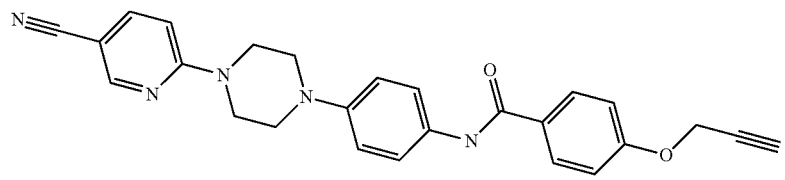 [SMILES: C#CCOc1ccc(C(=O)Nc2ccc(N3CCN(c4ccc(C#N)cn4)CC3)cc2)cc1]

A solution of 6-[4-(4-aminophenyl)piperazin-1-yl]pyridine-3-carbonitrile (Example 50, step a) (250 mg, 0.890 mmol), 4-prop-2-ynoxybenzoic acid (CAS Nr. 21926-55-6) (158 mg, 0.890 mmol), O-(7-azabenzotriazol-1-yl)-N,N,N,N-tetramethyluronium hexafluorophosphate (374 mg, 0.980 mmol) and triethylamine (0.25 mL, 1.79 mmol) in DMF (10 mL) was stirred at 25° C. for 16 h. The reaction was quenched with H₂O (20 mL). The solid was filtered and washed with EtOH (10 mL). The resulting solid was crystallized from DMSO/EtOH (25 mL/80 mL)) to afford the N-[4-[4-(5-cyano-2-pyridyl)piperazin-1-yl]phenyl]-4-prop-2-ynoxy-benzamide (209 mg, 52%) as pink solid. LC-MS: m/z=438.2 [M+H]⁺.

Example 175

N-[4-[4-(5-Cyano-2-pyridyl)piperazin-1-yl]phenyl]-4-(2-prop-2-ynoxyethoxy)benzamide

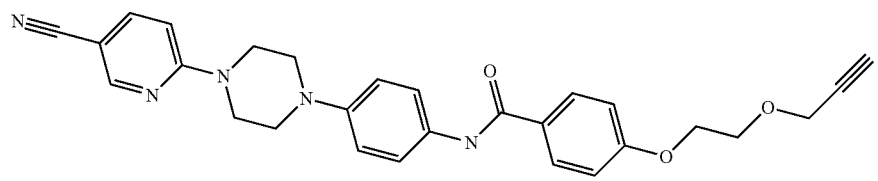 [SMILES: C#CCOCCOc1ccc(C(=O)Nc2ccc(N3CCN(c4ccc(C#N)cn4)CC3)cc2)cc1]

A solution of 6-[4-(4-aminophenyl)piperazin-1-yl]pyridine-3-carbonitrile (Example 50, step a) (250 mg, 0.890 mmol), 4-(2-prop-2-ynoxyethoxy)benzoic acid (CAS Nr. 1153245-98-7) (197 mg, 0.890 mmol), O-(7-azabenzotriazol-1-yl)-N,N,N,N-tetramethyluronium hexafluorophosphate (374 mg, 0.980 mmol) and triethylamine (0.31 mL, 2.24 mmol) in DMF (15 mL) was stirred at 25° C. for 16 h. The reaction was quenched with H₂O (35 mL). The resulting solid was collected by filtration and recrystallized from DMSO/EtOH (5 mL/10 mL). The solid was collected, washed with EtOH (50 mL) and dried under vacuum to afford N-[4-[4-(5-cyano-2-pyridyl)piperazin-1-yl]phenyl]-4-(2-prop-2-ynoxyethoxy)benzamide (140 mg, 32%) as the pink solid. LC-MS: m/z=482.2 [M+H]⁺.

Example 176

N-[4-[4-(5-Ethynyl-2-pyridyl)piperazin-1-yl]phenyl]-4-methoxy-benzamide

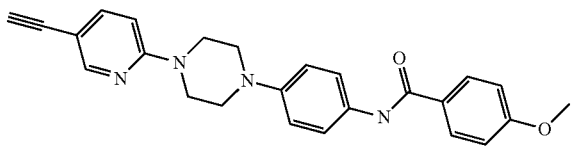 [SMILES: C#Cc1ccc(N2CCN(c3ccc(NC(=O)c4ccc(OC)cc4)cc3)CC2)nc1]

a) tert-Butyl 4-(5-ethynyl-2-pyridyl)piperazine-1-carboxylate

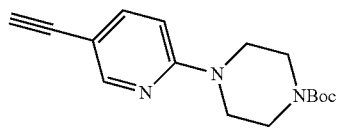 [SMILES: C#Cc1ccc(N2CCN(C(=O)OC(C)(C)C)CC2)nc1]

A solution of 5-ethynyl-2-fluoro-pyridine (500 mg, 4.13 mmol), 1-Boc-piperazine (923 mg, 4.95 mmol) and triethylamine (1.15 mL, 8.26 mmol) in MeCN (10 mL) was stirred at 60° C. for 16 h. The reaction was poured into H₂O (50 mL) and extracted with EtOAc (70 mL). The organic layer was separated, dried over Na₂SO₄, filtered and concentrated under vacuum. The residue was purified by silica gel chromatography (petroleum ehter:EtOAc, 10:1 to 2:1) to afford tert-butyl 4-(5-ethynyl-2-pyridyl)piperazine-1-carboxylate (630 mg, 79%) as white solid. ¹H NMR (CHLOROFORM-d, 400 MHz) δ 8.24 (d, 1H, J=2.2 Hz), 7.48 (dd, 1H, J=2.3, 8.9 Hz), 6.48 (d, 1H, J=8.8 Hz), 3.4-3.5 (m, 8H), 3.00 (s, 1H), 1.41 (s, 9H).

b) 1-(5-Ethynyl-2-pyridyl)piperazine hydrochloride

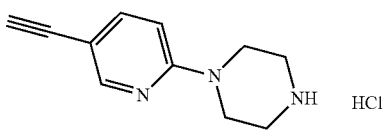

To a solution at 25° C. of tert-butyl 4-(5-ethynyl-2-pyridyl)piperazine-1-carboxylate (600 mg, 2.09 mmol) in EtOAc (10 mL) was added dropwise HCl in dioxane (10.4 mL, 41.76 mmol). The resulting mixture was stirred for 16 h. The reaction solution was concentrated under vacuum and the resulting solid was collected and was washed with EtOAc (20 mL) to afford 1-(5-ethynyl-2-pyridyl)piperazine hydrochloride (422 mg, 70%) as white solid. LC-MS: m/z=188.1 [M+H]$^+$.

c) 1-(5-Ethynyl-2-pyridyl)-4-(4-nitrophenyl)piperazine

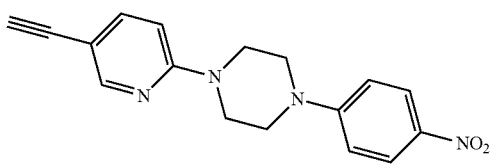

A solution of 1-(5-ethynyl-2-pyridyl)piperazine (460 mg, 2.46 mmol), 4-fluoronitrobenzene (347 mg, 2.46 mmol), and potassium carbonate (849 mg, 6.14 mmol) in DMSO (80 mL) was stirred at 90° C. for 1.5 h. The reaction solution was poured into H$_2$O (300 mL) and the solid was collected by filtration and washed with THF (20 mL) to afford 1-(5-ethynyl-2-pyridyl)-4-(4-nitrophenyl)piperazine (460 mg, 50%) as light yellow solid. LC-MS: m/z=309.0 [M+H]$^+$.

d) 4-[4-(5-Ethynyl-2-pyridyl)piperazin-1-yl]aniline

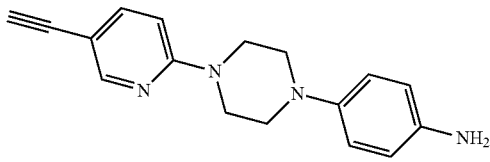 [SMILES: C#Cc1ccc(N2CCN(c3ccc([N+](=O)[O-])cc3)CC2)nc1]

To a solution of 1-(5-ethynyl-2-pyridyl)-4-(4-nitrophenyl)piperazine (430 mg, 1.39 mmol) and NH$_4$Cl (1.48 g, 27.9 mmol) in MeOH (20 mL) was added Zn (1.82 g, 27.9 mmol) and the mixture was stirred at 25° C. for 4 h. The reaction was filtered through Celite. The filtrate was concentrated under vacuum. The residue was washed with H$_2$O (50 mL), and the solid was collected to afford 4-[4-(5-ethynyl-2-pyridyl)piperazin-1-yl]aniline (282 mg, 62%) as yellow solid. LC-MS: m/z=279.1 [M+H]$^+$.

e) N-[4-[4-(5-Ethynyl-2-pyridyl)piperazin-1-yl]phenyl]-4-methoxy-benzamide

A solution of 4-[4-(5-ethynyl-2-pyridyl)piperazin-1-yl]aniline (200 mg, 0.720 mmol), 4-methoxybenzoic acid (109 mg, 0.720 mmol), 0-(7-azabenzotriazol-1-yl)-N,N,N'N'-tetramethyluronium hexafluorophosphate (328 mg, 0.860 mmol) and triethylamine (0.3 mL, 2.16 mmol) in DMF (9 mL) was stirred at 25° C. for 16 h. The reaction was filtered through Celite. The filtrate was purified by two consecutive preparative HPLCs (HCl$_{aq}$. as additive, then TFA$_{aq}$.) to afford N-[4-[4-(5-ethynyl-2-pyridyl)piperazin-1-yl]phenyl]-4-methoxy-benzamide (41 mg, 13%) as yellow solid. LC-MS: m/z=413.2 [M+H]$^+$.

Example 177

4-Prop-2-ynoxy-N-[4-[4-(2-pyridyl)piperazin-1-yl]phenyl]benzamide

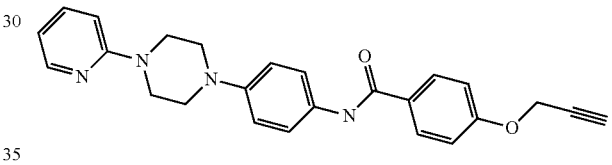

A solution of 4-[4-(2-pyridyl)piperazin-1-yl]aniline (Example 1, step b) (260 mg, 1.02 mmol), 4-prop-2-ynoxybenzoic acid (CAS Nr. 21926-55-6) (180 mg, 1.02 mmol), 0-(7-azabenzotriazol-1-yl)-N,N,N,N-tetramethyluronium hexafluorophosphate (428 mg, 1.12 mmol) and triethylamine (0.28 mL, 2.04 mmol) in DMF (10 mL) was stirred at 25° C. for 16 h. The reaction was quenched with H$_2$O (20 mL). The resulting solid was filtered and washed with EtOH (10 mL) before purification by Prep-HPLC (TFA as additive) to afford 4-prop-2-ynoxy-N-[4-[4-(2-pyridyl)piperazin-1-yl]phenyl]benzamide (62 mg, 15%) as pink solid. LCMS: m/z=413.2 [M+H]$^+$.

Example 178

4-(2-Prop-2-ynoxyethoxy)-N-[4-[4-(2-pyridyl)piperazin-1-yl]phenyl]benzamide

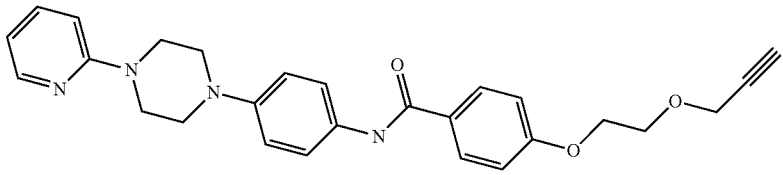 [SMILES: C#CCOCCOc1ccc(C(=O)Nc2ccc(N3CCN(c4ccccn4)CC3)cc2)cc1]

A solution of 4-(2-prop-2-ynoxyethoxy)benzoic acid (CAS Nr. 1153245-98-7) (260 mg, 1.18 mmol), 4-[4-(2-pyridyl)piperazin-1-yl]aniline (300.0 mg, 1.18 mmol), 0-(7-azabenzotriazol-1-yl)-N,N,N,N-tetramethyluronium hexafluorophosphate (493 mg, 1.3 mmol) and triethylamine (0.33 mL, 2.36 mmol) in DMF (10 mL) was stirred at 25° C. for 16 h. The reaction was quenched with H₂O (20 mL). The resulting solid was collected by filtration and washed with EtOH (10 mL). The crude product was re-crystallized from DMSO/EtOH (25 mL/80 mL) to afford 4-(2-prop-2-ynoxyethoxy)-N-[4-[4-(2-pyridyl)piperazin-1-yl]phenyl]benzamide (52 mg, 9%) as pink solid. LC-MS: m/z=457.3 [M+H]⁺.

Tritiation Procedures
General Methods

Reactions with tritium gas were performed on a stainless steel manifold purchased from RC Tritec AG. Liquid scintillation counting for tritium compounds was accomplished using a HIDEX 300 SL and ULTIMATE GOLD cocktail (PerkinElmer Inc., Waltham, Mass., USA). Pre-coated thin-layer chromatography sheets (TLC) were obtained from Merck KGaA (Darmstadt, Germany). Developed plates were visualized using an automatic TLC linear analyzer (Berthold Technologies, Bad Wildbad, Germany). Radiochemical purity was measured using the β-radioactivity HPLC detector RAMONA with internal solid scintillator (Raytest, Straubenhardt, Germany). Molar activity was determined by mass spectrometric isotopic peak intensity distribution, using 4000QTRAP system (AB Sciex GmbH, Zug, CH), flow injection mode with a CTC PAL, and an Agilent 1100 microLC pump without any separation.

2-Fluoro-4-[³H₃]methoxy-N-(4-(4-(pyridin-2-yl)piperazin-1-yl)phenyl)benzamide ([³H]Example 1)

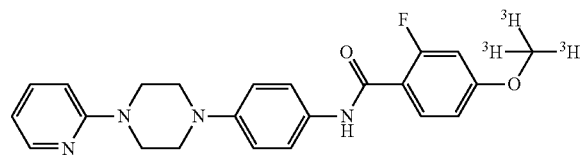 [SMILES: [3H]C([3H])([3H])Oc1ccc(C(=O)Nc2ccc(N3CCN(c4ccccn4)CC3)cc2)c(F)c1]

[³H]Methyl nosylate (152 μg, 1.85 GBq=50 mCi, 0.68 μmol), dissolved in 1 ml Tol, was transferred to a 5 ml reactor and concentrated under a stream of Ar to dryness. A solution of 2-fluoro-4-hydroxy-N-(4-(4-(pyridin-2-yl)piperazin-1-yl)phenyl)benzamide (785 μg, 2.0 μmol) in THF (0.4 ml) and Cs₂CO₃ (543 μg, 1.67 μmol) were added. The reactor was tightly closed, and the reaction mixture was stirred for 2.5 h at 50° C. The reaction mixture was filtered through a 0.22 μm membrane filter and purified by preparative HPLC (XBridge C18, 5 μm, 10 mm×250 mm) using MeCN/H₂O (70:30) as eluent (isocratic, run time 15 min) at a flow rate of 8 ml/min. An amount of 433 MBq (11.7 mCi) of the desired compound was obtained with a radiochemical purity of 99% and a molar activity of 2.7 TBq/mmol (73 Ci/mmol). The identity of the labeled compound was confirmed by MS and by co-injection of the cold reference standard with the radiolabeled material. MS m/z: 407.2 [M(H)+H]⁺ (5%), 409.2 [M(³H)+H]⁺ (3%), 411.2 [M(³H₂)+H]⁺ (24%), 413.2 [M(³H₃)+H]⁺ (68%).

4-[³H₃] Methoxy-N-[4-(4-pyridin-2-ylpiperazin-1-yl)phenyl]benzamide ([³H]Example 3)

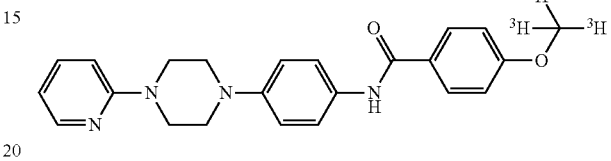

A solution of [³H]methyl nosylate (143 μg, 1.85 GBq=50 mCi, 0.64 μmol) in 5 ml Tol was transferred to a 5 ml reactor and concentrated under a stream of Ar to dryness. A solution of 4-hydroxy-N-(4-(4-(pyridin-2-yl)piperazin-1-yl)phenyl)benzamide (Example 2) (810 μg, 2.16 μmol) in THF (0.5 ml) and Cs₂CO₃ (460 μg, 1.41 μmol) were added. The reactor was tightly closed, and the reaction mixture was stirred for 16 h at 45° C. The reaction mixture was diluted with 1 ml MeCN/H₂O 1:1, filtered through a 0.22 μm membrane filter and purified by preparative HPLC (XBridge C18, 5 μm, 10 mm×250 mm) using 0.1 M ammonia formiate buffer, pH 9/MeCN/H₂O as eluent (isocratic 4 min: 1:1:8; gradient from 1:1:8 to 1:9:0 in 16 min) at a flow rate of 6 ml/min. An amount of 292 MBq (7.9 mCi) of the desired compound was obtained with a radiochemical purity of 96% and a molar activity of 2.9 TBq/mmol (78 Ci/mmol). The identity of the labeled compound was confirmed by MS and by co-injection of the cold reference standard with the radiolabeled material. MS m/z: 393.4 [M(³H₂)+H]⁺ (13%), 395.4 [M(³H₃)+H]⁺ (87%).

[³H]4-(2-(2-Fluoroethoxy)ethoxy)-N-(4-(4-(pyridin-2-yl)piperazin-1-yl)phenyl)benzamide ([³H]Example 12)

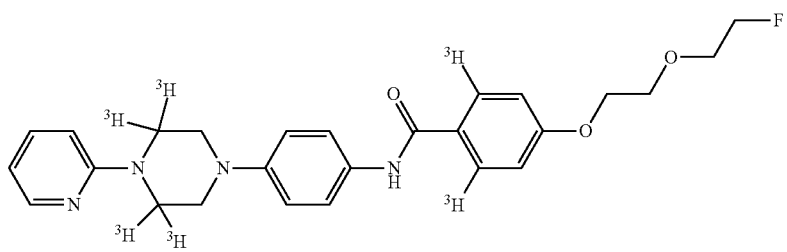 [SMILES: [3H]c1cc(OCCOCCF)cc([3H])c1C(=O)Nc1ccc(N2CC([3H])([3H])N(c3ccccn3)C([3H])([3H])C2)cc1]

In a 4 ml tritiation flask, 4-(2-(2-fluoroethoxy)ethoxy)-N-(4-(4-(pyridin-2-yl)piperazin-1-yl)phenyl) benzamide (Example 12) (2.0 mg, 4.31 μmol) and Kerr's catalyst ([Ir(Im- Mes)(PPhMe$_2$)(COD)]PF$_6$) (5.73 mg, 6.46 µmol) were dissolved in DMF (1 ml). The flask was attached to a RC Tritec tritium manifold and degassed by three freeze-thaw cycles. Tritium gas was introduced, and the light orange solution was vigorously stirred for 4 h in an atmosphere of tritium at 500 mbar. The solution was cooled by liquid nitrogen and the excess tritium gas in the reaction vessel was reabsorbed on a uranium trap for waste-tritium. The solvent was lyophilized off, and labile tritium was removed by lyophilization with a 9:1 mixture of EtOH and H$_2$O (3×1 ml) and Tol (2×1 ml). The remaining yellow oil was dissolved in DCM (0.3 ml), transferred in a 50 ml flask and the solution was diluted with 9 ml MeOH. Metal scavenger MP-TMT (macroporous polystyrene-bound trimercaptotriazine, Biotage, Uppsala, Sweden, 89.4 mg, load: 0.65 mmol/g, 58.1 µmol) was added and the mixture was shaken over night at room temperature. The scavenger was removed by filtering through a 0.45 m membrane filter. The crude product was purified by preparative HPLC (XBridge Prep, 5 µm, 10 mm×250 mm) using acetonitrile+0.01% TFA/water+ 0.01% TFA as eluent (gradient 1-15 min from 1:9 to 8:2, run time 17 min) at a flow rate of 7 ml/min. An amount of 148MBq (4 mCi) of the title compound was obtained with a radiochemical purity of 98% and a molar activity of 2.6 TBq/mmol (71.3 Ci/mmol), determined by MS spectrometry. The identity of the labeled compound was confirmed by MS and by co-injection of the cold reference standard with the radiolabeled material. MS: m/z=465.4 [M(H)+H]$^+$ (7%), 467.4 [M($^3$H)+H]$^+$ (19%), 469.4 [M($^3$H$_2$)+H]$^+$ (28%), 471.4 [M($^3$H$_3$)+H]$^+$ (24%), 473.4 [M($^3$H$_4$)+H]$^+$ (14%) 475.4 [M($^3$H$_5$)+H]$^+$ (5%), 467.4 [M($^3$H$_6$)+H]$^+$ (3%).

N-(4-(4-(5-Cyanopyridin-2-yl)piperazin-1-yl)phenyl)-4-[$^3$H$_3$]methoxybenzamide ([$^3$H]Example 50)

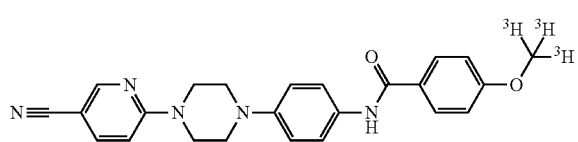 [SMILES: [3H]C([3H])([3H])Oc1ccc(C(=O)Nc2ccc(N3CCN(c4ccc(C#N)cn4)CC3)cc2)cc1]

A solution of [$^3$H]methyl nosylate (137 µg, 1.85 GBq=50 mCi, 0.62 µmol) in 5 ml Tol was transferred to a 5 ml round-bottomed flask and concentrated under a stream of Ar to dryness. A solution of N-(4-(4-(5-cyanopyridin-2-yl)piperazin-1-yl)phenyl)-4-hydroxybenzamide (Example 108) (1 mg, 2.50 µmol) in DMSO (0.5 ml) and Cs$_2$CO$_3$ (800 µg, 2.46 µmol) were added. The reactor was tightly closed, and the reaction mixture was stirred for 2 h at 70° C. The reaction mixture was diluted with 2 ml MeOH, filtered through a 500 mg SPE-HCO$_3$ cartridge (Agilent Technologies, Santa Clara, Calif., USA), washed with 10 ml MeOH and purified by preparative HPLC (XBridge C18, 5 µm, 10 mm×250 mm) using MeCN and H$_2$O as eluent (isocratic 3 min: 1:3; gradient from 1:3 to 3:2 in 15 min) at a flow rate of 6 ml/min. An amount of 163 MBq (4.4 mCi) of the desired compound was obtained with a radiochemical purity of 99% and a molar activity of 3.0 TBq/mmol (81 Ci/mmol). The identity of the labeled compound was confirmed by MS and by co-injection of the cold reference standard with the radiolabeled material. MS m/z: 414.3 [M(H)+H]$^+$ (3%), 416.3 [M($^3$H)+H]+(2%), 418.3 [M($^3$H$_2$)+H]$^+$ (5%), 420.3 [M($^3$H$_3$)+H]$^+$ (90%).

[$^3$H]N-(4-(4-(5-Cyanopyridin-2-yl)piperazin-1-yl)phenyl)-4-(2-(2-fluoroethoxy)ethoxy)benzamide ([$^3$H]Example 121)

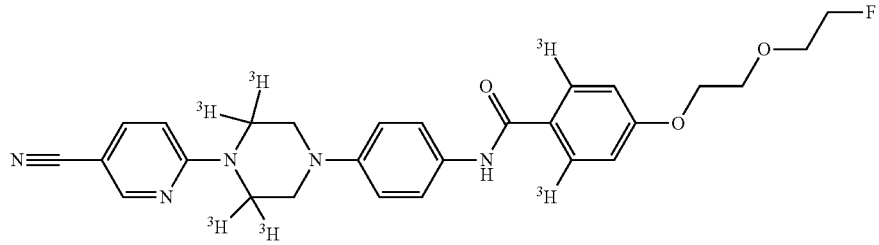 [SMILES: [3H]c1cc(OCCOCCF)cc([3H])c1C(=O)Nc1ccc(N2CC([3H])([3H])N(c3ccc(C#N)cn3)C([3H])([3H])C2)cc1]

In a 4 ml tritiation flask, N-(4-(4-(5-cyanopyridin-2-yl)piperazin-1-yl)phenyl)-4-(2-(2-fluoroethoxy)ethoxy)benzamide (Example 121) (2.0 mg, 4.09 µmol) and Crabtree's catalyst ([Ir(COD)(PCy$_3$)(Py)]PF$_6$) (4.32 mg, 5.31 µmol) were dissolved in DCM (1.0 ml). The reaction and the purification were performed in analogy to [$^3$H]4-(2-(2-fluoroethoxy)ethoxy)-N-(4-(4-(pyridin-2-yl)piperazin-1-yl)phenyl)benzamide ([$^3$H]Example 12) to provide 3.48 GBq (94 mCi) of the desired compound with a radiochemical purity of 98% and a molar activity of 3.81 TBq/mmol (103 Ci/mmol). The identity of the labeled compound was confirmed by MS and by co-injection of the cold reference standard with the radiolabeled material. MS m/z: 490.2 [M(H)+H]$^+$ (2%), 492.2 [M($^3$H)+H]$^+$ (3%), 494.2 [M($^3$H$_2$)+H]$^+$ (8%), 496.2 [M($^3$H$_3$)+H]$^+$ (26%), 498.2 [M($^3$H$_4$)+H]$^+$ (46%), 500.2 [M($^3$H$_5$)+H]$^+$ (15%).

[³H]N-(4-(4-(4-Cyanophenyl)piperazin-1-yl)phenyl)-4-(2-(2-fluoroethoxy)ethoxy)benzamide ([³H] Example 122)

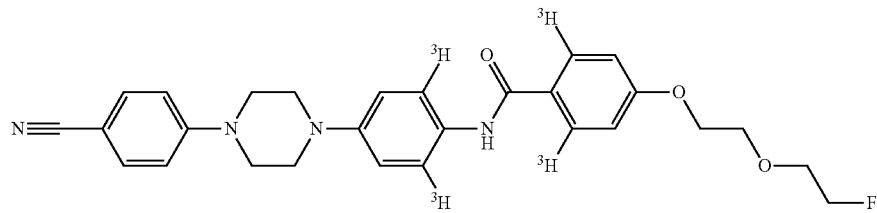 [SMILES: [3H]c1cc(N2CCN(c3ccc(C#N)cc3)CC2)cc([3H])c1NC(=O)c1c([3H])cc(OCCOCCF)cc1[3H]]

In a 4 ml tritiation flask, N-(4-(4-(4-cyanophenyl)piperazin-1-yl)phenyl)-4-(2-(2-fluoroethoxy)ethoxy) benzamide (Example 122) (2.0 mg, 7.8 µmol) and Kerr's catalyst ([Ir(Im-Mes)(PPhMe₂)(COD)]PF₆) (4.82 mg, 5.32 µmol) were dissolved in DCM (1.0 ml). The reaction and the purification were performed in analogy to [³H]4-(2-(2-fluoroethoxy)ethoxy)-N-(4-(4-(pyridin-2-yl)piperazin-1-yl)phenyl)benzamide ([³H]Example 12) to provide 777 GBq (21 mCi) of the desired compound with a radiochemical purity of 99% and a molar activity of 1.96 TBq/mmol (52.9 Ci/mmol). The identity of the labeled compound was confirmed by MS and by co-injection of the cold reference standard with the radiolabeled material. MS m/z: 491.4 [M(³H)+H]⁺ (4%), 493.4 [M(³H₂)+H]⁺ (11%), 495.4 [M(³H₃)+H]⁺ (34%), 497.4 [M(³H₄)+H]±(51%).

[³H]4-(Fluoromethoxy)-N-(4-(4-(pyridin-3-yl)piperazin-1-yl)phenyl)benzamide ([³H]Example 134)

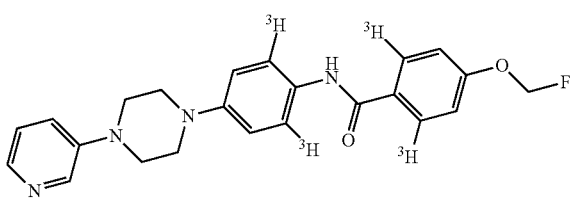 [SMILES: [3H]c1cc(N2CCN(c3cccnc3)CC2)cc([3H])c1NC(=O)c1c([3H])cc(OCF)cc1[3H]]

In a 4 ml tritiation flask, 4-(fluoromethoxy)-N-(4-(4-(pyridin-3-yl)piperazin-1-yl)phenyl)benzamide (Example 134) (4.66 mg, 11.5 µmol) and Crabtree's catalyst ([Ir(COD)(PCy₃)(Py)]PF₆) (14.51 mg, 18.0 µmol) were dissolved in chlorobenzene (0.8 ml). The reaction and the purification were performed in analogy to [³H]4-(2-(2-fluoroethoxy)ethoxy)-N-(4-(4-(pyridin-2-yl)piperazin-1-yl)phenyl)benzamide ([³H]Example 12), except for the reaction time of 3.5 h and the temperature that was increased to 90° C. 1.18 TBq (32 mCi) of the desired compound with a radiochemical purity of 98% and a molar activity of 1.66 TBq/mmol (44.9 Ci/mmol) were obtained. The identity of the labeled compound was confirmed by MS and by co-injection of the cold reference standard with the radiolabeled material. MS m/z: 407.2 [M(H)+H]⁺ (49%), 409.2 [M(³H)+H]⁺ (11%), 411.2 [M(³H₂)+H]⁺ (7%), 413.2 [M(³H₃)+H]⁺ (11%), 415.2 [M(³H₄)+H]⁺ (13%) 417.2 [M(³H₅)+H]⁺ (9%).

[³H]4-(Fluoromethoxy)-N-[4-(4-pyridin-2-ylpiperazin-1-yl)phenyl]benzamide ([³H]Example 135)

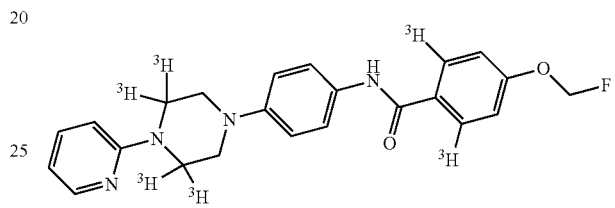

In a 4 ml tritiation flask, 4-(fluoromethoxy)-N-[4-(4-pyridin-2-ylpiperazin-1-yl)phenyl]benzamide (Example 135) (2.0 mg, 4.92 µmol) and Crabtree's catalyst ([Ir(COD)(PCy₃)(Py)]PF₆) (5.20 mg, 6.40 µmol) were dissolved in DCM (1.0 ml). The reaction and the purification were performed in analogy to [³H]4-(2-(2-fluoroethoxy)ethoxy)-N-(4-(4-(pyridin-2-yl)piperazin-1-yl)phenyl)benzamide ([³H]Example 12) to provide 3.33 TBq (90 mCi) of the desired compound with a radiochemical purity of 99% and a molar activity of 5.44 TBq/mmol (147 Ci/mmol). The identity of the labeled compound was confirmed by MS and by co-injection of the cold reference standard with the radiolabeled material. MS m/z: 407.2 [M(H)+H]⁺ (2%), 409.2 [M(³H)+H]⁺ (1%), 411.2 [M(³H₂)+H]⁺ (1%), 413.2 [M(³H₃)+H]⁺ (6%), 415.2 [M(³H₄)+H]⁺ (15%), 417.2 [M(³H₅)+H]⁺ (37%), 419.2 [M(³H₆)+H]⁺ (31%), 417.2 [M(³H₇)+H]⁺ (7%).

[³H]N-[4-[4-(5-Cyanopyridin-2-yl)piperazin-1-yl]phenyl]-4-(fluoromethoxy)benzamide ([³H]Example 136)

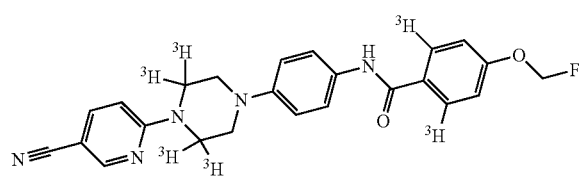 [SMILES: [3H]c1cc(OCF)cc([3H])c1C(=O)Nc1ccc(N2CC([3H])([3H])N(c3ccc(C#N)cn3)C([3H])([3H])C2)cc1]

In a 4 ml tritiation flask, N-(4-(4-(5-cyanopyridin-2-yl)piperazin-1-yl)phenyl)-4-(fluoromethoxy) benzamide (Example 136) (2.0 mg, 4.64 µmol) and Crabtree's catalyst ([Ir(COD)(PCy₃)(Py)]PF₆) (4.90 mg, 6.03 µmol) were dissolved in DCM (1.0 ml). The reaction and the purification were performed in analogy to [³H]4-(2-(2-fluoroethoxy)ethoxy)-N-(4-(4-(pyridin-2-yl)piperazin-1-yl)phenyl)benzamide ([³H]Example 12) to provide 1.44 TBq (39 mCi) of the desired compound with a radiochemical purity of 99% and a molar activity of 3.55 TBq/mmol (96 Ci/mmol). The identity of the labeled compound was confirmed by MS and by co-injection of the cold reference standard with the radiolabeled material. MS m/z: 432.2 $[M(H)+H]^+$ (2%), 434.2 $[M(^3H)+H]^+$ (3%), 436.2 $[M(^3H_2)+H]^+$ (16%), 438.2 $[M(^3H_3)+H]^+$ (36%), 440.2 $[M(^3H_4)+H]^+$ (30%), 442.2 $[M(^3H_5)+H]^+$ (9%), 444.2 $[M(^3H_6)+H]^+$ (4%).

TABLE 1

| | Displacement assay results | |
|---|---|---|
| Example No. | PCT_INHIB A30P @ 1 μM | sel. counterscreen PCT_INHIB AD @ 1 μM |
| 1 | 100 | 95 |
| 2 | 85 | 93 |
| 3 | 100% @ 3 μM | 100% @ 3 μM |
| 4 | 89 | 91 |
| 5 | 99 | 102 |
| 6 | 83 | 95 |
| 7 | 90 | 108 |
| 8 | 93 | 86 |
| 9 | 82 | 96 |
| 10 | 83 | 81 |
| 11 | 87 | 86 |
| 12 | 99 | 99 |
| 13 | 90 | 103 |
| 14 | 91 | 96 |
| 15 | 94 | 98 |
| 16 | 87 | 97 |
| 17 | 87 | 98 |
| 18 | 95 | 99 |
| 19 | 81 | |
| 20 | 90 | 103 |
| 21 | 85 | 91 |
| 22 | 84 | |
| 23 | 82 | |
| 24 | 94 | |
| 25 | 83 | |
| 26 | 93 | |
| 27 | 89 | |
| 28 | 82 | |
| 29 | 81 | 83 |
| 30 | 91 | 96 |
| 31 | 90 | 98 |
| 32 | 87 | 88 |
| 33 | 85 | 90 |
| 34 | 84 | 99 |
| 35 | 82 | 96 |
| 36 | 86 | 91 |
| 37 | 94 | 97 |
| 38 | 96 | 93 |
| 39 | 87 | 69 |
| 40 | 86 | 92 |
| 41 | 84 | 90 |
| 42 | 91 | 94 |
| 43 | 84 | 99 |
| 44 | 95 | 94 |
| 45 | 97 | 98 |
| 46 | 94 | 96 |
| 47 | 83 | 94 |
| 48 | 97 | 93 |
| 49 | 92 | 95 |
| 50 | 97 | 86 |
| 51 | 94 | 94 |
| 52 | 92 | 95 |
| 53 | 82 | 86 |
| 54 | 82 | 90 |
| 55 | 81 | 95 |
| 56 | 88 | 98 |
| 57 | 102 | 101 |
| 58 | 93 | 92 |
| 59 | 85 | 97 |
| 60 | 85 | 96 |
| 61 | 86 | 93 |
| 62 | 89 | 97 |
| 63 | 95 | 94 |
| 64 | 88 | 92 |
| 65 | 100 | 99 |
| 66 | 104 | 103 |
| 67 | 94 | 88 |
| 68 | 96 | 90 |
| 69 | 89 | 86 |
| 70 | 84 | 64 |
| 71 | 101 | 100 |
| 72 | 80 | 86 |
| 73 | 88 | 91 |
| 74 | 93 | 95 |
| 75 | 95 | 95 |
| 76 | 94 | 91 |
| 77 | 98 | 96 |
| 78 | 98 | 94 |
| 79 | 95 | 93 |
| 80 | 90 | 94 |
| 81 | 90 | 92 |
| 82 | 91 | 106 |
| 83 | 86 | 95 |
| 84 | 88 | 100 |
| 85 | 98 | 107 |
| 86 | 95 | 100 |
| 87 | 88 | 98 |
| 88 | 87 | 71 |
| 89 | 85 | 88 |
| 90 | 85 | 74 |
| 91 | 85 | 54 |
| 92 | 96 | 86 |
| 93 | 99 | 89 |
| 94 | 81 | 93 |
| 95 | 83 | 95 |
| 96 | 84 | 66 |
| 97 | 97 | 106 |
| 98 | 86 | 86 |
| 99 | 82 | 86 |
| 100 | 86 | 85 |
| 101 | 95 | 99 |
| 102 | 89 | 88 |
| 103 | 100 | 99 |
| 104 | 98 | 100 |
| 105 | 100 | 98 |
| 106 | 82 | 88 |
| 107 | 96 | 96 |
| 108 | 81 | 92 |
| 109 | 96 | 97 |
| 110 | 99 | 99 |
| 111 | 94 | 92 |
| 112 | 87 | 74 |
| 113 | 87 | 79 |
| 114 | 91 | 92 |
| 115 | 87 | 90 |
| 116 | 81 | 85 |
| 117 | 90 | 88 |
| 118 | 88 | 92 |
| 119 | 83 | 89 |
| 120 | 81 | 93 |
| 121 | 87 | 86 |
| 122 | 88 | 85 |
| 123 | 80 | 95 |
| 124 | 82 | 91 |
| 125 | 82 | 92 |
| 126 | 82 | 89 |
| 127 | 81 | 78 |
| 128 | 92 | 98 |
| 129 | 86 | 94 |
| 130 | 81 | 87 |
| 131 | 88 | 90 |
| 132 | 82 | 20 |
| 133 | 85 | 84 |
| 134 | 94 | 93 |

TABLE 1-continued

Displacement assay results

| Example No. | PCT_INHIB A30P @ 1 µM | sel. counterscreen PCT_INHIB AD @ 1 µM |
| --- | --- | --- |
| 135 | 97 | 98 |
| 136 | 91 | 92 |
| 137 | 80 | 92 |
| 138 | 82 | 89 |
| 139 | 94 | 94 |
| 140 | 94 | 93 |
| 141 | 96 | 94 |
| 142 | 91 | 91 |
| 143 | 91 | 91 |
| 144 | 89 | 92 |
| 145 | 98 | 97 |
| 146 | 95 | 91 |
| 147 | 88 | 91 |
| 148 | 86 | 89 |
| 149 | 93 | 91 |
| 150 | 98 | 94 |
| 151 | 93 | 91 |
| 152 | 90 | 88 |
| 153 | 92 | 87 |
| 154 | 98 | 96 |
| 155 | 85 | 97 |
| 156 | 81 | 76 |
| 157 | 91 | 92 |
| 158 | 83 | 87 |
| 159 | 88 | 89 |
| 160 | 96 | 95 |
| 161 | 84 | 87 |
| 162 | 84 | 78 |
| 163 | 94 | 92 |
| 164 | 80 | 90 |
| 165 | 86 | 90 |
| 166 | 81 | 70 |
| 167 | 91 | 88 |
| 168 | 95 | 96 |
| 169 | 83 | 82 |
| 170 | 86 | 82 |
| 171 | 89 | 92 |
| 172 | 93 | 84 |
| 173 | 83 | 82 |
| 174 | 87 @ 3 µM | 100 @ 3 µM |
| 175 | 85 @ 3 µM | 98 @ 3 µM |
| 176 | 102 @ 3 µM | 97 @ 3 µM |
| 177 | 96 @ 3 µM | 97 @ 3 µM |
| 178 | 97 @ 3 µM | 93 @ 3 µM |

What is claimed is:

1. A method of imaging alpha synuclein and/or Abeta deposits in a brain of a mammal, comprising:
   introducing into a mammal a detectable quantity of a radiolabeled compound selected from the group consisting of:
   2-Fluoro-4-methoxy-N-(4-(4-(pyridin-2-yl)piperazin-1-yl)phenyl)benzamide
   4-Hydroxy-N-[4-[4-(2-pyridyl)piperazin-1-yl]phenyl]benzamide
   4-Methoxy-N-[4-(4-pyridin-2-ylpiperazin-1-yl)phenyl]benzamide
   6-Methoxy-N-[4-[4-(5-methyl-2-pyridyl)piperazin-1-yl]phenyl]pyridine-3-carboxamide
   4-Methyl-N-(4-(4-(pyridin-2-yl)piperazin-1-yl)phenyl)benzamide
   4-(4-Methylpiperazin-1-yl)-N-(4-(4-(pyridin-2-yl)piperazin-1-yl)phenyl)benzamide
   4-(Dimethylamino)-N-(4-(4-(pyridin-2-yl)piperazin-1-yl)phenyl)benzamide
   4-Morpholino-N-(4-(4-(pyridin-2-yl)piperazin-1-yl)phenyl)benzamide
   2-Fluoro-N-(4-(4-(pyridin-2-yl)piperazin-1-yl)phenyl)benzamide
   2-Fluoro-4-methyl-N-N-(4-(4-(pyridin-2-yl)piperazin-1-yl)phenyl)benzamide
   4-Methoxy-2-methyl-N-(4-(4-(pyridin-2-yl)piperazin-1-yl)phenyl)benzamide
   4-(2-(2-Fluoroethoxy)ethoxy)-N-(4-(4-(pyridin-2-yl)piperazin-1-yl)phenyl)benzamide
   4-Methoxy-N-[4-[4-(1,3-thiazol-2-yl)piperazin-1-yl]phenyl]benzamide
   N-(4-(4-(Pyridin-2-yl)piperazin-1-yl)phenyl)-2,3-dihydrobenzo[b][1,4]dioxine-6-carboxamide
   N-(4-(4-(Pyridin-2-yl)piperazin-1-yl)phenyl)benzo[d][1,3]dioxole-5-carboxamide
   N-(4-(4-(Pyridin-2-yl)piperazin-1-yl)phenyl)imidazo[1,2-a]pyridine-7-carboxamide
   N-(4-(4-(Pyridin-2-yl)piperazin-1-yl)phenyl)imidazo[1,2-a]pyridine-6-carboxamide
   2-Fluoro-4-methoxy-N-[4-[4-(1,3-thiazol-2-yl)piperazin-1-yl]phenyl]benzamide
   4-Methoxy-2-methyl-N-[6-[4-(2-pyridyl)piperazin-1-yl]-3-pyridyl]benzamide
   4-(Dimethylamino)-N-[4-[4-(1,3-thiazol-2-yl)piperazin-1-yl]phenyl]benzamide
   2-Fluoro-4-methyl-N-[4-[4-(1,3-thiazol-2-yl)piperazin-1-yl]phenyl]benzamide
   4-(4-Methylpiperazin-1-yl)-N-[6-[4-(2-pyridyl)piperazin-1-yl]-3-pyridyl]benzamide
   2-Fluoro-4-methyl-N-[6-[4-(2-pyridyl)piperazin-1-yl]-3-pyridyl]benzamide
   4-Methoxy-N-[6-[4-(2-pyridyl)piperazin-1-yl]-3-pyridyl]benzamide
   5-Methyl-N-[4[4-(1,3-thiazol-2-yl)piperazin-1-yl]phenyl]pyridine-2-carboxamide
   4-Morpholin-4-yl-N-[4[4-(1,3-thiazol-2-yl)piperazin-1-yl]phenyl]benzamide
   4-Methyl-N-[4-[4-(1,3-thiazol-2-yl)piperazin-1-yl]phenyl]benzamide
   4-(4-Methylpiperazin-1-yl)-N-[4[4-(1,3-thiazol-2-yl)piperazin-1-yl]phenyl]benzamide
   2-Fluoro-4-methoxy-N-[2-methyl-4[4-(2-pyridyl)piperazin-1-yl]phenyl]benzamide
   4-(Dimethylamino)-N-[4[4-(6-methyl-2-pyridyl)piperazin-1-yl]phenyl]benzamide
   4-(Dimethylamino)-N-[6-[4-(2-pyridyl)piperazin-1-yl]-3-pyridyl]benzamide
   4-Morpholino-N-6[4-(2-pyridyl)piperazin-1-yl]-3-pyridyl]benzamide
   5-Methyl-N-[6-[4-(2-pyridyl)piperazin-1-yl]-3-pyridyl]pyridine-2-carboxamide
   2-Fluoro-4-methoxy-N-[6-[4-(2-pyridyl)piperazin-1-yl]-3-pyridyl]benzamide
   4-Methyl-N-[6-[4-(2-pyridyl)piperazin-1-yl]-3-pyridyl]benzamide
   4-(Dimethylamino)-N-[6-[4-(2-pyridyl)piperazin-1-yl]pyridazin-3-yl]benzamide
   4-Methyl-N-(4-(4-(pyridin-3-yl)piperazin-1-yl)phenyl)benzamide
   4-Methoxy-N-(4-(4-(pyridin-3-yl)piperazin-1-yl)phenyl)benzamide
   4-Morpholino-N-(4-(4-(pyridin-3-yl)piperazin-1-yl)phenyl)benzamide
   2-Fluoro-4-methoxy-N-[6-[4-(2-pyridyl)piperazin-1-yl]pyridazin-3-yl]benzamide
   4-Methoxy-N-[4-[4-(4-pyridyl)piperazin-1-yl]phenyl]benzamide 4-Methyl-N-(4-(4-(pyridin-2-yl)piperazin-1-yl)phenyl)-3,4-dihydro-2H-benzo[b][1,4]oxazine-7-carboxamide
4-Methoxy-N-(5-(4-(pyridin-2-yl)piperazin-1-yl)pyridin-2-yl)benzamide
2-Fluoro-4-methoxy-N-(5-(4-(pyridin-2-yl)piperazin-1-yl)pyridin-2-yl)benzamide
4-Methyl-N-(5-(4-(pyridin-2-yl)piperazin-1-yl)pyridin-2-yl)benzamide
4-(Dimethylamino)-N-(5-(4-(pyridin-2-yl)piperazin-1-yl)pyridin-2-yl)benzamide
2-Fluoro-N-(5-(4-(pyridin-2-yl)piperazin-1-yl)pyridin-2-yl)benzamide
4-Morpholino-N-[6-[4-(2-pyridyl)piperazin-1-yl]pyridazin-3-yl]benzamide
4-Methoxy-N-{4-[4-(pyrimidin-2-yl)piperazin-1-yl]phenyl}benzamide
N-(4-(4-(5-Cyanopyridin-2-yl)piperazin-1-yl)phenyl)-4-methoxybenzamide
4-Morpholino-N-(5-(4-(pyridin-2-yl)piperazin-1-yl)pyridin-2-yl)benzamide
2-Fluoro-4-methyl-N-(5-(4-(pyridin-2-yl)piperazin-1-yl)pyridin-2-yl)benzamide
5-Methyl-N-(5-(4-(pyridin-2-yl)piperazin-1-yl)pyridin-2-yl)picolinamide
3-Methyl-N-(5-(4-(pyridin-2-yl)piperazin-1-yl)pyridin-2-yl)benzamide
4-Methoxy-N-{4-[4-(1,3,5-triazin-2-yl)piperazin-1-yl]phenyl}benzamide
4-Methoxy-N-{4-[4-(pyrimidin-4-yl)piperazin-1-yl]phenyl}benzamide
N-[4-[4-(4-Cyanophenyl)piperazin-1-yl]phenyl]-4-methoxy-benzamide
4-Methoxy-N-[4-[4-(6-methoxypyridin-3-yl)piperazin-1-yl]phenyl]benzamide
4-Methoxy-N-(2-(4-(pyridin-2-yl)piperazin-1-yl)pyrimidin-5-yl)benzamide
2-Fluoro-4-methoxy-N-(2-(4-(pyridin-2-yl)piperazin-1-yl)pyrimidin-5-yl)benzamide
2-Fluoro-N-(2-(4-(pyridin-2-yl)piperazin-1-yl)pyrimidin-5-yl)benzamide
4-(Dimethylamino)-N-(2-(4-(pyridin-2-yl)piperazin-1-yl)pyrimidin-5-yl)benzamide
4-Morpholino-N-(2-(4-(pyridin-2-yl)piperazin-1-yl)pyrimidin-5-yl)benzamide
3-Methyl-N-(2-(4-(pyridin-2-yl)piperazin-1-yl)pyrimidin-5-yl)benzamide
N-[4-[4-(4-Cyano-2-pyridyl)piperazin-1-yl]phenyl]-4-methoxy-benzamide
4-Methoxy-N-{4-[4-(thiophen-2-yl)piperazin-1-yl]phenyl}benzamide
4-Methoxy-N-{4-[4-(2-methoxypyridin-3-yl)piperazin-1-yl]phenyl}benzamide
4-Methoxy-N-{4-[4-(6-methoxypyridin-2-yl)piperazin-1-yl]phenyl}benzamide
4-Methoxy-N-{4-[4-(2-methoxyphenyl)piperazin-1-yl]phenyl}benzamide
N-{4-[4-(2-Cyanophenyl)piperazin-1-yl]phenyl 1-4-methoxybenzamide
N-{4-[4-(2-Fluorophenyl)piperazin-1-yl]phenyl 1-4-methoxybenzamide
4-Methoxy-2-methyl-N-(2-(4-(pyridin-2-yl)piperazin-1-yl)pyrimidin-5-yl)benzamide
4-(4-Methylpiperazin-1-yl)-N-(2-(4-(pyridin-2-yl)piperazin-1-yl)pyrimidin-5-yl)benzamide
4-Methyl-N-(2-(4-(pyridin-2-yl)piperazin-1-yl)pyrimidin-5-yl)benzamide
5-Methyl-N-(2-(4-(pyridin-2-yl)piperazin-1-yl)pyrimidin-5-yl)picolinamide
5-Methoxy-N-(5-(4-(pyridin-2-yl)piperazin-1-yl)pyridin-2-yl)picolinamide
5-Methoxy-N-(4-(4-(pyridin-3-yl)piperazin-1-yl)phenyl)picolinamide
5-Methoxy-N-(4-(4-(pyridin-2-yl)piperazin-1-yl)phenyl)picolinamide
5-Methoxy-N-(2-(4-(pyridin-2-yl)piperazin-1-yl)pyrimidin-5-yl)picolinamide
4-Methoxy-2-methyl-N-[5-(4-pyridin-2-ylpiperazin-1-yl)pyridin-2-yl]benzamide
4-(4-Methylpiperazin-1-yl)-N-5-(4-pyridin-2-ylpiperazin-1-yl)pyridin-2-yl]benzamide
4-Methoxy-N-[4-[4-(4-methoxy-2-pyridyl)piperazin-1-yl]phenyl]benzamide
Acetic acid; 4-Methoxy-N-[4-[4-(3-methyl-4-pyridyl)piperazin-1-yl]phenyl]benzamide
2-Fluoro-4-methoxy-N-(5-(4-(pyridin-2-yl)piperazin-1-yl)pyrazin-2-yl)benzamide
4-Methoxy-N-(5-(4-(pyridin-2-yl)piperazin-1-yl)pyrazin-2-yl)benzamide
4-(Dimethylamino)-N-(5-(4-(pyridin-2-yl)piperazin-1-yl)pyrazin-2-yl)benzamide
4-(4-Methylpiperazin-1-yl)-N-(5-(4-(pyridin-2-yl)piperazin-1-yl)pyrazin-2-yl)benzamide
4-Morpholino-N-(5-(4-(pyridin-2-yl)piperazin-1-yl)pyrazin-2-yl)benzamide
4-Methyl-N-(5-(4-(pyridin-2-yl)piperazin-1-yl)pyrazin-2-yl)benzamide
5-Methyl-N-(5-(4-(pyridin-2-yl)piperazin-1-yl)pyrazin-2-yl)picolinamide
N-(4-(4-(5-Cyanopyridin-2-yl)piperazin-1-yl)phenyl)-6-methoxypicolinamide
N-(4-(4-(4-Cyanophenyl)piperazin-1-yl)phenyl)-4-morpholinobenzamide
N-(4-(4-(4-Cyanophenyl)piperazin-1-yl)phenyl)-6-methoxypicolinamide
4-Morpholino-N-(4-(4-(thiophen-2-yl)piperazin-1-yl)phenyl)benzamide
N-(5-(4-(5-Cyanopyridin-2-yl)piperazin-1-yl)pyridin-2-yl)-4-methoxybenzamide
N-(5-(4-(4-Cyanophenyl)piperazin-1-yl)pyridin-2-yl)-4-methoxybenzamide
N-(2-(4-(4-Cyanophenyl)piperazin-1-yl)pyrimidin-5-yl)-4-methoxybenzamide
N-(2-(4-(5-Cyanopyridin-2-yl)piperazin-1-yl)pyrimidin-5-yl)-4-methoxybenzamide
N-(2-(4-(5-Cyanopyridin-2-yl)piperazin-1-yl)pyrimidin-5-yl)-4-morpholinobenzamide
N-[4-[4-(6-Cyano-2-pyridyl)piperazin-1-yl]phenyl]-4-methoxy-benzamide
4-Methoxy-N-[4-(4-phenylpiperazin-1-yl)phenyl]benzamide
4-Methoxy-N-[4-[4-(4-methyl-2-pyridyl)piperazin-1-yl]phenyl]benzamide
N-[4-[4-(3-Cyanophenyl)piperazin-1-yl]phenyl]-4-methoxy-benzamide
N-[4-[4-(3-Fluorophenyl)piperazin-1-yl]phenyl]-4-methoxy-benzamide
N-[4-[4-(4-Fluorophenyl)piperazin-1-yl]phenyl]-4-methoxy-benzamide
N-[3-Fluoro-4-[4-(2-pyridyl)piperazin-1-yl]phenyl]-4-methoxy-benzamide
N-[4-[4-(5-Cyano-2-pyridyl)piperazin-1-yl]-3-fluoro-phenyl]-4-methoxy-benzamide N-(4-(4-(5-Cyanopyridin-2-yl)piperazin-1-yl)phenyl)-4-hydroxybenzamide
4-Methoxy-N-[4-[4-(p-tolyl)piperazin-1-yl]phenyl]benzamide
4-Methoxy-N-[4-[4-(4-methoxyphenyl)piperazin-1-yl]phenyl]benzamide
4-Methoxy-N-[4-[4-(4-methylsulfonylphenyl)piperazin-1-yl]phenyl]benzamide
N-[4-[4-(4-Cyanophenyl)piperazin-1-yl]-3-methyl-phenyl]-4-methoxy-benzamide
N-[4-[4-(5-Cyano-2-pyridyl)piperazin-1-yl]-3-methyl-phenyl]-4-methoxy-benzamide
N-[4-[4-(4-Cyanophenyl)piperazin-1-yl]phenyl]-2-fluoro-4-methoxy-benzamide
N-[4-[4-(5-Cyano-2-pyridyl)piperazin-1-yl]phenyl]-2-fluoro-4-methoxy-benzamide
N-[4-[4-(5-Cyano-2-pyridyl)piperazin-1-yl]phenyl]-4-(2-fluoroethoxy)benzamide
N-[4-[4-(4-Cyanophenyl)piperazin-1-yl]phenyl]-4-(2-fluoroethoxy)benzamide
4-(2-Fluoroethoxy)-N-[4-[4-(2-pyridyl)piperazin-1-yl]phenyl]benzamide
4-(2-Fluoroethoxy)-N-[4-(4-thiazol-2-ylpiperazin-1-yl)phenyl]benzamide
4-[2-[2-(2-Fluoroethoxy)ethoxy]ethoxy]-N-[4-(4-thiazol-2-ylpiperazin-1-yl)phenyl]benzamide
N-(4-(4-(5-Cyanopyridin-2-yl)piperazin-1-yl)phenyl)-4-(2-(2-fluoroethoxy)ethoxy)benzamide
N-(4-(4-(4-Cyanophenyl)piperazin-1-yl)phenyl)-4-(2-(2-fluoroethoxy)ethoxy)benzamide
N-[4-[4-(4-Cyanophenyl)piperazin-1-yl]phenyl]-4-[2-[2-(2-fluoroethoxy)ethoxy]ethoxy]benzamide
rac-4-(2-((tert-Butyldimethylsilyl)oxy)-3-fluoropropoxy)-N-(4-(4-(pyridin-2-yl)piperazin-1-yl)phenyl)benzamide
rac-4-(3-Fluoro-2-hydroxypropoxy)-N-(4-(4-(pyridin-2-yl)piperazin-1-yl)phenyl)benzamide
rac-4-(2-((tert-Butyldimethylsilyl)oxy)-3-fluoropropoxy)-N-(4-(4-(thiazol-2-yl)piperazin-1-yl)phenyl)benzamide
rac-4-(2-((tert-Butyldimethylsilyl)oxy)-3-fluoropropoxy)-N-(4-(4-(4-cyanophenyl)piperazin-1-yl)phenyl)benzamide
rac-4-(2-((tert-Butyldimethylsilyl)oxy)-3-fluoropropoxy)-N-(4-(4-(4-cyanopyridin-2-yl)piperazin-1-yl)phenyl)benzamide
rac-N-(4-(4-(5-Cyanopyridin-2-yl)piperazin-1-yl)phenyl)-4-(3-fluoro-2-hydroxypropoxy)benzamide
rac-4-(3-Fluoro-2-hydroxypropoxy)-N-(4-(4-(thiazol-2-yl)piperazin-1-yl)phenyl)benzamide
rac-N-(4-(4-(4-Cyanophenyl)piperazin-1-yl)phenyl)-4-(3-fluoro-2-hydroxypropoxy)benzamide
4-Methoxy-N-(4-((3 aS,6aS)-5-(pyridin-2-yl)hexahydropyrrolo[3,4-c]pyrrol-2(1H)-yl)phenyl)benzamide
4-Methoxy-N-(4-((3aR,6aR)-5-(pyridin-2-yl)hexahydropyrrolo[3,4-c]pyrrol-2(1H)-yl)phenyl)benzamide
4-(Fluoromethoxy)-N-(4-(4-(pyridin-3-yl)piperazin-1-yl)phenyl)benzamide
4-(Fluoromethoxy)-N-[4-(4-pyridin-2-ylpiperazin-1-yl)phenyl]benzamide
N-[4-[4-(5-Cyanopyridin-2-yl)piperazin-1-yl]phenyl]-4-(fluoromethoxy)benzamide
4-(2-(2-Hydroxyethoxy)ethoxy)-N-(4-(4-(pyridin-2-yl)piperazin-1-yl)phenyl)benzamide
4-Hydroxy-N-[4-(4-pyridin-3-ylpiperazin-1-yl)phenyl]benzamide
N-(4-(4-(4-Cyano-2-methoxyphenyl)piperazin-1-yl)phenyl)-4-methoxybenzamide
N-(4-(4-(4-Cyano-3-methoxyphenyl)piperazin-1-yl)phenyl)-4-methoxybenzamide
N-(4-(4-(5-Fluoropyridin-2-yl)piperazin-1-yl)phenyl)-4-methoxybenzamide
N-(4-(4-(5-(Dimethylamino)pyridin-2-yl)piperazin-1-yl)phenyl)-4-methoxybenzamide
N-(4-(4-(5-Cyanopyrimidin-2-yl)piperazin-1-yl)phenyl)-4-methoxybenzamide
N-(4-(4-(4-Cyano-2-methylphenyl)piperazin-1-yl)phenyl)-4-methoxybenzamide
N-(4-(4-(4-Cyano-2-fluorophenyl)piperazin-1-yl)phenyl)-4-methoxybenzamide
N-(4-(4-(6-Fluoropyridin-2-yl)piperazin-1-yl)phenyl)-4-methoxybenzamide
N-(4-(4-(5-Cyanopyrazin-2-yl)piperazin-1-yl)phenyl)-4-methoxybenzamide
N-(4-(4-(3-Fluoropyridin-2-yl)piperazin-1-yl)phenyl)-4-methoxybenzamide
N-(4-(4-(4-Chloropyridin-2-yl)piperazin-1-yl)phenyl)-4-methoxybenzamide
N-(4-(4-(4-Cyano-3-fluorophenyl)piperazin-1-yl)phenyl)-4-methoxybenzamide
N-(4-(4-(5-Cyano-4-methylpyridin-2-yl)piperazin-1-yl)phenyl)-4-methoxybenzamide
N-(4-(4-(4-Chloro-5-cyanopyridin-2-yl)piperazin-1-yl)phenyl)-4-methoxybenzamide
N-(4-(4-(4-Cyano-3-methylphenyl)piperazin-1-yl)phenyl)-4-methoxybenzamide
N-(4-(4-(6-Cyanopyridin-3-yl)piperazin-1-yl)phenyl)-4-methoxybenzamide
4-Methoxy-N-(4-(4-(2-methoxypyridin-4-yl)piperazin-1-yl)phenyl)benzamide
4-Methoxy-N-(4-(4-(6-methylpyridin-3-yl)piperazin-1-yl)phenyl)benzamide
N-(4-(4-(4-Cyanophenyl)piperazin-1-yl)phenyl)-6-methoxynicotinamide
N-(4-(4-(4-Cyanophenyl)piperazin-1-yl)phenyl)-1-methyl-1H-pyrazole-4-carboxamide
N-(4-(4-(5-Cyanopyridin-2-yl)piperazin-1-yl)phenyl)-3,4-dimethoxybenzamide
N-(4-(4-(5-Cyanopyridin-2-yl)piperazin-1-yl)phenyl)-3-fluoro-4-methoxybenzamide
N-(4-(4-(5-Cyanopyridin-2-yl)piperazin-1-yl)phenyl)isonicotinamide
N-(4-(4-(5-Cyanopyridin-2-yl)piperazin-1-yl)phenyl)-5-methoxypicolinamide
N-(4-(4-(4-Cyanophenyl)piperazin-1-yl)phenyl)-3-fluoro-4-methoxybenzamide
4-Cyano-N-(4-(4-(5-cyanopyridin-2-yl)piperazin-1-yl)phenyl)benzamide
N-(4-(4-(4-Cyanophenyl)piperazin-1-yl)phenyl)pyrimidine-4-carboxamide
N-(4-(4-(4-Cyanophenyl)piperazin-1-yl)phenyl)-5-methoxypicolinamide
N-(4-(4-(4-Cyanophenyl)piperazin-1-yl)phenyl)-4-methoxy-3-methylbenzamide
N-(4-(4-(4-Cyanophenyl)piperazin-1-yl)phenyl)-4-methoxy-2-methylbenzamide
N-(4-(4-(4-Cyanophenyl)piperazin-1-yl)phenyl)-3,4-dimethoxybenzamide
N-(4-(4-(5-Cyanopyridin-2-yl)piperazin-1-yl)phenyl)-4-methoxy-3-methylbenzamide
N-(4-(4-(5-Cyanopyridin-2-yl)piperazin-1-yl)phenyl)-6-methoxynicotinamide Methyl 6-(4-(4-(4-methoxybenzamido)phenyl)piperazin-1-yl)nicotinate N-(4-(4-(6-Cyanopyridin-3-yl)piperazin-1-yl)phenyl)-5-methoxypicolinamide N-[4-[4-(5-Cyano-2-pyridyl)piperazin-1-yl]phenyl]-4-prop-2-ynoxy-benzamide N-[4-[4-(5-Cyano-2-pyridyl)piperazin-1-yl]phenyl]-4-(2-prop-2-ynoxyethoxy)benzamide N-[4-[4-(5-Ethynyl-2-pyridyl)piperazin-1-yl]phenyl]-4-methoxy-benzamide 4-Prop-2-ynoxy-N-[4-[4-(2-pyridyl)piperazin-1-yl]phenyl]benzamide and 4-(2-Prop-2-ynoxyethoxy)-N-[4-[4-(2-pyridyl)piperazin-1-yl]phenyl]benzamide, wherein the compounds are labeled with the radionuclide $^3$H.

2. The method of claim 1, wherein the radiolabeled compound is selected from the group consisting of:

2-Fluoro-4-methoxy-N-(4-(4-(pyridin-2-yl)piperazin-1-yl)phenyl)benzamide

4-Methoxy-N-[4-(4-pyridin-2-ylpiperazin-1-yl)phenyl]benzamide 4-(2-(2-Fluoroethoxy)ethoxy)-N-(4-(4-(pyridin-2-yl)piperazin-1-yl)phenyl)benzamide N-(4-(4-(5-Cyanopyridin-2-yl)piperazin-1-yl)phenyl)-4-methoxybenzamide N-(4-(4-(5-Cyanopyridin-2-yl)piperazin-1-yl)phenyl)-4-(2-(2-fluoroethoxy)ethoxy)benzamide N-(4-(4-(4-Cyanophenyl)piperazin-1-yl)phenyl)-4-(2-(2-fluoroethoxy)ethoxy)benzamide 4-(Fluoromethoxy)-N-(4-(4-(pyridin-3-yl)piperazin-1-yl)phenyl)benzamide 4-(Fluoromethoxy)-N-[4-(4-pyridin-2-ylpiperazin-1-yl)phenyl]benzamide and N-[4-[4-(5-Cyanopyridin-2-yl)piperazin-1-yl]phenyl]-4-(fluoromethoxy)benzamide, wherein the compounds are labeled with the radionuclide $^3$H.

3. The method of claim 1, wherein the radiolabeled compound is selected from the group consisting of:

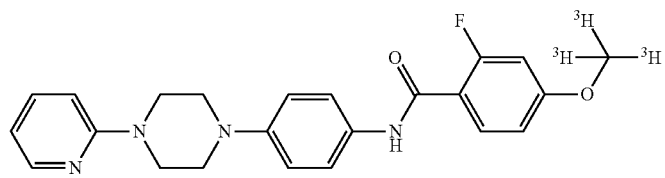

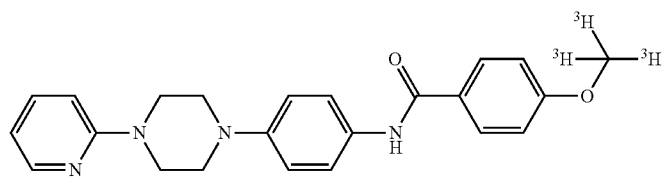

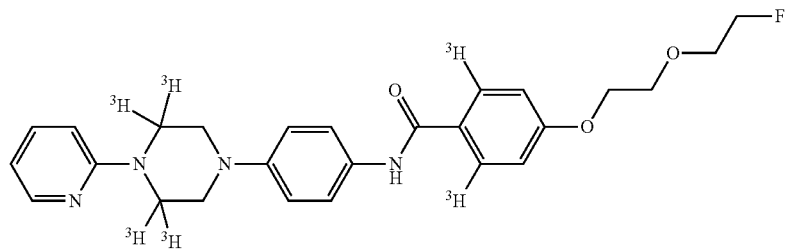

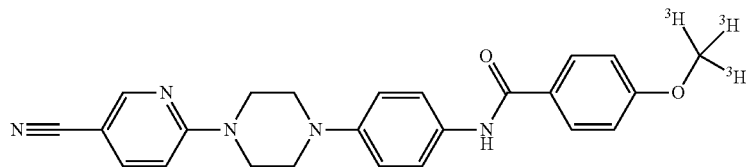

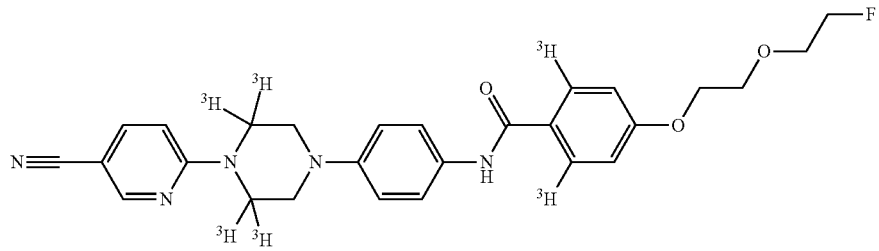

-continued
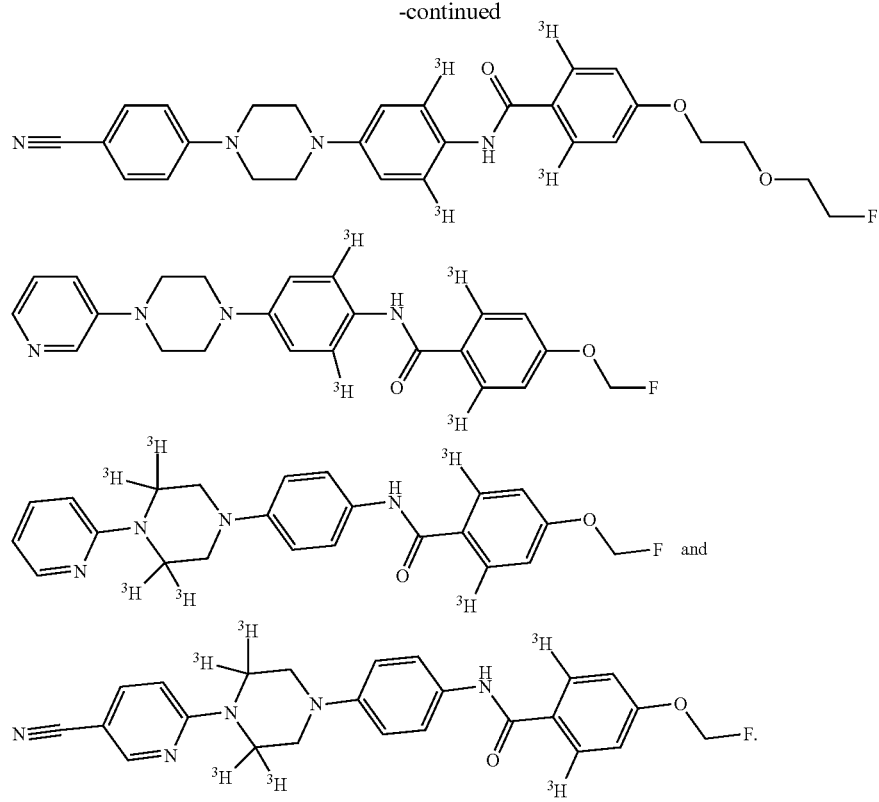
4. The method of claim 1, wherein the radiolabeled compound is in a pharmaceutical composition further comprising a pharmaceutical acceptable carrier.
* * * * *